US007186515B1

(12) United States Patent
Srivastava et al.

(10) Patent No.: US 7,186,515 B1
(45) Date of Patent: Mar. 6, 2007

(54) ALPHA(2) MACROGLOBULIN RECEPTOR AS A HEAT SHOCK PROTEIN RECEPTOR AND USES THEREOF

(75) Inventors: Pramod K. Srivastava, Avon, CT (US); Robert J. Binder, Farmington, CT (US)

(73) Assignee: University of Connecticut Health Center, Farmington, CT (US)

( * ) Notice: Subject to any disclaimer, the term of this patent is extended or adjusted under 35 U.S.C. 154(b) by 0 days.

(21) Appl. No.: 09/625,137

(22) Filed: Jul. 25, 2000

Related U.S. Application Data

(60) Provisional application No. 60/209,095, filed on Jun. 2, 2000.

(51) Int. Cl.
*G01N 33/53* (2006.01)
*G01N 33/567* (2006.01)
*G01N 33/00* (2006.01)

(52) U.S. Cl. ..................... 435/7.1; 435/7.21; 435/7.24; 435/7.8

(58) Field of Classification Search ................. 435/7.1, 435/7.8, 7.21, 7.24
See application file for complete search history.

(56) References Cited

U.S. PATENT DOCUMENTS

| | | | |
|---|---|---|---|
| 5,112,298 | A | 5/1992 | Prince et al. |
| 5,554,293 | A | 9/1996 | Uhoch |
| 5,637,082 | A | 6/1997 | Pages et al. |
| 5,830,464 | A | 11/1998 | Srivastava |
| 5,837,251 | A | 11/1998 | Srivastava |
| 5,846,928 | A | 12/1998 | Kishida |
| 5,935,576 | A | 8/1999 | Srivastava |
| 5,961,979 | A | 10/1999 | Srivastava |
| 5,968,526 | A | 10/1999 | Garman et al. |
| 5,985,270 | A | 11/1999 | Srivastava |
| 6,007,821 | A | 12/1999 | Srivastava et al. |
| 6,017,540 | A | 1/2000 | Srivastava |
| 6,027,731 | A | 2/2000 | Pauza |
| 6,033,561 | A | 3/2000 | Schoendorfer |
| 6,156,311 | A | 12/2000 | Strickland et al. |
| 6,333,311 | B1 | 12/2001 | Nuijens et al. |
| 2002/0001841 | A1 | 1/2002 | Kaltoft et al. |

FOREIGN PATENT DOCUMENTS

| | | |
|---|---|---|
| WO | WO 94/14471 | 7/1994 |
| WO | WO 94/14976 | 7/1994 |
| WO | WO 96/10411 | 4/1996 |
| WO | WO 97/04794 | 2/1997 |
| WO | WO 97/10002 | 3/1997 |
| WO | WO 98/46739 | 7/1997 |
| WO | WO 98/42752 | 10/1998 |
| WO | WO 98/46743 | 10/1998 |
| WO | WO 99/50303 | 10/1999 |
| WO | WO 00/03003 | 1/2000 |
| WO | WO 00/34494 | 6/2000 |
| WO | WO 00/38760 | 7/2000 |
| WO | WO 00/46246 | 8/2000 |
| WO | WO 00/54801 | 9/2000 |
| WO | WO 02/07755 | 1/2002 |

OTHER PUBLICATIONS

Agostoni et al., 1994, "Activation of complement and kinin systems after thrombolytic therapy in patients with acute myocardial infarction. A comparison between streptokinase and recombinant tissue-type plasminogen activator." Circulation. 90(6):2666-70.
Bednar et al., 1997, "Activation of complement by tissue plasminogen activator, but not acute cerebral ischemia, in a rabbit model of thromboembolic stroke." J. Neurosurg. 86(1):139-42.
Collen et al., 1989, "Tissue-type plasminogen activator. A review of its pharmacology and therapeutic use as a thrombolytic agent." Drugs. 38(3):346-88.
Hanover et al., 1986, "Monoclonal antibodies against a glycoprotein localized in coated pits and endocytic vesicles inhibit alpha2-macroglobulin binding and uptake", J. of Biol. Chem, 261(35): 16732-16737.
Herz et al., 1990, "Low density lipoprotein receptor-related protein mediates endocytosis of monoclonal antibodies in cultured cells and rabbit liver", J. of Biol. Chem. 265(34): 21355-21362.
Herz et al., 1991, "39-kDa protein modulates binding of ligands to low density lipoprotein recpetor-related protein/alpha-2-macroglobulin receptor." J.Biol.Chem. 266(31):21232-21238.
Hey et al., 1988, "Cloning of a novel member of the low-density lipoprotein receptor family", Gene 216: 103-111.
Horn et al., 1995, "Analysis of the binding of Pro-urokinase and urokinase-plasminogen activator inhibitor-1 complex to the low density lipoprotein recepetor-related protein using a Fab fragment selected from a phage-displayed Fab library", J. of Biol. Chem. 270 (20): 11770-11775.
Huang et al., 1996, "The immunodominant major histocompatability complex class I-restricted antigen of a murine colon tumor derives from an endogenous retroviral gene product", Proc. Natl. Acad. Sci. USA. 93:9730-9735.
Hughes et al., 1981, "Characterization of plasma membrane proteins identified by monoclonal antibodies", J. of Biol./Chem. 256(2): 664-671.
Isaacs et al., 1988, "Use of anti-idiotypic antibodies to establish that monoclonal antibody 7H11D6 binds to the alpha2-macroglobulin receptor recognition site", J. Biol. Chem. 263(14): 6709-6714.
Katsutani et al., 1992, "Immunogenic properties of structurally modified human tissue plasminogen activators in chimpanzees and mice." Fundam Appl Toxicol. 19(4):555-62.
Kim et al., 1998, "A new low density lipoprotein receptor related protein, LRP5, is expressed in hepatocytes and adrenal cortex, and recognized apolipoprotein E", J. Biochem. 124: 1072-1076.

(Continued)

*Primary Examiner*—Christopher H. Yaen
(74) *Attorney, Agent, or Firm*—Jones Day

(57) ABSTRACT

The present invention relates to the use of alpha (2) macroglobulin ("α2M") receptor as a heat shock protein receptor, cells that express the α2M receptor bound to an HSP, and antibodies and other molecules that bind the α2M receptor-HSP complex. The invention also relates to screening assays to identify compounds that modulate the interaction of an HSP with the α2M receptor, and methods for using compositions comprising α2M-receptor sequences for the diagnosis and treatment of immune disorders, proliferative disorders, and infectious diseases.

27 Claims, 103 Drawing Sheets

OTHER PUBLICATIONS

Figure 1A:
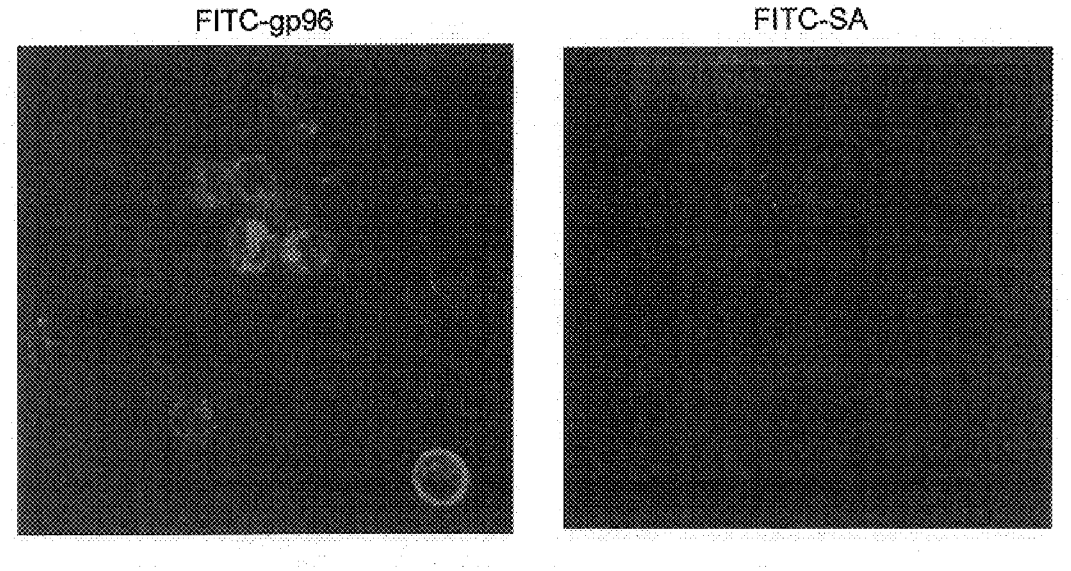

Kimber et al., 2002, "Lactoferrin: influences on langerhans cells, epidermal cytokines, and cutaneous inflammation." Biochem Cell Biol. 2002;80(1):103-7.
Moestrup et al., 1990, "Immunocytochemical identification of the human aplpha 2-macroglobulin receptor in monocytes and fibroblasts: monoclonal antibodies define the receptor as a monocyte differentiation antigen", Exper. Cell Res. 190: 195-203.
Moestrup et al., 1991, Analysis of Ligand Recognition by the purified alpha-2M-macroglobulin receptor (low density lipoprotein receptor-related protein). J. Biol. Chem. 266(21):14011-14017.
Opekun et al., 1999, "Novel therapies for *Heliobacter pylori* infection." Aliment Pharmacol Ther, 13(1):35-42.
Reed et al., 1990, "Low incidence of antibodies to recombinant human tissue-type plasminogen activator in treated patients." Thromb Haemost. 64(2):276-80.
Warshawaky et al., 1993, "Identification of domains in the 39-kDa protein that inhibit the binding of ligands to the low density lipoprotein receptor-related protein," J. Biol. Chem. 268(29):22046-22054.
Yamauchi et al., 2000, "Oral administration of bovine lactoferrin for treatment of *tinea pedis*. A placebo-controlled, double-blind study." Mycoses.43(5):197-202.
Zimecki et al., 1999, "Lactoferrin increases the output of neutrophil precursors and attenuates the spontaneous production of TNT-alpha and IL-6 by peripheral blood cells." Arch Immunol Ther Exp (Warsz). 47(2):113-8.
Zimecki et al., 1998, "Immnunoregulatory effects of a nutritional preparation containing bovine lactoferrin taken orally by healthy individuals." Arch Immunol Ther Exp (Warsz). 46(4):231-40.
U.S. Appl. No. 09/411,075, P. Srivastava.
U.S. Appl. No. 60/209,095, P. Srivastava.
Arnold et al., 1995, , "Cross-priming of minor histocompaibility antigen-specific cytotoxic T cells upon immunization with the heat shock protein gp96", J Exp Med. 182(3):885-9.
Arnold-Schild et al., 1999, "Cutting edge: receptor-mediated endocytosis of heat shock proteins by professional antigen-presenting cells", J. Immunol. 1999, 162: 3757-3760.
Asea et al., 2000, "HSP70 stimulates cytokine production through a CD14 dependent pathway, demostrating its dual role as a chaperone and cytokine", Nature Med. 6: 435-42.
Bevan, 1995, "Antigen presentation to cytotoxic T lymphocytes in vivo", J.Exp. Med. 192: 639-41.
Binder et al., 1998, Cell Stress & Chaperones 3 (Supp.1): 2.
Castellino et al., 2000, "Receptor-mediated Uptake of Antigen/Heat Shock Protein Complexes Results in Major Histocompatibility Complex Class I Antigen Presentation via Two Distinct Processing Pathways", J. Exp. Med. 191: 1957-64.
Chen et al., 1999, "Human 60-kDa Heat-Shock Protein: A Danger Signal to the Innate Immune System", J. Immunology 162: 3212-3219.
Chu and Pizzo, 1993, "Receptor mediated antigen delivery into macrophages. Complexing antigen to $\alpha_2$-macroglobulin enhances presentation into T cells", J. Immun. 150(1):48-58.
Chu et al., 1994, "Adjuvant-Free in Vivo Targeting. Antigen Delivery by a $\alpha_2$-macroglobulin enhances antibody formation", J. Immun. 152(4):1538-45.
Ciupitu et al., 1998, "Immunization with a lymphocytic choriomeningitis virus peptide mixed with heat shock protein 70 results in protective antiviral immunity and specific cytotoxic T lymphocytes", J Exp Med. 187(5):685-91.
Coutinho et al., 1998, "Alpha-2-macroglobulin receptor is differently expressed in peritoneal macrophages from C3H and C57/B16 mice and up-regulated during *Trypanosoma cruzi* infection", Tissue and Cell 30: 407-15.
Day et al., "Direct delivery of exogenous MHC class I molecule-binding oligopeptides to the endoplasmic reticulum of viable cells", 1997, Proc Natl Acad Sci. USA 94: 8064-8069.
Dennis et al., 1989, "Alpha 2-macroglobulin is a binding protein for basic fibroblast growth factor", J Biol Chem. 264 (13) :7210-6.
Fadok et al., 2000, "A receptor for phosphatidylserine-specific clearance of apoptotic cells", Nature 405(6782):85-90.
Forrester et al., 1983, "Effect of modified alpha 2macroglobulin on leucocyte locomotion and chemotaxis", Immunology. 50(2):251-9.
Haas et al., 1988, "cDNA cloning of the immunoglobulin heavy chain binding protein", Proc Natl Acad Sci U S A. 85(7):2250-4.
Hertz et al., 1988, "Surface location and high affinity for calcium of a 500-kd liver membrane protein closely related to the LDL-receptor suggest a physiological role as lipoprotein receptor", EMBO J. 7(13):4119-27.
Hickey et al., 1986, "Sequence and organization of genes encoding the human 27 kDa heat shock protein", Nucleic Acids Res. 14(10):4127-45.
Hickey et al., 1989, "Sequence and regulation of a gene encoding the human 89-kilodalton heat shock protein", Mol Cell Biol. 9(6):2615-26.
Hilliker et al., "Assignment of the gene coding for the alpha 2-macroglobulin receptor to mouse chromosome 15 and to human chromosome 12q13-q14 by isotopic and nonisotopic in situ hybridization", Genomics. 13(2):472-4.
Holtet et al., 1994, "Recombinant $\alpha$-$_2$M Receptor binding domain binds to the $\alpha$-$_2$M receptor with high affinity", Ann N Y Acad Sci 737:480-2.
Huang et al., 1999, "NMR solution structure of complement-like repeat CR8 from the low density lipoprotein receptor -related protein", J. of Biolog. Chem. 274: 14130-14136.
Huang et al., 1984, Specific covalent binding of platelet-derived growth factor to human plasma alpha 2-macroglobulin. Proc Natl Acad Sci U S A. 81(2):342-6.
Hunt et al., 1990, "Characterization and sequence of a mouse hsp70 gene and its expression in mouse cell lines", Gene. 87(2):199-204.
Jensen et al., 1989, "Comparison of $\alpha$-macroglobulin receptors from human, baboon, rat and mouse liver", Biochem. Arch. 5:171-6.
Jindai et al., 1989, Primary structure of a human mitochondrial protein homologous to the bacterial and plant chaperonins and to the 65-kilodalton mycobacterial antigen. Mol Cell Biol. 9(5):2279-83.
Kol et al., 2000, "Cutting edge: heat shock protein (HSP)60 activates the innate immune response: CD14 is an essential receptor to HSP60 activation of mononuclear cells", J. Immunol. 164(1):13-17.
Krieger and Herz, 1994, "Structures and functions of multiligand lipoprotein: macrophage scavenger receptors and LDL receptor-related protein (LRP)", Annu Rev Biochem. 63:601-37.
Kristensen et al., 1990, "Evidence that the newly cloned low-density-lipoprotein receptor related protein (LRP) is the alpha 2-macroglobulin receptor", FEBS Lett. 276(1-2):151-5.
Maki et al., 1990, "Human homologue of murine tumor rejection antigen gp96: 5'-regulatory and coding regions and relationship to stress-induced proteins", Proc Natl Acad Sci U S A. 87(15):5658-62.
Maki et al., 1993, "Mapping of the genes for human endoplasmic reticular heat shock protein gp96/grp9", Somat Cell Mol Genet. 19(1):73-81.
Misra et al., 1993, "Receptor-recognized alpha 2-macroglobulin-methylamine elevates intracellular calcium, Inositol phosphates and cyclic AMP in murine peritoneal macrophages", Biochem J. 290 (Pt 3):885-91.
Mitsuda et al., 1993, "A receptor-mediated antigen delivery and incorporation system", Biochem. and Biophys. Res. Comm. 191:1326-31.
Mitsuda et al., 1993, "A receptor-mediated delivery of an HIV 1 derived peptide vaccine", Biochem Biophys Res Commun 194(3): 1155-60.
Moestrup et al., 1993, "$\alpha$-$_2$ macroglobulin-proteinase complexes, plasminogen activator inhibitor type-1-plasminogen activator complexes, and receptor-associated protein bind to a region of the $\alpha$-$_2$-macroglobulin receptor containing a cluster of eight complement type repeats", J. of Biolog. Chem. 268: 13691-13696.
Moestrup et al., 1992, "Distribution of the alpha 2-macroglobulin receptor/low density lipoprotein receptor-related protein in human tissues", Cell Tissue Res. 269(3):375-82.
Nicchitta et al., 1998, "Biochemical, cell biological and immunological issues surrounding the endoplasmic recticulum chaperone GRP94/gp96", Curr Opin Immunol. 10(1):103-9.

Nielsen et al., 1996, "Identification of residues in alpha-macroglubulins important for binding to the alpha2-macroglobulin receptor/Low density lipoprotein receptor-related protein", J Biol Chem. 271(22):12909-12.
Nykjaer et al., 1992, "Purified alpha 2-macroglobulin receptor/LDL receptor-related protein binds urokinase.plasminogen activator inhibitor type-1 complex. Evidence that the alpha 2-macroglobulin receptor mediates cellular degradation of urokinase receptor-bound complexes", J Biol Chem. 267(21):14543-6.
O'Connor-McCourt et al., 1987, "Latent transforming growth factor-beta in serum. A specific complex with alpha 2-macroglobulin", J. Biol Chem. 262(29):14090-9.
Orth et al., 1992, "Complexes of tissue-type plasminogen activator and its serpin inhibitor plasminogen-activator inhibitor type 1 are internalized by means of the low density lipoprotein receptor-related protein/alpha 2-macroglobulin receptor", Proc Natl Acad Sci U S A. 89(16):7422-6.
Osada et al., 1987, "Murine T cell proliferation can be specifically augmented by macrophages fed with specific antigen: α-2-macroglobulin conjugate", Biochem. and Biophys. Res. Comm. 146: 26-31.
Osada et al., 1988, "Antibodies against viral proteins can be produced effectively in response to the increased uptake of alpha 2 macroglobulin: viral protein conjugate by macrophages", Biochem and Biophys. Res. Comm. 150: 883-889.
Sargent et al., 1989, "Human major histocompatibility complex contains genes for the major heat shock protein HSP70", Proc Natl Acad Sci U S A. 86(6):1968-72.
Savill et al., 1992, "Thrombospondin cooperates with CD36 and the vitronectin receptor in macrophage recognition of neutrophils undergoing apoptosis", J Clin Invest. 90(4):1513-22.
Singh-Jasjua et al., 2000, "Cross Presentation of Glycoprotein 96-associated antigens on major histocompatibility complex class molecules requires receptor-mediated endocytosis", J. Exp. Med. 191:1965-74.
Soeiro et al., 2000, "*Trypanosoma cruzi*: Acute Infection Affects Expression of α-a-macroglobulin and A2MR/LRP Receptor Differently in C3H and C57BL/6 Mice", Exper. Parasitology 96: 97-107.
Srivastava et al., 1998, "Heat shock proteins come of age: primitive functions acquire new roles in an adaptive world", Immunity. 8(6):657-65.
Srivastava et al., 1994, "Stress-induced proteins in immune repsonse to cancer", Curr Top Microbiol Immunol. 167:109-23.
Srivastava et al., 1987, "5'-structural analysis of genes encoding polymorphic antigens of chemically induced tumors." Proc. Natl. Acad. Sci USA 85:3807-3811.
Srivastava et al., 1993, "Peptide-binding heat shock proteins in the endoplasmic reticulum: role in immune response to cancer and in antigen presentation", Adv Cancer Res. 62:153-77.
Srivastava et al., 1994, "Heat shock proteins in immune response to cancer: the Fourth Paradigm", Experientia. 50(11-12):1054-60.
Srivastava et al., 1994, "Heat shock proteins transfer peptides during antigen processing and CTL priming", Immunogenetics. 39(2):93-8. Review.
Strickland et al., 1990, "Sequence identity between the alpha 2-macroglobulin receptor and low density lipoprotein receptor-related protein suggests that this molecule is a multifunctional receptor", J Biol Chem. 15:265(29):17401-4.
Suto and Srivastava, 1995, "A mechanism for the specific immunogenicity of heat shock protein-chaperoned peptides", Science 269(5230):1585-8.
Ting et al., 1988, "Human gene encoding the 78,000-dalton glucose-regulated protein and its pseudogene: structure, conservation, and regulation", DNA, 7(4):275-86.
Van Leuven et al., 1993, "Molecular cloning and sequencing of the murine alpha-2-macroglobulin receptor cDNA", Biochem Biophys Acta. 1173(1):71-4.
Wassenberg et al., 1999, Receptor mediated and fluid phase pathways for internalization of the ER Hsp90 chaperone GRP94 n murine macrophagesJ. Cell Science 112: 2167-2175.
Willnow et al., 1994, "Molecular dissection of ligand binding sites on the low density lipoprotein receptor-related protein", J. of Biolog. Chem. 269: 15827-15832.
Yamazaki et al., 1989, "Nucleotide sequence of a full-length cDNA for 90 kDa heat-shock protein from human peripheral blood lymphocytes", Nucleic Acids Res. 17(17):7108.
Willnow et al., 1996, "The low-density-lipoprotein receptor-related protein (LRP) is processed by furin in vivo and in vitro." The Biochemical Journal. England 313:71-76.
U.S. Appl. No. 09/668,724, filed Sep. 22, 2000 , Srivastava et al.
Basu et al., 2001, "CD91 is a common receptor for heat shock proteins gp96, hsp90, hsp70, and calrecticulin," Immunity 14:303-313.
Bellone et al., 1999, "Cancer Immunotherapy: synthetic and natural peptides in balance," Immunology Today 20(10): 457-462.
Binder and Srivastava, 2004, "Essential role of CD91 in re-presentation of gp96-chaperoned peptides," Proc. Natl. Acad. Sci. U.S.A. 101-6128-6133.
Binder et al., 2001, "Adjuvanticity of alpha 2-macroglobulin, an independent ligand for the heat shock protein receptor CD91 , " J. Immunol. 166(8):4968-72.
Binder et al., 2001, "Heat shock protein-chaperoned peptides but not free peptides introduced into the cytosol are presented efficiently by major histocompatability complex I molecules ," J. Biol. Chem. 276(20): 17163-17171.
Binder et al., 2002, "Naturally formed artificially reconstituted non-covalent alpha 2-macrophages-peptide complexes elicit CD91-dependent cellular immunity," Cancer Immunity 2:16-24.
Binder et al., 2000, "CD91: a receptor for heat shock protein gp96," Nature Immunol. 1(2):151-155.
Bosch et al., 1999, "State of the art of therapeutic apheresis in Europe", Ther. Apher. 3(3):197-8.
D'Andrea, 2005, "Add Alzheimer's disease to the list of autoimmune diseases," Med. Hypotheses 64(3):458-463.
Dermer, 1994, "Another Anniversary for the War on Cancer," Biotechnology 12:320.
Epplen et al., 1997, "Genetic predisposition to multiple sclerosis as revealed by immunoprinting," Ann. Neurol. 41(3):341-52.
Fay et al., 1979, "Leukopheresis Therapy of Leukemic Reticuloendotheliosis (Hairy Cell Leukemia)", Blood 54: 747-749.
Freshney, 1983, "Culture of Animal Cells, A Manual of Basic Technique," Alan R. Liss Inc., New York p4.
Gaiger et al., 2000, "Immunity to WTI in the animal model and in patients with acute myeloid leukemia," Blood 96(4):1480-1489.
Goto and Tanzi, 2002, "The role of the low-density lipoprotein receptor-related protein (LRPI) in Alzheimer's Abeta generation," J. Mol. Neurosci. 19:37-41.
Gura, 1997, "Systems for identifying new drugs are often faulty," Science 278:1041-1042.
Herz and Strickland, 2001, "LRP: a multifunctional scavenger and signaling receptor," J. Clin. Invest. 108:779-784.
Houghten et al., 1991, "Generation and use of synthetic peptide combinatorial libraries for basic research and drup discovery," Science 354:84-86.
Hunter, N. et al., 1991, "Supression of experimental allergic encephalomyelitis by alpha(2)-macroglobulin," Immunology 73:58-63.
James, K., 1980, "Alpha (2) macroglobulin and its possible importance in immune systems," Trends in Biol. Sci. p. 43-47.
Kornfeld et al., 1980, "Plasmapheresis in *Myasthenia gravis*," Plasma Therapy, 2(3): 127-133.
Kuhlmann et al., 1997, "Drug Research: from the idea to the product," International Journal of Pharmacology and Therapeutics 35:541-552.
McKee and Collins, 1974, "Intravascular Leukocyte thrombi and aggregates as a cause of mobidity and mortality in leukemia," Medicine 53:463-478.
The Merck Manual of Diagnosis and Therapy, 1999, Beers and Berkow eds., Merck Research Laboratories, Whitehouse Station N.J., pp. 1871-1872.
Millward and Hoeltge, 1982, "The Historical Development of Automated Hemapheresis", J. of Clin. Apheresis 1: 25-32.
Pineda et al., 1994, "Applications of therapeutic apheresis," Mayo Clin. Proc. 69(9):893-4.
Proud, G. et al., 1979, "Blood transfusion and renal transplantation," Br. J. Sur. 66:678-82.

Report of the AMA Panel on Therapeutic Plasmapheresis, Current Status of Therapeutic Plasmapheresis and Related Techniques, Dec. 1984.

Singh, 1997, "Neuroautoimmunity: pathogenic implications for Alzheimer's disease," Gerontology 43:79-94.

Sotgiu et al., 1998, "Genetic susceptibility to multiple sclerosis in Sardinians: an immunological study," Acta. Neurol. Scand. 98(5):314-7.

Spero et al., 1980, "Plasma Exchange in Preparation of Mild Factor IX Deficient Hemophiliacs for Surgical Procedures," 19-22.

Srivastava, 2002, "Roles of heat-shock proteins in innate and adaptive immunity," Nature Rev. Immunol. 2(3): 185-194.

Tait, BD, 1990, "Genetic susceptibility to type I diabetes: a review," J. Autoimmun. 3 Suppl. 1:3-11.

Urbaniak and Robinson, 1990, "ABC of transfusion. Therapeutic apheresis," BMJ 300(6725):662-5 Review.

Weiner et al., 1980, "Plasmapheresis in multiple sclerosis: preliminary study," Neurology 30: 1029-33.

Weiner et al., 2002, "Inflammation and therapeutic vaccination in CNS diseases," Nature 420:879-884.

Wong et al., 1991, "Susceptibility to type I diabetes in woman is associated with the CD3 epsilon locus on chromosome 1 1," Clin. Exp. Immunol. 83(1):69-73.

| Seq | # | b | y | +1 |
|---|---|---|---|---|
| G | 1 | 58.1 | – | 10 |
| G | 2 | 115.1 | 1095.2 | 9 |
| A | 3 | 186.2 | 1038.2 | 8 |
| L | 4 | 299.3 | 967.1 | 7 |
| H | 5 | 436.5 | 853.9 | 6 |
| I | 6 | 549.6 | 716.8 | 5 |
| Y | 7 | 712.8 | 603.6 | 4 |
| H | 8 | 850.0 | 440.5 | 3 |
| Q | 9 | 978.1 | 303.3 | 2 |
| R | 10 | – | 175.2 | 1 |

FIG.3A

| POSITION | MH+ | SEQUENCE | |
|---|---|---|---|
| 509-518 | 955.0122 | SGFSLGSDGK | (SEQ ID NO: 54) |
| 328-337 | 973.1753 | GIALDPAMGK | (SEQ ID NO: 55) |
| 460-469 | 1152.3010 | GGALHIYHQR | (SEQ ID NO: 56) |
| 338-348 | 1315.5116 | VFFTDYGQIPK | (SEQ ID NO: 57) |

FIG.3C

```
CGCTGCTCCC CGCCAGTGCA CTGAGGAGGC GGAAACGGGG GAGCCCCTAG TGCTCCATCA    60
GGCCCCTACC AAGGCACCCC CATCGGGTCC ACGCCCCCCA CCCCCCACCC CGCCTCCTCC   120
CAATTGTGCA TTTTTGCAGC CGGAGTCGGC TCCGAGATGG GGCTGTGAGC TTCGCCCTGG   180
GAGGGGGAGA GGAGCGAGGA GTAAAGCAGG GGTGAAGGGT TCGAATTTGG GGGCAGGGGG   240
CGCACCCGCG TCAGCAGGCC CTTCCCAGGG GGCTCGGAAC TGTACCATTT CACCTATGCC   300
CCTGGTTCGC TTTGCTTAAG GAAGGATAAG ATAGAAGAGT CGGGGAGAGG AAGATAAAGG   360
GGGACCCCCC AATTGGGGGG GGCGAGGACA AGAAGTAACA GGACCAGAGG GTGGGGGCTG   420
CTGTTTGCAT CGGCCCACAC C ATG CTG ACC CCG CCG TTG CTG CTG CTC GTG     471
                        Met Leu Thr Pro Pro Leu Leu Leu Leu Val
                         1               5                  10

CCG CTG CTT TCA GCT CTG GTC TCC GGG GCC ACT ATG GAT GCC CCT AAA     519
Pro Leu Leu Ser Ala Leu Val Ser Gly Ala Thr Met Asp Ala Pro Lys
                15                  20                  25

ACT TGC AGC CCT AAG CAG TTT GCC TGC AGA GAC CAA ATC ACC TGT ATC     567
Thr Cys Ser Pro Lys Gln Phe Ala Cys Arg Asp Gln Ile Thr Cys Ile
            30                  35                  40

TCA AAG GGC TGG CGG TGT GAC GGT GAA AGA GAT TGC CCC GAC GGC TCT     615
Ser Lys Gly Trp Arg Cys Asp Gly Glu Arg Asp Cys Pro Asp Gly Ser
        45                  50                  55

GAT GAA GCC CCT GAG ATC TGT CCA CAG AGT AAA GCC CAG AGA TGC CCG     663
Asp Glu Ala Pro Glu Ile Cys Pro Gln Ser Lys Ala Gln Arg Cys Pro
    60                  65                  70

CCA AAT GAG CAC AGT TGT CTG GGG ACT GAG CTA TGT GTC CCC ATG TCT     711
Pro Asn Glu His Ser Cys Leu Gly Thr Glu Leu Cys Val Pro Met Ser
75                  80                  85                  90

CGT CTC TGC AAC GGG ATC CAG GAC TGC ATG GAT GGC TCA GAC GAG GGT     759
Arg Leu Cys Asn Gly Ile Gln Asp Cys Met Asp Gly Ser Asp Glu Gly
                95                  100                 105

GCT CAC TGC CGA GAG CTC CGA GCC AAC TGT TCT CGA ATG GGT TGT CAA     807
Ala His Cys Arg Glu Leu Arg Ala Asn Cys Ser Arg Met Gly Cys Gln
            110                 115                 120

CAC CAT TGT GTA CCT ACA CCC AGT GGG CCC ACG TGC TAC TGT AAC AGC     855
His His Cys Val Pro Thr Pro Ser Gly Pro Thr Cys Tyr Cys Asn Ser
        125                 130                 135
```

FIG.6A-1

```
AGC TTC CAG CTC GAG GCA GAT GGC AAG ACG TGC AAA GAT TTT GAC GAG      903
Ser Phe Gln Leu Glu Ala Asp Gly Lys Thr Cys Lys Asp Phe Asp Glu
    140                 145                 150

TGT TCC GTG TAT GGC ACC TGC AGC CAG CTT TGC ACC AAC ACA GAT GGC      951
Cys Ser Val Tyr Gly Thr Cys Ser Gln Leu Cys Thr Asn Thr Asp Gly
155                 160                 165                 170

TCC TTC ACA TGT GGC TGT GTT GAA GGC TAC CTG CTG CAA CCG GAC AAC      999
Ser Phe Thr Cys Gly Cys Val Glu Gly Tyr Leu Leu Gln Pro Asp Asn
                175                 180                 185

CGC TCC TGC AAG GCC AAG AAT GAG CCA GTA GAT CGG CCG CCA GTG CTA     1047
Arg Ser Cys Lys Ala Lys Asn Glu Pro Val Asp Arg Pro Pro Val Leu
            190                 195                 200

CTG ATT GCC AAC TCT CAG AAC ATC CTA GCT ACG TAC CTG AGT GGG GCC     1095
Leu Ile Ala Asn Ser Gln Asn Ile Leu Ala Thr Tyr Leu Ser Gly Ala
        205                 210                 215

CAA GTG TCT ACC ATC ACA CCC ACC AGC ACC CGA CAA ACC ACG GCC ATG     1143
Gln Val Ser Thr Ile Thr Pro Thr Ser Thr Arg Gln Thr Thr Ala Met
    220                 225                 230

GAC TTC AGT TAT GCC AAT GAG ACC GTA TGC TGG GTG CAC GTT GGG GAC     1191
Asp Phe Ser Tyr Ala Asn Glu Thr Val Cys Trp Val His Val Gly Asp
235                 240                 245                 250

AGT GCT GCC CAG ACA CAG CTC AAG TGT GCC CGG ATG CCT GGC CTG AAG     1239
Ser Ala Ala Gln Thr Gln Leu Lys Cys Ala Arg Met Pro Gly Leu Lys
                255                 260                 265

GGC TTT GTG GAT GAG CAT ACC ATC AAC ATC TCC CTC AGC CTG CAC CAC     1287
Gly Phe Val Asp Glu His Thr Ile Asn Ile Ser Leu Ser Leu His His
            270                 275                 280

GTG GAG CAG ATG GCA ATC GAC TGG CTG ACG GGA AAC TTC TAC TTT GTC     1335
Val Glu Gln Met Ala Ile Asp Trp Leu Thr Gly Asn Phe Tyr Phe Val
        285                 290                 295

GAC GAC ATT GAC GAC AGG ATC TTT GTC TGT AAC CGA AAC GGG GAC ACC     1383
Asp Asp Ile Asp Asp Arg Ile Phe Val Cys Asn Arg Asn Gly Asp Thr
    300                 305                 310
```

FIG.6A-2

```
TGT GTC ACT CTG CTG GAC CTG GAA CTC TAC AAC CCC AAA GGC ATC GCC     1431
Cys Val Thr Leu Leu Asp Leu Glu Leu Tyr Asn Pro Lys Gly Ile Ala
315                 320                 325                 330

TTG GAC CCC GCC ATG GGG AAG GTG TTC TTC ACT GAC TAC GGG CAG ATC     1479
Leu Asp Pro Ala Met Gly Lys Val Phe Phe Thr Asp Tyr Gly Gln Ile
                335                 340                 345

CCA AAG GTG GAG CGC TGT GAC ATG GAT GGA CAG AAC CGC ACC AAG CTG     1527
Pro Lys Val Glu Arg Cys Asp Met Asp Gly Gln Asn Arg Thr Lys Leu
            350                 355                 360

GTG GAT AGC AAG ATC GTG TTT CCA CAC GGC ATC ACC CTG GAC CTG GTC     1575
Val Asp Ser Lys Ile Val Phe Pro His Gly Ile Thr Leu Asp Leu Val
        365                 370                 375

AGC CGC CTC GTC TAC TGG GCG GAC GCC TAC CTA GAC TAC ATC GAG GTG     1623
Ser Arg Leu Val Tyr Trp Ala Asp Ala Tyr Leu Asp Tyr Ile Glu Val
    380                 385                 390

GTA GAC TAC GAA GGG AAG GGT CGG CAG ACC ATC ATC CAA GGC ATC CTG     1671
Val Asp Tyr Glu Gly Lys Gly Arg Gln Thr Ile Ile Gln Gly Ile Leu
395                 400                 405                 410

ATC GAG CAC CTG TAC GGC CTG ACC GTG TTT GAG AAC TAT CTC TAC GCC     1719
Ile Glu His Leu Tyr Gly Leu Thr Val Phe Glu Asn Tyr Leu Tyr Ala
                415                 420                 425

ACC AAC TCG GAC AAT GCC AAC ACG CAG CAG AAG ACG AGC GTG ATC CGA     1767
Thr Asn Ser Asp Asn Ala Asn Thr Gln Gln Lys Thr Ser Val Ile Arg
            430                 435                 440

GTG AAC CGG TTC AAC AGT ACT GAG TAC CAG GTC GTC ACC CGT GTG GAC     1815
Val Asn Arg Phe Asn Ser Thr Glu Tyr Gln Val Val Thr Arg Val Asp
        445                 450                 455

AAG GGT GGT GCC CTG CAT ATC TAC CAC CAG CGA CGC CAG CCC CGA GTG     1863
Lys Gly Gly Ala Leu His Ile Tyr His Gln Arg Arg Gln Pro Arg Val
    460                 465                 470

CGG AGT CAC GCC TGT GAG AAT GAC CAG TAC GGG AAG CCA GGT GGC TGC     1911
Arg Ser His Ala Cys Glu Asn Asp Gln Tyr Gly Lys Pro Gly Gly Cys
475                 480                 485                 490
```

FIG.6A-3

```
TCC GAC ATC TGC CTC CTG GCC AAC AGT CAC AAG GCA AGG ACC TGC AGG     1959
Ser Asp Ile Cys Leu Leu Ala Asn Ser His Lys Ala Arg Thr Cys Arg
                495                 500                 505

TGC AGG TCT GGC TTC AGC CTG GGA AGT GAT GGG AAG TCT TGT AAG AAA     2007
Cys Arg Ser Gly Phe Ser Leu Gly Ser Asp Gly Lys Ser Cys Lys Lys
            510                 515                 520

CCT GAA CAT GAG CTG TTC CTC GTG TAT GGC AAG GGC CGA CCA GGC ATC     2055
Pro Glu His Glu Leu Phe Leu Val Tyr Gly Lys Gly Arg Pro Gly Ile
        525                 530                 535

ATT AGA GGC ATG GAC ATG GGG GCC AAG GTC CCA GAT GAG CAC ATG ATC     2103
Ile Arg Gly Met Asp Met Gly Ala Lys Val Pro Asp Glu His Met Ile
    540                 545                 550

CCC ATC GAG AAC CTT ATG AAT CCA CGC GCT CTG GAC TTC CAC GCC GAG     2151
Pro Ile Glu Asn Leu Met Asn Pro Arg Ala Leu Asp Phe His Ala Glu
555                 560                 565                 570

ACC GGC TTC ATC TAC TTT GCT GAC ACC ACC AGC TAC CTC ATT GGC CGC     2199
Thr Gly Phe Ile Tyr Phe Ala Asp Thr Thr Ser Tyr Leu Ile Gly Arg
                575                 580                 585

CAG AAA ATT GAT GGC ACG GAG AGA GAG ACT ATC CTG AAG GAT GGC ATC     2247
Gln Lys Ile Asp Gly Thr Glu Arg Glu Thr Ile Leu Lys Asp Gly Ile
            590                 595                 600

CAC AAT GTG GAG GGC GTA GCC GTG GAC TGG ATG GGA GAC AAT CTT TAC     2295
His Asn Val Glu Gly Val Ala Val Asp Trp Met Gly Asp Asn Leu Tyr
        605                 610                 615

TGG ACT GAT GAT GGC CCC AAG AAG ACC ATT AGT GTG GCC AGG CTG GAG     2343
Trp Thr Asp Asp Gly Pro Lys Lys Thr Ile Ser Val Ala Arg Leu Glu
    620                 625                 630

AAA GCC GCT CAG ACC CGG AAG ACT CTA ATT GAG GGC AAG ATG ACA CAC     2391
Lys Ala Ala Gln Thr Arg Lys Thr Leu Ile Glu Gly Lys Met Thr His
635                 640                 645                 650

CCC AGG GCC ATT GTA GTG GAT CCA CTC AAT GGG TGG ATG TAC TGG ACA     2439
Pro Arg Ala Ile Val Val Asp Pro Leu Asn Gly Trp Met Tyr Trp Thr
                655                 660                 665
```

FIG.6A-4

```
GAC TGG GAG GAG GAC CCC AAG GAC AGT CGG CGA GGG CGG CTC GAG AGG     2487
Asp Trp Glu Glu Asp Pro Lys Asp Ser Arg Arg Gly Arg Leu Glu Arg
            670                 675                 680

GCT TGG ATG GAC GGC TCA CAC CGA GAT ATC TTT GTC ACC TCC AAG ACA     2535
Ala Trp Met Asp Gly Ser His Arg Asp Ile Phe Val Thr Ser Lys Thr
        685                 690                 695

GTG CTT TGG CCC AAT GGG CTA AGC CTG GAT ATC CCA GCC GGA CGC CTC     2583
Val Leu Trp Pro Asn Gly Leu Ser Leu Asp Ile Pro Ala Gly Arg Leu
    700                 705                 710

TAC TGG GTG GAT GCC TTC TAT GAC CGA ATT GAG ACC ATA CTG CTC AAT     2631
Tyr Trp Val Asp Ala Phe Tyr Asp Arg Ile Glu Thr Ile Leu Leu Asn
715                 720                 725                 730

GGC ACA GAC CGG AAG ATT GTA TAT GAG GGT CCT GAA CTG AAT CAT GCC     2679
Gly Thr Asp Arg Lys Ile Val Tyr Glu Gly Pro Glu Leu Asn His Ala
                735                 740                 745

TTC GGC CTG TGT CAC CAT GGC AAC TAC CTC TTT TGG ACC GAG TAC CGG     2727
Phe Gly Leu Cys His His Gly Asn Tyr Leu Phe Trp Thr Glu Tyr Arg
            750                 755                 760

AGC GGC AGC GTC TAC CGC TTG GAA CGG GGC GTG GCA GGC GCA CCG CCC     2775
Ser Gly Ser Val Tyr Arg Leu Glu Arg Gly Val Ala Gly Ala Pro Pro
        765                 770                 775

ACT GTG ACC CTT CTG CGC AGC GAG AGA CCG CCT ATC TTT GAG ATC CGA     2823
Thr Val Thr Leu Leu Arg Ser Glu Arg Pro Pro Ile Phe Glu Ile Arg
    780                 785                 790

ATG TAC GAC GCG CAC GAG CAG CAA GTG GGT ACC AAC AAA TGC CGG GTA     2871
Met Tyr Asp Ala His Glu Gln Gln Val Gly Thr Asn Lys Cys Arg Val
795                 800                 805                 810

AAT AAC GGA GGC TGC AGC AGC CTG TGC CTC GCC ACC CCC GGG AGC CGC     2919
Asn Asn Gly Gly Cys Ser Ser Leu Cys Leu Ala Thr Pro Gly Ser Arg
                815                 820                 825

CAG TGT GCC TGT GCC GAG GAC CAG GTG TTG GAC ACA GAT GGT GTC ACC     2967
Gln Cys Ala Cys Ala Glu Asp Gln Val Leu Asp Thr Asp Gly Val Thr
            830                 835                 840
```

FIG.6A-5

TGC TTG GCG AAC CCA TCC TAC GTG CCC CCA CCC CAG TGC CAG CCG GGC 3015
Cys Leu Ala Asn Pro Ser Tyr Val Pro Pro Pro Gln Cys Gln Pro Gly
845 850 855

CAG TTT GCC TGT GCC AAC AAC CGC TGC ATC CAG GAG CGC TGG AAG TGT 3063
Gln Phe Ala Cys Ala Asn Asn Arg Cys Ile Gln Glu Arg Trp Lys Cys
860 865 870

GAC GGA GAC AAC GAC TGT CTG GAC AAC AGC GAT GAG GCC CCA GCA CTG 3111
Asp Gly Asp Asn Asp Cys Leu Asp Asn Ser Asp Glu Ala Pro Ala Leu
875 880 885 890

TGC CAT CAA CAC ACC TGT CCC TCG GAC CGA TTC AAG TGT GAG AAC AAC 3159
Cys His Gln His Thr Cys Pro Ser Asp Arg Phe Lys Cys Glu Asn Asn
895 900 905

CGG TGT ATC CCC AAC CGC TGG CTC TGT GAT GGG GAT AAT GAT TGT GGC 3207
Arg Cys Ile Pro Asn Arg Trp Leu Cys Asp Gly Asp Asn Asp Cys Gly
910 915 920

AAC AGC GAG GAC GAA TCC AAT GCC ACG TGC TCA GCC CGC ACC TGT CCA 3255
Asn Ser Glu Asp Glu Ser Asn Ala Thr Cys Ser Ala Arg Thr Cys Pro
925 930 935

CCC AAC CAG TTC TCC TGT GCC AGT GGC CGA TGC ATT CCT ATC TCA TGG 3303
Pro Asn Gln Phe Ser Cys Ala Ser Gly Arg Cys Ile Pro Ile Ser Trp
940 945 950

ACC TGT GAT CTG GAT GAT GAC TGT GGG GAC CGG TCC GAT GAG TCA GCC 3351
Thr Cys Asp Leu Asp Asp Asp Cys Gly Asp Arg Ser Asp Glu Ser Ala
955 960 965 970

TCA TGC GCC TAC CCC ACC TGC TTC CCC CTG ACT CAA TTT ACC TGC AAC 3399
Ser Cys Ala Tyr Pro Thr Cys Phe Pro Leu Thr Gln Phe Thr Cys Asn
975 980 985

AAT GGC AGA TGT ATT AAC ATC AAC TGG CGG TGT GAC AAC GAC AAT GAC 3447
Asn Gly Arg Cys Ile Asn Ile Asn Trp Arg Cys Asp Asn Asp Asn Asp
990 995 1000

TGT GGG GAC AAC AGC GAC GAA GCC GGC TGC AGT CAC TCC TGC TCC AGT 3495
Cys Gly Asp Asn Ser Asp Glu Ala Gly Cys Ser His Ser Cys Ser Ser
1005 1010 1015

FIG.6A-6

```
ACC CAG TTC AAG TGC AAC AGT GGC AGA TGC ATC CCC GAG CAC TGG ACG      3543
Thr Gln Phe Lys Cys Asn Ser Gly Arg Cys Ile Pro Glu His Trp Thr
   1020                1025                1030

TGT GAT GGG GAC AAT GAT TGT GGG GAC TAC AGC GAC GAG ACA CAC GCC      3591
Cys Asp Gly Asp Asn Asp Cys Gly Asp Tyr Ser Asp Glu Thr His Ala
1035                1040                1045                1050

AAC TGT ACC AAC CAG GCT ACA AGA CCT CCT GGT GGC TGC CAC TCG GAT      3639
Asn Cys Thr Asn Gln Ala Thr Arg Pro Pro Gly Gly Cys His Ser Asp
                1055                1060                1065

GAG TTC CAG TGC CCG CTA GAT GGC CTG TGC ATC CCC CTG AGG TGG CGC      3687
Glu Phe Gln Cys Pro Leu Asp Gly Leu Cys Ile Pro Leu Arg Trp Arg
            1070                1075                1080

TGC GAC GGG GAC ACC GAC TGC ATG GAT TCC AGC GAT GAG AAG AGC TGT      3735
Cys Asp Gly Asp Thr Asp Cys Met Asp Ser Ser Asp Glu Lys Ser Cys
        1085                1090                1095

GAG GGC GTG ACC CAT GTT TGT GAC CCG AAT GTC AAG TTT GGC TGC AAG      3783
Glu Gly Val Thr His Val Cys Asp Pro Asn Val Lys Phe Gly Cys Lys
   1100                1105                1110

GAC TCC GCC CGG TGC ATC AGC AAG GCG TGG GTG TGT GAT GGC GAC AGC      3831
Asp Ser Ala Arg Cys Ile Ser Lys Ala Trp Val Cys Asp Gly Asp Ser
1115                1120                1125                1130

GAC TGT GAA GAT AAC TCC GAC GAG GAG AAC TGT GAG GCC CTG GCC TGC      3879
Asp Cys Glu Asp Asn Ser Asp Glu Glu Asn Cys Glu Ala Leu Ala Cys
                1135                1140                1145

AGG CCA CCC TCC CAT CCC TGC GCC AAC AAC ACC TCT GTC TGC CTG CCT      3927
Arg Pro Pro Ser His Pro Cys Ala Asn Asn Thr Ser Val Cys Leu Pro
            1150                1155                1160

CCT GAC AAG CTG TGC GAC GGC AAG GAT GAC TGT GGA GAC GGC TCG GAT      3975
Pro Asp Lys Leu Cys Asp Gly Lys Asp Asp Cys Gly Asp Gly Ser Asp
        1165                1170                1175

GAG GGC GAG CTC TGT GAC CAG TGT TCT CTG AAT AAT GGT GGC TGT AGT      4023
Glu Gly Glu Leu Cys Asp Gln Cys Ser Leu Asn Asn Gly Gly Cys Ser
   1180                1185                1190
```

FIG.6A-7

CAC AAC TGC TCA GTG GCC CCT GGT GAA GGC ATC GTG TGC TCT TGC CCT 4071
His Asn Cys Ser Val Ala Pro Gly Glu Gly Ile Val Cys Ser Cys Pro
1195 1200 1205 1210

CTG GGC ATG GAG CTG GGC TCT GAC AAC CAC ACC TGC CAG ATC CAG AGC 4119
Leu Gly Met Glu Leu Gly Ser Asp Asn His Thr Cys Gln Ile Gln Ser
1215 1220 1225

TAC TGT GCC AAG CAC CTC AAA TGC AGC CAG AAG TGT GAC CAG AAC AAG 4167
Tyr Cys Ala Lys His Leu Lys Cys Ser Gln Lys Cys Asp Gln Asn Lys
1230 1235 1240

TTC AGT GTG AAG TGC TCC TGC TAC GAG GGC TGG GTC TTG GAG CCT GAC 4215
Phe Ser Val Lys Cys Ser Cys Tyr Glu Gly Trp Val Leu Glu Pro Asp
1245 1250 1255

GGG GAA ACG TGC CGC AGT CTG GAT CCC TTC AAA CTG TTC ATC ATC TTC 4263
Gly Glu Thr Cys Arg Ser Leu Asp Pro Phe Lys Leu Phe Ile Ile Phe
1260 1265 1270

TCC AAC CGC CAC GAG ATC AGG CGC ATT GAC CTT CAC AAG GGG GAC TAC 4311
Ser Asn Arg His Glu Ile Arg Arg Ile Asp Leu His Lys Gly Asp Tyr
1275 1280 1285 1290

AGC GTC CTA GTG CCT GGC CTG CGC AAC ACT ATT GCC CTG GAC TTC CAC 4359
Ser Val Leu Val Pro Gly Leu Arg Asn Thr Ile Ala Leu Asp Phe His
1295 1300 1305

CTC AGC CAG AGT GCC CTC TAC TGG ACC GAC GCG GTA GAG GAC AAG ATC 4407
Leu Ser Gln Ser Ala Leu Tyr Trp Thr Asp Ala Val Glu Asp Lys Ile
1310 1315 1320

TAC CGT GGG AAA CTC CTG GAC AAC GGA GCC CTG ACC AGC TTT GAG GTG 4455
Tyr Arg Gly Lys Leu Leu Asp Asn Gly Ala Leu Thr Ser Phe Glu Val
1325 1330 1335

GTG ATT CAG TAT GGC TTG GCC ACA CCA GAG GGC CTG GCT GTA GAT TGG 4503
Val Ile Gln Tyr Gly Leu Ala Thr Pro Glu Gly Leu Ala Val Asp Trp
1340 1345 1350

ATT GCA GGC AAC ATC TAC TGG GTG GAG AGC AAC CTG GAC CAG ATC GAA 4551
Ile Ala Gly Asn Ile Tyr Trp Val Glu Ser Asn Leu Asp Gln Ile Glu
1355 1360 1365 1370

FIG.6A-8

```
GTG GCC AAG CTG GAC GGA ACC CTC CGA ACC ACT CTG CTG GCG GGT GAC    4599
Val Ala Lys Leu Asp Gly Thr Leu Arg Thr Thr Leu Leu Ala Gly Asp
                1375                1380                1385

ATT GAG CAC CCG AGG GCC ATC GCT CTG GAC CCT CGG GAT GGG ATT CTG    4647
Ile Glu His Pro Arg Ala Ile Ala Leu Asp Pro Arg Asp Gly Ile Leu
            1390                1395                1400

TTT TGG ACA GAC TGG GAT GCC AGC CTG CCA CGA ATC GAG GCT GCA TCC    4695
Phe Trp Thr Asp Trp Asp Ala Ser Leu Pro Arg Ile Glu Ala Ala Ser
        1405                1410                1415

ATG AGT GGA GCT GGC CGC CGA ACC ATC CAC CGG GAG ACA GGC TCT GGG    4743
Met Ser Gly Ala Gly Arg Arg Thr Ile His Arg Glu Thr Gly Ser Gly
    1420                1425                1430

GGC TGC GCC AAT GGG CTC ACC GTG GAT TAC CTG GAG AAG CGC ATC CTC    4791
Gly Cys Ala Asn Gly Leu Thr Val Asp Tyr Leu Glu Lys Arg Ile Leu
1435                1440                1445                1450

TGG ATT GAT GCT AGG TCA GAT GCC ATC TAT TCA GCC CGG TAT GAC GGC    4839
Trp Ile Asp Ala Arg Ser Asp Ala Ile Tyr Ser Ala Arg Tyr Asp Gly
                1455                1460                1465

TCC GGC CAC ATG GAG GTG CTT CGG GGA CAC GAG TTC CTG TCA CAC CCA    4887
Ser Gly His Met Glu Val Leu Arg Gly His Glu Phe Leu Ser His Pro
            1470                1475                1480

TTT GCC GTG ACA CTG TAC GGT GGG GAG GTG TAC TGG ACC GAC TGG CGA    4935
Phe Ala Val Thr Leu Tyr Gly Gly Glu Val Tyr Trp Thr Asp Trp Arg
        1485                1490                1495

ACA AAT ACA CTG GCT AAG GCC AAC AAG TGG ACT GGC CAC AAC GTC ACC    4983
Thr Asn Thr Leu Ala Lys Ala Asn Lys Trp Thr Gly His Asn Val Thr
    1500                1505                1510

GTG GTA CAG AGG ACC AAC ACC CAG CCC TTC GAC CTG CAG GTG TAT CAC    5031
Val Val Gln Arg Thr Asn Thr Gln Pro Phe Asp Leu Gln Val Tyr His
1515                1520                1525                1530

CCT TCC CGG CAG CCC ATG GCT CCA AAC CCA TGT GAG GCC AAT GGC GGC    5079
Pro Ser Arg Gln Pro Met Ala Pro Asn Pro Cys Glu Ala Asn Gly Gly
                1535                1540                1545
```

FIG.6A-9

```
CGG GGC CCC TGT TCC CAT CTG TGC CTC ATC AAC TAC AAC CGG ACC GTC     5127
Arg Gly Pro Cys Ser His Leu Cys Leu Ile Asn Tyr Asn Arg Thr Val
            1550                1555                1560

TCC TGG GCC TGT CCC CAC CTC ATG AAG CTG CAC AAG GAC AAC ACC ACC     5175
Ser Trp Ala Cys Pro His Leu Met Lys Leu His Lys Asp Asn Thr Thr
        1565                1570                1575

TGC TAT GAG TTT AAG AAG TTC CTG CTG TAC GCA CGT CAG ATG GAG ATC     5223
Cys Tyr Glu Phe Lys Lys Phe Leu Leu Tyr Ala Arg Gln Met Glu Ile
    1580                1585                1590

CGG GGC GTG GAC CTG GAT GCC CCG TAC TAC AAT TAT ATC ATC TCC TTC     5271
Arg Gly Val Asp Leu Asp Ala Pro Tyr Tyr Asn Tyr Ile Ile Ser Phe
1595                1600                1605                1610

ACG GTG CCT GAT ATC GAC AAT GTC ACG GTG CTG GAC TAT GAT GCC CGA     5319
Thr Val Pro Asp Ile Asp Asn Val Thr Val Leu Asp Tyr Asp Ala Arg
                1615                1620                1625

GAG CAG CGA GTT TAC TGG TCT GAT GTG CGG ACT CAA GCC ATC AAA AGG     5367
Glu Gln Arg Val Tyr Trp Ser Asp Val Arg Thr Gln Ala Ile Lys Arg
            1630                1635                1640

GCA TTT ATC AAC GGC ACT GGC GTG GAG ACC GTT GTC TCT GCA GAC TTG     5415
Ala Phe Ile Asn Gly Thr Gly Val Glu Thr Val Val Ser Ala Asp Leu
        1645                1650                1655

CCC AAC GCC CAC GGG CTG GCT GTG GAC TGG GTC TCC CGA AAT CTG TTT     5463
Pro Asn Ala His Gly Leu Ala Val Asp Trp Val Ser Arg Asn Leu Phe
    1660                1665                1670

TGG ACA AGT TAC GAC ACC AAC AAG AAG CAG ATT AAC GTG GCC CGG CTG     5511
Trp Thr Ser Tyr Asp Thr Asn Lys Lys Gln Ile Asn Val Ala Arg Leu
1675                1680                1685                1690

GAC GGC TCC TTC AAG AAT GCG GTG GTG CAG GGC CTG GAG CAG CCC CAC     5559
Asp Gly Ser Phe Lys Asn Ala Val Val Gln Gly Leu Glu Gln Pro His
                1695                1700                1705

GGC CTG GTC GTC CAC CCG CTT CGT GGC AAG CTC TAC TGG ACT GAT GGG     5607
Gly Leu Val Val His Pro Leu Arg Gly Lys Leu Tyr Trp Thr Asp Gly
            1710                1715                1720
```

FIG.6A-10

```
GAC AAC ATC AGC ATG GCC AAC ATG GAT GGG AGC AAC CAC ACT CTG CTC     5655
Asp Asn Ile Ser Met Ala Asn Met Asp Gly Ser Asn His Thr Leu Leu
         1725                1730                1735

TTC AGT GGC CAG AAG GGC CCT GTG GGG TTG GCC ATT GAC TTC CCT GAG     5703
Phe Ser Gly Gln Lys Gly Pro Val Gly Leu Ala Ile Asp Phe Pro Glu
    1740                1745                1750

AGC AAA CTC TAC TGG ATC AGC TCT GGG AAC CAC ACA ATC AAC CGT TGC     5751
Ser Lys Leu Tyr Trp Ile Ser Ser Gly Asn His Thr Ile Asn Arg Cys
1755                1760                1765                1770

AAT CTG GAT GGG AGC GAG CTG GAG GTC ATC GAC ACC ATG CGG AGC CAG     5799
Asn Leu Asp Gly Ser Glu Leu Glu Val Ile Asp Thr Met Arg Ser Gln
                1775                1780                1785

CTG GGC AAG GCC ACT GCC CTG GCC ATC ATG GGG GAC AAG CTG TGG TGG     5847
Leu Gly Lys Ala Thr Ala Leu Ala Ile Met Gly Asp Lys Leu Trp Trp
            1790                1795                1800

GCA GAT CAG GTG TCA GAG AAG ATG GGC ACG TGC AAC AAA GCC GAT GGC     5895
Ala Asp Gln Val Ser Glu Lys Met Gly Thr Cys Asn Lys Ala Asp Gly
         1805                1810                1815

TCT GGG TCC GTG GTG CTG CGG AAC AGT ACC ACG TTG GTT ATG CAC ATG     5943
Ser Gly Ser Val Val Leu Arg Asn Ser Thr Thr Leu Val Met His Met
    1820                1825                1830

AAG GTG TAT GAC GAG AGC ATC CAG CTA GAG CAT GAG GGC ACC AAC CCC     5991
Lys Val Tyr Asp Glu Ser Ile Gln Leu Glu His Glu Gly Thr Asn Pro
1835                1840                1845                1850

TGC AGT GTC AAC AAC GGA GAC TGT TCC CAG CTC TGC CTG CCA ACA TCA     6039
Cys Ser Val Asn Asn Gly Asp Cys Ser Gln Leu Cys Leu Pro Thr Ser
                1855                1860                1865

GAG ACG ACT CGC TCC TGT ATG TGT ACA GCC GGT TAC AGC CTC CGG AGC     6087
Glu Thr Thr Arg Ser Cys Met Cys Thr Ala Gly Tyr Ser Leu Arg Ser
            1870                1875                1880

GGA CAG CAG GCC TGT GAG GGT GTG GGC TCT TTT CTC CTG TAC TCT GTA     6135
Gly Gln Gln Ala Cys Glu Gly Val Gly Ser Phe Leu Leu Tyr Ser Val
         1885                1890                1895
```

FIG.6A-11

CAT GAG GGA ATT CGG GGG ATT CCA CTA GAT CCC AAT GAC AAG TCG GAT 6183
His Glu Gly Ile Arg Gly Ile Pro Leu Asp Pro Asn Asp Lys Ser Asp
1900 1905 1910

GCC CTG GTC CCA GTG TCC GGA ACT TCA CTG GCT GTC GGA ATC GAC TTC 6231
Ala Leu Val Pro Val Ser Gly Thr Ser Leu Ala Val Gly Ile Asp Phe
1915 1920 1925 1930

CAT GCC GAA AAT GAC ACT ATT TAT TGG GTG GAT ATG GGC CTA AGC ACC 6279
His Ala Glu Asn Asp Thr Ile Tyr Trp Val Asp Met Gly Leu Ser Thr
1935 1940 1945

ATC AGC AGG GCC AAG CGT GAC CAG ACA TGG CGA GAG GAT GTG GTG ACC 6327
Ile Ser Arg Ala Lys Arg Asp Gln Thr Trp Arg Glu Asp Val Val Thr
1950 1955 1960

AAC GGT ATT GGC CGT GTG GAG GGC ATC GCC GTG GAC TGG ATC GCA GGC 6375
Asn Gly Ile Gly Arg Val Glu Gly Ile Ala Val Asp Trp Ile Ala Gly
1965 1970 1975

AAC ATA TAC TGG ACG GAC CAG GGC TTC GAT GTC ATC GAG GTT GCC CGG 6423
Asn Ile Tyr Trp Thr Asp Gln Gly Phe Asp Val Ile Glu Val Ala Arg
1980 1985 1990

CTC AAT GGC TCT TTT CGT TAT GTG GTC ATT TCC CAG GGT CTG GAC AAG 6471
Leu Asn Gly Ser Phe Arg Tyr Val Val Ile Ser Gln Gly Leu Asp Lys
1995 2000 2005 2010

CCT CGG GCC ATC ACT GTC CAC CCA GAG AAG GGG TAC TTG TTC TGG ACC 6519
Pro Arg Ala Ile Thr Val His Pro Glu Lys Gly Tyr Leu Phe Trp Thr
2015 2020 2025

GAG TGG GGT CAT TAC CCA CGT ATT GAG CGG TCT CGC CTT GAT GGC ACA 6567
Glu Trp Gly His Tyr Pro Arg Ile Glu Arg Ser Arg Leu Asp Gly Thr
2030 2035 2040

GAG AGA GTG GTG TTG GTT AAT GTC AGC ATC AGC TGG CCC AAT GGC ATC 6615
Glu Arg Val Val Leu Val Asn Val Ser Ile Ser Trp Pro Asn Gly Ile
2045 2050 2055

TCA GTA GAC TAT CAG GGC GGC AAG CTC TAC TGG TGT GAT GCT CGG ATG 6663
Ser Val Asp Tyr Gln Gly Gly Lys Leu Tyr Trp Cys Asp Ala Arg Met
2060 2065 2070

FIG.6A-12

```
GAC AAG ATC GAG CGC ATC GAC CTG GAA ACG GGC GAG AAC CGG GAG GTG    6711
Asp Lys Ile Glu Arg Ile Asp Leu Glu Thr Gly Glu Asn Arg Glu Val
2075                2080                2085                2090

GTC CTG TCC AGC AAT AAC ATG GAT ATG TTC TCC GTG TCC GTG TTT GAG    6759
Val Leu Ser Ser Asn Asn Met Asp Met Phe Ser Val Ser Val Phe Glu
                2095                2100                2105

GAC TTC ATC TAC TGG AGT GAC AGA ACT CAC GCC AAT GGC TCC ATC AAG    6807
Asp Phe Ile Tyr Trp Ser Asp Arg Thr His Ala Asn Gly Ser Ile Lys
            2110                2115                2120

CGC GGC TGC AAA GAC AAT GCT ACA GAC TCC GTG CCT CTG AGG ACA GGC    6855
Arg Gly Cys Lys Asp Asn Ala Thr Asp Ser Val Pro Leu Arg Thr Gly
        2125                2130                2135

ATT GGT GTT CAG CTT AAA GAC ATC AAG GTC TTC AAC AGG GAC AGG CAG    6903
Ile Gly Val Gln Leu Lys Asp Ile Lys Val Phe Asn Arg Asp Arg Gln
    2140                2145                2150

AAG GGT ACC AAT GTG TGC GCG GTA GCC AAC GGC GGG TGC CAG CAG CTC    6951
Lys Gly Thr Asn Val Cys Ala Val Ala Asn Gly Gly Cys Gln Gln Leu
2155                2160                2165                2170

TGC TTG TAT CGG GGT GGC GGA CAG CGA GCC TGT GCC TGT GCC CAC GGG    6999
Cys Leu Tyr Arg Gly Gly Gly Gln Arg Ala Cys Ala Cys Ala His Gly
                2175                2180                2185

ATG CTG GCA GAA GAC GGG GCC TCA TGC CGA GAG TAC GCT GGC TAC CTG    7047
Met Leu Ala Glu Asp Gly Ala Ser Cys Arg Glu Tyr Ala Gly Tyr Leu
            2190                2195                2200

CTC TAC TCA GAG CGG ACC ATC CTC AAG AGC ATC CAC CTG TCG GAT GAG    7095
Leu Tyr Ser Glu Arg Thr Ile Leu Lys Ser Ile His Leu Ser Asp Glu
        2205                2210                2215

CGT AAC CTC AAC GCA CCG GTG CAG CCC TTT GAA GAC CCC GAG CAC ATG    7143
Arg Asn Leu Asn Ala Pro Val Gln Pro Phe Glu Asp Pro Glu His Met
    2220                2225                2230

AAA AAT GTC ATC GCC CTG GCC TTT GAC TAC CGA GCA GGC ACC TCC CCG    7191
Lys Asn Val Ile Ala Leu Ala Phe Asp Tyr Arg Ala Gly Thr Ser Pro
2235                2240                2245                2250
```

FIG.6A-13

GGG ACC CCT AAC CGC ATC TTC TTC AGT GAC ATC CAC TTT GGG AAC ATC 7239
Gly Thr Pro Asn Arg Ile Phe Phe Ser Asp Ile His Phe Gly Asn Ile
2255 2260 2265

CAG CAG ATC AAT GAC GAT GGC TCG GGC AGG ACC ACC ATC GTG GAA AAT 7287
Gln Gln Ile Asn Asp Asp Gly Ser Gly Arg Thr Thr Ile Val Glu Asn
2270 2275 2280

GTG GGC TCT GTG GAA GGC CTG GCC TAT CAC CGT GGC TGG GAC ACA CTG 7335
Val Gly Ser Val Glu Gly Leu Ala Tyr His Arg Gly Trp Asp Thr Leu
2285 2290 2295

TAC TGG ACA AGC TAC ACC ACA TCC ACC ATC ACC CGC CAC ACC GTG GAC 7383
Tyr Trp Thr Ser Tyr Thr Thr Ser Thr Ile Thr Arg His Thr Val Asp
2300 2305 2310

CAG ACT CGC CCA GGG GCC TTC GAG AGG GAG ACA GTC ATC ACC ATG TCC 7431
Gln Thr Arg Pro Gly Ala Phe Glu Arg Glu Thr Val Ile Thr Met Ser
2315 2320 2325 2330

GGA GAC GAC CAC CCG AGA GCC TTT GTG CTG GAT GAG TGC CAG AAC CTG 7479
Gly Asp Asp His Pro Arg Ala Phe Val Leu Asp Glu Cys Gln Asn Leu
2335 2340 2345

ATG TTC TGG ACC AAT TGG AAC GAG CTC CAT CCA AGC ATC ATG CGG GCA 7527
Met Phe Trp Thr Asn Trp Asn Glu Leu His Pro Ser Ile Met Arg Ala
2350 2355 2360

GCC CTA TCC GGA GCC AAC GTC CTG ACC CTC ATT GAG AAG GAC ATC CGC 7575
Ala Leu Ser Gly Ala Asn Val Leu Thr Leu Ile Glu Lys Asp Ile Arg
2365 2370 2375

ACG CCC AAT GGG TTG GCC ATC GAC CAC CGG GCG GAG AAG CTG TAC TTC 7623
Thr Pro Asn Gly Leu Ala Ile Asp His Arg Ala Glu Lys Leu Tyr Phe
2380 2385 2390

TCG GAT GCC ACC TTG GAC AAG ATC GAG CGC TGC GAG TAC GAC GGC TCC 7671
Ser Asp Ala Thr Leu Asp Lys Ile Glu Arg Cys Glu Tyr Asp Gly Ser
2395 2400 2405 2410

CAC CGC TAT GTG ATC CTA AAG TCG GAG CCC GTC CAC CCC TTT GGG TTG 7719
His Arg Tyr Val Ile Leu Lys Ser Glu Pro Val His Pro Phe Gly Leu
2415 2420 2425

FIG.6A-14

```
GCG GTG TAC GGA GAG CAC ATT TTC TGG ACT GAC TGG GTG CGG CGG GCT      7767
Ala Val Tyr Gly Glu His Ile Phe Trp Thr Asp Trp Val Arg Arg Ala
            2430                2435                2440

GTG CAG CGA GCC AAC AAG TAT GTG GGC AGC GAC ATG AAG CTG CTT CGG      7815
Val Gln Arg Ala Asn Lys Tyr Val Gly Ser Asp Met Lys Leu Leu Arg
        2445                2450                2455

GTG GAC ATT CCC CAG CAA CCC ATG GGC ATC ATC GCC GTG GCC AAT GAC      7863
Val Asp Ile Pro Gln Gln Pro Met Gly Ile Ile Ala Val Ala Asn Asp
    2460                2465                2470

ACC AAC AGC TGT GAA CTC TCC CCC TGC CGT ATC AAC AAT GGA GGC TGC      7911
Thr Asn Ser Cys Glu Leu Ser Pro Cys Arg Ile Asn Asn Gly Gly Cys
2475                2480                2485                2490

CAG GAT CTG TGT CTG CTC ACC CAC CAA GGC CAC GTC AAC TGT TCC TGT      7959
Gln Asp Leu Cys Leu Leu Thr His Gln Gly His Val Asn Cys Ser Cys
                2495                2500                2505

CGA GGG GGC CGG ATC CTC CAG GAG GAC TTC ACC TGC CGG GCT GTG AAC      8007
Arg Gly Gly Arg Ile Leu Gln Glu Asp Phe Thr Cys Arg Ala Val Asn
            2510                2515                2520

TCC TCT TGT CGG GCA CAA GAT GAG TTT GAG TGT GCC AAT GGG GAA TGT      8055
Ser Ser Cys Arg Ala Gln Asp Glu Phe Glu Cys Ala Asn Gly Glu Cys
        2525                2530                2535

ATC AGC TTC AGC CTC ACC TGT GAT GGC GTC TCC CAC TGC AAG GAC AAG      8103
Ile Ser Phe Ser Leu Thr Cys Asp Gly Val Ser His Cys Lys Asp Lys
    2540                2545                2550

TCC GAT GAG AAG CCC TCC TAC TGC AAC TCA CGC CGC TGC AAG AAG ACT      8151
Ser Asp Glu Lys Pro Ser Tyr Cys Asn Ser Arg Arg Cys Lys Lys Thr
2555                2560                2565                2570

TTC CGC CAG TGT AAC AAT GGC CGC TGT GTA TCC AAC ATG CTG TGG TGC      8199
Phe Arg Gln Cys Asn Asn Gly Arg Cys Val Ser Asn Met Leu Trp Cys
                2575                2580                2585

AAT GGG GTG GAT TAC TGT GGG GAT GGC TCT GAT GAG ATA CCT TGC AAC      8247
Asn Gly Val Asp Tyr Cys Gly Asp Gly Ser Asp Glu Ile Pro Cys Asn
            2590                2595                2600
```

FIG.6A-15

AAG ACT GCC TGT GGT GTG GGT GAG TTC CGC TGC CGG GAT GGG TCC TGC 8295
Lys Thr Ala Cys Gly Val Gly Glu Phe Arg Cys Arg Asp Gly Ser Cys
2605 2610 2615

ATC GGG AAC TCC AGT CGC TGC AAC CAG TTT GTG GAT TGT GAG GAT GCC 8343
Ile Gly Asn Ser Ser Arg Cys Asn Gln Phe Val Asp Cys Glu Asp Ala
2620 2625 2630

TCG GAT GAG ATG AAT TGC AGT GCC ACA GAC TGC AGC AGC TAT TTC CGC 8391
Ser Asp Glu Met Asn Cys Ser Ala Thr Asp Cys Ser Ser Tyr Phe Arg
2635 2640 2645 2650

CTG GGC GTG AAA GGT GTC CTC TTC CAG CCG TGC GAG CGG ACA TCC CTG 8439
Leu Gly Val Lys Gly Val Leu Phe Gln Pro Cys Glu Arg Thr Ser Leu
2655 2660 2665

TGC TAC GCA CCT AGC TGG GTG TGT GAT GGC GCC AAC GAC TGT GGA GAC 8487
Cys Tyr Ala Pro Ser Trp Val Cys Asp Gly Ala Asn Asp Cys Gly Asp
2670 2675 2680

TAC AGC GAT GAA CGT GAC TGT CCA GGT GTG AAG CGC CCT AGG TGC CCG 8535
Tyr Ser Asp Glu Arg Asp Cys Pro Gly Val Lys Arg Pro Arg Cys Pro
2685 2690 2695

CTC AAT TAC TTT GCC TGC CCC AGC GGG CGC TGT ATC CCC ATG AGC TGG 8583
Leu Asn Tyr Phe Ala Cys Pro Ser Gly Arg Cys Ile Pro Met Ser Trp
2700 2705 2710

ACG TGT GAC AAG GAG GAT GAC TGT GAG AAC GGC GAG GAT GAG ACC CAC 8631
Thr Cys Asp Lys Glu Asp Asp Cys Glu Asn Gly Glu Asp Glu Thr His
2715 2720 2725 2730

TGC AAC AAG TTC TGC TCA GAG GCA CAG TTC GAG TGC CAG AAC CAC CGG 8679
Cys Asn Lys Phe Cys Ser Glu Ala Gln Phe Glu Cys Gln Asn His Arg
2735 2740 2745

TGT ATC TCC AAG CAG TGG CTG TGT GAC GGT AGC GAT GAT TGC GGG GAT 8727
Cys Ile Ser Lys Gln Trp Leu Cys Asp Gly Ser Asp Asp Cys Gly Asp
2750 2755 2760

GGC TCC GAT GAG GCA GCT CAC TGT GAA GGC AAG ACA TGT GGC CCC TCC 8775
Gly Ser Asp Glu Ala Ala His Cys Glu Gly Lys Thr Cys Gly Pro Ser
2765 2770 2775

FIG.6A-16

```
TCC TTC TCC TGT CCC GGC ACC CAC GTG TGT GTC CCT GAG CGC TGG CTC     8823
Ser Phe Ser Cys Pro Gly Thr His Val Cys Val Pro Glu Arg Trp Leu
    2780                2785                2790

TGT GAT GGC GAC AAG GAC TGT ACC GAT GGC GCG GAT GAG AGT GTC ACT     8871
Cys Asp Gly Asp Lys Asp Cys Thr Asp Gly Ala Asp Glu Ser Val Thr
2795                2800                2805                2810

GCT GGC TGC CTG TAC AAC AGC ACC TGT GAT GAC CGT GAG TTC ATG TGC     8919
Ala Gly Cys Leu Tyr Asn Ser Thr Cys Asp Asp Arg Glu Phe Met Cys
                2815                2820                2825

CAG AAC CGC TTG TGT ATT CCC AAG CAT TTC GTG TGC GAC CAT GAC CGT     8967
Gln Asn Arg Leu Cys Ile Pro Lys His Phe Val Cys Asp His Asp Arg
            2830                2835                2840

GAC TGT GCT GAT GGC TCT GAT GAA TCC CCT GAG TGT GAG TAC CCA ACC     9015
Asp Cys Ala Asp Gly Ser Asp Glu Ser Pro Glu Cys Glu Tyr Pro Thr
        2845                2850                2855

TGC GGG CCC AAT GAA TTC CGC TGT GCC AAT GGG CGT TGT CTG AGC TCC     9063
Cys Gly Pro Asn Glu Phe Arg Cys Ala Asn Gly Arg Cys Leu Ser Ser
    2860                2865                2870

CGT CAG TGG GAA TGT GAT GGG GAG AAT GAC TGT CAC GAC CAC AGC GAT     9111
Arg Gln Trp Glu Cys Asp Gly Glu Asn Asp Cys His Asp His Ser Asp
2875                2880                2885                2890

GAG GCT CCC AAG AAC CCA CAC TGC ACC AGC CCA GAG CAC AAA TGC AAT     9159
Glu Ala Pro Lys Asn Pro His Cys Thr Ser Pro Glu His Lys Cys Asn
                2895                2900                2905

GCC TCA TCA CAG TTC CTG TGC AGC AGC GGG CGC TGC GTG GCT GAG GCG     9207
Ala Ser Ser Gln Phe Leu Cys Ser Ser Gly Arg Cys Val Ala Glu Ala
            2910                2915                2920

TTG CTC TGC AAC GGC CAG GAC GAC TGT GGG GAC GGT TCA GAC GAA CGC     9255
Leu Leu Cys Asn Gly Gln Asp Asp Cys Gly Asp Gly Ser Asp Glu Arg
        2925                2930                2935

GGG TGC CAT GTC AAC GAG TGT CTC AGC CGC AAG CTC AGT GGC TGC AGT     9303
Gly Cys His Val Asn Glu Cys Leu Ser Arg Lys Leu Ser Gly Cys Ser
    2940                2945                2950
```

FIG.6A-17

CAG GAC TGC GAG GAC CTC AAG ATA GGC TTT AAG TGC CGC TGT CGC CCG 9351
Gln Asp Cys Glu Asp Leu Lys Ile Gly Phe Lys Cys Arg Cys Arg Pro
2955 2960 2965 2970

GGC TTC CGG CTA AAG GAC GAT GGC AGG ACC TGT GCC GAC CTG GAT GAG 9399
Gly Phe Arg Leu Lys Asp Asp Gly Arg Thr Cys Ala Asp Leu Asp Glu
2975 2980 2985

TGC AGC ACC ACC TTC CCC TGC AGC CAG CTC TGC ATC AAC ACC CAC GGA 9447
Cys Ser Thr Thr Phe Pro Cys Ser Gln Leu Cys Ile Asn Thr His Gly
2990 2995 3000

AGT TAC AAG TGT CTG TGT GTG GAG GGC TAT GCA CCC CGT GGC GGT GAC 9495
Ser Tyr Lys Cys Leu Cys Val Glu Gly Tyr Ala Pro Arg Gly Gly Asp
3005 3010 3015

CCC CAC AGC TGC AAA GCT GTG ACC GAT GAG GAG CCA TTT CTC ATC TTT 9543
Pro His Ser Cys Lys Ala Val Thr Asp Glu Glu Pro Phe Leu Ile Phe
3020 3025 3030

GCC AAC CGG TAC TAC CTG CGG AAG CTC AAC CTG GAC GGC TCC AAC TAC 9591
Ala Asn Arg Tyr Tyr Leu Arg Lys Leu Asn Leu Asp Gly Ser Asn Tyr
3035 3040 3045 3050

ACA CTG CTT AAG CAG GGC CTG AAC AAT GCG GTC GCC TTG GCA TTT GAC 9639
Thr Leu Leu Lys Gln Gly Leu Asn Asn Ala Val Ala Leu Ala Phe Asp
3055 3060 3065

TAC CGA GAG CAG ATG ATC TAC TGG ACG GGC GTG ACC ACC CAG GGC AGC 9687
Tyr Arg Glu Gln Met Ile Tyr Trp Thr Gly Val Thr Thr Gln Gly Ser
3070 3075 3080

ATG ATT CGC AGG ATG CAC CTC AAC GGC AGC AAC GTG CAG GTT CTG CAC 9735
Met Ile Arg Arg Met His Leu Asn Gly Ser Asn Val Gln Val Leu His
3085 3090 3095

CGG ACG GGC CTT AGT AAC CCA GAT GGG CTC GCT GTG GAC TGG GTG GGT 9783
Arg Thr Gly Leu Ser Asn Pro Asp Gly Leu Ala Val Asp Trp Val Gly
3100 3105 3110

GGC AAC CTG TAC TGG TGT GAC AAG GGC AGA GAT ACC ATT GAG GTG TCC 9831
Gly Asn Leu Tyr Trp Cys Asp Lys Gly Arg Asp Thr Ile Glu Val Ser
3115 3120 3125 3130

FIG.6A-18

AAG CTT AAC GGG GCC TAT CGG ACA GTG CTG GTC AGC TCT GGC CTC CGG 9879
Lys Leu Asn Gly Ala Tyr Arg Thr Val Leu Val Ser Ser Gly Leu Arg
3135 3140 3145

GAG CCC AGA GCT CTG GTA GTG GAT GTA CAG AAT GGG TAC CTG TAC TGG 9927
Glu Pro Arg Ala Leu Val Val Asp Val Gln Asn Gly Tyr Leu Tyr Trp
3150 3155 3160

ACA GAC TGG GGT GAC CAC TCA CTG ATC GGC CGG ATT GGC ATG GAT GGA 9975
Thr Asp Trp Gly Asp His Ser Leu Ile Gly Arg Ile Gly Met Asp Gly
3165 3170 3175

TCT GGC CGC AGC ATC ATC GTG GAC ACT AAG ATC ACA TGG CCC AAT GGC 10023
Ser Gly Arg Ser Ile Ile Val Asp Thr Lys Ile Thr Trp Pro Asn Gly
3180 3185 3190

CTG ACC GTG GAC TAC GTC ACG GAA CGC ATC TAC TGG GCT GAC GCC CGT 10071
Leu Thr Val Asp Tyr Val Thr Glu Arg Ile Tyr Trp Ala Asp Ala Arg
3195 3200 3205 3210

GAG GAC TAC ATC GAG TTC GCC AGC CTG GAT GGC TCC AAC CGT CAC GTT 10119
Glu Asp Tyr Ile Glu Phe Ala Ser Leu Asp Gly Ser Asn Arg His Val
3215 3220 3225

GTG CTG AGC CAA GAC ATC CCA CAC ATC TTT GCG CTG ACC CTA TTT GAA 10167
Val Leu Ser Gln Asp Ile Pro His Ile Phe Ala Leu Thr Leu Phe Glu
3230 3235 3240

GAC TAC GTC TAC TGG ACA GAC TGG GAA ACG AAG TCC ATC AAC CGG GCC 10215
Asp Tyr Val Tyr Trp Thr Asp Trp Glu Thr Lys Ser Ile Asn Arg Ala
3245 3250 3255

CAC AAG ACC ACG GGT GCC AAC AAA ACA CTC CTC ATC AGC ACC CTG CAC 10263
His Lys Thr Thr Gly Ala Asn Lys Thr Leu Leu Ile Ser Thr Leu His
3260 3265 3270

CGG CCC ATG GAC TTA CAT GTA TTC CAC GCC CTG CGC CAG CCA GAT GTG 10311
Arg Pro Met Asp Leu His Val Phe His Ala Leu Arg Gln Pro Asp Val
3275 3280 3285 3290

CCC AAT CAC CCC TGC AAA GTC AAC AAT GGT GGC TGC AGC AAC CTG TGC 10359
Pro Asn His Pro Cys Lys Val Asn Asn Gly Gly Cys Ser Asn Leu Cys
3295 3300 3305

FIG.6A-19

CTG CTG TCC CCT GGG GGT GGT CAC AAG TGC GCC TGC CCC ACC AAC TTC 10407
Leu Leu Ser Pro Gly Gly Gly His Lys Cys Ala Cys Pro Thr Asn Phe
3310 3315 3320

TAT CTG GGT GGC GAT GGC CGT ACC TGT GTG TCC AAC TGC ACA GCA AGC 10455
Tyr Leu Gly Gly Asp Gly Arg Thr Cys Val Ser Asn Cys Thr Ala Ser
3325 3330 3335

CAG TTT GTG TGC AAA AAT GAC AAG TGC ATC CCC TTC TGG TGG AAG TGT 10503
Gln Phe Val Cys Lys Asn Asp Lys Cys Ile Pro Phe Trp Trp Lys Cys
3340 3345 3350

GAC ACG GAG GAC GAC TGT GGG GAT CAC TCA GAC GAG CCT CCA GAC TGT 10551
Asp Thr Glu Asp Asp Cys Gly Asp His Ser Asp Glu Pro Pro Asp Cys
3355 3360 3365 3370

CCC GAG TTC AAG TGC CGC CCA GGC CAG TTC CAG TGC TCC ACC GGC ATC 10599
Pro Glu Phe Lys Cys Arg Pro Gly Gln Phe Gln Cys Ser Thr Gly Ile
3375 3380 3385

TGC ACC AAC CCT GCC TTC ATC TGT GAT GGG GAC AAT GAC TGC CAA GAC 10647
Cys Thr Asn Pro Ala Phe Ile Cys Asp Gly Asp Asn Asp Cys Gln Asp
3390 3395 3400

AAT AGT GAC GAG GCC AAT TGC GAC ATT CAC GTC TGC TTG CCC AGC CAA 10695
Asn Ser Asp Glu Ala Asn Cys Asp Ile His Val Cys Leu Pro Ser Gln
3405 3410 3415

TTC AAG TGC ACC AAC ACC AAC CGC TGC ATT CCT GGC ATC TTC CGT TGC 10743
Phe Lys Cys Thr Asn Thr Asn Arg Cys Ile Pro Gly Ile Phe Arg Cys
3420 3425 3430

AAT GGG CAG GAC AAC TGC GGG GAC GGC GAG GAT GAG CGG GAT TGC CCT 10791
Asn Gly Gln Asp Asn Cys Gly Asp Gly Glu Asp Glu Arg Asp Cys Pro
3435 3440 3445 3450

GAG GTG ACC TGC GCC CCC AAC CAG TTC CAG TGC TCC ATC ACC AAG CGC 10839
Glu Val Thr Cys Ala Pro Asn Gln Phe Gln Cys Ser Ile Thr Lys Arg
3455 3460 3465

TGC ATC CCT CGC GTC TGG GTC TGT GAC AGG GAT AAT CAC TGT GTG GAC 10887
Cys Ile Pro Arg Val Trp Val Cys Asp Arg Asp Asn His Cys Val Asp
3470 3475 3480

FIG.6A-20

```
GGC AGT GAT GAG CCT GCC AAC TGT ACC CAA ATG ACC TGT GGA GTG GAT   10935
Gly Ser Asp Glu Pro Ala Asn Cys Thr Gln Met Thr Cys Gly Val Asp
        3485                3490                3495

GAG TTC CGC TGC AAG GAT TCT GGC CGC TGC ATC CCC GCG CGC TGG AAG   10983
Glu Phe Arg Cys Lys Asp Ser Gly Arg Cys Ile Pro Ala Arg Trp Lys
    3500                3505                3510

TGT GAC GGA GAA GAT GAC TGT GGG GAT GGT TCA GAT GAG CCC AAG GAA   11031
Cys Asp Gly Glu Asp Asp Cys Gly Asp Gly Ser Asp Glu Pro Lys Glu
3515                3520                3525                3530

GAG TGT GAT GAG CGC ACC TGT GAG CCA TAC CAG TTC CGC TGC AAA AAC   11079
Glu Cys Asp Glu Arg Thr Cys Glu Pro Tyr Gln Phe Arg Cys Lys Asn
                3535                3540                3545

AAC CGC TGT GTC CCA GGC CGT TGG CAA TGT GAC TAC GAC AAC GAC TGC   11127
Asn Arg Cys Val Pro Gly Arg Trp Gln Cys Asp Tyr Asp Asn Asp Cys
            3550                3555                3560

GGA GAT AAC TCG GAC GAG GAG AGC TGC ACA CCT CGG CCC TGC TCT GAG   11175
Gly Asp Asn Ser Asp Glu Glu Ser Cys Thr Pro Arg Pro Cys Ser Glu
        3565                3570                3575

AGT GAG TTT TTC TGT GCC AAT GGC CGC TGC ATC GCT GGG CGC TGG AAG   11223
Ser Glu Phe Phe Cys Ala Asn Gly Arg Cys Ile Ala Gly Arg Trp Lys
    3580                3585                3590

TGT GAT GGG GAC CAT GAC TGT GCC GAC GGC TCA GAC GAG AAA GAC TGC   11271
Cys Asp Gly Asp His Asp Cys Ala Asp Gly Ser Asp Glu Lys Asp Cys
3595                3600                3605                3610

ACC CCC CGC TGT GAT ATG GAC CAG TTC CAG TGC AAG AGT GGC CAC TGC   11319
Thr Pro Arg Cys Asp Met Asp Gln Phe Gln Cys Lys Ser Gly His Cys
                3615                3620                3625

ATC CCC CTG CGC TGG CCG TGT GAC GCG GAT GCT GAC TGT ATG GAC GGC   11367
Ile Pro Leu Arg Trp Pro Cys Asp Ala Asp Ala Asp Cys Met Asp Gly
            3630                3635                3640

AGT GAC GAG GAA GCC TGT GGC ACT GGG GTG AGG ACC TGC CCA TTG GAT   11415
Ser Asp Glu Glu Ala Cys Gly Thr Gly Val Arg Thr Cys Pro Leu Asp
        3645                3650                3655
```

FIG.6A-21

```
GAG TTT CAA TGT AAC AAC ACC TTG TGC AAG CCG CTG GCC TGG AAG TGT   11463
Glu Phe Gln Cys Asn Asn Thr Leu Cys Lys Pro Leu Ala Trp Lys Cys
   3660                3665                3670

GAT GGA GAG GAC GAC TGT GGG GAC AAC TCA GAT GAG AAC CCC GAG GAA   11511
Asp Gly Glu Asp Asp Cys Gly Asp Asn Ser Asp Glu Asn Pro Glu Glu
3675                3680                3685                3690

TGC GCC CGG TTC ATC TGC CCT CCC AAC CGG CCT TTC CGC TGC AAG AAT   11559
Cys Ala Arg Phe Ile Cys Pro Pro Asn Arg Pro Phe Arg Cys Lys Asn
            3695                3700                3705

GAC CGA GTC TGC CTG TGG ATT GGG CGC CAG TGT GAT GGC GTG GAC AAC   11607
Asp Arg Val Cys Leu Trp Ile Gly Arg Gln Cys Asp Gly Val Asp Asn
        3710                3715                3720

TGT GGA GAT GGG ACT GAC GAG GAG GAC TGT GAG CCC CCC ACG GCC CAG   11655
Cys Gly Asp Gly Thr Asp Glu Glu Asp Cys Glu Pro Pro Thr Ala Gln
    3725                3730                3735

AAC CCC CAC TGC AAA GAC AAG AAG GAG TTC CTG TGC CGA AAC CAG CGC   11703
Asn Pro His Cys Lys Asp Lys Lys Glu Phe Leu Cys Arg Asn Gln Arg
   3740                3745                3750

TGT CTA TCA TCC TCC CTG CGC TGT AAC ATG TTC GAT GAC TGC GGC GAT   11751
Cys Leu Ser Ser Ser Leu Arg Cys Asn Met Phe Asp Asp Cys Gly Asp
3755                3760                3765                3770

GGC TCC GAT GAA GAA GAT TGC AGC ATC GAC CCC AAG CTG ACC AGC TGT   11799
Gly Ser Asp Glu Glu Asp Cys Ser Ile Asp Pro Lys Leu Thr Ser Cys
            3775                3780                3785

GCC ACC AAT GCC AGC ATG TGT GGG GAC GAA GCT CGT TGT GTG CGC ACT   11847
Ala Thr Asn Ala Ser Met Cys Gly Asp Glu Ala Arg Cys Val Arg Thr
        3790                3795                3800

GAG AAA GCT GCC TAC TGT GCC TGC CGC TCG GGC TTC CAT ACT GTG CCG   11895
Glu Lys Ala Ala Tyr Cys Ala Cys Arg Ser Gly Phe His Thr Val Pro
    3805                3810                3815

GGC CAG CCC GGA TGC CAG GAC ATC AAC GAG TGC CTG CGC TTT GGT ACC   11943
Gly Gln Pro Gly Cys Gln Asp Ile Asn Glu Cys Leu Arg Phe Gly Thr
   3820                3825                3830
```

FIG.6A-22

```
TGC TCT CAG CTC TGG AAC AAA CCC AAG GGA GGC CAC CTC TGC AGC TGT   11991
Cys Ser Gln Leu Trp Asn Lys Pro Lys Gly Gly His Leu Cys Ser Cys
3835                3840                3845                3850

GCC CGC AAC TTC ATG AAG ACA CAC AAC ACC TGC AAA GCT GAA GGC TCC   12039
Ala Arg Asn Phe Met Lys Thr His Asn Thr Cys Lys Ala Glu Gly Ser
            3855                3860                3865

GAG TAC CAG GTG CTA TAC ATC GCG GAT GAC AAC GAG ATC CGC AGC TTG   12087
Glu Tyr Gln Val Leu Tyr Ile Ala Asp Asp Asn Glu Ile Arg Ser Leu
        3870                3875                3880

TTC CCG GGC CAC CCC CAC TCA GCC TAC GAG CAG ACA TTC CAG GGC GAT   12135
Phe Pro Gly His Pro His Ser Ala Tyr Glu Gln Thr Phe Gln Gly Asp
    3885                3890                3895

GAG AGT GTC CGC ATA GAT GCC ATG GAT GTC CAT GTC AAG GCC GGC CGT   12183
Glu Ser Val Arg Ile Asp Ala Met Asp Val His Val Lys Ala Gly Arg
3900                3905                3910

GTC TAC TGG ACT AAC TGG CAC ACG GGC ACA ATC TCC TAC AGG AGC CTG   12231
Val Tyr Trp Thr Asn Trp His Thr Gly Thr Ile Ser Tyr Arg Ser Leu
3915                3920                3925                3930

CCC CCT GCC GCC CCT CCT ACC ACT TCC AAC CGC CAC CGG AGG CAG ATC   12279
Pro Pro Ala Ala Pro Pro Thr Thr Ser Asn Arg His Arg Arg Gln Ile
            3935                3940                3945

GAC CGG GGT GTC ACC CAC CTC AAT ATT TCA GGG CTG AAG ATG CCG AGG   12327
Asp Arg Gly Val Thr His Leu Asn Ile Ser Gly Leu Lys Met Pro Arg
        3950                3955                3960

GGT ATC GCT ATC GAC TGG GTG GCC GGG AAT GTG TAC TGG ACC GAT TCC   12375
Gly Ile Ala Ile Asp Trp Val Ala Gly Asn Val Tyr Trp Thr Asp Ser
    3965                3970                3975

GGC CGA GAC GTG ATT GAG GTG GCG CAA ATG AAG GGC GAG AAC CGC AAG   12423
Gly Arg Asp Val Ile Glu Val Ala Gln Met Lys Gly Glu Asn Arg Lys
3980                3985                3990

ACG CTC ATC TCG GGC ATG ATT GAT GAG CCC CAT GCC ATC GTG GTG GAC   12471
Thr Leu Ile Ser Gly Met Ile Asp Glu Pro His Ala Ile Val Val Asp
3995                4000                4005                4010
```

FIG.6A-23

```
CCT CTG AGG GGC ACC ATG TAC TGG TCA GAC TGG GGG AAC CAC CCC AAG   12519
Pro Leu Arg Gly Thr Met Tyr Trp Ser Asp Trp Gly Asn His Pro Lys
                4015                4020                4025

ATT GAA ACA GCA GCG ATG GAT GGC ACC CTT CGG GAG ACT CTC GTG CAA   12567
Ile Glu Thr Ala Ala Met Asp Gly Thr Leu Arg Glu Thr Leu Val Gln
            4030                4035                4040

GAC AAC ATT CAG TGG CCT ACA GGG CTG GCT GTG GAC TAT CAC AAT GAA   12615
Asp Asn Ile Gln Trp Pro Thr Gly Leu Ala Val Asp Tyr His Asn Glu
        4045                4050                4055

CGG CTC TAC TGG GCA GAT GCC AAG CTT TCG GTC ATC GGC AGC ATC CGG   12663
Arg Leu Tyr Trp Ala Asp Ala Lys Leu Ser Val Ile Gly Ser Ile Arg
    4060                4065                4070

CTC AAC GGC ACT GAC CCC ATT GTG GCT GCT GAC AGC AAA CGA GGC CTA   12711
Leu Asn Gly Thr Asp Pro Ile Val Ala Ala Asp Ser Lys Arg Gly Leu
4075                4080                4085                4090

AGT CAC CCC TTC AGC ATC GAT GTG TTT GAA GAC TAC ATC TAC GGA GTC   12759
Ser His Pro Phe Ser Ile Asp Val Phe Glu Asp Tyr Ile Tyr Gly Val
                4095                4100                4105

ACT TAC ATC AAT AAT CGT GTC TTC AAG ATC CAC AAG TTT GGA CAC AGC   12807
Thr Tyr Ile Asn Asn Arg Val Phe Lys Ile His Lys Phe Gly His Ser
            4110                4115                4120

CCC TTG TAC AAC CTA ACT GGG GGC CTG AGC CAT GCC TCT GAT GTA GTC   12855
Pro Leu Tyr Asn Leu Thr Gly Gly Leu Ser His Ala Ser Asp Val Val
        4125                4130                4135

CTT TAC CAT CAA CAC AAG CAG CCT GAA GTG ACC AAC CCC TGT GAC CGC   12903
Leu Tyr His Gln His Lys Gln Pro Glu Val Thr Asn Pro Cys Asp Arg
    4140                4145                4150

AAG AAA TGC GAA TGG CTG TGT CTG CTG AGC CCC AGC GGG CCT GTC TGC   12951
Lys Lys Cys Glu Trp Leu Cys Leu Leu Ser Pro Ser Gly Pro Val Cys
4155                4160                4165                4170

ACC TGT CCC AAT GGA AAG AGG CTG GAT AAT GGC ACC TGT GTG CCT GTG   12999
Thr Cys Pro Asn Gly Lys Arg Leu Asp Asn Gly Thr Cys Val Pro Val
                4175                4180                4185
```

FIG.6A-24

```
CCC TCT CCA ACA CCC CCT CCA GAT GCC CCT AGG CCT GGA ACC TGC ACT   13047
Pro Ser Pro Thr Pro Pro Pro Asp Ala Pro Arg Pro Gly Thr Cys Thr
                4190                4195                4200

CTG CAG TGC TTC AAT GGT GGT AGT TGT TTC CTC AAC GCT CGG AGG CAG   13095
Leu Gln Cys Phe Asn Gly Gly Ser Cys Phe Leu Asn Ala Arg Arg Gln
        4205                4210                4215

CCC AAG TGC CGT TGC CAG CCC CGT TAC ACA GGC GAT AAG TGT GAG CTG   13143
Pro Lys Cys Arg Cys Gln Pro Arg Tyr Thr Gly Asp Lys Cys Glu Leu
    4220                4225                4230

GAT CAG TGC TGG GAA TAC TGT CAC AAC GGA GGC ACC TGT GCG GCT TCC   13191
Asp Gln Cys Trp Glu Tyr Cys His Asn Gly Gly Thr Cys Ala Ala Ser
4235                4240                4245                4250

CCA TCT GGC ATG CCC ACG TGC CGC TGT CCC ACT GGC TTC ACG GGC CCC   13239
Pro Ser Gly Met Pro Thr Cys Arg Cys Pro Thr Gly Phe Thr Gly Pro
                    4255                4260                4265

AAA TGC ACC GCA CAG GTG TGT GCA GGC TAC TGC TCT AAC AAC AGC ACC   13287
Lys Cys Thr Ala Gln Val Cys Ala Gly Tyr Cys Ser Asn Asn Ser Thr
                4270                4275                4280

TGC ACC GTC AAC CAG GGC AAC CAG CCC CAG TGC CGA TGT CTA CCT GGC   13335
Cys Thr Val Asn Gln Gly Asn Gln Pro Gln Cys Arg Cys Leu Pro Gly
        4285                4290                4295

TTC CTG GGC GAC CGT TGC CAG TAC CGG CAG TGC TCT GGC TTC TGT GAG   13383
Phe Leu Gly Asp Arg Cys Gln Tyr Arg Gln Cys Ser Gly Phe Cys Glu
    4300                4305                4310

AAC TTT GGC ACC TGT CAG ATG GCT GCT GAT GGC TCC CGA CAA TGT CGC   13431
Asn Phe Gly Thr Cys Gln Met Ala Ala Asp Gly Ser Arg Gln Cys Arg
4315                4320                4325                4330

TGC ACC GTC TAC TTT GAG GGA CCA AGG TGT GAG GTG AAC AAG TGT AGT   13479
Cys Thr Val Tyr Phe Glu Gly Pro Arg Cys Glu Val Asn Lys Cys Ser
                    4335                4340                4345

CGC TGT CTC CAA GGC GCC TGT GTG GTC AAT AAG CAG ACC GGA GAT GTC   13527
Arg Cys Leu Gln Gly Ala Cys Val Val Asn Lys Gln Thr Gly Asp Val
                4350                4355                4360
```

FIG.6A-25

```
ACA TGC AAC TGC ACT GAT GGC CGG GTA GCC CCC AGT TGT CTC ACC TGC    13575
Thr Cys Asn Cys Thr Asp Gly Arg Val Ala Pro Ser Cys Leu Thr Cys
        4365                4370                4375

ATC GAT CAC TGT AGC AAT GGT GGC TCC TGC ACC ATG AAC AGC AAG ATG    13623
Ile Asp His Cys Ser Asn Gly Gly Ser Cys Thr Met Asn Ser Lys Met
    4380                4385                4390

ATG CCT GAG TGC CAG TGC CCG CCC CAT ATG ACA GGA CCC CGG TGC CAG    13671
Met Pro Glu Cys Gln Cys Pro Pro His Met Thr Gly Pro Arg Cys Gln
4395                4400                4405                4410

GAG CAG GTT GTT AGT CAG CAA CAG CCT GGG CAT ATG GCC TCC ATC CTG    13719
Glu Gln Val Val Ser Gln Gln Gln Pro Gly His Met Ala Ser Ile Leu
            4415                4420                4425

ATC CCT CTG CTG CTG CTT CTC CTG CTG CTT CTG GTG GCT GGC GTG GTG    13767
Ile Pro Leu Leu Leu Leu Leu Leu Leu Leu Leu Val Ala Gly Val Val
        4430                4435                4440

TTC TGG TAT AAG CGG CGA GTC CGA GGG GCT AAG GGC TTC CAG CAC CAG    13815
Phe Trp Tyr Lys Arg Arg Val Arg Gly Ala Lys Gly Phe Gln His Gln
        4445                4450                4455

CGG ATG ACC AAT GGG GCC ATG AAT GTG GAA ATT GGA AAC CCT ACC TAC    13863
Arg Met Thr Asn Gly Ala Met Asn Val Glu Ile Gly Asn Pro Thr Tyr
    4460                4465                4470

AAG ATG TAT GAA GGT GGA GAG CCC GAT GAT GTC GGG GGC CTA CTG GAT    13911
Lys Met Tyr Glu Gly Gly Glu Pro Asp Asp Val Gly Gly Leu Leu Asp
4475                4480                4485                4490

GCT GAT TTT GCC CTT GAC CCT GAC AAG CCT ACC AAC TTC ACC AAC CCA    13959
Ala Asp Phe Ala Leu Asp Pro Asp Lys Pro Thr Asn Phe Thr Asn Pro
            4495                4500                4505

GTG TAT GCC ACG CTC TAC ATG GGG GGC CAC GGC AGC CGC CAT TCC CTG    14007
Val Tyr Ala Thr Leu Tyr Met Gly Gly His Gly Ser Arg His Ser Leu
        4510                4515                4520

GCC AGC ACG GAC GAG AAG CGA GAA CTG CTG GGC CGG GGA CCT GAA GAC    14055
Ala Ser Thr Asp Glu Lys Arg Glu Leu Leu Gly Arg Gly Pro Glu Asp
        4525                4530                4535
```

FIG.6A-26

```
GAG ATA GGA GAT CCC TTG GCA TAGGGCCCTG CCCCGACGGA TGTCCCCAGA AAGC  14110
CCCCTGCCAC ATGAGTCTTT CAATGAACCC CCTCCCCAGC CGGCCCTTCT CCGGCCCTGC  14170
Glu Ile Gly Asp Pro Leu Ala
   4540                4545

CGGGTGTACA AATGTAAAAA TGAAGGAATT ACTTTTTATA TGTGAGCGAG CAAGCGAGCA  14230
AGCACAGTAT TATCTCTTTG CATTTCCTTC CTGCCTGCTC CTCAGTATCC CCCCCATGCT  14290
GCCTTGAGGG GGCGGGGAGG GCTTTGTGGC TCAAAGGTAT GAAGGAGTCC ACATGTTCCC  14350
TACCGAGCAT ACCCCTGGAA GCCTGGCGGC ACGGCCTCCC CACCACGCCT GTGCAAGACA  14410
CTCAACGGGG CTCCGTGTCC CAGCTTTCCT TTCCTTGGCT CTCTGGGGTT AGTTCAGGGG  14470
AGGTGGAGTC CTCTGCTGAC CCTGTCTGGA AGATTTGGCT CTAGCTGAGG AAGGAGTCTT  14530
TTAGTTGAGG GAAGTCACCC CAAACCCCAG CTCCCACTTT CAGGGGCACC TCTCAGATGG  14590
CCATGCTCAG TATCCCTTCC AGACAGGCCC TCCCCTCTCT AGCGCCCCCT CTGTGGCTCC  14650
TAGGGCTGAA CACATTCTTT GGTAACTGTC CCCCAAGCCT CCCATCCCCC TGAGGGCCAG  14710
GAAGAGTCGG GGCACACCAA GGAAGGGCAA GCGGGCAGCC CCATTTTGGG GACGTGAACG  14770
TTTTAATAAT TTTTGCTGAA TTCCTTTACA ACTAAATAAC ACAGATATTG TTATAAATAA  14830
AATTGTAAAA AAAAAAAAA
```

FIG.6A-27

Met Leu Thr Pro Pro Leu Leu Leu Leu Val Pro Leu Leu Ser Ala Leu
1 5 10 15
Val Ser Gly Ala Thr Met Asp Ala Pro Lys Thr Cys Ser Pro Lys Gln
20 25 30
Phe Ala Cys Arg Asp Gln Ile Thr Cys Ile Ser Lys Gly Trp Arg Cys
35 40 45
Asp Gly Glu Arg Asp Cys Pro Asp Gly Ser Asp Glu Ala Pro Glu Ile
50 55 60
Cys Pro Gln Ser Lys Ala Gln Arg Cys Pro Pro Asn Glu His Ser Cys
65 70 75 80
Leu Gly Thr Glu Leu Cys Val Pro Met Ser Arg Leu Cys Asn Gly Ile
85 90 95
Gln Asp Cys Met Asp Gly Ser Asp Glu Gly Ala His Cys Arg Glu Leu
100 105 110
Arg Ala Asn Cys Ser Arg Met Gly Cys Gln His His Cys Val Pro Thr
115 120 125
Pro Ser Gly Pro Thr Cys Tyr Cys Asn Ser Ser Phe Gln Leu Glu Ala
130 135 140
Asp Gly Lys Thr Cys Lys Asp Phe Asp Glu Cys Ser Val Tyr Gly Thr
145 150 155 160
Cys Ser Gln Leu Cys Thr Asn Thr Asp Gly Ser Phe Thr Cys Gly Cys
165 170 175
Val Glu Gly Tyr Leu Leu Gln Pro Asp Asn Arg Ser Cys Lys Ala Lys
180 185 190
Asn Glu Pro Val Asp Arg Pro Pro Val Leu Leu Ile Ala Asn Ser Gln
195 200 205
Asn Ile Leu Ala Thr Tyr Leu Ser Gly Ala Gln Val Ser Thr Ile Thr
210 215 220
Pro Thr Ser Thr Arg Gln Thr Thr Ala Met Asp Phe Ser Tyr Ala Asn
225 230 235 240
Glu Thr Val Cys Trp Val His Val Gly Asp Ser Ala Ala Gln Thr Gln
245 250 255
Leu Lys Cys Ala Arg Met Pro Gly Leu Lys Gly Phe Val Asp Glu His
260 265 270
Thr Ile Asn Ile Ser Leu Ser Leu His His Val Glu Gln Met Ala Ile
275 280 285
Asp Trp Leu Thr Gly Asn Phe Tyr Phe Val Asp Asp Ile Asp Asp Arg
290 295 300
Ile Phe Val Cys Asn Arg Asn Gly Asp Thr Cys Val Thr Leu Leu Asp
305 310 315 320
Leu Glu Leu Tyr Asn Pro Lys Gly Ile Ala Leu Asp Pro Ala Met Gly
325 330 335

FIG.6B-1

Lys Val Phe Phe Thr Asp Tyr Gly Gln Ile Pro Lys Val Glu Arg Cys
340 345 350
Asp Met Asp Gly Gln Asn Arg Thr Lys Leu Val Asp Ser Lys Ile Val
355 360 365
Phe Pro His Gly Ile Thr Leu Asp Leu Val Ser Arg Leu Val Tyr Trp
370 375 380
Ala Asp Ala Tyr Leu Asp Tyr Ile Glu Val Val Asp Tyr Glu Gly Lys
385 390 395 400
Gly Arg Gln Thr Ile Ile Gln Gly Ile Leu Ile Glu His Leu Tyr Gly
405 410 415
Leu Thr Val Phe Glu Asn Tyr Leu Tyr Ala Thr Asn Ser Asp Asn Ala
420 425 430
Asn Thr Gln Gln Lys Thr Ser Val Ile Arg Val Asn Arg Phe Asn Ser
435 440 445
Thr Glu Tyr Gln Val Val Thr Arg Val Asp Lys Gly Gly Ala Leu His
450 455 460
Ile Tyr His Gln Arg Arg Gln Pro Arg Val Arg Ser His Ala Cys Glu
465 470 475 480
Asn Asp Gln Tyr Gly Lys Pro Gly Gly Cys Ser Asp Ile Cys Leu Leu
485 490 495
Ala Asn Ser His Lys Ala Arg Thr Cys Arg Cys Arg Ser Gly Phe Ser
500 505 510
Leu Gly Ser Asp Gly Lys Ser Cys Lys Lys Pro Glu His Glu Leu Phe
515 520 525
Leu Val Tyr Gly Lys Gly Arg Pro Gly Ile Ile Arg Gly Met Asp Met
530 535 540
Gly Ala Lys Val Pro Asp Glu His Met Ile Pro Ile Glu Asn Leu Met
545 550 555 560
Asn Pro Arg Ala Leu Asp Phe His Ala Glu Thr Gly Phe Ile Tyr Phe
565 570 575
Ala Asp Thr Thr Ser Tyr Leu Ile Gly Arg Gln Lys Ile Asp Gly Thr
580 585 590
Glu Arg Glu Thr Ile Leu Lys Asp Gly Ile His Asn Val Glu Gly Val
595 600 605
Ala Val Asp Trp Met Gly Asp Asn Leu Tyr Trp Thr Asp Asp Gly Pro
610 615 620
Lys Lys Thr Ile Ser Val Ala Arg Leu Glu Lys Ala Ala Gln Thr Arg
625 630 635 640
Lys Thr Leu Ile Glu Gly Lys Met Thr His Pro Arg Ala Ile Val Val
645 650 655
Asp Pro Leu Asn Gly Trp Met Tyr Trp Thr Asp Trp Glu Glu Asp Pro
660 665 670

FIG.6B-2

```
Leu Ser Leu Asp Ile Pro Ala Gly Arg Leu Tyr Trp Val Asp Ala Phe
705                 710                 715                 720
Tyr Asp Arg Ile Glu Thr Ile Leu Leu Asn Gly Thr Asp Arg Lys Ile
                725                 730                 735
Val Tyr Glu Gly Pro Glu Leu Asn His Ala Phe Gly Leu Cys His His
            740                 745                 750
Gly Asn Tyr Leu Phe Trp Thr Glu Tyr Arg Ser Gly Ser Val Tyr Arg
        755                 760                 765
Leu Glu Arg Gly Val Ala Gly Ala Pro Pro Thr Val Thr Leu Leu Arg
    770                 775                 780
Ser Glu Arg Pro Pro Ile Phe Glu Ile Arg Met Tyr Asp Ala His Glu
785                 790                 795                 800
Gln Gln Val Gly Thr Asn Lys Cys Arg Val Asn Asn Gly Gly Cys Ser
                805                 810                 815
Ser Leu Cys Leu Ala Thr Pro Gly Ser Arg Gln Cys Ala Cys Ala Glu
            820                 825                 830
Asp Gln Val Leu Asp Thr Asp Gly Val Thr Cys Leu Ala Asn Pro Ser
        835                 840                 845
Tyr Val Pro Pro Pro Gln Cys Gln Pro Gly Gln Phe Ala Cys Ala Asn
    850                 855                 860
Asn Arg Cys Ile Gln Glu Arg Trp Lys Cys Asp Gly Asp Asn Asp Cys
865                 870                 875                 880
Leu Asp Asn Ser Asp Glu Ala Pro Ala Leu Cys His Gln His Thr Cys
                885                 890                 895
Pro Ser Asp Arg Phe Lys Cys Glu Asn Asn Arg Cys Ile Pro Asn Arg
            900                 905                 910
Trp Leu Cys Asp Gly Asp Asn Asp Cys Gly Asn Ser Glu Asp Glu Ser
        915                 920                 925
Asn Ala Thr Cys Ser Ala Arg Thr Cys Pro Pro Asn Gln Phe Ser Cys
    930                 935                 940
Ala Ser Gly Arg Cys Ile Pro Ile Ser Trp Thr Cys Asp Leu Asp Asp
945                 950                 955                 960
Asp Cys Gly Asp Arg Ser Asp Glu Ser Ala Ser Cys Ala Tyr Pro Thr
                965                 970                 975
Cys Phe Pro Leu Thr Gln Phe Thr Cys Asn Asn Gly Arg Cys Ile Asn
            980                 985                 990
Ile Asn Trp Arg Cys Asp Asn Asp Asn Asp Cys Gly Asp Asn Ser Asp
        995                1000                1005
Glu Ala Gly Cys Ser His Ser Cys Ser Ser Thr Gln Phe Lys Cys Asn
   1010                1015                1020
Ser Gly Arg Cys Ile Pro Glu His Trp Thr Cys Asp Gly Asp Asn Asp
025                1030                1035                1040
```

FIG.6B-3

```
Cys Gly Asp Tyr Ser Asp Glu Thr His Ala Asn Cys Thr Asn Gln Ala
                1045                1050                1055
Thr Arg Pro Pro Gly Gly Cys His Ser Asp Glu Phe Gln Cys Pro Leu
            1060                1065                1070
Asp Gly Leu Cys Ile Pro Leu Arg Trp Arg Cys Asp Gly Asp Thr Asp
        1075                1080                1085
Cys Met Asp Ser Ser Asp Glu Lys Ser Cys Glu Gly Val Thr His Val
    1090                1095                1100
Cys Asp Pro Asn Val Lys Phe Gly Cys Lys Asp Ser Ala Arg Cys Ile
105                 1110                1115                1120
Ser Lys Ala Trp Val Cys Asp Gly Asp Ser Asp Cys Glu Asp Asn Ser
                1125                1130                1135
Asp Glu Glu Asn Cys Glu Ala Leu Ala Cys Arg Pro Pro Ser His Pro
            1140                1145                1150
Cys Ala Asn Asn Thr Ser Val Cys Leu Pro Pro Asp Lys Leu Cys Asp
        1155                1160                1165
Gly Lys Asp Asp Cys Gly Asp Gly Ser Asp Glu Gly Glu Leu Cys Asp
    1170                1175                1180
Gln Cys Ser Leu Asn Asn Gly Gly Cys Ser His Asn Cys Ser Val Ala
185                 1190                1195                1200
Pro Gly Glu Gly Ile Val Cys Ser Cys Pro Leu Gly Met Glu Leu Gly
                1205                1210                1215
Ser Asp Asn His Thr Cys Gln Ile Gln Ser Tyr Cys Ala Lys His Leu
            1220                1225                1230
Lys Cys Ser Gln Lys Cys Asp Gln Asn Lys Phe Ser Val Lys Cys Ser
        1235                1240                1245
Cys Tyr Glu Gly Trp Val Leu Glu Pro Asp Gly Glu Thr Cys Arg Ser
    1250                1255                1260
Leu Asp Pro Phe Lys Leu Phe Ile Ile Phe Ser Asn Arg His Glu Ile
265                 1270                1275                1280
Arg Arg Ile Asp Leu His Lys Gly Asp Tyr Ser Val Leu Val Pro Gly
                1285                1290                1295
Leu Arg Asn Thr Ile Ala Leu Asp Phe His Leu Ser Gln Ser Ala Leu
            1300                1305                1310
Tyr Trp Thr Asp Ala Val Glu Asp Lys Ile Tyr Arg Gly Lys Leu Leu
        1315                1320                1325
Asp Asn Gly Ala Leu Thr Ser Phe Glu Val Val Ile Gln Tyr Gly Leu
    1330                1335                1340
Ala Thr Pro Glu Gly Leu Ala Val Asp Trp Ile Ala Gly Asn Ile Tyr
345                 1350                1355                1360
Trp Val Glu Ser Asn Leu Asp Gln Ile Glu Val Ala Lys Leu Asp Gly
                1365                1370                1375
```

FIG.6B-4

Thr Leu Arg Thr Thr Leu Leu Ala Gly Asp Ile Glu His Pro Arg Ala
1380 1385 1390
Ile Ala Leu Asp Pro Arg Asp Gly Ile Leu Phe Trp Thr Asp Trp Asp
1395 1400 1405
Ala Ser Leu Pro Arg Ile Glu Ala Ala Ser Met Ser Gly Ala Gly Arg
1410 1415 1420
Arg Thr Ile His Arg Glu Thr Gly Ser Gly Gly Cys Ala Asn Gly Leu
425 1430 1435 1440
Thr Val Asp Tyr Leu Glu Lys Arg Ile Leu Trp Ile Asp Ala Arg Ser
1445 1450 1455
Asp Ala Ile Tyr Ser Ala Arg Tyr Asp Gly Ser Gly His Met Glu Val
1460 1465 1470
Leu Arg Gly His Glu Phe Leu Ser His Pro Phe Ala Val Thr Leu Tyr
1475 1480 1485
Gly Gly Glu Val Tyr Trp Thr Asp Trp Arg Thr Asn Thr Leu Ala Lys
1490 1495 1500
Ala Asn Lys Trp Thr Gly His Asn Val Thr Val Val Gln Arg Thr Asn
505 1510 1515 1520
Thr Gln Pro Phe Asp Leu Gln Val Tyr His Pro Ser Arg Gln Pro Met
1525 1530 1535
Ala Pro Asn Pro Cys Glu Ala Asn Gly Gly Arg Gly Pro Cys Ser His
1540 1545 1550
Leu Cys Leu Ile Asn Tyr Asn Arg Thr Val Ser Trp Ala Cys Pro His
1555 1560 1565
Leu Met Lys Leu His Lys Asp Asn Thr Thr Cys Tyr Glu Phe Lys Lys
1570 1575 1580
Phe Leu Leu Tyr Ala Arg Gln Met Glu Ile Arg Gly Val Asp Leu Asp
585 1590 1595 1600
Ala Pro Tyr Tyr Asn Tyr Ile Ile Ser Phe Thr Val Pro Asp Ile Asp
1605 1610 1615
Asn Val Thr Val Leu Asp Tyr Asp Ala Arg Glu Gln Arg Val Tyr Trp
1620 1625 1630
Ser Asp Val Arg Thr Gln Ala Ile Lys Arg Ala Phe Ile Asn Gly Thr
1635 1640 1645
Gly Val Glu Thr Val Val Ser Ala Asp Leu Pro Asn Ala His Gly Leu
1650 1655 1660
Ala Val Asp Trp Val Ser Arg Asn Leu Phe Trp Thr Ser Tyr Asp Thr
665 1670 1675 1680
Asn Lys Lys Gln Ile Asn Val Ala Arg Leu Asp Gly Ser Phe Lys Asn
1685 1690 1695
Ala Val Val Gln Gly Leu Glu Gln Pro His Gly Leu Val Val His Pro
1700 1705 1710

FIG.6B-5

```
Leu Arg Gly Lys Leu Tyr Trp Thr Asp Gly Asp Asn Ile Ser Met Ala
      1715                1720                1725
Asn Met Asp Gly Ser Asn His Thr Leu Leu Phe Ser Gly Gln Lys Gly
   1730                1735                1740
Pro Val Gly Leu Ala Ile Asp Phe Pro Glu Ser Lys Leu Tyr Trp Ile
745                1750                1755                1760
Ser Ser Gly Asn His Thr Ile Asn Arg Cys Asn Leu Asp Gly Ser Glu
               1765                1770                1775
Leu Glu Val Ile Asp Thr Met Arg Ser Gln Leu Gly Lys Ala Thr Ala
            1780                1785                1790
Leu Ala Ile Met Gly Asp Lys Leu Trp Trp Ala Asp Gln Val Ser Glu
      1795                1800                1805
Lys Met Gly Thr Cys Asn Lys Ala Asp Gly Ser Gly Ser Val Val Leu
   1810                1815                1820
Arg Asn Ser Thr Thr Leu Val Met His Met Lys Val Tyr Asp Glu Ser
825                1830                1835                1840
Ile Gln Leu Glu His Glu Gly Thr Asn Pro Cys Ser Val Asn Asn Gly
               1845                1850                1855
Asp Cys Ser Gln Leu Cys Leu Pro Thr Ser Glu Thr Thr Arg Ser Cys
            1860                1865                1870
Met Cys Thr Ala Gly Tyr Ser Leu Arg Ser Gly Gln Gln Ala Cys Glu
      1875                1880                1885
Gly Val Gly Ser Phe Leu Leu Tyr Ser Val His Glu Gly Ile Arg Gly
   1890                1895                1900
Ile Pro Leu Asp Pro Asn Asp Lys Ser Asp Ala Leu Val Pro Val Ser
905                1910                1915                1920
Gly Thr Ser Leu Ala Val Gly Ile Asp Phe His Ala Glu Asn Asp Thr
               1925                1930                1935
Ile Tyr Trp Val Asp Met Gly Leu Ser Thr Ile Ser Arg Ala Lys Arg
            1940                1945                1950
Asp Gln Thr Trp Arg Glu Asp Val Val Thr Asn Gly Ile Gly Arg Val
      1955                1960                1965
Glu Gly Ile Ala Val Asp Trp Ile Ala Gly Asn Ile Tyr Trp Thr Asp
   1970                1975                1980
Gln Gly Phe Asp Val Ile Glu Val Ala Arg Leu Asn Gly Ser Phe Arg
985                1990                1995                2000
Tyr Val Val Ile Ser Gln Gly Leu Asp Lys Pro Arg Ala Ile Thr Val
               2005                2010                2015
His Pro Glu Lys Gly Tyr Leu Phe Trp Thr Glu Trp Gly His Tyr Pro
            2020                2025                2030
Arg Ile Glu Arg Ser Arg Leu Asp Gly Thr Glu Arg Val Val Leu Val
      2035                2040                2045
```

FIG. 6B-6

Asn Val Ser Ile Ser Trp Pro Asn Gly Ile Ser Val Asp Tyr Gln Gly
2050 2055 2060
Gly Lys Leu Tyr Trp Cys Asp Ala Arg Met Asp Lys Ile Glu Arg Ile
065 2070 2075 2080
Asp Leu Glu Thr Gly Glu Asn Arg Glu Val Val Leu Ser Ser Asn Asn
2085 2090 2095
Met Asp Met Phe Ser Val Ser Val Phe Glu Asp Phe Ile Tyr Trp Ser
2100 2105 2110
Asp Arg Thr His Ala Asn Gly Ser Ile Lys Arg Gly Cys Lys Asp Asn
2115 2120 2125
Ala Thr Asp Ser Val Pro Leu Arg Thr Gly Ile Gly Val Gln Leu Lys
2130 2135 2140
Asp Ile Lys Val Phe Asn Arg Asp Arg Gln Lys Gly Thr Asn Val Cys
145 2150 2155 2160
Ala Val Ala Asn Gly Gly Cys Gln Gln Leu Cys Leu Tyr Arg Gly Gly
2165 2170 2175
Gly Gln Arg Ala Cys Ala Cys Ala His Gly Met Leu Ala Glu Asp Gly
2180 2185 2190
Ala Ser Cys Arg Glu Tyr Ala Gly Tyr Leu Leu Tyr Ser Glu Arg Thr
2195 2200 2205
Ile Leu Lys Ser Ile His Leu Ser Asp Glu Arg Asn Leu Asn Ala Pro
2210 2215 2220
Val Gln Pro Phe Glu Asp Pro Glu His Met Lys Asn Val Ile Ala Leu
225 2230 2235 2240
Ala Phe Asp Tyr Arg Ala Gly Thr Ser Pro Gly Thr Pro Asn Arg Ile
2245 2250 2255
Phe Phe Ser Asp Ile His Phe Gly Asn Ile Gln Gln Ile Asn Asp Asp
2260 2265 2270
Gly Ser Gly Arg Thr Thr Ile Val Glu Asn Val Gly Ser Val Glu Gly
2275 2280 2285
Leu Ala Tyr His Arg Gly Trp Asp Thr Leu Tyr Trp Thr Ser Tyr Thr
2290 2295 2300
Thr Ser Thr Ile Thr Arg His Thr Val Asp Gln Thr Arg Pro Gly Ala
305 2310 2315 2320
Phe Glu Arg Glu Thr Val Ile Thr Met Ser Gly Asp Asp His Pro Arg
2325 2330 2335
Ala Phe Val Leu Asp Glu Cys Gln Asn Leu Met Phe Trp Thr Asn Trp
2340 2345 2350
Asn Glu Leu His Pro Ser Ile Met Arg Ala Ala Leu Ser Gly Ala Asn
2355 2360 2365
Val Leu Thr Leu Ile Glu Lys Asp Ile Arg Thr Pro Asn Gly Leu Ala
2370 2375 2380

FIG.6B-7

Ile Asp His Arg Ala Glu Lys Leu Tyr Phe Ser Asp Ala Thr Leu Asp
385 2390 2395 2400
Lys Ile Glu Arg Cys Glu Tyr Asp Gly Ser His Arg Tyr Val Ile Leu
2405 2410 2415
Lys Ser Glu Pro Val His Pro Phe Gly Leu Ala Val Tyr Gly Glu His
2420 2425 2430
Ile Phe Trp Thr Asp Trp Val Arg Arg Ala Val Gln Arg Ala Asn Lys
2435 2440 2445
Tyr Val Gly Ser Asp Met Lys Leu Leu Arg Val Asp Ile Pro Gln Gln
2450 2455 2460
Pro Met Gly Ile Ile Ala Val Ala Asn Asp Thr Asn Ser Cys Glu Leu
465 2470 2475 2480
Ser Pro Cys Arg Ile Asn Asn Gly Gly Cys Gln Asp Leu Cys Leu Leu
2485 2490 2495
Thr His Gln Gly His Val Asn Cys Ser Cys Arg Gly Gly Arg Ile Leu
2500 2505 2510
Gln Glu Asp Phe Thr Cys Arg Ala Val Asn Ser Ser Cys Arg Ala Gln
2515 2520 2525
Asp Glu Phe Glu Cys Ala Asn Gly Glu Cys Ile Ser Phe Ser Leu Thr
2530 2535 2540
Cys Asp Gly Val Ser His Cys Lys Asp Lys Ser Asp Glu Lys Pro Ser
545 2550 2555 2560
Tyr Cys Asn Ser Arg Arg Cys Lys Lys Thr Phe Arg Gln Cys Asn Asn
2565 2570 2575
Gly Arg Cys Val Ser Asn Met Leu Trp Cys Asn Gly Val Asp Tyr Cys
2580 2585 2590
Gly Asp Gly Ser Asp Glu Ile Pro Cys Asn Lys Thr Ala Cys Gly Val
2595 2600 2605
Gly Glu Phe Arg Cys Arg Asp Gly Ser Cys Ile Gly Asn Ser Ser Arg
2610 2615 2620
Cys Asn Gln Phe Val Asp Cys Glu Asp Ala Ser Asp Glu Met Asn Cys
625 2630 2635 2640
Ser Ala Thr Asp Cys Ser Ser Tyr Phe Arg Leu Gly Val Lys Gly Val
2645 2650 2655
Leu Phe Gln Pro Cys Glu Arg Thr Ser Leu Cys Tyr Ala Pro Ser Trp
2660 2665 2670
Val Cys Asp Gly Ala Asn Asp Cys Gly Asp Tyr Ser Asp Glu Arg Asp
2675 2680 2685
Cys Pro Gly Val Lys Arg Pro Arg Cys Pro Leu Asn Tyr Phe Ala Cys
2690 2695 2700
Pro Ser Gly Arg Cys Ile Pro Met Ser Trp Thr Cys Asp Lys Glu Asp
705 2710 2715 2720

FIG.6B-8

Asp Cys Glu Asn Gly Glu Asp Glu Thr His Cys Asn Lys Phe Cys Ser
2725 2730 2735
Glu Ala Gln Phe Glu Cys Gln Asn His Arg Cys Ile Ser Lys Gln Trp
2740 2745 2750
Leu Cys Asp Gly Ser Asp Asp Cys Gly Asp Gly Ser Asp Glu Ala Ala
2755 2760 2765
His Cys Glu Gly Lys Thr Cys Gly Pro Ser Ser Phe Ser Cys Pro Gly
2770 2775 2780
Thr His Val Cys Val Pro Glu Arg Trp Leu Cys Asp Gly Asp Lys Asp
785 2790 2795 2800
Cys Thr Asp Gly Ala Asp Glu Ser Val Thr Ala Gly Cys Leu Tyr Asn
2805 2810 2815
Ser Thr Cys Asp Asp Arg Glu Phe Met Cys Gln Asn Arg Leu Cys Ile
2820 2825 2830
Pro Lys His Phe Val Cys Asp His Asp Arg Asp Cys Ala Asp Gly Ser
2835 2840 2845
Asp Glu Ser Pro Glu Cys Glu Tyr Pro Thr Cys Gly Pro Asn Glu Phe
2850 2855 2860
Arg Cys Ala Asn Gly Arg Cys Leu Ser Ser Arg Gln Trp Glu Cys Asp
865 2870 2875 2880
Gly Glu Asn Asp Cys His Asp His Ser Asp Glu Ala Pro Lys Asn Pro
2885 2890 2895
His Cys Thr Ser Pro Glu His Lys Cys Asn Ala Ser Ser Gln Phe Leu
2900 2905 2910
Cys Ser Ser Gly Arg Cys Val Ala Glu Ala Leu Leu Cys Asn Gly Gln
2915 2920 2925
Asp Asp Cys Gly Asp Gly Ser Asp Glu Arg Gly Cys His Val Asn Glu
2930 2935 2940
Cys Leu Ser Arg Lys Leu Ser Gly Cys Ser Gln Asp Cys Glu Asp Leu
945 2950 2955 2960
Lys Ile Gly Phe Lys Cys Arg Cys Arg Pro Gly Phe Arg Leu Lys Asp
2965 2970 2975
Asp Gly Arg Thr Cys Ala Asp Leu Asp Glu Cys Ser Thr Thr Phe Pro
2980 2985 2990
Cys Ser Gln Leu Cys Ile Asn Thr His Gly Ser Tyr Lys Cys Leu Cys
2995 3000 3005
Val Glu Gly Tyr Ala Pro Arg Gly Gly Asp Pro His Ser Cys Lys Ala
3010 3015 3020
Val Thr Asp Glu Glu Pro Phe Leu Ile Phe Ala Asn Arg Tyr Tyr Leu
025 3030 3035 3040
Arg Lys Leu Asn Leu Asp Gly Ser Asn Tyr Thr Leu Leu Lys Gln Gly
3045 3050 3055

FIG.6B-9

Leu Asn Asn Ala Val Ala Leu Ala Phe Asp Tyr Arg Glu Gln Met Ile
3060 3065 3070
Tyr Trp Thr Gly Val Thr Thr Gln Gly Ser Met Ile Arg Arg Met His
3075 3080 3085
Leu Asn Gly Ser Asn Val Gln Val Leu His Arg Thr Gly Leu Ser Asn
3090 3095 3100
Pro Asp Gly Leu Ala Val Asp Trp Val Gly Gly Asn Leu Tyr Trp Cys
105 3110 3115 3120
Asp Lys Gly Arg Asp Thr Ile Glu Val Ser Lys Leu Asn Gly Ala Tyr
3125 3130 3135
Arg Thr Val Leu Val Ser Ser Gly Leu Arg Glu Pro Arg Ala Leu Val
3140 3145 3150
Val Asp Val Gln Asn Gly Tyr Leu Tyr Trp Thr Asp Trp Gly Asp His
3155 3160 3165
Ser Leu Ile Gly Arg Ile Gly Met Asp Gly Ser Gly Arg Ser Ile Ile
3170 3175 3180
Val Asp Thr Lys Ile Thr Trp Pro Asn Gly Leu Thr Val Asp Tyr Val
185 3190 3195 3200
Thr Glu Arg Ile Tyr Trp Ala Asp Ala Arg Glu Asp Tyr Ile Glu Phe
3205 3210 3215
Ala Ser Leu Asp Gly Ser Asn Arg His Val Val Leu Ser Gln Asp Ile
3220 3225 3230
Pro His Ile Phe Ala Leu Thr Leu Phe Glu Asp Tyr Val Tyr Trp Thr
3235 3240 3245
Asp Trp Glu Thr Lys Ser Ile Asn Arg Ala His Lys Thr Thr Gly Ala
3250 3255 3260
Asn Lys Thr Leu Leu Ile Ser Thr Leu His Arg Pro Met Asp Leu His
265 3270 3275 3280
Val Phe His Ala Leu Arg Gln Pro Asp Val Pro Asn His Pro Cys Lys
3285 3290 3295
Val Asn Asn Gly Gly Cys Ser Asn Leu Cys Leu Leu Ser Pro Gly Gly
3300 3305 3310
Gly His Lys Cys Ala Cys Pro Thr Asn Phe Tyr Leu Gly Gly Asp Gly
3315 3320 3325
Arg Thr Cys Val Ser Asn Cys Thr Ala Ser Gln Phe Val Cys Lys Asn
3330 3335 3340
Asp Lys Cys Ile Pro Phe Trp Trp Lys Cys Asp Thr Glu Asp Asp Cys
345 3350 3355 3360
Gly Asp His Ser Asp Glu Pro Pro Asp Cys Pro Glu Phe Lys Cys Arg
3365 3370 3375
Pro Gly Gln Phe Gln Cys Ser Thr Gly Ile Cys Thr Asn Pro Ala Phe
3380 3385 3390

FIG.6B-10

Ile Cys Asp Gly Asp Asn Asp Cys Gln Asp Asn Ser Asp Glu Ala Asn
3395 3400 3405
Cys Asp Ile His Val Cys Leu Pro Ser Gln Phe Lys Cys Thr Asn Thr
3410 3415 3420
Asn Arg Cys Ile Pro Gly Ile Phe Arg Cys Asn Gly Gln Asp Asn Cys
425 3430 3435 3440
Gly Asp Gly Glu Asp Glu Arg Asp Cys Pro Glu Val Thr Cys Ala Pro
3445 3450 3455
Asn Gln Phe Gln Cys Ser Ile Thr Lys Arg Cys Ile Pro Arg Val Trp
3460 3465 3470
Val Cys Asp Arg Asp Asn His Cys Val Asp Gly Ser Asp Glu Pro Ala
3475 3480 3485
Asn Cys Thr Gln Met Thr Cys Gly Val Asp Glu Phe Arg Cys Lys Asp
3490 3495 3500
Ser Gly Arg Cys Ile Pro Ala Arg Trp Lys Cys Asp Gly Glu Asp Asp
505 3510 3515 3520
Cys Gly Asp Gly Ser Asp Glu Pro Lys Glu Glu Cys Asp Glu Arg Thr
3525 3530 3535
Cys Glu Pro Tyr Gln Phe Arg Cys Lys Asn Asn Arg Cys Val Pro Gly
3540 3545 3550
Arg Trp Gln Cys Asp Tyr Asp Asn Asp Cys Gly Asp Asn Ser Asp Glu
3555 3560 3565
Glu Ser Cys Thr Pro Arg Pro Cys Ser Glu Ser Glu Phe Phe Cys Ala
3570 3575 3580
Asn Gly Arg Cys Ile Ala Gly Arg Trp Lys Cys Asp Gly Asp His Asp
585 3590 3595 3600
Cys Ala Asp Gly Ser Asp Glu Lys Asp Cys Thr Pro Arg Cys Asp Met
3605 3610 3615
Asp Gln Phe Gln Cys Lys Ser Gly His Cys Ile Pro Leu Arg Trp Pro
3620 3625 3630
Cys Asp Ala Asp Ala Asp Cys Met Asp Gly Ser Asp Glu Glu Ala Cys
3635 3640 3645
Gly Thr Gly Val Arg Thr Cys Pro Leu Asp Glu Phe Gln Cys Asn Asn
3650 3655 3660
Thr Leu Cys Lys Pro Leu Ala Trp Lys Cys Asp Gly Glu Asp Asp Cys
665 3670 3675 3680
Gly Asp Asn Ser Asp Glu Asn Pro Glu Glu Cys Ala Arg Phe Ile Cys
3685 3690 3695
Pro Pro Asn Arg Pro Phe Arg Cys Lys Asn Asp Arg Val Cys Leu Trp
3700 3705 3710
Ile Gly Arg Gln Cys Asp Gly Val Asp Asn Cys Gly Asp Gly Thr Asp
3715 3720 3725

FIG.6B-11

Glu Glu Asp Cys Glu Pro Pro Thr Ala Gln Asn Pro His Cys Lys Asp
3730 3735 3740
Lys Lys Glu Phe Leu Cys Arg Asn Gln Arg Cys Leu Ser Ser Ser Leu
745 3750 3755 3760
Arg Cys Asn Met Phe Asp Asp Cys Gly Asp Gly Ser Asp Glu Glu Asp
3765 3770 3775
Cys Ser Ile Asp Pro Lys Leu Thr Ser Cys Ala Thr Asn Ala Ser Met
3780 3785 3790
Cys Gly Asp Glu Ala Arg Cys Val Arg Thr Glu Lys Ala Ala Tyr Cys
3795 3800 3805
Ala Cys Arg Ser Gly Phe His Thr Val Pro Gly Gln Pro Gly Cys Gln
3810 3815 3820
Asp Ile Asn Glu Cys Leu Arg Phe Gly Thr Cys Ser Gln Leu Trp Asn
825 3830 3835 3840
Lys Pro Lys Gly Gly His Leu Cys Ser Cys Ala Arg Asn Phe Met Lys
3845 3850 3855
Thr His Asn Thr Cys Lys Ala Glu Gly Ser Glu Tyr Gln Val Leu Tyr
3860 3865 3870
Ile Ala Asp Asp Asn Glu Ile Arg Ser Leu Phe Pro Gly His Pro His
3875 3880 3885
Ser Ala Tyr Glu Gln Thr Phe Gln Gly Asp Glu Ser Val Arg Ile Asp
3890 3895 3900
Ala Met Asp Val His Val Lys Ala Gly Arg Val Tyr Trp Thr Asn Trp
905 3910 3915 3920
His Thr Gly Thr Ile Ser Tyr Arg Ser Leu Pro Pro Ala Ala Pro Pro
3925 3930 3935
Thr Thr Ser Asn Arg His Arg Arg Gln Ile Asp Arg Gly Val Thr His
3940 3945 3950
Leu Asn Ile Ser Gly Leu Lys Met Pro Arg Gly Ile Ala Ile Asp Trp
3955 3960 3965
Val Ala Gly Asn Val Tyr Trp Thr Asp Ser Gly Arg Asp Val Ile Glu
3970 3975 3980
Val Ala Gln Met Lys Gly Glu Asn Arg Lys Thr Leu Ile Ser Gly Met
985 3990 3995 4000
Ile Asp Glu Pro His Ala Ile Val Val Asp Pro Leu Arg Gly Thr Met
4005 4010 4015
Tyr Trp Ser Asp Trp Gly Asn His Pro Lys Ile Glu Thr Ala Ala Met
4020 4025 4030
Asp Gly Thr Leu Arg Glu Thr Leu Val Gln Asp Asn Ile Gln Trp Pro
4035 4040 4045
Thr Gly Leu Ala Val Asp Tyr His Asn Glu Arg Leu Tyr Trp Ala Asp
4050 4055 4060

FIG.6B-12

Ala Lys Leu Ser Val Ile Gly Ser Ile Arg Leu Asn Gly Thr Asp Pro
065 4070 4075 4080
Ile Val Ala Ala Asp Ser Lys Arg Gly Leu Ser His Pro Phe Ser Ile
4085 4090 4095
Asp Val Phe Glu Asp Tyr Ile Tyr Gly Val Thr Tyr Ile Asn Asn Arg
4100 4105 4110
Val Phe Lys Ile His Lys Phe Gly His Ser Pro Leu Tyr Asn Leu Thr
4115 4120 4125
Gly Gly Leu Ser His Ala Ser Asp Val Val Leu Tyr His Gln His Lys
4130 4135 4140
Gln Pro Glu Val Thr Asn Pro Cys Asp Arg Lys Lys Cys Glu Trp Leu
145 4150 4155 4160
Cys Leu Leu Ser Pro Ser Gly Pro Val Cys Thr Cys Pro Asn Gly Lys
4165 4170 4175
Arg Leu Asp Asn Gly Thr Cys Val Pro Val Pro Ser Pro Thr Pro Pro
4180 4185 4190
Pro Asp Ala Pro Arg Pro Gly Thr Cys Thr Leu Gln Cys Phe Asn Gly
4195 4200 4205
Gly Ser Cys Phe Leu Asn Ala Arg Arg Gln Pro Lys Cys Arg Cys Gln
4210 4215 4220
Pro Arg Tyr Thr Gly Asp Lys Cys Glu Leu Asp Gln Cys Trp Glu Tyr
225 4230 4235 4240
Cys His Asn Gly Gly Thr Cys Ala Ala Ser Pro Ser Gly Met Pro Thr
4245 4250 4255
Cys Arg Cys Pro Thr Gly Phe Thr Gly Pro Lys Cys Thr Ala Gln Val
4260 4265 4270
Cys Ala Gly Tyr Cys Ser Asn Asn Ser Thr Cys Thr Val Asn Gln Gly
4275 4280 4285
Asn Gln Pro Gln Cys Arg Cys Leu Pro Gly Phe Leu Gly Asp Arg Cys
4290 4295 4300
Gln Tyr Arg Gln Cys Ser Gly Phe Cys Glu Asn Phe Gly Thr Cys Gln
305 4310 4315 4320
Met Ala Ala Asp Gly Ser Arg Gln Cys Arg Cys Thr Val Tyr Phe Glu
4325 4330 4335
Gly Pro Arg Cys Glu Val Asn Lys Cys Ser Arg Cys Leu Gln Gly Ala
4340 4345 4350
Cys Val Val Asn Lys Gln Thr Gly Asp Val Thr Cys Asn Cys Thr Asp
4355 4360 4365
Gly Arg Val Ala Pro Ser Cys Leu Thr Cys Ile Asp His Cys Ser Asn
4370 4375 4380
Gly Gly Ser Cys Thr Met Asn Ser Lys Met Met Pro Glu Cys Gln Cys
385 4390 4395 4400

FIG.6B-13

Pro Pro His Met Thr Gly Pro Arg Cys Gln Glu Gln Val Val Ser Gln
4405 4410 4415
Gln Gln Pro Gly His Met Ala Ser Ile Leu Ile Pro Leu Leu Leu Leu
4420 4425 4430
Leu Leu Leu Leu Leu Val Ala Gly Val Val Phe Trp Tyr Lys Arg Arg
4435 4440 4445
Val Arg Gly Ala Lys Gly Phe Gln His Gln Arg Met Thr Asn Gly Ala
4450 4455 4460
Met Asn Val Glu Ile Gly Asn Pro Thr Tyr Lys Met Tyr Glu Gly Gly
465 4470 4475 4480
Glu Pro Asp Asp Val Gly Gly Leu Leu Asp Ala Asp Phe Ala Leu Asp
4485 4490 4495
Pro Asp Lys Pro Thr Asn Phe Thr Asn Pro Val Tyr Ala Thr Leu Tyr
4500 4505 4510
Met Gly Gly His Gly Ser Arg His Ser Leu Ala Ser Thr Asp Glu Lys
4515 4520 4525
Arg Glu Leu Leu Gly Arg Gly Pro Glu Asp Glu Ile Gly Asp Pro Leu
4530 4535 4540
Ala
545

FIG.6B-14

GCTACAATCC ATCTGGTCTC CTCCAGCTCC TTCTTTCTGC AAC ATG GGG AAG AAC 55
Met Gly Lys Asn
1

AAA CTC CTT CAT CCA AGT CTG GTT CTT CTC CTC TTG GTC CTC CTG CCC 103
Lys Leu Leu His Pro Ser Leu Val Leu Leu Leu Leu Val Leu Leu Pro
5 10 15 20

ACA GAC GCC TCA GTC TCT GGA AAA CCG CAG TAT ATG GTT CTG GTC CCC 151
Thr Asp Ala Ser Val Ser Gly Lys Pro Gln Tyr Met Val Leu Val Pro
25 30 35

TCC CTG CTC CAC ACT GAG ACC ACT GAG AAG GGC TGT GTC CTT CTG AGC 199
Ser Leu Leu His Thr Glu Thr Thr Glu Lys Gly Cys Val Leu Leu Ser
40 45 50

TAC CTG AAT GAG ACA GTG ACT GTA AGT GCT TCC TTG GAG TCT GTC AGG 247
Tyr Leu Asn Glu Thr Val Thr Val Ser Ala Ser Leu Glu Ser Val Arg
55 60 65

GGA AAC AGG AGC CTC TTC ACT GAC CTG GAG GCG GAG AAT GAC GTA CTC 295
Gly Asn Arg Ser Leu Phe Thr Asp Leu Glu Ala Glu Asn Asp Val Leu
70 75 80

CAC TGT GTC GCC TTC GCT GTC CCA AAG TCT TCA TCC AAT GAG GAG GTA 343
His Cys Val Ala Phe Ala Val Pro Lys Ser Ser Ser Asn Glu Glu Val
85 90 95 100

ATG TTC CTC ACT GTC CAA GTG AAA GGA CCA ACC CAA GAA TTT AAG AAG 391
Met Phe Leu Thr Val Gln Val Lys Gly Pro Thr Gln Glu Phe Lys Lys
105 110 115

CGG ACC ACA GTG ATG GTT AAG AAC GAG GAC AGT CTG GTC TTT GTC CAG 439
Arg Thr Thr Val Met Val Lys Asn Glu Asp Ser Leu Val Phe Val Gln
120 125 130

ACA GAC AAA TCA ATC TAC AAA CCA GGG CAG ACA GTG AAA TTT CGT GTT 487
Thr Asp Lys Ser Ile Tyr Lys Pro Gly Gln Thr Val Lys Phe Arg Val
135 140 145

GTC TCC ATG GAT GAA AAC TTT CAC CCC CTG AAT GAG TTG ATT CCA CTA 535
Val Ser Met Asp Glu Asn Phe His Pro Leu Asn Glu Leu Ile Pro Leu
150 155 160

FIG.7A-1

GTA TAC ATT CAG GAT CCC AAA GGA AAT CGC ATC GCA CAA TGG CAG AGT 583
Val Tyr Ile Gln Asp Pro Lys Gly Asn Arg Ile Ala Gln Trp Gln Ser
165 170 175 180

TTC CAG TTA GAG GGT GGC CTC AAG CAA TTT TCT TTT CCC CTC TCA TCA 631
Phe Gln Leu Glu Gly Gly Leu Lys Gln Phe Ser Phe Pro Leu Ser Ser
185 190 195

GAG CCC TTC CAG GGC TCC TAC AAG GTG GTG GTA CAG AAG AAA TCA GGT 679
Glu Pro Phe Gln Gly Ser Tyr Lys Val Val Val Gln Lys Lys Ser Gly
200 205 210

GGA AGG ACA GAG CAC CCT TTC ACC GTG GAG GAA TTT GTT CTT CCC AAG 727
Gly Arg Thr Glu His Pro Phe Thr Val Glu Glu Phe Val Leu Pro Lys
215 220 225

TTT GAA GTA CAA GTA ACA GTG CCA AAG ATA ATC ACC ATC TTG GAA GAA 775
Phe Glu Val Gln Val Thr Val Pro Lys Ile Ile Thr Ile Leu Glu Glu
230 235 240

GAG ATG AAT GTA TCA GTG TGT GGC CTA TAC ACA TAT GGG AAG CCT GTC 823
Glu Met Asn Val Ser Val Cys Gly Leu Tyr Thr Tyr Gly Lys Pro Val
245 250 255 260

CCT GGA CAT GTG ACT GTG AGC ATT TGC AGA AAG TAT AGT GAC GCT TCC 871
Pro Gly His Val Thr Val Ser Ile Cys Arg Lys Tyr Ser Asp Ala Ser
265 270 275

GAC TGC CAC GGT GAA GAT TCA CAG GCT TTC TGT GAG AAA TTC AGT GGA 919
Asp Cys His Gly Glu Asp Ser Gln Ala Phe Cys Glu Lys Phe Ser Gly
280 285 290

CAG CTA AAC AGC CAT GGC TGC TTC TAT CAG CAA GTA AAA ACC AAG GTC 967
Gln Leu Asn Ser His Gly Cys Phe Tyr Gln Gln Val Lys Thr Lys Val
295 300 305

TTC CAG CTG AAG AGG AAG GAG TAT GAA ATG AAA CTT CAC ACT GAG GCC 1015
Phe Gln Leu Lys Arg Lys Glu Tyr Glu Met Lys Leu His Thr Glu Ala
310 315 320

CAG ATC CAA GAA GAA GGA ACA GTG GTG GAA TTG ACT GGA AGG CAG TCC 1063
Gln Ile Gln Glu Glu Gly Thr Val Val Glu Leu Thr Gly Arg Gln Ser
325 330 335 340

FIG.7A-2

AGT GAA ATC ACA AGA ACC ATA ACC AAA CTC TCA TTT GTG AAA GTG GAC 1111
Ser Glu Ile Thr Arg Thr Ile Thr Lys Leu Ser Phe Val Lys Val Asp
345 350 355

TCA CAC TTT CGA CAG GGA ATT CCC TTC TTT GGG CAG GTG CGC CTA GTA 1159
Ser His Phe Arg Gln Gly Ile Pro Phe Phe Gly Gln Val Arg Leu Val
360 365 370

GAT GGG AAA GGC GTC CCT ATA CCA AAT AAA GTC ATA TTC ATC AGA GGA 1207
Asp Gly Lys Gly Val Pro Ile Pro Asn Lys Val Ile Phe Ile Arg Gly
375 380 385

AAT GAA GCA AAC TAT TAC TCC AAT GCT ACC ACG GAT GAG CAT GGC CTT 1255
Asn Glu Ala Asn Tyr Tyr Ser Asn Ala Thr Thr Asp Glu His Gly Leu
390 395 400

GTA CAG TTC TCT ATC AAC ACC ACC AAC GTT ATG GGT ACC TCT CTT ACT 1303
Val Gln Phe Ser Ile Asn Thr Thr Asn Val Met Gly Thr Ser Leu Thr
405 410 415 420

GTT AGG GTC AAT TAC AAG GAT CGT AGT CCC TGT TAC GGC TAC CAG TGG 1351
Val Arg Val Asn Tyr Lys Asp Arg Ser Pro Cys Tyr Gly Tyr Gln Trp
425 430 435

GTG TCA GAA GAA CAC GAA GAG GCA CAT CAC ACT GCT TAT CTT GTG TTC 1399
Val Ser Glu Glu His Glu Glu Ala His His Thr Ala Tyr Leu Val Phe
440 445 450

TCC CCA AGC AAG AGC TTT GTC CAC CTT GAG CCC ATG TCT CAT GAA CTA 1447
Ser Pro Ser Lys Ser Phe Val His Leu Glu Pro Met Ser His Glu Leu
455 460 465

CCC TGT GGC CAT ACT CAG ACA GTC CAG GCA CAT TAT ATT CTG AAT GGA 1495
Pro Cys Gly His Thr Gln Thr Val Gln Ala His Tyr Ile Leu Asn Gly
470 475 480

GGC ACC CTG CTG GGG CTG AAG AAG CTC TCC TTT TAT TAT CTG ATA ATG 1543
Gly Thr Leu Leu Gly Leu Lys Lys Leu Ser Phe Tyr Tyr Leu Ile Met
485 490 495 500

GCA AAG GGA GGC ATT GTC CGA ACT GGG ACT CAT GGA CTG CTT GTG AAG 1591
Ala Lys Gly Gly Ile Val Arg Thr Gly Thr His Gly Leu Leu Val Lys
505 510 515

FIG.7A-3

```
CAG GAA GAC ATG AAG GGC CAT TTT TCC ATC TCA ATC CCT GTG AAG TCA     1639
Gln Glu Asp Met Lys Gly His Phe Ser Ile Ser Ile Pro Val Lys Ser
            520                 525                 530

GAC ATT GCT CCT GTC GCT CGG TTG CTC ATC TAT GCT GTT TTA CCT ACC     1687
Asp Ile Ala Pro Val Ala Arg Leu Leu Ile Tyr Ala Val Leu Pro Thr
        535                 540                 545

GGG GAC GTG ATT GGG GAT TCT GCA AAA TAT GAT GTT GAA AAT TGT CTG     1735
Gly Asp Val Ile Gly Asp Ser Ala Lys Tyr Asp Val Glu Asn Cys Leu
    550                 555                 560

GCC AAC AAG GTG GAT TTG AGC TTC AGC CCA TCA CAA AGT CTC CCA GCC     1783
Ala Asn Lys Val Asp Leu Ser Phe Ser Pro Ser Gln Ser Leu Pro Ala
565                 570                 575                 580

TCA CAC GCC CAC CTG CGA GTC ACA GCG GCT CCT CAG TCC GTC TGC GCC     1831
Ser His Ala His Leu Arg Val Thr Ala Ala Pro Gln Ser Val Cys Ala
                585                 590                 595

CTC CGT GCT GTG GAC CAA AGC GTG CTG CTC ATG AAG CCT GAT GCT GAG     1879
Leu Arg Ala Val Asp Gln Ser Val Leu Leu Met Lys Pro Asp Ala Glu
            600                 605                 610

CTC TCG GCG TCC TCG GTT TAC AAC CTG CTA CCA GAA AAG GAC CTC ACT     1927
Leu Ser Ala Ser Ser Val Tyr Asn Leu Leu Pro Glu Lys Asp Leu Thr
        615                 620                 625

GGC TTC CCT GGG CCT TTG AAT GAC CAG GAC GAT GAA GAC TGC ATC AAT     1975
Gly Phe Pro Gly Pro Leu Asn Asp Gln Asp Asp Glu Asp Cys Ile Asn
    630                 635                 640

CGT CAT AAT GTC TAT ATT AAT GGA ATC ACA TAT ACT CCA GTA TCA AGT     2023
Arg His Asn Val Tyr Ile Asn Gly Ile Thr Tyr Thr Pro Val Ser Ser
645                 650                 655                 660

ACA AAT GAA AAG GAT ATG TAC AGC TTC CTA GAG GAC ATG GGC TTA AAG     2071
Thr Asn Glu Lys Asp Met Tyr Ser Phe Leu Glu Asp Met Gly Leu Lys
                665                 670                 675

GCA TTC ACC AAC TCA AAG ATT CGT AAA CCC AAA ATG TGT CCA CAG CTT     2119
Ala Phe Thr Asn Ser Lys Ile Arg Lys Pro Lys Met Cys Pro Gln Leu
            680                 685                 690
```

FIG.7A-4

```
CAA CAG TAT GAA ATG CAT GGA CCT GAA GGT CTA CGT GTA GGT TTT TAT    2167
Gln Gln Tyr Glu Met His Gly Pro Glu Gly Leu Arg Val Gly Phe Tyr
        695                 700                 705

GAG TCA GAT GTA ATG GGA AGA GGC CAT GCA CGC CTG GTG CAT GTT GAA    2215
Glu Ser Asp Val Met Gly Arg Gly His Ala Arg Leu Val His Val Glu
    710                 715                 720

GAG CCT CAC ACG GAG ACC GTA CGA AAG TAC TTC CCT GAG ACA TGG ATC    2263
Glu Pro His Thr Glu Thr Val Arg Lys Tyr Phe Pro Glu Thr Trp Ile
725                 730                 735                 740

TGG GAT TTG GTG GTG GTA AAC TCA GCA GGG GTG GCT GAG GTA GGA GTA    2311
Trp Asp Leu Val Val Val Asn Ser Ala Gly Val Ala Glu Val Gly Val
                745                 750                 755

ACA GTC CCT GAC ACC ATC ACC GAG TGG AAG GCA GGG GCC TTC TGC CTG    2359
Thr Val Pro Asp Thr Ile Thr Glu Trp Lys Ala Gly Ala Phe Cys Leu
            760                 765                 770

TCT GAA GAT GCT GGA CTT GGT ATC TCT TCC ACT GCC TCT CTC CGA GCC    2407
Ser Glu Asp Ala Gly Leu Gly Ile Ser Ser Thr Ala Ser Leu Arg Ala
        775                 780                 785

TTC CAG CCC TTC TTT GTG GAG CTT ACA ATG CCT TAC TCT GTG ATT CGT    2455
Phe Gln Pro Phe Phe Val Glu Leu Thr Met Pro Tyr Ser Val Ile Arg
    790                 795                 800

GGA GAG GCC TTC ACA CTC AAG GCC ACG GTC CTA AAC TAC CTT CCC AAA    2503
Gly Glu Ala Phe Thr Leu Lys Ala Thr Val Leu Asn Tyr Leu Pro Lys
805                 810                 815                 820

TGC ATC CGG GTC AGT GTG CAG CTG GAA GCC TCT CCC GCC TTC CTT GCT    2551
Cys Ile Arg Val Ser Val Gln Leu Glu Ala Ser Pro Ala Phe Leu Ala
                825                 830                 835

GTC CCA GTG GAG AAG GAA CAA GCG CCT CAC TGC ATC TGT GCA AAC GGG    2599
Val Pro Val Glu Lys Glu Gln Ala Pro His Cys Ile Cys Ala Asn Gly
            840                 845                 850

CGG CAA ACT GTG TCC TGG GCA GTA ACC CCA AAG TCA TTA GGA AAT GTG    2647
Arg Gln Thr Val Ser Trp Ala Val Thr Pro Lys Ser Leu Gly Asn Val
        855                 860                 865
```

FIG.7A-5

```
AAT TTC ACT GTG AGC GCA GAG GCA CTA GAG TCT CAA GAG CTG TGT GGG     2695
Asn Phe Thr Val Ser Ala Glu Ala Leu Glu Ser Gln Glu Leu Cys Gly
    870                 875                 880

ACT GAG GTG CCT TCA GTT CCT GAA CAC GGA AGG AAA GAC ACA GTC ATC     2743
Thr Glu Val Pro Ser Val Pro Glu His Gly Arg Lys Asp Thr Val Ile
885                 890                 895                 900

AAG CCT CTG TTG GTT GAA CCT GAA GGA CTA GAG AAG GAA ACA ACA TTC     2791
Lys Pro Leu Leu Val Glu Pro Glu Gly Leu Glu Lys Glu Thr Thr Phe
                905                 910                 915

AAC TCC CTA CTT TGT CCA TCA GGT GGT GAG GTT TCT GAA GAA TTA TCC     2839
Asn Ser Leu Leu Cys Pro Ser Gly Gly Glu Val Ser Glu Glu Leu Ser
            920                 925                 930

CTG AAA CTG CCA CCA AAT GTG GTA GAA GAA TCT GCC CGA GCT TCT GTC     2887
Leu Lys Leu Pro Pro Asn Val Val Glu Glu Ser Ala Arg Ala Ser Val
        935                 940                 945

TCA GTT TTG GGA GAC ATA TTA GGC TCT GCC ATG CAA AAC ACA CAA AAT     2935
Ser Val Leu Gly Asp Ile Leu Gly Ser Ala Met Gln Asn Thr Gln Asn
    950                 955                 960

CTT CTC CAG ATG CCC TAT GGC TGT GGA GAG CAG AAT ATG GTC CTC TTT     2983
Leu Leu Gln Met Pro Tyr Gly Cys Gly Glu Gln Asn Met Val Leu Phe
965                 970                 975                 980

GCT CCT AAC ATC TAT GTA CTG GAT TAT CTA AAT GAA ACA CAG CAG CTT     3031
Ala Pro Asn Ile Tyr Val Leu Asp Tyr Leu Asn Glu Thr Gln Gln Leu
                985                 990                 995

ACT CCA GAG GTC AAG TCC AAG GCC ATT GGC TAT CTC AAC ACT GGT TAC     3079
Thr Pro Glu Val Lys Ser Lys Ala Ile Gly Tyr Leu Asn Thr Gly Tyr
           1000                1005                1010

CAG AGA CAG TTG AAC TAC AAA CAC TAT GAT GGC TCC TAC AGC ACC TTT     3127
Gln Arg Gln Leu Asn Tyr Lys His Tyr Asp Gly Ser Tyr Ser Thr Phe
       1015                1020                1025

GGG GAG CGA TAT GGC AGG AAC CAG GGC AAC ACC TGG CTC ACA GCC TTT     3175
Gly Glu Arg Tyr Gly Arg Asn Gln Gly Asn Thr Trp Leu Thr Ala Phe
   1030                1035                1040
```

FIG.7A-6

GTT CTG AAG ACT TTT GCC CAA GCT CGA GCC TAC ATC TTC ATC GAT GAA 3223
Val Leu Lys Thr Phe Ala Gln Ala Arg Ala Tyr Ile Phe Ile Asp Glu
1045 1050 1055 1060

GCA CAC ATT ACC CAA GCC CTC ATA TGG CTC TCC CAG AGG CAG AAG GAC 3271
Ala His Ile Thr Gln Ala Leu Ile Trp Leu Ser Gln Arg Gln Lys Asp
1065 1070 1075

AAT GGC TGT TTC AGG AGC TCT GGG TCA CTG CTC AAC AAT GCC ATA AAG 3319
Asn Gly Cys Phe Arg Ser Ser Gly Ser Leu Leu Asn Asn Ala Ile Lys
1080 1085 1090

GGA GGA GTA GAA GAT GAA GTG ACC CTC TCC GCC TAT ATC ACC ATC GCC 3367
Gly Gly Val Glu Asp Glu Val Thr Leu Ser Ala Tyr Ile Thr Ile Ala
1095 1100 1105

CTT CTG GAG ATT CCT CTC ACA GTC ACT CAC CCT GTT GTC CGC AAT GCC 3415
Leu Leu Glu Ile Pro Leu Thr Val Thr His Pro Val Val Arg Asn Ala
1110 1115 1120

CTG TTT TGC CTG GAG TCA GCC TGG AAG ACA GCA CAA GAA GGG GAC CAT 3463
Leu Phe Cys Leu Glu Ser Ala Trp Lys Thr Ala Gln Glu Gly Asp His
1125 1130 1135 1140

GGC AGC CAT GTA TAT ACC AAA GCA CTG CTG GCC TAT GCT TTT GCC CTG 3511
Gly Ser His Val Tyr Thr Lys Ala Leu Leu Ala Tyr Ala Phe Ala Leu
1145 1150 1155

GCA GGT AAC CAG GAC AAG AGG AAG GAA GTA CTC AAG TCA CTT AAT GAG 3559
Ala Gly Asn Gln Asp Lys Arg Lys Glu Val Leu Lys Ser Leu Asn Glu
1160 1165 1170

GAA GCT GTG AAG AAA GAC AAC TCT GTC CAT TGG GAG CGC CCT CAG AAA 3607
Glu Ala Val Lys Lys Asp Asn Ser Val His Trp Glu Arg Pro Gln Lys
1175 1180 1185

CCC AAG GCA CCA GTG GGG CAT TTT TAC GAA CCC CAG GCT CCC TCT GCT 3655
Pro Lys Ala Pro Val Gly His Phe Tyr Glu Pro Gln Ala Pro Ser Ala
1190 1195 1200

GAG GTG GAG ATG ACA TCC TAT GTG CTC CTC GCT TAT CTC ACG GCC CAG 3703
Glu Val Glu Met Thr Ser Tyr Val Leu Leu Ala Tyr Leu Thr Ala Gln
1205 1210 1215 1220

FIG.7A-7

```
CCA GCC CCA ACC TCG GAG GAC CTG ACC TCT GCA ACC AAC ATC GTG AAG    3751
Pro Ala Pro Thr Ser Glu Asp Leu Thr Ser Ala Thr Asn Ile Val Lys
                1225                1230                1235

TGG ATC ACG AAG CAG CAG AAT GCC CAG GGC GGT TTC TCC TCC ACC CAG    3799
Trp Ile Thr Lys Gln Gln Asn Ala Gln Gly Gly Phe Ser Ser Thr Gln
            1240                1245                1250

GAC ACA GTG GTG GCT CTC CAT GCT CTG TCC AAA TAT GGA GCC GCC ACA    3847
Asp Thr Val Val Ala Leu His Ala Leu Ser Lys Tyr Gly Ala Ala Thr
        1255                1260                1265

TTT ACC AGG ACT GGG AAG GCT GCA CAG GTG ACT ATC CAG TCT TCA GGG    3895
Phe Thr Arg Thr Gly Lys Ala Ala Gln Val Thr Ile Gln Ser Ser Gly
    1270                1275                1280

ACA TTT TCC AGC AAA TTC CAA GTG GAC AAC AAC AAT CGC CTG TTA CTG    3943
Thr Phe Ser Ser Lys Phe Gln Val Asp Asn Asn Asn Arg Leu Leu Leu
1285                1290                1295                1300

CAG CAG GTC TCA TTG CCA GAG CTG CCT GGG GAA TAC AGC ATG AAA GTG    3991
Gln Gln Val Ser Leu Pro Glu Leu Pro Gly Glu Tyr Ser Met Lys Val
                1305                1310                1315

ACA GGA GAA GGA TGT GTC TAC CTC CAG ACC TCC TTG AAA TAC AAT ATT    4039
Thr Gly Glu Gly Cys Val Tyr Leu Gln Thr Ser Leu Lys Tyr Asn Ile
            1320                1325                1330

CTC CCA GAA AAG GAA GAG TTC CCC TTT GCT TTA GGA GTG CAG ACT CTG    4087
Leu Pro Glu Lys Glu Glu Phe Pro Phe Ala Leu Gly Val Gln Thr Leu
        1335                1340                1345

CCT CAA ACT TGT GAT GAA CCC AAA GCC CAC ACC AGC TTC CAA ATC TCC    4135
Pro Gln Thr Cys Asp Glu Pro Lys Ala His Thr Ser Phe Gln Ile Ser
    1350                1355                1360

CTA AGT GTC AGT TAC ACA GGG AGC CGC TCT GCC TCC AAC ATG GCG ATC    4183
Leu Ser Val Ser Tyr Thr Gly Ser Arg Ser Ala Ser Asn Met Ala Ile
1365                1370                1375                1380

GTT GAT GTG AAG ATG GTC TCT GGC TTC ATT CCC CTG AAG CCA ACA GTG    4231
Val Asp Val Lys Met Val Ser Gly Phe Ile Pro Leu Lys Pro Thr Val
                1385                1390                1395
```

FIG.7A-8

```
AAA ATG CTT GAA AGA TCT AAC CAT GTG AGC CGG ACA GAA GTC AGC AGC     4279
Lys Met Leu Glu Arg Ser Asn His Val Ser Arg Thr Glu Val Ser Ser
              1400                1405                1410

AAC CAT GTC TTG ATT TAC CTT GAT AAG GTG TCA AAT CAG ACA CTG AGC     4327
Asn His Val Leu Ile Tyr Leu Asp Lys Val Ser Asn Gln Thr Leu Ser
          1415                1420                1425

TTG TTC TTC ACG GTT CTG CAA GAT GTC CCA GTA AGA GAT CTC AAA CCA     4375
Leu Phe Phe Thr Val Leu Gln Asp Val Pro Val Arg Asp Leu Lys Pro
      1430                1435                1440

GCC ATA GTG AAA GTC TAT GAT TAC TAC GAG ACG GAT GAG TTT GCA ATC     4423
Ala Ile Val Lys Val Tyr Asp Tyr Tyr Glu Thr Asp Glu Phe Ala Ile
1445                1450                1455                1460

GCT GAG TAC AAT GCT CCT TGC AGC AAA GAT CTT GGA AAT GCT TGAAGACCA  4474
Ala Glu Tyr Asn Ala Pro Cys Ser Lys Asp Leu Gly Asn Ala
                  1465                1470                1

CAAGGCTGAA AAGTGCTTTG CTGGAGTCCT GTTCTCTGAG CTCCACAGAA GACACGTGTT  4534
TTTGTATCTT TAAAGACTTG ATGAATAAAC ACTTTTTCTG GTC                    4577
```

FIG.7A-9

```
Ser Val Ser Gly Lys Pro Gln Tyr Met Val Leu Val Pro Ser Leu Leu
1               5                   10                  15
His Thr Glu Thr Thr Glu Lys Gly Cys Val Leu Leu Ser Tyr Leu Asn
            20                  25                  30
Glu Thr Val Thr Val Ser Ala Ser Leu Glu Ser Val Arg Gly Asn Arg
        35                  40                  45
Ser Leu Phe Thr Asp Leu Glu Ala Glu Asn Asp Val Leu His Cys Val
    50                  55                  60
Ala Phe Ala Val Pro Lys Ser Ser Ser Asn Glu Glu Val Met Phe Leu
65                  70                  75                  80
Thr Val Gln Val Lys Gly Pro Thr Gln Glu Phe Lys Lys Arg Thr Thr
                85                  90                  95
Val Met Val Lys Asn Glu Asp Ser Leu Val Phe Val Gln Thr Asp Lys
            100                 105                 110
Ser Ile Tyr Lys Pro Gly Gln Thr Val Lys Phe Arg Val Val Ser Met
        115                 120                 125
Asp Glu Asn Phe His Pro Leu Asn Glu Leu Ile Pro Leu Val Tyr Ile
    130                 135                 140
Gln Asp Pro Lys Gly Asn Arg Ile Ala Gln Trp Gln Ser Phe Gln Leu
145                 150                 155                 160
Glu Gly Gly Leu Lys Gln Phe Ser Phe Pro Leu Ser Ser Glu Pro Phe
                165                 170                 175
Gln Gly Ser Tyr Lys Val Val Val Gln Lys Lys Ser Gly Gly Arg Thr
            180                 185                 190
Glu His Pro Phe Thr Val Glu Glu Phe Val Leu Pro Lys Phe Glu Val
        195                 200                 205
Gln Val Thr Val Pro Lys Ile Ile Thr Ile Leu Glu Glu Glu Met Asn
    210                 215                 220
Val Ser Val Cys Gly Leu Tyr Thr Tyr Gly Lys Pro Val Pro Gly His
225                 230                 235                 240
Val Thr Val Ser Ile Cys Arg Lys Tyr Ser Asp Ala Ser Asp Cys His
                245                 250                 255
Gly Glu Asp Ser Gln Ala Phe Cys Glu Lys Phe Ser Gly Gln Leu Asn
            260                 265                 270
Ser His Gly Cys Phe Tyr Gln Gln Val Lys Thr Lys Val Phe Gln Leu
        275                 280                 285
Lys Arg Lys Glu Tyr Glu Met Lys Leu His Thr Glu Ala Gln Ile Gln
    290                 295                 300
Glu Glu Gly Thr Val Val Glu Leu Thr Gly Arg Gln Ser Ser Glu Ile
305                 310                 315                 320
```

FIG.7B-1

Thr Arg Thr Ile Thr Lys Leu Ser Phe Val Lys Val Asp Ser His Phe
325 330 335
Arg Gln Gly Ile Pro Phe Phe Gly Gln Val Arg Leu Val Asp Gly Lys
340 345 350
Gly Val Pro Ile Pro Asn Lys Val Ile Phe Ile Arg Gly Asn Glu Ala
355 360 365
Asn Tyr Tyr Ser Asn Ala Thr Thr Asp Glu His Gly Leu Val Gln Phe
370 375 380
Ser Ile Asn Thr Thr Asn Val Met Gly Thr Ser Leu Thr Val Arg Val
385 390 395 400
Asn Tyr Lys Asp Arg Ser Pro Cys Tyr Gly Tyr Gln Trp Val Ser Glu
405 410 415
Glu His Glu Glu Ala His His Thr Ala Tyr Leu Val Phe Ser Pro Ser
420 425 430
Lys Ser Phe Val His Leu Glu Pro Met Ser His Glu Leu Pro Cys Gly
435 440 445
His Thr Gln Thr Val Gln Ala His Tyr Ile Leu Asn Gly Gly Thr Leu
450 455 460
Leu Gly Leu Lys Lys Leu Ser Phe Tyr Tyr Leu Ile Met Ala Lys Gly
465 470 475 480
Gly Ile Val Arg Thr Gly Thr His Gly Leu Leu Val Lys Gln Glu Asp
485 490 495
Met Lys Gly His Phe Ser Ile Ser Ile Pro Val Lys Ser Asp Ile Ala
500 505 510
Pro Val Ala Arg Leu Leu Ile Tyr Ala Val Leu Pro Thr Gly Asp Val
515 520 525
Ile Gly Asp Ser Ala Lys Tyr Asp Val Glu Asn Cys Leu Ala Asn Lys
530 535 540
Val Asp Leu Ser Phe Ser Pro Ser Gln Ser Leu Pro Ala Ser His Ala
545 550 555 560
His Leu Arg Val Thr Ala Ala Pro Gln Ser Val Cys Ala Leu Arg Ala
565 570 575
Val Asp Gln Ser Val Leu Leu Met Lys Pro Asp Ala Glu Leu Ser Ala
580 585 590
Ser Ser Val Tyr Asn Leu Leu Pro Glu Lys Asp Leu Thr Gly Phe Pro
595 600 605
Gly Pro Leu Asn Asp Gln Asp Asp Glu Asp Cys Ile Asn Arg His Asn
610 615 620
Val Tyr Ile Asn Gly Ile Thr Tyr Thr Pro Val Ser Ser Thr Asn Glu
625 630 635 640

FIG.7B-2

Lys Asp Met Tyr Ser Phe Leu Glu Asp Met Gly Leu Lys Ala Phe Thr
645 650 655
Asn Ser Lys Ile Arg Lys Pro Lys Met Cys Pro Gln Leu Gln Gln Tyr
660 665 670
Thr Glu Thr Val Arg Lys Tyr Phe Pro Glu Thr Trp Ile Trp Asp Leu
705 710 715 720
Val Val Val Asn Ser Ala Gly Val Ala Glu Val Gly Val Thr Val Pro
725 730 735
Asp Thr Ile Thr Glu Trp Lys Ala Gly Ala Phe Cys Leu Ser Glu Asp
740 745 750
Ala Gly Leu Gly Ile Ser Ser Thr Ala Ser Leu Arg Ala Phe Gln Pro
755 760 765
Phe Phe Val Glu Leu Thr Met Pro Tyr Ser Val Ile Arg Gly Glu Ala
770 775 780
Phe Thr Leu Lys Ala Thr Val Leu Asn Tyr Leu Pro Lys Cys Ile Arg
785 790 795 800
Val Ser Val Gln Leu Glu Ala Ser Pro Ala Phe Leu Ala Val Pro Val
805 810 815
Glu Lys Glu Gln Ala Pro His Cys Ile Cys Ala Asn Gly Arg Gln Thr
820 825 830
Val Ser Trp Ala Val Thr Pro Lys Ser Leu Gly Asn Val Asn Phe Thr
835 840 845
Val Ser Ala Glu Ala Leu Glu Ser Gln Glu Leu Cys Gly Thr Glu Val
850 855 860
Pro Ser Val Pro Glu His Gly Arg Lys Asp Thr Val Ile Lys Pro Leu
865 870 875 880
Leu Val Glu Pro Glu Gly Leu Glu Lys Glu Thr Thr Phe Asn Ser Leu
885 890 895
Leu Cys Pro Ser Gly Gly Glu Val Ser Glu Glu Leu Ser Leu Lys Leu
900 905 910
Pro Pro Asn Val Val Glu Glu Ser Ala Arg Ala Ser Val Ser Val Leu
915 920 925
Gly Asp Ile Leu Gly Ser Ala Met Gln Asn Thr Gln Asn Leu Leu Gln
930 935 940
Met Pro Tyr Gly Cys Gly Glu Gln Asn Met Val Leu Phe Ala Pro Asn
945 950 955 960
Ile Tyr Val Leu Asp Tyr Leu Asn Glu Thr Gln Gln Leu Thr Pro Glu
965 970 975
Val Lys Ser Lys Ala Ile Gly Tyr Leu Asn Thr Gly Tyr Gln Arg Gln
980 985 990

FIG.7B-3

Leu Asn Tyr Lys His Tyr Asp Gly Ser Tyr Ser Thr Phe Gly Glu Arg
995 1000 1005
Tyr Gly Arg Asn Gln Gly Asn Thr Trp Leu Thr Ala Phe Val Leu Lys
1010 1015 1020
Thr Phe Ala Gln Ala Arg Ala Tyr Ile Phe Ile Asp Glu Ala His Ile
025 1030 1035 1040
Thr Gln Ala Leu Ile Trp Leu Ser Gln Arg Gln Lys Asp Asn Gly Cys
1045 1050 1055
Phe Arg Ser Ser Gly Ser Leu Leu Asn Asn Ala Ile Lys Gly Gly Val
1060 1065 1070
Glu Asp Glu Val Thr Leu Ser Ala Tyr Ile Thr Ile Ala Leu Leu Glu
1075 1080 1085
Ile Pro Leu Thr Val Thr His Pro Val Val Arg Asn Ala Leu Phe Cys
1090 1095 1100
Leu Glu Ser Ala Trp Lys Thr Ala Gln Glu Gly Asp His Gly Ser His
105 1110 1115 1120
Val Tyr Thr Lys Ala Leu Leu Ala Tyr Ala Phe Ala Leu Ala Gly Asn
1125 1130 1135
Gln Asp Lys Arg Lys Glu Val Leu Lys Ser Leu Asn Glu Glu Ala Val
1140 1145 1150
Lys Lys Asp Asn Ser Val His Trp Glu Arg Pro Gln Lys Pro Lys Ala
1155 1160 1165
Pro Val Gly His Phe Tyr Glu Pro Gln Ala Pro Ser Ala Glu Val Glu
1170 1175 1180
Met Thr Ser Tyr Val Leu Leu Ala Tyr Leu Thr Ala Gln Pro Ala Pro
185 1190 1195 1200
Thr Ser Glu Asp Leu Thr Ser Ala Thr Asn Ile Val Lys Trp Ile Thr
1205 1210 1215
Lys Gln Gln Asn Ala Gln Gly Gly Phe Ser Ser Thr Gln Asp Thr Val
1220 1225 1230
Val Ala Leu His Ala Leu Ser Lys Tyr Gly Ala Ala Thr Phe Thr Arg
1235 1240 1245
Thr Gly Lys Ala Ala Gln Val Thr Ile Gln Ser Ser Gly Thr Phe Ser
1250 1255 1260
Ser Lys Phe Gln Val Asp Asn Asn Asn Arg Leu Leu Leu Gln Gln Val
265 1270 1275 1280
Ser Leu Pro Glu Leu Pro Gly Glu Tyr Ser Met Lys Val Thr Gly Glu
1285 1290 1295
Gly Cys Val Tyr Leu Gln Thr Ser Leu Lys Tyr Asn Ile Leu Pro Glu
1300 1305 1310

FIG.7B-4

Lys Glu Glu Phe Pro Phe Ala Leu Gly Val Gln Thr Leu Pro Gln Thr
1315 1320 1325

Cys Asp Glu Pro Lys Ala His Thr Ser Phe Gln Ile Ser Leu Ser Val
1330 1335 1340

Ser Tyr Thr Gly Ser Arg Ser Ala Ser Asn Met Ala Ile Val Asp Val
345 1350 1355 1360

Lys Met Val Ser Gly *Phe Ile Pro Leu* Lys *Pro Thr Val* Lys *Met Leu*
1365 1370 1375

*Glu Arg Ser Asn His Val Ser Arg Thr Glu Val Ser Ser Asn His Val*
1380 1385 1390

Leu Ile Tyr Leu Asp Lys Val Ser Asn Gln Thr Leu Ser Leu Phe Phe

Thr Val Leu Gln Asp Val Pro Val Arg Asp Leu Lys Pro Ala Ile Val
1410 1415 1420

Lys Val Tyr Asp Tyr Tyr Glu Thr Asp Glu Phe Ala Ile Ala Glu Tyr
425 1430 1435 1440

Asn Ala Pro Cys Ser Lys Asp Leu Gly Asn Ala
1445 1450

FIG.7B-5

```
CAGCGGTGCG AGCTCCAGGC CCATGCACTG AGGAGGCGGA AACAAGGGGA GCCCCCAGAG    60
CTCCATCAAG CCCCCTCCAA AGGCTCCCCT ACCCGGTCCA CGCCCCCCAC CCCCCCTCCC   120
CGCCTCCTCC CAATTGTGCA TTTTTGCAGC CGGAGGCGGC TCCGAGATGG GGCTGTGAGC   180
TTCGCCCGGG GAGGGGGAAA GAGCAGCGAG GAGTGAAGCG GGGGGGTGGG GTGAAGGGTT   240
TGGATTTCGG GGCAGGGGGC GCACCCCCGT CAGCAGGCCC TCCCCAAGGG GCTCGGAACT   300
CTACCTCTTC ACCCACGCCC CTGGTGCGCT TTGCCGAAGG AAAGAATAAG AACAGAGAAG   360
GAGGAGGGGG AAAGGAGGAA AAGGGGGACC CCCCAACTGG GGGGGGTGAA GGGAGAGAAGT  420
AGCAGGACCA GAGGGGAAGG GGCTGCTGCT TGCATCAGCC CACACC ATG CTG ACC      475
                                                   Met Leu Thr
                                                    1

CCG CCG TTG CTC CTG CTG CTG CCC CTG CTC TCA GCT CTG GTC GCG GCG     523
Pro Pro Leu Leu Leu Leu Leu Pro Leu Leu Ser Ala Leu Val Ala Ala
     5                  10                  15

GCT ATC GAC GCC CCT AAG ACT TGC AGC CCC AAG CAG TTT GCC TGC AGA     571
Ala Ile Asp Ala Pro Lys Thr Cys Ser Pro Lys Gln Phe Ala Cys Arg
20                  25                  30                  35

GAT CAA ATA ACC TGT ATC TCA AAG GGC TGG CGG TGC GAC GGT GAG AGG     619
Asp Gln Ile Thr Cys Ile Ser Lys Gly Trp Arg Cys Asp Gly Glu Arg
                40                  45                  50

GAC TGC CCA GAC GGA TCT GAC GAG GCC CCT GAG ATT TGT CCA CAG AGT     667
Asp Cys Pro Asp Gly Ser Asp Glu Ala Pro Glu Ile Cys Pro Gln Ser
            55                  60                  65

AAG GCC CAG CGA TGC CAG CCA AAC GAG CAT AAC TGC CTG GGT ACT GAG     715
Lys Ala Gln Arg Cys Gln Pro Asn Glu His Asn Cys Leu Gly Thr Glu
        70                  75                  80

CTG TGT GTT CCC ATG TCC CGC CTC TGC AAT GGG GTC CAG GAC TGC ATG     763
Leu Cys Val Pro Met Ser Arg Leu Cys Asn Gly Val Gln Asp Cys Met
    85                  90                  95

GAC GGC TCA GAT GAG GGG CCC CAC TGC CGA GAG CTC CAA GGC AAC TGC     811
Asp Gly Ser Asp Glu Gly Pro His Cys Arg Glu Leu Gln Gly Asn Cys
100                 105                 110                 115

TCT CGC CTG GGC TGC CAG CAC CAT TGT GTC CCC ACA CTC GAT GGG CCC     859
Ser Arg Leu Gly Cys Gln His His Cys Val Pro Thr Leu Asp Gly Pro
                120                 125                 130
```

FIG.8A-1

ACC TGC TAC TGC AAC AGC AGC TTT CAG CTT CAG GCA GAT GGC AAG ACC 907
Thr Cys Tyr Cys Asn Ser Ser Phe Gln Leu Gln Ala Asp Gly Lys Thr
135 140 145

TGC AAA GAT TTT GAT GAG TGC TCA GTG TAC GGC ACC TGC AGC CAG CTA 955
Cys Lys Asp Phe Asp Glu Cys Ser Val Tyr Gly Thr Cys Ser Gln Leu
150 155 160

TGC ACC AAC ACA GAC GGC TCC TTC ATA TGT GGC TGT GTT GAA GGA TAC 1003
Cys Thr Asn Thr Asp Gly Ser Phe Ile Cys Gly Cys Val Glu Gly Tyr
165 170 175

CTC CTG CAG CCG GAT AAC CGC TCC TGC AAG GCC AAG AAC GAG CCA GTA 1051
Leu Leu Gln Pro Asp Asn Arg Ser Cys Lys Ala Lys Asn Glu Pro Val
180 185 190 195

GAC CGG CCC CCT GTG CTG TTG ATA GCC AAC TCC CAG AAC ATC TTG GCC 1099
Asp Arg Pro Pro Val Leu Leu Ile Ala Asn Ser Gln Asn Ile Leu Ala
200 205 210

ACG TAC CTG AGT GGG GCC CAG GTG TCT ACC ATC ACA CCT ACG AGC ACG 1147
Thr Tyr Leu Ser Gly Ala Gln Val Ser Thr Ile Thr Pro Thr Ser Thr
215 220 225

CGG CAG ACC ACA GCC ATG GAC TTC AGC TAT GCC AAC GAG ACC GTA TGC 1195
Arg Gln Thr Thr Ala Met Asp Phe Ser Tyr Ala Asn Glu Thr Val Cys
230 235 240

TGG GTG CAT GTT GGG GAC AGT GCT GCT CAG ACG CAG CTC AAG TGT GCC 1243
Trp Val His Val Gly Asp Ser Ala Ala Gln Thr Gln Leu Lys Cys Ala
245 250 255

CGC ATG CCT GGC CTA AAG GGC TTC GTG GAT GAG CAC ACC ATC AAC ATC 1291
Arg Met Pro Gly Leu Lys Gly Phe Val Asp Glu His Thr Ile Asn Ile
260 265 270 275

TCC CTC AGT CTG CAC CAC GTG GAA CAG ATG GCC ATC GAC TGG CTG ACA 1339
Ser Leu Ser Leu His His Val Glu Gln Met Ala Ile Asp Trp Leu Thr
280 285 290

GGC AAC TTC TAC TTT GTG GAT GAC ATC GAT GAT AGG ATC TTT GTC TGC 1387
Gly Asn Phe Tyr Phe Val Asp Asp Ile Asp Asp Arg Ile Phe Val Cys
295 300 305

FIG.8A-2

```
AAC AGA AAT GGG GAC ACA TGT GTC ACA TTG CTA GAC CTG GAA CTC TAC     1435
Asn Arg Asn Gly Asp Thr Cys Val Thr Leu Leu Asp Leu Glu Leu Tyr
        310                 315                 320

AAC CCC AAG GGC ATT GCC CTG GAC CCT GCC ATG GGG AAG GTG TTT TTC     1483
Asn Pro Lys Gly Ile Ala Leu Asp Pro Ala Met Gly Lys Val Phe Phe
    325                 330                 335

ACT GAC TAT GGG CAG ATC CCA AAG GTG GAA CGC TGT GAC ATG GAT GGG     1531
Thr Asp Tyr Gly Gln Ile Pro Lys Val Glu Arg Cys Asp Met Asp Gly
340                 345                 350                 355

CAG AAC CGC ACC AAG CTC GTC GAC AGC AAG ATT GTG TTT CCT CAT GGC     1579
Gln Asn Arg Thr Lys Leu Val Asp Ser Lys Ile Val Phe Pro His Gly
                360                 365                 370

ATC ACG CTG GAC CTG GTC AGC CGC CTT GTC TAC TGG GCA GAT GCC TAT     1627
Ile Thr Leu Asp Leu Val Ser Arg Leu Val Tyr Trp Ala Asp Ala Tyr
            375                 380                 385

CTG GAC TAT ATT GAA GTG GTG GAC TAT GAG GGC AAG GGC CGC CAG ACC     1675
Leu Asp Tyr Ile Glu Val Val Asp Tyr Glu Gly Lys Gly Arg Gln Thr
        390                 395                 400

ATC ATC CAG GGC ATC CTG ATT GAG CAC CTG TAC GGC CTG ACT GTG TTT     1723
Ile Ile Gln Gly Ile Leu Ile Glu His Leu Tyr Gly Leu Thr Val Phe
    405                 410                 415

GAG AAT TAT CTC TAT GCC ACC AAC TCG GAC AAT GCC AAT GCC CAG CAG     1771
Glu Asn Tyr Leu Tyr Ala Thr Asn Ser Asp Asn Ala Asn Ala Gln Gln
420                 425                 430                 435

AAG ACG AGT GTG ATC CGT GTG AAC CGC TTT AAC AGC ACC GAG TAC CAG     1819
Lys Thr Ser Val Ile Arg Val Asn Arg Phe Asn Ser Thr Glu Tyr Gln
                440                 445                 450

GTT GTC ACC CGG GTG GAC AAG GGT GGT GCC CTC CAC ATC TAC CAC CAG     1867
Val Val Thr Arg Val Asp Lys Gly Gly Ala Leu His Ile Tyr His Gln
            455                 460                 465

AGG CGT CAG CCC CGA GTG AGG AGC CAT GCC TGT GAA AAC GAC CAG TAT     1915
Arg Arg Gln Pro Arg Val Arg Ser His Ala Cys Glu Asn Asp Gln Tyr
        470                 475                 480
```

FIG.8A-3

```
GGG AAG CCG GGT GGC TGC TCT GAC ATC TGC CTG CTG GCC AAC AGC CAC     1963
Gly Lys Pro Gly Gly Cys Ser Asp Ile Cys Leu Leu Ala Asn Ser His
    485                 490                 495

AAG GCG CGG ACC TGC CGC TGC CGT TCC GGC TTC AGC CTG GGC AGT GAC     2011
Lys Ala Arg Thr Cys Arg Cys Arg Ser Gly Phe Ser Leu Gly Ser Asp
500                 505                 510                 515

GGG AAG TCA TGC AAG AAG CCG GAG CAT GAG CTG TTC CTC GTG TAT GGC     2059
Gly Lys Ser Cys Lys Lys Pro Glu His Glu Leu Phe Leu Val Tyr Gly
                520                 525                 530

AAG GGC CGG CCA GGC ATC ATC CGG GGC ATG GAT ATG GGG GCC AAG GTC     2107
Lys Gly Arg Pro Gly Ile Ile Arg Gly Met Asp Met Gly Ala Lys Val
            535                 540                 545

CCG GAT GAG CAC ATG ATC CCC ATT GAA AAC CTC ATG AAC CCC CGA GCC     2155
Pro Asp Glu His Met Ile Pro Ile Glu Asn Leu Met Asn Pro Arg Ala
        550                 555                 560

CTG GAC TTC CAC GCT GAG ACC GGC TTC ATC TAC TTT GCC GAC ACC ACC     2203
Leu Asp Phe His Ala Glu Thr Gly Phe Ile Tyr Phe Ala Asp Thr Thr
    565                 570                 575

AGC TAC CTC ATT GGC CGC CAG AAG ATT GAT GGC ACT GAG CGG GAG ACC     2251
Ser Tyr Leu Ile Gly Arg Gln Lys Ile Asp Gly Thr Glu Arg Glu Thr
580                 585                 590                 595

ATC CTG AAG GAC GGC ATC CAC AAT GTG GAG GGT GTG GCC GTG GAC TGG     2299
Ile Leu Lys Asp Gly Ile His Asn Val Glu Gly Val Ala Val Asp Trp
                600                 605                 610

ATG GGA GAC AAT CTG TAC TGG ACG GAC GAT GGG CCC AAA AAG ACA ATC     2347
Met Gly Asp Asn Leu Tyr Trp Thr Asp Asp Gly Pro Lys Lys Thr Ile
            615                 620                 625

AGC GTG GCC AGG CTG GAG AAA GCT GCT CAG ACC CGC AAG ACT TTA ATC     2395
Ser Val Ala Arg Leu Glu Lys Ala Ala Gln Thr Arg Lys Thr Leu Ile
        630                 635                 640

GAG GGC AAA ATG ACA CAC CCC AGG GCT ATT GTG GTG GAT CCA CTC AAT     2443
Glu Gly Lys Met Thr His Pro Arg Ala Ile Val Val Asp Pro Leu Asn
    645                 650                 655
```

FIG.8A-4

GGG TGG ATG TAC TGG ACA GAC TGG GAG GAG GAC CCC AAG GAC AGT CGG 2491
Gly Trp Met Tyr Trp Thr Asp Trp Glu Glu Asp Pro Lys Asp Ser Arg
660 665 670 675

CGT GGG CGG CTG GAG AGG GCG TGG ATG GAT GGC TCA CAC CGA GAC ATC 2539
Arg Gly Arg Leu Glu Arg Ala Trp Met Asp Gly Ser His Arg Asp Ile
680 685 690

TTT GTC ACC TCC AAG ACA GTG CTT TGG CCC AAT GGG CTA AGC CTG GAC 2587
Phe Val Thr Ser Lys Thr Val Leu Trp Pro Asn Gly Leu Ser Leu Asp
695 700 705

ATC CCG GCT GGG CGC CTC TAC TGG GTG GAT GCC TTC TAC GAC CGC ATC 2635
Ile Pro Ala Gly Arg Leu Tyr Trp Val Asp Ala Phe Tyr Asp Arg Ile
710 715 720

GAG ACG ATA CTG CTC AAT GGC ACA GAC CGG AAG ATT GTG TAT GAA GGT 2683
Glu Thr Ile Leu Leu Asn Gly Thr Asp Arg Lys Ile Val Tyr Glu Gly
725 730 735

CCT GAG CTG AAC CAC GCC TTT GGC CTG TGT CAC CAT GGC AAC TAC CTC 2731
Pro Glu Leu Asn His Ala Phe Gly Leu Cys His His Gly Asn Tyr Leu
740 745 750 755

TTC TGG ACT GAG TAT CGG AGT GGC AGT GTC TAC CGC TTG GAA CGG GGT 2779
Phe Trp Thr Glu Tyr Arg Ser Gly Ser Val Tyr Arg Leu Glu Arg Gly
760 765 770

GTA GGA GGC GCA CCC CCC ACT GTG ACC CTT CTG CGC AGT GAG CGG CCC 2827
Val Gly Gly Ala Pro Pro Thr Val Thr Leu Leu Arg Ser Glu Arg Pro
775 780 785

CCC ATC TTT GAG ATC CGA ATG TAT GAT GCC CAG CAG CAG CAA GTT GGC 2875
Pro Ile Phe Glu Ile Arg Met Tyr Asp Ala Gln Gln Gln Gln Val Gly
790 795 800

ACC AAC AAA TGC CGG GTG AAC AAT GGC GGC TGC AGC AGC CTG TGC TTG 2923
Thr Asn Lys Cys Arg Val Asn Asn Gly Gly Cys Ser Ser Leu Cys Leu
805 810 815

GCC ACC CCT GGG AGC CGC CAG TGC GCC TGT GCT GAG GAC CAG GTG TTG 2971
Ala Thr Pro Gly Ser Arg Gln Cys Ala Cys Ala Glu Asp Gln Val Leu
820 825 830 835

FIG.8A-5

```
GAC GCA GAC GGC GTC ACT TGC TTG GCG AAC CCA TCC TAC GTG CCT CCA      3019
Asp Ala Asp Gly Val Thr Cys Leu Ala Asn Pro Ser Tyr Val Pro Pro
                840                 845                 850

CCC CAG TGC CAG CCA GGC GAG TTT GCC TGT GCC AAC AGC CGC TGC ATC      3067
Pro Gln Cys Gln Pro Gly Glu Phe Ala Cys Ala Asn Ser Arg Cys Ile
            855                 860                 865

CAG GAG CGC TGG AAG TGT GAC GGA GAC AAC GAT TGC CTG GAC AAC AGT      3115
Gln Glu Arg Trp Lys Cys Asp Gly Asp Asn Asp Cys Leu Asp Asn Ser
        870                 875                 880

GAT GAG GCC CCA GCC CTC TGC CAT CAG CAC ACC TGC CCC TCG GAC CGA      3163
Asp Glu Ala Pro Ala Leu Cys His Gln His Thr Cys Pro Ser Asp Arg
    885                 890                 895

TTC AAG TGC GAG AAC AAC CGG TGC ATC CCC AAC CGC TGG CTC TGC GAC      3211
Phe Lys Cys Glu Asn Asn Arg Cys Ile Pro Asn Arg Trp Leu Cys Asp
900                 905                 910                 915

GGG GAC AAT GAC TGT GGG AAC AGT GAA GAT GAG TCC AAT GCC ACT TGT      3259
Gly Asp Asn Asp Cys Gly Asn Ser Glu Asp Glu Ser Asn Ala Thr Cys
                920                 925                 930

TCA GCC CGC ACC TGC CCC CCC AAC CAG TTC TCC TGT GCC AGT GGC CGC      3307
Ser Ala Arg Thr Cys Pro Pro Asn Gln Phe Ser Cys Ala Ser Gly Arg
            935                 940                 945

TGC ATC CCC ATC TCC TGG ACG TGT GAT CTG GAT GAC GAC TGT GGG GAC      3355
Cys Ile Pro Ile Ser Trp Thr Cys Asp Leu Asp Asp Asp Cys Gly Asp
        950                 955                 960

CGC TCT GAT GAG TCT GCT TCG TGT GCC TAT CCC ACC TGC TTC CCC CTG      3403
Arg Ser Asp Glu Ser Ala Ser Cys Ala Tyr Pro Thr Cys Phe Pro Leu
    965                 970                 975

ACT CAG TTT ACC TGC AAC AAT GGC AGA TGT ATC AAC ATC AAC TGG AGA      3451
Thr Gln Phe Thr Cys Asn Asn Gly Arg Cys Ile Asn Ile Asn Trp Arg
980                 985                 990                 995

TGC GAC AAT GAC AAT GAC TGT GGG GAC AAC AGT GAC GAA GCC GGC TGC      3499
Cys Asp Asn Asp Asn Asp Cys Gly Asp Asn Ser Asp Glu Ala Gly Cys
               1000                1005                1010
```

FIG.8A-6

AGC CAC TCC TGT TCT AGC ACC CAG TTC AAG TGC AAC AGC GGG CGT TGC 3547
Ser His Ser Cys Ser Ser Thr Gln Phe Lys Cys Asn Ser Gly Arg Cys
1015 1020 1025

ATC CCC GAG CAC TGG ACC TGC GAT GGG GAC AAT GAC TGC GGA GAC TAC 3595
Ile Pro Glu His Trp Thr Cys Asp Gly Asp Asn Asp Cys Gly Asp Tyr
1030 1035 1040

AGT GAT GAG ACA CAC GCC AAC TGC ACC AAC CAG GCC ACG AGG CCC CCT 3643
Ser Asp Glu Thr His Ala Asn Cys Thr Asn Gln Ala Thr Arg Pro Pro
1045 1050 1055

GGT GGC TGC CAC ACT GAT GAG TTC CAG TGC CGG CTG GAT GGA CTA TGC 3691
Gly Gly Cys His Thr Asp Glu Phe Gln Cys Arg Leu Asp Gly Leu Cys
1060 1065 1070 1075

ATC CCC CTG CGG TGG CGC TGC GAT GGG GAC ACT GAC TGC ATG GAC TCC 3739
Ile Pro Leu Arg Trp Arg Cys Asp Gly Asp Thr Asp Cys Met Asp Ser
1080 1085 1090

AGC GAT GAG AAG AGC TGT GAG GGA GTG ACC CAC GTC TGC GAT CCC AGT 3787
Ser Asp Glu Lys Ser Cys Glu Gly Val Thr His Val Cys Asp Pro Ser
1095 1100 1105

GTC AAG TTT GGC TGC AAG GAC TCA GCT CGG TGC ATC AGC AAA GCG TGG 3835
Val Lys Phe Gly Cys Lys Asp Ser Ala Arg Cys Ile Ser Lys Ala Trp
1110 1115 1120

GTG TGT GAT GGC GAC AAT GAC TGT GAG GAT AAC TCG GAC GAG GAG AAC 3883
Val Cys Asp Gly Asp Asn Asp Cys Glu Asp Asn Ser Asp Glu Glu Asn
1125 1130 1135

TGC GAG TCC CTG GCC TGC AGG CCA CCC TCG CAC CCT TGT GCC AAC AAC 3931
Cys Glu Ser Leu Ala Cys Arg Pro Pro Ser His Pro Cys Ala Asn Asn
1140 1145 1150 1155

ACC TCA GTC TGC CTG CCC CCT GAC AAG CTG TGT GAT GGC AAC GAC GAC 3979
Thr Ser Val Cys Leu Pro Pro Asp Lys Leu Cys Asp Gly Asn Asp Asp
1160 1165 1170

TGT GGC GAC GGC TCA GAT GAG GGC GAG CTC TGC GAC CAG TGC TCT CTG 4027
Cys Gly Asp Gly Ser Asp Glu Gly Glu Leu Cys Asp Gln Cys Ser Leu
1175 1180 1185

FIG.8A-7

AAT AAC GGT GGC TGC AGC CAC AAC TGC TCA GTG GCA CCT GGC GAA GGC 4075
Asn Asn Gly Gly Cys Ser His Asn Cys Ser Val Ala Pro Gly Glu Gly
1190 1195 1200

ATT GTG TGT TCC TGC CCT CTG GGC ATG GAG CTG GGG CCC GAC AAC CAC 4123
Ile Val Cys Ser Cys Pro Leu Gly Met Glu Leu Gly Pro Asp Asn His
1205 1210 1215

ACC TGC CAG ATC CAG AGC TAC TGT GCC AAG CAT CTC AAA TGC AGC CAA 4171
Thr Cys Gln Ile Gln Ser Tyr Cys Ala Lys His Leu Lys Cys Ser Gln
1220 1225 1230 1235

AAG TGC GAC CAG AAC AAG TTC AGC GTG AAG TGC TCC TGC TAC GAG GGC 4219
Lys Cys Asp Gln Asn Lys Phe Ser Val Lys Cys Ser Cys Tyr Glu Gly
1240 1245 1250

TGG GTC CTG GAA CCT GAC GGC GAG AGC TGC CGC AGC CTG GAC CCC TTC 4267
Trp Val Leu Glu Pro Asp Gly Glu Ser Cys Arg Ser Leu Asp Pro Phe
1255 1260 1265

AAG CCG TTC ATC ATT TTC TCC AAC CGC CAT GAA ATC CGG CGC ATC GAT 4315
Lys Pro Phe Ile Ile Phe Ser Asn Arg His Glu Ile Arg Arg Ile Asp
1270 1275 1280

CTT CAC AAA GGA GAC TAC AGC GTC CTG GTG CCC GGC CTG CGC AAC ACC 4363
Leu His Lys Gly Asp Tyr Ser Val Leu Val Pro Gly Leu Arg Asn Thr
1285 1290 1295

ATC GCC CTG GAC TTC CAC CTC AGC CAG AGC GCC CTC TAC TGG ACC GAC 4411
Ile Ala Leu Asp Phe His Leu Ser Gln Ser Ala Leu Tyr Trp Thr Asp
1300 1305 1310 1315

GTG GTG GAG GAC AAG ATC TAC CGC GGG AAG CTG CTG GAC AAC GGA GCC 4459
Val Val Glu Asp Lys Ile Tyr Arg Gly Lys Leu Leu Asp Asn Gly Ala
1320 1325 1330

CTG ACT AGT TTC GAG GTG GTG ATT CAG TAT GGC CTG GCC ACA CCC GAG 4507
Leu Thr Ser Phe Glu Val Val Ile Gln Tyr Gly Leu Ala Thr Pro Glu
1335 1340 1345

GGC CTG GCT GTA GAC TGG ATT GCA GGC AAC ATC TAC TGG GTG GAG AGT 4555
Gly Leu Ala Val Asp Trp Ile Ala Gly Asn Ile Tyr Trp Val Glu Ser
1350 1355 1360

FIG.8A-8

```
AAC CTG GAT CAG ATC GAG GTG GCC AAG CTG GAT GGG ACC CTC CGG ACC     4603
Asn Leu Asp Gln Ile Glu Val Ala Lys Leu Asp Gly Thr Leu Arg Thr
    1365                1370                1375

ACC CTG CTG GCC GGT GAC ATT GAG CAC CCA AGG GCA ATC GCA CTG GAT     4651
Thr Leu Leu Ala Gly Asp Ile Glu His Pro Arg Ala Ile Ala Leu Asp
1380                1385                1390                1395

CCC CGG GAT GGG ATC CTG TTT TGG ACA GAC TGG GAT GCC AGC CTG CCC     4699
Pro Arg Asp Gly Ile Leu Phe Trp Thr Asp Trp Asp Ala Ser Leu Pro
                1400                1405                1410

CGC ATT GAG GCA GCC TCC ATG AGT GGG GCT GGG CGC CGC ACC GTG CAC     4747
Arg Ile Glu Ala Ala Ser Met Ser Gly Ala Gly Arg Arg Thr Val His
            1415                1420                1425

CGG GAG ACC GGC TCT GGG GGC TGG CCC AAC GGG CTC ACC GTG GAC TAC     4795
Arg Glu Thr Gly Ser Gly Gly Trp Pro Asn Gly Leu Thr Val Asp Tyr
        1430                1435                1440

CTG GAG AAG CGC ATC CTT TGG ATT GAC GCC AGG TCA GAT GCC ATT TAC     4843
Leu Glu Lys Arg Ile Leu Trp Ile Asp Ala Arg Ser Asp Ala Ile Tyr
    1445                1450                1455

TCA GCC CGT TAC GAC GGC TCT GGC CAC ATG GAG GTG CTT CGG GGA CAC     4891
Ser Ala Arg Tyr Asp Gly Ser Gly His Met Glu Val Leu Arg Gly His
1460                1465                1470                1475

GAG TTC CTG TCG CAC CCG TTT GCA GTG ACG CTG TAC GGG GGG GAG GTC     4939
Glu Phe Leu Ser His Pro Phe Ala Val Thr Leu Tyr Gly Gly Glu Val
                1480                1485                1490

TAC TGG ACT GAC TGG CGA ACA AAC ACA CTG GCT AAG GCC AAC AAG TGG     4987
Tyr Trp Thr Asp Trp Arg Thr Asn Thr Leu Ala Lys Ala Asn Lys Trp
            1495                1500                1505

ACC GGC CAC AAT GTC ACC GTG GTA CAG AGG ACC AAC ACC CAG CCC TTT     5035
Thr Gly His Asn Val Thr Val Val Gln Arg Thr Asn Thr Gln Pro Phe
        1510                1515                1520

GAC CTG CAG GTG TAC CAC CCC TCC CGC CAG CCC ATG GCT CCC AAT CCC     5083
Asp Leu Gln Val Tyr His Pro Ser Arg Gln Pro Met Ala Pro Asn Pro
    1525                1530                1535
```

FIG.8A-9

```
 TGT GAG GCC AAT GGG GGC CAG GGC CCC TGC TCC CAC CTG TGT CTC ATC    5131
 Cys Glu Ala Asn Gly Gly Gln Gly Pro Cys Ser His Leu Cys Leu Ile
1540                1545                1550                1555

 AAC TAC AAC CGG ACC GTG TCC TGC GCC TGC CCC CAC CTC ATG AAG CTC    5179
 Asn Tyr Asn Arg Thr Val Ser Cys Ala Cys Pro His Leu Met Lys Leu
                1560                1565                1570

 CAC AAG GAC AAC ACC ACC TGC TAT GAG TTT AAG AAG TTC CTG CTG TAC    5227
 His Lys Asp Asn Thr Thr Cys Tyr Glu Phe Lys Lys Phe Leu Leu Tyr
            1575                1580                1585

 GCA CGT CAG ATG GAG ATC CGA GGT GTG GAC CTG GAT GCT CCC TAC TAC    5275
 Ala Arg Gln Met Glu Ile Arg Gly Val Asp Leu Asp Ala Pro Tyr Tyr
        1590                1595                1600

 AAC TAC ATC ATC TCC TTC ACG GTG CCC GAC ATC GAC AAC GTC ACA GTG    5323
 Asn Tyr Ile Ile Ser Phe Thr Val Pro Asp Ile Asp Asn Val Thr Val
    1605                1610                1615

 CTA GAC TAC GAT GCC CGC GAG CAG CGT GTG TAC TGG TCT GAC GTG CGG    5371
 Leu Asp Tyr Asp Ala Arg Glu Gln Arg Val Tyr Trp Ser Asp Val Arg
1620                1625                1630                1635

 ACA CAG GCC ATC AAG CGG GCC TTC ATC AAC GGC ACA GGC GTG GAG ACA    5419
 Thr Gln Ala Ile Lys Arg Ala Phe Ile Asn Gly Thr Gly Val Glu Thr
                1640                1645                1650

 GTC GTC TCT GCA GAC TTG CCA AAT GCC CAC GGG CTG GCT GTG GAC TGG    5467
 Val Val Ser Ala Asp Leu Pro Asn Ala His Gly Leu Ala Val Asp Trp
            1655                1660                1665

 GTC TCC CGA AAC CTG TTC TGG ACA AGC TAT GAC ACC AAT AAG AAG CAG    5515
 Val Ser Arg Asn Leu Phe Trp Thr Ser Tyr Asp Thr Asn Lys Lys Gln
        1670                1675                1680

 ATC AAT GTG GCC CGG CTG GAT GGC TCC TTC AAG AAC GCA GTG GTG CAG    5563
 Ile Asn Val Ala Arg Leu Asp Gly Ser Phe Lys Asn Ala Val Val Gln
    1685                1690                1695

 GGC CTG GAG CAG CCC CAT GGC CTT GTC GTC CAC CCT CTG CGT GGG AAG    5611
 Gly Leu Glu Gln Pro His Gly Leu Val Val His Pro Leu Arg Gly Lys
1700                1705                1710                1715
```

FIG.8A-10

CTC TAC TGG ACC GAT GGT GAC AAC ATC AGC ATG GCC AAC ATG GAT GGC 5659
Leu Tyr Trp Thr Asp Gly Asp Asn Ile Ser Met Ala Asn Met Asp Gly
1720 1725 1730

AGC AAT CGC ACC CTG CTC TTC AGT GGC CAG AAG GGC CCC GTG GGC CTG 5707
Ser Asn Arg Thr Leu Leu Phe Ser Gly Gln Lys Gly Pro Val Gly Leu
1735 1740 1745

GCT ATT GAC TTC CCT GAA AGC AAA CTC TAC TGG ATC AGC TCC GGG AAC 5755
Ala Ile Asp Phe Pro Glu Ser Lys Leu Tyr Trp Ile Ser Ser Gly Asn
1750 1755 1760

CAT ACC ATC AAC CGC TGC AAC CTG GAT GGG AGT GGG CTG GAG GTC ATC 5803
His Thr Ile Asn Arg Cys Asn Leu Asp Gly Ser Gly Leu Glu Val Ile
1765 1770 1775

GAT GCC ATG CGG AGC CAG CTG GGC AAG GCC ACC GCC CTG GCC ATC ATG 5851
Asp Ala Met Arg Ser Gln Leu Gly Lys Ala Thr Ala Leu Ala Ile Met
1780 1785 1790 1795

GGG GAC AAG CTG TGG TGG GCT GAT CAG GTG TCG GAA AAG ATG GGC ACA 5899
Gly Asp Lys Leu Trp Trp Ala Asp Gln Val Ser Glu Lys Met Gly Thr
1800 1805 1810

TGC AGC AAG GCT GAC GGC TCG GGC TCC GTG GTC CTT CGG AAC AGC ACC 5947
Cys Ser Lys Ala Asp Gly Ser Gly Ser Val Val Leu Arg Asn Ser Thr
1815 1820 1825

ACC CTG GTG ATG CAC ATG AAG GTC TAT GAC GAG AGC ATC CAG CTG GAC 5995
Thr Leu Val Met His Met Lys Val Tyr Asp Glu Ser Ile Gln Leu Asp
1830 1835 1840

CAT AAG GGC ACC AAC CCC TGC AGT GTC AAC AAC GGT GAC TGC TCC CAG 6043
His Lys Gly Thr Asn Pro Cys Ser Val Asn Asn Gly Asp Cys Ser Gln
1845 1850 1855

CTC TGC CTG CCC ACG TCA GAG ACG ACC CGC TCC TGC ATG TGC ACA GCC 6091
Leu Cys Leu Pro Thr Ser Glu Thr Thr Arg Ser Cys Met Cys Thr Ala
1860 1865 1870 1875

GGC TAT AGC CTC CGG AGT GGC CAG CAG GCC TGC GAG GGC GTA GGT TCC 6139
Gly Tyr Ser Leu Arg Ser Gly Gln Gln Ala Cys Glu Gly Val Gly Ser
1880 1885 1890

FIG.8A-11

TTT CTC CTG TAC TCT GTG CAT GAG GGA ATC AGG GGA ATT CCC CTG GAT 6187
Phe Leu Leu Tyr Ser Val His Glu Gly Ile Arg Gly Ile Pro Leu Asp
1895 1900 1905

CCC AAT GAC AAG TCA GAT GCC CTG GTC CCA GTG TCC GGG ACC TCG CTG 6235
Pro Asn Asp Lys Ser Asp Ala Leu Val Pro Val Ser Gly Thr Ser Leu
1910 1915 1920

GCT GTC GGC ATC GAC TTC CAC GCT GAA AAT GAC ACC ATC TAC TGG GTG 6283
Ala Val Gly Ile Asp Phe His Ala Glu Asn Asp Thr Ile Tyr Trp Val
1925 1930 1935

GAC ATG GGC CTG AGC ACG ATC AGC CGG GCC AAG CGG GAC CAG ACG TGG 6331
Asp Met Gly Leu Ser Thr Ile Ser Arg Ala Lys Arg Asp Gln Thr Trp
1940 1945 1950 1955

CGT GAA GAC GTG GTG ACC AAT GGC ATT GGC CGT GTG GAG GGC ATT GCA 6379
Arg Glu Asp Val Val Thr Asn Gly Ile Gly Arg Val Glu Gly Ile Ala
1960 1965 1970

GTG GAC TGG ATC GCA GGC AAC ATC TAC TGG ACA GAC CAG GGC TTT GAT 6427
Val Asp Trp Ile Ala Gly Asn Ile Tyr Trp Thr Asp Gln Gly Phe Asp
1975 1980 1985

GTC ATC GAG GTC GCC CGG CTC AAT GGC TCC TTC CGC TAC GTG GTG ATC 6475
Val Ile Glu Val Ala Arg Leu Asn Gly Ser Phe Arg Tyr Val Val Ile
1990 1995 2000

TCC CAG GGT CTA GAC AAG CCC CGG GCC ATC ACC GTC CAC CCG GAG AAA 6523
Ser Gln Gly Leu Asp Lys Pro Arg Ala Ile Thr Val His Pro Glu Lys
2005 2010 2015

GGG TAC TTG TTC TGG ACT GAG TGG GGT CAG TAT CCG CGT ATT GAG CGG 6571
Gly Tyr Leu Phe Trp Thr Glu Trp Gly Gln Tyr Pro Arg Ile Glu Arg
2020 2025 2030 2035

TCT CGG CTA GAT GGC ACG GAG CGT GTG GTG CTG GTC AAC GTC AGC ATC 6619
Ser Arg Leu Asp Gly Thr Glu Arg Val Val Leu Val Asn Val Ser Ile
2040 2045 2050

AGC TGG CCC AAC GGC ATC TCA GTG GAC TAC CAG GAT GGG AAG CTG TAC 6667
Ser Trp Pro Asn Gly Ile Ser Val Asp Tyr Gln Asp Gly Lys Leu Tyr
2055 2060 2065

FIG.8A-12

```
TGG TGC GAT GCA CGG ACA GAC AAG ATT GAA CGG ATC GAC CTG GAG ACA    6715
Trp Cys Asp Ala Arg Thr Asp Lys Ile Glu Arg Ile Asp Leu Glu Thr
        2070                2075                2080

GGT GAG AAC CGC GAG GTG GTT CTG TCC AGC AAC AAC ATG GAC ATG TTT    6763
Gly Glu Asn Arg Glu Val Val Leu Ser Ser Asn Asn Met Asp Met Phe
    2085                2090                2095

TCA GTG TCT GTG TTT GAG GAT TTC ATC TAC TGG AGT GAC AGG ACT CAT    6811
Ser Val Ser Val Phe Glu Asp Phe Ile Tyr Trp Ser Asp Arg Thr His
2100                2105                2110                2115

GCC AAC GGC TCT ATC AAG CGC GGG AGC AAA GAC AAT GCC ACA GAC TCC    6859
Ala Asn Gly Ser Ile Lys Arg Gly Ser Lys Asp Asn Ala Thr Asp Ser
                2120                2125                2130

GTG CCC CTG CGA ACC GGC ATC GGC GTC CAG CTT AAA GAC ATC AAA GTC    6907
Val Pro Leu Arg Thr Gly Ile Gly Val Gln Leu Lys Asp Ile Lys Val
            2135                2140                2145

TTC AAC CGG GAC CGG CAG AAA GGC ACC AAC GTG TGC GCG GTG GCC AAT    6955
Phe Asn Arg Asp Arg Gln Lys Gly Thr Asn Val Cys Ala Val Ala Asn
        2150                2155                2160

GGC GGG TGC CAG CAG CTG TGC CTG TAC CGG GGC CGT GGG CAG CGG GCC    7003
Gly Gly Cys Gln Gln Leu Cys Leu Tyr Arg Gly Arg Gly Gln Arg Ala
    2165                2170                2175

TGC GCC TGT GCC CAC GGG ATG CTG GCT GAA GAC GGA GCA TCG TGC CGC    7051
Cys Ala Cys Ala His Gly Met Leu Ala Glu Asp Gly Ala Ser Cys Arg
2180                2185                2190                2195

GAG TAT GCC GGC TAC CTG CTC TAC TCA GAG CGC ACC ATT CTC AAG AGT    7099
Glu Tyr Ala Gly Tyr Leu Leu Tyr Ser Glu Arg Thr Ile Leu Lys Ser
                2200                2205                2210

ATC CAC CTG TCG GAT GAG CGC AAC CTC AAT GCG CCC GTG CAG CCC TTC    7147
Ile His Leu Ser Asp Glu Arg Asn Leu Asn Ala Pro Val Gln Pro Phe
            2215                2220                2225

GAG GAC CCT GAG CAC ATG AAG AAC GTC ATC GCC CTG GCC TTT GAC TAC    7195
Glu Asp Pro Glu His Met Lys Asn Val Ile Ala Leu Ala Phe Asp Tyr
        2230                2235                2240
```

FIG.8A-13

CGG GCA GGC ACC TCT CCG GGC ACC CCC AAT CGC ATC TTC TTC AGC GAC 7243
Arg Ala Gly Thr Ser Pro Gly Thr Pro Asn Arg Ile Phe Phe Ser Asp
2245 2250 2255

ATC CAC TTT GGG AAC ATC CAA CAG ATC AAC GAC GAT GGC TCC AGG AGG 7291
Ile His Phe Gly Asn Ile Gln Gln Ile Asn Asp Asp Gly Ser Arg Arg
2260 2265 2270 2275

ATC ACC ATT GTG GAA AAC GTG GGC TCC GTG GAA GGC CTG GCC TAT CAC 7339
Ile Thr Ile Val Glu Asn Val Gly Ser Val Glu Gly Leu Ala Tyr His
2280 2285 2290

CGT GGC TGG GAC ACT CTC TAT TGG ACA AGC TAC ACG ACA TCC ACC ATC 7387
Arg Gly Trp Asp Thr Leu Tyr Trp Thr Ser Tyr Thr Thr Ser Thr Ile
2295 2300 2305

ACG CGC CAC ACA GTG GAC CAG ACC CGC CCA GGG GCC TTC GAG CGT GAG 7435
Thr Arg His Thr Val Asp Gln Thr Arg Pro Gly Ala Phe Glu Arg Glu
2310 2315 2320

ACC GTC ATC ACT ATG TCT GGA GAT GAC CAC CCA CGG GCC TTC GTT TTG 7483
Thr Val Ile Thr Met Ser Gly Asp Asp His Pro Arg Ala Phe Val Leu
2325 2330 2335

GAC GAG TGC CAG AAC CTC ATG TTC TGG ACC AAC TGG AAT GAG CAG CAT 7531
Asp Glu Cys Gln Asn Leu Met Phe Trp Thr Asn Trp Asn Glu Gln His
2340 2345 2350 2355

CCC AGC ATC ATG CGG GCG GCG CTC TCG GGA GCC AAT GTC CTG ACC CTT 7579
Pro Ser Ile Met Arg Ala Ala Leu Ser Gly Ala Asn Val Leu Thr Leu
2360 2365 2370

ATC GAG AAG GAC ATC CGT ACC CCC AAT GGC CTG GCC ATC GAC CAC CGT 7627
Ile Glu Lys Asp Ile Arg Thr Pro Asn Gly Leu Ala Ile Asp His Arg
2375 2380 2385

GCC GAG AAG CTC TAC TTC TCT GAC GCC ACC CTG GAC AAG ATC GAG CGG 7675
Ala Glu Lys Leu Tyr Phe Ser Asp Ala Thr Leu Asp Lys Ile Glu Arg
2390 2395 2400

TGC GAG TAT GAC GGC TCC CAC CGC TAT GTG ATC CTA AAG TCA GAG CCT 7723
Cys Glu Tyr Asp Gly Ser His Arg Tyr Val Ile Leu Lys Ser Glu Pro
2405 2410 2415

FIG.8A-14

```
 GTC CAC CCC TTC GGG CTG GCC GTG TAT GGG GAG CAC ATT TTC TGG ACT     7771
 Val His Pro Phe Gly Leu Ala Val Tyr Gly Glu His Ile Phe Trp Thr
2420                2425                2430                2435

 GAC TGG GTG CGG CGG GCA GTG CAG CGG GCC AAC AAG CAC GTG GGC AGC     7819
 Asp Trp Val Arg Arg Ala Val Gln Arg Ala Asn Lys His Val Gly Ser
                2440                2445                2450

 AAC ATG AAG CTG CTG CGC GTG GAC ATC CCC CAG CAG CCC ATG GGC ATC     7867
 Asn Met Lys Leu Leu Arg Val Asp Ile Pro Gln Gln Pro Met Gly Ile
            2455                2460                2465

 ATC GCC GTG GCC AAC GAC ACC AAC AGC TGT GAA CTC TCT CCA TGC CGA     7915
 Ile Ala Val Ala Asn Asp Thr Asn Ser Cys Glu Leu Ser Pro Cys Arg
        2470                2475                2480

 ATC AAC AAC GGT GGC TGC CAG GAC CTG TGT CTG CTC ACT CAC CAG GGC     7963
 Ile Asn Asn Gly Gly Cys Gln Asp Leu Cys Leu Leu Thr His Gln Gly
    2485                2490                2495

 CAT GTC AAC TGC TCA TGC CGA GGG GGC CGA ATC CTC CAG GAT GAC CTC     8011
 His Val Asn Cys Ser Cys Arg Gly Gly Arg Ile Leu Gln Asp Asp Leu
2500                2505                2510                2515

 ACC TGC CGA GCG GTG AAT TCC TCT TGC CGA GCA CAA GAT GAG TTT GAG     8059
 Thr Cys Arg Ala Val Asn Ser Ser Cys Arg Ala Gln Asp Glu Phe Glu
                2520                2525                2530

 TGT GCC AAT GGC GAG TGC ATC AAC TTC AGC CTG ACC TGC GAC GGC GTC     8107
 Cys Ala Asn Gly Glu Cys Ile Asn Phe Ser Leu Thr Cys Asp Gly Val
            2535                2540                2545

 CCC CAC TGC AAG GAC AAG TCC GAT GAG AAG CCA TCC TAC TGC AAC TCC     8155
 Pro His Cys Lys Asp Lys Ser Asp Glu Lys Pro Ser Tyr Cys Asn Ser
        2550                2555                2560

 CGC CGC TGC AAG AAG ACT TTC CGG CAG TGC AGC AAT GGG CGC TGT GTG     8203
 Arg Arg Cys Lys Lys Thr Phe Arg Gln Cys Ser Asn Gly Arg Cys Val
    2565                2570                2575

 TCC AAC ATG CTG TGG TGC AAC GGG GCC GAC GAC TGT GGG GAT GGC TCT     8251
 Ser Asn Met Leu Trp Cys Asn Gly Ala Asp Asp Cys Gly Asp Gly Ser
2580                2585                2590                2595
```

FIG.8A-15

GAC GAG ATC CCT TGC AAC AAG ACA GCC TGT GGT GTG GGC GAG TTC CGC 8299
Asp Glu Ile Pro Cys Asn Lys Thr Ala Cys Gly Val Gly Glu Phe Arg
2600 2605 2610

TGC CGG GAC GGG ACC TGC ATC GGG AAC TCC AGC CGC TGC AAC CAG TTT 8347
Cys Arg Asp Gly Thr Cys Ile Gly Asn Ser Ser Arg Cys Asn Gln Phe
2615 2620 2625

GTG GAT TGT GAG GAC GCC TCA GAT GAG ATG AAC TGC AGT GCC ACC GAC 8395
Val Asp Cys Glu Asp Ala Ser Asp Glu Met Asn Cys Ser Ala Thr Asp
2630 2635 2640

TGC AGC AGC TAC TTC CGC CTG GGC GTG AAG GGC GTG CTC TTC CAG CCC 8443
Cys Ser Ser Tyr Phe Arg Leu Gly Val Lys Gly Val Leu Phe Gln Pro
2645 2650 2655

TGC GAG CGG ACC TCA CTC TGC TAC GCA CCC AGC TGG GTG TGT GAT GGC 8491
Cys Glu Arg Thr Ser Leu Cys Tyr Ala Pro Ser Trp Val Cys Asp Gly
2660 2665 2670 2675

GCC AAT GAC TGT GGG GAC TAC AGT GAT GAG CGC GAC TGC CCA GGT GTG 8539
Ala Asn Asp Cys Gly Asp Tyr Ser Asp Glu Arg Asp Cys Pro Gly Val
2680 2685 2690

AAA CGC CCC AGA TGC CCT CTG AAT TAC TTC GCC TGC CCT AGT GGG CGC 8587
Lys Arg Pro Arg Cys Pro Leu Asn Tyr Phe Ala Cys Pro Ser Gly Arg
2695 2700 2705

TGC ATC CCC ATG AGC TGG ACG TGT GAC AAA GAG GAT GAC TGT GAA CAT 8635
Cys Ile Pro Met Ser Trp Thr Cys Asp Lys Glu Asp Asp Cys Glu His
2710 2715 2720

GGC GAG GAC GAG ACC CAC TGC AAC AAG TTC TGC TCA GAG GCC CAG TTT 8683
Gly Glu Asp Glu Thr His Cys Asn Lys Phe Cys Ser Glu Ala Gln Phe
2725 2730 2735

GAG TGC CAG AAC CAT CGC TGC ATC TCC AAG CAG TGG CTG TGT GAC GGC 8731
Glu Cys Gln Asn His Arg Cys Ile Ser Lys Gln Trp Leu Cys Asp Gly
2740 2745 2750 2755

AGC GAT GAC TGT GGG GAT GGC TCA GAC GAG GCT GCT CAC TGT GAA GGC 8779
Ser Asp Asp Cys Gly Asp Gly Ser Asp Glu Ala Ala His Cys Glu Gly
2760 2765 2770

FIG.8A-16

```
AAG ACG TGC GGC CCC TCC TCC TTC TCC TGC CCT GGC ACC CAC GTG TGC      8827
Lys Thr Cys Gly Pro Ser Ser Phe Ser Cys Pro Gly Thr His Val Cys
            2775                2780                2785

GTC CCC GAG CGC TGG CTC TGT GAC GGT GAC AAA GAC TGT GCT GAT GGT      8875
Val Pro Glu Arg Trp Leu Cys Asp Gly Asp Lys Asp Cys Ala Asp Gly
        2790                2795                2800

GCA GAC GAG AGC ATC GCA GCT GGT TGC TTG TAC AAC AGC ACT TGT GAC      8923
Ala Asp Glu Ser Ile Ala Ala Gly Cys Leu Tyr Asn Ser Thr Cys Asp
    2805                2810                2815

GAC CGT GAG TTC ATG TGC CAG AAC CGC CAG TGC ATC CCC AAG CAC TTC      8971
Asp Arg Glu Phe Met Cys Gln Asn Arg Gln Cys Ile Pro Lys His Phe
2820                2825                2830                2835

GTG TGT GAC CAC GAC CGT GAC TGT GCA GAT GGC TCT GAT GAG TCC CCC      9019
Val Cys Asp His Asp Arg Asp Cys Ala Asp Gly Ser Asp Glu Ser Pro
                2840                2845                2850

GAG TGT GAG TAC CCG ACC TGC GGC CCC AGT GAG TTC CGC TGT GCC AAT      9067
Glu Cys Glu Tyr Pro Thr Cys Gly Pro Ser Glu Phe Arg Cys Ala Asn
            2855                2860                2865

GGG CGC TGT CTG AGC TCC CGC CAG TGG GAG TGT GAT GGC GAG AAT GAC      9115
Gly Arg Cys Leu Ser Ser Arg Gln Trp Glu Cys Asp Gly Glu Asn Asp
        2870                2875                2880

TGC CAC GAC CAG AGT GAC GAG GCT CCC AAG AAC CCA CAC TGC ACC AGC      9163
Cys His Asp Gln Ser Asp Glu Ala Pro Lys Asn Pro His Cys Thr Ser
    2885                2890                2895

CCA GAG CAC AAG TGC AAT GCC TCG TCA CAG TTC CTG TGC AGC AGT GGG      9211
Pro Glu His Lys Cys Asn Ala Ser Ser Gln Phe Leu Cys Ser Ser Gly
2900                2905                2910                2915

CGC TGT GTG GCT GAG GCA CTG CTC TGC AAC GGC CAG GAT GAC TGT GGC      9259
Arg Cys Val Ala Glu Ala Leu Leu Cys Asn Gly Gln Asp Asp Cys Gly
                2920                2925                2930

GAC AGC TCG GAC GAG CGT GGC TGC CAC ATC AAT GAG TGT CTC AGC CGC      9307
Asp Ser Ser Asp Glu Arg Gly Cys His Ile Asn Glu Cys Leu Ser Arg
            2935                2940                2945
```

FIG.8A-17

```
AAG CTC AGT GGC TGC AGC CAG GAC TGT GAG GAC CTC AAG ATC GGC TTC      9355
Lys Leu Ser Gly Cys Ser Gln Asp Cys Glu Asp Leu Lys Ile Gly Phe
        2950                2955                2960

AAG TGC CGC TGT CGC CCT GGC TTC CGG CTG AAG GAT GAC GGC CGG ACG      9403
Lys Cys Arg Cys Arg Pro Gly Phe Arg Leu Lys Asp Asp Gly Arg Thr
    2965                2970                2975

TGT GCT GAT GTG GAC GAG TGC AGC ACC ACC TTC CCC TGC AGC CAG CGC      9451
Cys Ala Asp Val Asp Glu Cys Ser Thr Thr Phe Pro Cys Ser Gln Arg
2980                2985                2990                2995

TGC ATC AAC ACC CAT GGC AGC TAT AAG TGT CTG TGT GTG GAG GGC TAT      9499
Cys Ile Asn Thr His Gly Ser Tyr Lys Cys Leu Cys Val Glu Gly Tyr
                3000                3005                3010

GCA CCC CGC GGC GGC GAC CCC CAC AGC TGC AAG GCT GTG ACT GAC GAG      9547
Ala Pro Arg Gly Gly Asp Pro His Ser Cys Lys Ala Val Thr Asp Glu
            3015                3020                3025

GAA CCG TTT CTG ATC TTC GCC AAC CGG TAC TAC CTG CGC AAG CTC AAC      9595
Glu Pro Phe Leu Ile Phe Ala Asn Arg Tyr Tyr Leu Arg Lys Leu Asn
        3030                3035                3040

CTG GAC GGG TCC AAC TAC ACG TTA CTT AAG CAG GGC CTG AAC AAC GCC      9643
Leu Asp Gly Ser Asn Tyr Thr Leu Leu Lys Gln Gly Leu Asn Asn Ala
    3045                3050                3055

GTT GCC TTG GAT TTT GAC TAC CGA GAG CAG ATG ATC TAC TGG ACA GAT      9691
Val Ala Leu Asp Phe Asp Tyr Arg Glu Gln Met Ile Tyr Trp Thr Asp
3060                3065                3070                3075

GTG ACC ACC CAG GGC AGC ATG ATC CGA AGG ATG CAC CTT AAC GGG AGC      9739
Val Thr Thr Gln Gly Ser Met Ile Arg Arg Met His Leu Asn Gly Ser
                3080                3085                3090

AAT GTG CAG GTC CTA CAC CGT ACA GGC CTC AGC AAC CCC GAT GGG CTG      9787
Asn Val Gln Val Leu His Arg Thr Gly Leu Ser Asn Pro Asp Gly Leu
            3095                3100                3105

GCT GTG GAC TGG GTG GGT GGC AAC CTG TAC TGG TGC GAC AAA GGC CGG      9835
Ala Val Asp Trp Val Gly Gly Asn Leu Tyr Trp Cys Asp Lys Gly Arg
        3110                3115                3120
```

FIG.8A-18

```
GAC ACC ATC GAG GTG TCC AAG CTC AAT GGG GCC TAT CGG ACG GTG CTG     9883
Asp Thr Ile Glu Val Ser Lys Leu Asn Gly Ala Tyr Arg Thr Val Leu
    3125                3130                3135

GTC AGC TCT GGC CTC CGT GAG CCC AGG GCT CTG GTG GTG GAT GTG CAG     9931
Val Ser Ser Gly Leu Arg Glu Pro Arg Ala Leu Val Val Asp Val Gln
3140                3145                3150                3155

AAT GGG TAC CTG TAC TGG ACA GAC TGG GGT GAC CAT TCA CTG ATC GGC     9979
Asn Gly Tyr Leu Tyr Trp Thr Asp Trp Gly Asp His Ser Leu Ile Gly
                3160                3165                3170

CGC ATC GGC ATG GAT GGG TCC AGC CGC AGC GTC ATC GTG GAC ACC AAG    10027
Arg Ile Gly Met Asp Gly Ser Ser Arg Ser Val Ile Val Asp Thr Lys
            3175                3180                3185

ATC ACA TGG CCC AAT GGC CTG ACG CTG GAC TAT GTC ACT GAG CGC ATC    10075
Ile Thr Trp Pro Asn Gly Leu Thr Leu Asp Tyr Val Thr Glu Arg Ile
        3190                3195                3200

TAC TGG GCC GAC GCC CGC GAG GAC TAC ATT GAA TTT GCC AGC CTG GAT    10123
Tyr Trp Ala Asp Ala Arg Glu Asp Tyr Ile Glu Phe Ala Ser Leu Asp
    3205                3210                3215

GGC TCC AAT CGC CAC GTT GTG CTG AGC CAG GAC ATC CCG CAC ATC TTT    10171
Gly Ser Asn Arg His Val Val Leu Ser Gln Asp Ile Pro His Ile Phe
3220                3225                3230                3235

GCA CTG ACC CTG TTT GAG GAC TAC GTC TAC TGG ACC GAC TGG GAA ACA    10219
Ala Leu Thr Leu Phe Glu Asp Tyr Val Tyr Trp Thr Asp Trp Glu Thr
                3240                3245                3250

AAG TCC ATT AAC CGA GCC CAC AAG ACC ACG GGC ACC AAC AAA ACG CTC    10267
Lys Ser Ile Asn Arg Ala His Lys Thr Thr Gly Thr Asn Lys Thr Leu
            3255                3260                3265

CTC ATC AGC ACG CTG CAC CGG CCC ATG GAC CTG CAT GTC TTC CAT GCC    10315
Leu Ile Ser Thr Leu His Arg Pro Met Asp Leu His Val Phe His Ala
        3270                3275                3280

CTG CGC CAG CCA GAC GTG CCC AAT CAC CCC TGC AAG GTC AAC AAT GGT    10363
Leu Arg Gln Pro Asp Val Pro Asn His Pro Cys Lys Val Asn Asn Gly
    3285                3290                3295
```

FIG.8A-19

```
GGC TGC AGC AAC CTG TGC CTG CTG TCC CCC GGG GGA GGG CAC AAA TGT   10411
Gly Cys Ser Asn Leu Cys Leu Leu Ser Pro Gly Gly Gly His Lys Cys
3300                3305                3310                3315

GCC TGC CCC ACC AAC TTC TAC CTG GGC AGC GAT GGG CGC ACC TGT GTG   10459
Ala Cys Pro Thr Asn Phe Tyr Leu Gly Ser Asp Gly Arg Thr Cys Val
                3320                3325                3330

TCC AAC TGC ACG GCT AGC CAG TTT GTA TGC AAG AAC GAC AAG TGC ATC   10507
Ser Asn Cys Thr Ala Ser Gln Phe Val Cys Lys Asn Asp Lys Cys Ile
            3335                3340                3345

CCC TTC TGG TGG AAG TGT GAC ACC GAG GAC GAC TGC GGG GAC CAC TCA   10555
Pro Phe Trp Trp Lys Cys Asp Thr Glu Asp Asp Cys Gly Asp His Ser
        3350                3355                3360

GAC GAG CCC CCG GAC TGC CCT GAG TTC AAG TGC CGG CCC GGA CAG TTC   10603
Asp Glu Pro Pro Asp Cys Pro Glu Phe Lys Cys Arg Pro Gly Gln Phe
    3365                3370                3375

CAG TGC TCC ACA GGT ATC TGC ACA AAC CCT GCC TTC ATC TGC GAT GGC   10651
Gln Cys Ser Thr Gly Ile Cys Thr Asn Pro Ala Phe Ile Cys Asp Gly
3380                3385                3390                3395

GAC AAT GAC TGC CAG GAC AAC AGT GAC GAG GCC AAC TGT GAC ATC CAC   10699
Asp Asn Asp Cys Gln Asp Asn Ser Asp Glu Ala Asn Cys Asp Ile His
                3400                3405                3410

GTC TGC TTG CCC AGT CAG TTC AAA TGC ACC AAC ACC AAC CGC TGT ATT   10747
Val Cys Leu Pro Ser Gln Phe Lys Cys Thr Asn Thr Asn Arg Cys Ile
            3415                3420                3425

CCC GGC ATC TTC CGC TGC AAT GGG CAG GAC AAC TGC GGA GAT GGG GAG   10795
Pro Gly Ile Phe Arg Cys Asn Gly Gln Asp Asn Cys Gly Asp Gly Glu
        3430                3435                3440

GAT GAG AGG GAC TGC CCC GAG GTG ACC TGC GCC CCC AAC CAG TTC CAG   10843
Asp Glu Arg Asp Cys Pro Glu Val Thr Cys Ala Pro Asn Gln Phe Gln
    3445                3450                3455

TGC TCC ATT ACC AAA CGG TGC ATC CCC CGG GTC TGG GTC TGC GAC CGG   10891
Cys Ser Ile Thr Lys Arg Cys Ile Pro Arg Val Trp Val Cys Asp Arg
3460                3465                3470                3475
```

FIG.8A-20

GAC AAT GAC TGT GTG GAT GGC AGT GAT GAG CCC GCC AAC TGC ACC CAG 10939
Asp Asn Asp Cys Val Asp Gly Ser Asp Glu Pro Ala Asn Cys Thr Gln
3480 3485 3490

ATG ACC TGT GGT GTG GAC GAG TTC CGC TGC AAG GAT TCG GGC CGC TGC 10987
Met Thr Cys Gly Val Asp Glu Phe Arg Cys Lys Asp Ser Gly Arg Cys
3495 3500 3505

ATC CCA GCG CGT TGG AAG TGT GAC GGA GAG GAT GAC TGT GGG GAT GGC 11035
Ile Pro Ala Arg Trp Lys Cys Asp Gly Glu Asp Asp Cys Gly Asp Gly
3510 3515 3520

TCG GAT GAG CCC AAG GAA GAG TGT GAT GAA CGC ACC TGT GAG CCA TAC 11083
Ser Asp Glu Pro Lys Glu Glu Cys Asp Glu Arg Thr Cys Glu Pro Tyr
3525 3530 3535

CAG TTC CGC TGC AAG AAC AAC CGC TGC GTG CCC GGC CGC TGG CAG TGC 11131
Gln Phe Arg Cys Lys Asn Asn Arg Cys Val Pro Gly Arg Trp Gln Cys
3540 3545 3550 3555

GAC TAC GAC AAC GAT TGC GGT GAC AAC TCC GAT GAA GAG AGC TGC ACC 11179
Asp Tyr Asp Asn Asp Cys Gly Asp Asn Ser Asp Glu Glu Ser Cys Thr
3560 3565 3570

CCT CGG CCC TGC TCC GAG AGT GAG TTC TCC TGT GCC AAC GGC CGC TGC 11227
Pro Arg Pro Cys Ser Glu Ser Glu Phe Ser Cys Ala Asn Gly Arg Cys
3575 3580 3585

ATC GCG GGG CGC TGG AAA TGC GAT GGA GAC CAC GAC TGC GCG GAC GGC 11275
Ile Ala Gly Arg Trp Lys Cys Asp Gly Asp His Asp Cys Ala Asp Gly
3590 3595 3600

TCG GAC GAG AAA GAC TGC ACC CCC CGC TGT GAC ATG GAC CAG TTC CAG 11323
Ser Asp Glu Lys Asp Cys Thr Pro Arg Cys Asp Met Asp Gln Phe Gln
3605 3610 3615

TGC AAG AGC GGC CAC TGC ATC CCC CTG CGC TGG CGC TGT GAC GCA GAC 11371
Cys Lys Ser Gly His Cys Ile Pro Leu Arg Trp Arg Cys Asp Ala Asp
3620 3625 3630 3635

GCC GAC TGC ATG GAC GGC AGC GAC GAG GAG GCC TGC GGC ACT GGC GTG 11419
Ala Asp Cys Met Asp Gly Ser Asp Glu Glu Ala Cys Gly Thr Gly Val
3640 3645 3650

FIG.8A-21

CGG ACC TGC CCC CTG GAC GAG TTC CAG TGC AAC AAC ACC TTG TGC AAG 11467
Arg Thr Cys Pro Leu Asp Glu Phe Gln Cys Asn Asn Thr Leu Cys Lys
3655 3660 3665

CCG CTG GCC TGG AAG TGC GAT GGC GAG GAT GAC TGT GGG GAC AAC TCA 11515
Pro Leu Ala Trp Lys Cys Asp Gly Glu Asp Asp Cys Gly Asp Asn Ser
3670 3675 3680

GAT GAG AAC CCC GAG GAG TGT GCC CGG TTC GTG TGC CCT CCC AAC CGG 11563
Asp Glu Asn Pro Glu Glu Cys Ala Arg Phe Val Cys Pro Pro Asn Arg
3685 3690 3695

CCC TTC CGT TGC AAG AAT GAC CGC GTC TGT CTG TGG ATC GGG CGC CAA 11611
Pro Phe Arg Cys Lys Asn Asp Arg Val Cys Leu Trp Ile Gly Arg Gln
3700 3705 3710 3715

TGC GAT GGC ACG GAC AAC TGT GGG GAT GGG ACT GAT GAA GAG GAC TGT 11659
Cys Asp Gly Thr Asp Asn Cys Gly Asp Gly Thr Asp Glu Glu Asp Cys
3720 3725 3730

GAG CCC CCC ACA GCC CAC ACC ACC CAC TGC AAA GAC AAG AAG GAG TTT 11707
Glu Pro Pro Thr Ala His Thr Thr His Cys Lys Asp Lys Lys Glu Phe
3735 3740 3745

CTG TGC CGG AAC CAG CGC TGC CTC TCC TCC TCC CTG CGC TGC AAC ATG 11755
Leu Cys Arg Asn Gln Arg Cys Leu Ser Ser Ser Leu Arg Cys Asn Met
3750 3755 3760

TTC GAT GAC TGC GGG GAC GGC TCT GAC GAG GAG GAC TGC AGC ATC GAC 11803
Phe Asp Asp Cys Gly Asp Gly Ser Asp Glu Glu Asp Cys Ser Ile Asp
3765 3770 3775

CCC AAG CTG ACC AGC TGC GCC ACC AAT GCC AGC ATC TGT GGG GAC GAG 11851
Pro Lys Leu Thr Ser Cys Ala Thr Asn Ala Ser Ile Cys Gly Asp Glu
3780 3785 3790 3795

GCA CGC TGC GTG CGC ACC GAG AAA GCG GCC TAC TGT GCC TGC CGC TCG 11899
Ala Arg Cys Val Arg Thr Glu Lys Ala Ala Tyr Cys Ala Cys Arg Ser
3800 3805 3810

GGC TTC CAC ACC GTG CCC GGC CAG CCC GGA TGC CAA GAC ATC AAC GAG 11947
Gly Phe His Thr Val Pro Gly Gln Pro Gly Cys Gln Asp Ile Asn Glu
3815 3820 3825

FIG.8A-22

TGC CTG CGC TTC GGC ACC TGC TCC CAG CTC TGC AAC AAC ACC AAG GGC 11995
Cys Leu Arg Phe Gly Thr Cys Ser Gln Leu Cys Asn Asn Thr Lys Gly
3830 3835 3840

GGC CAC CTC TGC AGC TGC GCT CGG AAC TTC ATG AAG ACG CAC AAC ACC 12043
Gly His Leu Cys Ser Cys Ala Arg Asn Phe Met Lys Thr His Asn Thr
3845 3850 3855

TGC AAG GCC GAA GGC TCT GAG TAC CAG GTC CTG TAC ATC GCT GAT GAC 12091
Cys Lys Ala Glu Gly Ser Glu Tyr Gln Val Leu Tyr Ile Ala Asp Asp
3860 3865 3870 3875

AAT GAG ATC CGC AGC CTG TTC CCC GGC CAC CCC CAT TCG GCT TAC GAG 12139
Asn Glu Ile Arg Ser Leu Phe Pro Gly His Pro His Ser Ala Tyr Glu
3880 3885 3890

CAG GCA TTC CAG GGT GAC GAG AGT GTC CGC ATT GAT GCT ATG GAT GTC 12187
Gln Ala Phe Gln Gly Asp Glu Ser Val Arg Ile Asp Ala Met Asp Val
3895 3900 3905

CAT GTC AAG GCT GGC CGT GTC TAT TGG ACC AAC TGG CAC ACG GGC ACC 12235
His Val Lys Ala Gly Arg Val Tyr Trp Thr Asn Trp His Thr Gly Thr
3910 3915 3920

ATC TCC TAC CGC AGC CTG CCA CCT GCT GCG CCT CCT ACC ACT TCC AAC 12283
Ile Ser Tyr Arg Ser Leu Pro Pro Ala Ala Pro Pro Thr Thr Ser Asn
3925 3930 3935

CGC CAC CGG CGA CAG ATT GAC CGG GGT GTC ACC CAC CTC AAC ATT TCA 12331
Arg His Arg Arg Gln Ile Asp Arg Gly Val Thr His Leu Asn Ile Ser
3940 3945 3950 3955

GGG CTG AAG ATG CCC AGA GGC ATC GCC ATC GAC TGG GTG GCC GGA AAC 12379
Gly Leu Lys Met Pro Arg Gly Ile Ala Ile Asp Trp Val Ala Gly Asn
3960 3965 3970

GTG TAC TGG ACC GAC TCG GGC CGA GAT GTG ATT GAG GTG GCG CAG ATG 12427
Val Tyr Trp Thr Asp Ser Gly Arg Asp Val Ile Glu Val Ala Gln Met
3975 3980 3985

AAG GGC GAG AAC CGC AAG ACG CTC ATC TCG GGC ATG ATT GAC GAG CCC 12475
Lys Gly Glu Asn Arg Lys Thr Leu Ile Ser Gly Met Ile Asp Glu Pro
3990 3995 4000

FIG.8A-23

CAC GCC ATT GTG GTG GAC CCA CTG AGG GGG ACC ATG TAC TGG TCA GAC 12523
His Ala Ile Val Val Asp Pro Leu Arg Gly Thr Met Tyr Trp Ser Asp
4005 4010 4015

TGG GGC AAC CAC CCC AAG ATT GAG ACG GCA GCG ATG GAT GGG ACG CTT 12571
Trp Gly Asn His Pro Lys Ile Glu Thr Ala Ala Met Asp Gly Thr Leu
4020 4025 4030 4035

CGG GAG ACA CTG GTG CAG GAC AAC ATT CAG TGG CCC ACA GGC CTG GCC 12619
Arg Glu Thr Leu Val Gln Asp Asn Ile Gln Trp Pro Thr Gly Leu Ala
4040 4045 4050

GTG GAT TAT CAC AAT GAG CGG CTG TAC TGG GCA GAC GCC AAG CTT TCA 12667
Val Asp Tyr His Asn Glu Arg Leu Tyr Trp Ala Asp Ala Lys Leu Ser
4055 4060 4065

GTC ATC GGC AGC ATC CGG CTC AAT GGC ACG GAC CCC ATT GTG GCT GCT 12715
Val Ile Gly Ser Ile Arg Leu Asn Gly Thr Asp Pro Ile Val Ala Ala
4070 4075 4080

GAC AGC AAA CGA GGC CTA AGT CAC CCC TTC AGC ATC GAC GTC TTT GAG 12763
Asp Ser Lys Arg Gly Leu Ser His Pro Phe Ser Ile Asp Val Phe Glu
4085 4090 4095

GAT TAC ATC TAT GGT GTC ACC TAC ATC AAT AAT CGT GTC TTC AAG ATC 12811
Asp Tyr Ile Tyr Gly Val Thr Tyr Ile Asn Asn Arg Val Phe Lys Ile
4100 4105 4110 4115

CAT AAG TTT GGC CAC AGC CCC TTG GTC AAC CTG ACA GGG GGC CTG AGC 12859
His Lys Phe Gly His Ser Pro Leu Val Asn Leu Thr Gly Gly Leu Ser
4120 4125 4130

CAC GCC TCT GAC GTG GTC CTT TAC CAT CAG CAC AAG CAG CCC GAA GTG 12907
His Ala Ser Asp Val Val Leu Tyr His Gln His Lys Gln Pro Glu Val
4135 4140 4145

ACC AAC CCA TGT GAC CGC AAG AAA TGC GAG TGG CTC TGC CTG CTG AGC 12955
Thr Asn Pro Cys Asp Arg Lys Lys Cys Glu Trp Leu Cys Leu Leu Ser
4150 4155 4160

CCC AGT GGG CCT GTC TGC ACC TGT CCC AAT GGG AAG CGG CTG GAC AAC 13003
Pro Ser Gly Pro Val Cys Thr Cys Pro Asn Gly Lys Arg Leu Asp Asn
4165 4170 4175

FIG.8A-24

GGC ACA TGC GTG CCT GTG CCC TCT CCA ACG CCC CCC CCA GAT GCT CCC 13051
Gly Thr Cys Val Pro Val Pro Ser Pro Thr Pro Pro Pro Asp Ala Pro
4180 4185 4190 4195

CGG CCT GGA ACC TGT AAC CTG CAG TGC TTC AAC GGT GGC AGC TGT TTC 13099
Arg Pro Gly Thr Cys Asn Leu Gln Cys Phe Asn Gly Gly Ser Cys Phe
4200 4205 4210

CTC AAT GCA CGG AGG CAG CCC AAG TGC CGC TGC CAA CCC CGC TAC ACG 13147
Leu Asn Ala Arg Arg Gln Pro Lys Cys Arg Cys Gln Pro Arg Tyr Thr
4215 4220 4225

GGT GAC AAG TGT GAA CTG GAC CAG TGC TGG GAG CAC TGT CGC AAT GGG 13195
Gly Asp Lys Cys Glu Leu Asp Gln Cys Trp Glu His Cys Arg Asn Gly
4230 4235 4240

GGC ACC TGT GCT GCC TCC CCC TCT GGC ATG CCC ACG TGC CGG TGC CCC 13243
Gly Thr Cys Ala Ala Ser Pro Ser Gly Met Pro Thr Cys Arg Cys Pro
4245 4250 4255

ACG GGC TTC ACG GGC CCC AAA TGC ACC CAG CAG GTG TGT GCG GGC TAC 13291
Thr Gly Phe Thr Gly Pro Lys Cys Thr Gln Gln Val Cys Ala Gly Tyr
4260 4265 4270 4275

TGT GCC AAC AAC AGC ACC TGC ACT GTC AAC CAG GGC AAC CAG CCC CAG 13339
Cys Ala Asn Asn Ser Thr Cys Thr Val Asn Gln Gly Asn Gln Pro Gln
4280 4285 4290

TGC CGA TGC CTA CCC GGC TTC CTG GGC GAC CGC TGC CAG TAC CGG CAG 13387
Cys Arg Cys Leu Pro Gly Phe Leu Gly Asp Arg Cys Gln Tyr Arg Gln
4295 4300 4305

TGC TCT GGC TAC TGT GAG AAC TTT GGC ACA TGC CAG ATG GCT GCT GAT 13435
Cys Ser Gly Tyr Cys Glu Asn Phe Gly Thr Cys Gln Met Ala Ala Asp
4310 4315 4320

GGC TCC CGA CAA TGC CGC TGC ACT GCC TAC TTT GAG GGA TCG AGG TGT 13483
Gly Ser Arg Gln Cys Arg Cys Thr Ala Tyr Phe Glu Gly Ser Arg Cys
4325 4330 4335

GAG GTG AAC AAG TGC AGC CGC TGT CTC GAA GGG GCC TGT GTG GTC AAC 13531
Glu Val Asn Lys Cys Ser Arg Cys Leu Glu Gly Ala Cys Val Val Asn
4340 4345 4350 4355

FIG.8A-25

AAG CAG AGT GGG GAT GTC ACC TGC AAC TGC ACG GAT GGC CGG GTG GCC 13579
Lys Gln Ser Gly Asp Val Thr Cys Asn Cys Thr Asp Gly Arg Val Ala
4360 4365 4370

CCC AGC TGT CTG ACC TGC GTC GGC CAC TGC AGC AAT GGC GGC TCC TGT 13627
Pro Ser Cys Leu Thr Cys Val Gly His Cys Ser Asn Gly Gly Ser Cys
4375 4380 4385

ACC ATG AAC AGC AAA ATG ATG CCT GAG TGC CAG TGC CCA CCC CAC ATG 13675
Thr Met Asn Ser Lys Met Met Pro Glu Cys Gln Cys Pro Pro His Met
4390 4395 4400

ACA GGG CCC CGG TGT GAG GAG CAC GTC TTC AGC CAG CAG CAG CCA GGA 13723
Thr Gly Pro Arg Cys Glu Glu His Val Phe Ser Gln Gln Gln Pro Gly
4405 4410 4415

CAT ATA GCC TCC ATC CTA ATC CCT CTG CTG TTG CTG CTG CTG CTG GTT 13771
His Ile Ala Ser Ile Leu Ile Pro Leu Leu Leu Leu Leu Leu Leu Val
4420 4425 4430 4435

CTG GTG GCC GGA GTG GTA TTC TGG TAT AAG CGG CGA GTC CAA GGG GCT 13819
Leu Val Ala Gly Val Val Phe Trp Tyr Lys Arg Arg Val Gln Gly Ala
4440 4445 4450

AAG GGC TTC CAG CAC CAA CGG ATG ACC AAC GGG GCC ATG AAC GTG GAG 13867
Lys Gly Phe Gln His Gln Arg Met Thr Asn Gly Ala Met Asn Val Glu
4455 4460 4465

ATT GGA AAC CCC ACC TAC AAG ATG TAC GAA GGC GGA GAG CCT GAT GAT 13915
Ile Gly Asn Pro Thr Tyr Lys Met Tyr Glu Gly Gly Glu Pro Asp Asp
4470 4475 4480

GTG GGA GGC CTA CTG GAC GCT GAC TTT GCC CTG GAC CCT GAC AAG CCC 13963
Val Gly Gly Leu Leu Asp Ala Asp Phe Ala Leu Asp Pro Asp Lys Pro
4485 4490 4495

ACC AAC TTC ACC AAC CCC GTG TAT GCC ACA CTC TAC ATG GGG GGC CAT 14011
Thr Asn Phe Thr Asn Pro Val Tyr Ala Thr Leu Tyr Met Gly Gly His
4500 4505 4510 4515

GGC AGT CGC CAC TCC CTG GCC AGC ACG GAC GAG AAG CGA GAA CTC CTG 14059
Gly Ser Arg His Ser Leu Ala Ser Thr Asp Glu Lys Arg Glu Leu Leu
4520 4525 4530

FIG.8A-26

GGC CGG GGC CCT GAG GAC GAG ATA GGG GAC CCC TTG GCA TAGGGCCCTG CC 14110
CCGTCGGACT GCCCCCAGAA AGCCTCCTGC CCCCTGCCGG TGAAGTCCTT CAGTGAGCCC 14170
Gly Arg Gly Pro Glu Asp Glu Ile Gly Asp Pro Leu Ala
4535 4540

CTCCCCAGCC AGCCCTTCCC TGGCCCCGCC GGATGTATAA ATGTAAAAAT GAAGGAATTA
14230
CATTTTATAT GTGAGCGAGC AAGCCGGCAA GCGAGCACAG TATTATTTCT CCATCCCCTC 14290
CCTGCCTGCT CCTTGGCACC CCCATGCTGC CTTCAGGGAG ACAGGCAGGG AGGGCTTGGG 14350
GCTGCACCTC CTACCCTCCC ACCAGAACGC ACCCCACTGG GAGAGCTGGT GGTGCAGCCT 14410
TCCCCTCCCT GTATAAGACA CTTTGCCAAG GCTCTCCCCT CTCGCCCCAT CCCTGCTTGC 14470
CCGCTCCCAC AGCTTCCTGA GGGCTAATTC TGGGAAGGGA GAGTTCTTTG CTGCCCCTGT 14530
CTGGAAGACG TGGCTCTGGG TGAGGTAGGC GGGAAAGGAT GGAGTGTTTT AGTTCTTGGG 14590
GGAGGCCACC CCAAACCCCA GCCCCAACTC CAGGGGCACC TATGAGATGG CCATGCTCAA 14650
CCCCCCTCCC AGACAGGCCC TCCCTGTCTC CAGGGCCCCC ACCGAGGTTC CCAGGGCTGG 14710
AGACTTCCTC TGGTAAACAT TCCTCCAGCC TCCCCTCCCC TGGGGACGCC AAGGAGGTGG 14770
GCCACACCCA GGAAGGGAAA GCGGGCAGCC CCGTTTTGGG GACGTGAACG TTTTAATAAT 14830
TTTTGCTGAA TTCTTTACAA CTAAATAACA CAGATATTCT TATAAATAAA ATTGTAAAAA 14890
AAAAAA 14896

FIG.8A-27

Met Leu Thr Pro Pro Leu Leu Leu Leu Leu Pro Leu Leu Ser Ala Leu
1 5 10 15
Val Ala Ala Ala Ile Asp Ala Pro Lys Thr Cys Ser Pro Lys Gln Phe
20 25 30
Ala Cys Arg Asp Gln Ile Thr Cys Ile Ser Lys Gly Trp Arg Cys Asp
35 40 45
Gly Glu Arg Asp Cys Pro Asp Gly Ser Asp Glu Ala Pro Glu Ile Cys
50 55 60
Pro Gln Ser Lys Ala Gln Arg Cys Gln Pro Asn Glu His Asn Cys Leu
65 70 75 80
Gly Thr Glu Leu Cys Val Pro Met Ser Arg Leu Cys Asn Gly Val Gln
85 90 95
Asp Cys Met Asp Gly Ser Asp Glu Gly Pro His Cys Arg Glu Leu Gln
100 105 110
Gly Asn Cys Ser Arg Leu Gly Cys Gln His His Cys Val Pro Thr Leu
115 120 125
Asp Gly Pro Thr Cys Tyr Cys Asn Ser Ser Phe Gln Leu Gln Ala Asp
130 135 140
Gly Lys Thr Cys Lys Asp Phe Asp Glu Cys Ser Val Tyr Gly Thr Cys
145 150 155 160
Ser Gln Leu Cys Thr Asn Thr Asp Gly Ser Phe Ile Cys Gly Cys Val
165 170 175
Glu Gly Tyr Leu Leu Gln Pro Asp Asn Arg Ser Cys Lys Ala Lys Asn
180 185 190
Glu Pro Val Asp Arg Pro Pro Val Leu Leu Ile Ala Asn Ser Gln Asn
195 200 205
Ile Leu Ala Thr Tyr Leu Ser Gly Ala Gln Val Ser Thr Ile Thr Pro
210 215 220
Thr Ser Thr Arg Gln Thr Thr Ala Met Asp Phe Ser Tyr Ala Asn Glu
225 230 235 240
Thr Val Cys Trp Val His Val Gly Asp Ser Ala Ala Gln Thr Gln Leu
245 250 255
Lys Cys Ala Arg Met Pro Gly Leu Lys Gly Phe Val Asp Glu His Thr
260 265 270
Ile Asn Ile Ser Leu Ser Leu His His Val Glu Gln Met Ala Ile Asp
275 280 285
Trp Leu Thr Gly Asn Phe Tyr Phe Val Asp Asp Ile Asp Asp Arg Ile
290 295 300
Phe Val Cys Asn Arg Asn Gly Asp Thr Cys Val Thr Leu Leu Asp Leu
305 310 315 320
Glu Leu Tyr Asn Pro Lys Gly Ile Ala Leu Asp Pro Ala Met Gly Lys
325 330 335
Val Phe Phe Thr Asp Tyr Gly Gln Ile Pro Lys Val Glu Arg Cys Asp
340 345 350
Met Asp Gly Gln Asn Arg Thr Lys Leu Val Asp Ser Lys Ile Val Phe
355 360 365
Pro His Gly Ile Thr Leu Asp Leu Val Ser Arg Leu Val Tyr Trp Ala
370 375 380
Asp Ala Tyr Leu Asp Tyr Ile Glu Val Val Asp Tyr Glu Gly Lys Gly
385 390 395 400
Arg Gln Thr Ile Ile Gln Gly Ile Leu Ile Glu His Leu Tyr Gly Leu
405 410 415

FIG.8B-1

Thr Val Phe Glu Asn Tyr Leu Tyr Ala Thr Asn Ser Asp Asn Ala Asn
420 425 430
Ala Gln Gln Lys Thr Ser Val Ile Arg Val Asn Arg Phe Asn Ser Thr
435 440 445
Glu Tyr Gln Val Val Thr Arg Val Asp Lys Gly Gly Ala Leu His Ile
450 455 460
Tyr His Gln Arg Arg Gln Pro Arg Val Arg Ser His Ala Cys Glu Asn
465 470 475 480
Asp Gln Tyr Gly Lys Pro Gly Gly Cys Ser Asp Ile Cys Leu Leu Ala
485 490 495
Asn Ser His Lys Ala Arg Thr Cys Arg Cys Arg Ser Gly Phe Ser Leu
500 505 510
Gly Ser Asp Gly Lys Ser Cys Lys Lys Pro Glu His Glu Leu Phe Leu
515 520 525
Val Tyr Gly Lys Gly Arg Pro Gly Ile Ile Arg Gly Met Asp Met Gly
530 535 540
Ala Lys Val Pro Asp Glu His Met Ile Pro Ile Glu Asn Leu Met Asn
545 550 555 560
Pro Arg Ala Leu Asp Phe His Ala Glu Thr Gly Phe Ile Tyr Phe Ala
565 570 575
Asp Thr Thr Ser Tyr Leu Ile Gly Arg Gln Lys Ile Asp Gly Thr Glu
580 585 590
Arg Glu Thr Ile Leu Lys Asp Gly Ile His Asn Val Glu Gly Val Ala
595 600 605
Val Asp Trp Met Gly Asp Asn Leu Tyr Trp Thr Asp Asp Gly Pro Lys
610 615 620
Lys Thr Ile Ser Val Ala Arg Leu Glu Lys Ala Ala Gln Thr Arg Lys
625 630 635 640
Thr Leu Ile Glu Gly Lys Met Thr His Pro Arg Ala Ile Val Val Asp
645 650 655
Pro Leu Asn Gly Trp Met Tyr Trp Thr Asp Trp Glu Glu Asp Pro Lys
660 665 670
Asp Ser Arg Arg Gly Arg Leu Glu Arg Ala Trp Met Asp Gly Ser His
675 680 685
Arg Asp Ile Phe Val Thr Ser Lys Thr Val Leu Trp Pro Asn Gly Leu
690 695 700
Ser Leu Asp Ile Pro Ala Gly Arg Leu Tyr Trp Val Asp Ala Phe Tyr
705 710 715 720
Asp Arg Ile Glu Thr Ile Leu Leu Asn Gly Thr Asp Arg Lys Ile Val
725 730 735
Tyr Glu Gly Pro Glu Leu Asn His Ala Phe Gly Leu Cys His His Gly
740 745 750
Asn Tyr Leu Phe Trp Thr Glu Tyr Arg Ser Gly Ser Val Tyr Arg Leu
755 760 765
Glu Arg Gly Val Gly Gly Ala Pro Pro Thr Val Thr Leu Leu Arg Ser
770 775 780
Glu Arg Pro Pro Ile Phe Glu Ile Arg Met Tyr Asp Ala Gln Gln Gln
785 790 795 800
Gln Val Gly Thr Asn Lys Cys Arg Val Asn Asn Gly Gly Cys Ser Ser
805 810 815
Leu Cys Leu Ala Thr Pro Gly Ser Arg Gln Cys Ala Cys Ala Glu Asp
820 825 830

FIG.8B-2

Gln Val Leu Asp Ala Asp Gly Val Thr Cys Leu Ala Asn Pro Ser Tyr
835 840 845
Val Pro Pro Pro *Gln Cys Gln Pro Gly Glu Phe Ala Cys Ala Asn Ser*
850 855 860
*Arg Cys Ile Gln Glu Arg Trp Lys Cys Asp Gly Asp Asn Asp Cys Leu*
865 870 875 880
*Asp Asn Ser Asp Glu Ala Pro Ala Leu Cys His Gln His* Thr Cys Pro
885 890 895
Ser Asp Arg Phe Lys Cys Glu Asn Asn Arg Cys Ile Pro Asn Arg Trp
900 905 910
Leu Cys Asp Gly Asp Asn Asp Cys Gly Asn Ser Glu Asp Glu Ser Asn
915 920 925
Ala Thr Cys Ser Ala Arg *Thr Cys Pro Pro Asn Gln Phe Ser Cys Ala*
930 935 940
*Ser Gly Arg Cys Ile Pro Ile Ser Trp Thr Cys Asp Leu Asp Asp Asp*
945 950 955 960
*Cys Gly Asp Arg Ser Asp Glu Ser Ala Ser Cys Ala Tyr Pro* Thr Cys
965 970 975
Phe Pro Leu Thr Gln Phe Thr Cys Asn Asn Gly Arg Cys Ile Asn Ile
980 985 990
Asn Trp Arg Cys Asp Asn Asp Asn Asp Cys Gly Asp Asn Ser Asp Glu
995 1000 1005
*Arg Pro Pro Gly* Gly Cys His Thr Asp Glu Phe Gln Cys Arg Leu Asp
1060 1065 1070
Gly Leu Cys Ile Pro Leu Arg Trp Arg Cys Asp Gly Asp Thr Asp Cys
1075 1080 1085
Met Asp Ser Ser Asp Glu Lys Ser Cys Glu Gly Val Thr His *Val Cys*
1090 1095 1100
*Asp Pro Ser Val Lys Phe Gly Cys Lys Asp Ser Ala Arg Cys Ile Ser*
105 1110 1115 1120
*Lys Ala Trp Val Cys Asp Gly Asp Asn Asp Cys Glu Asp Asn Ser Asp*
1125 1130 1135
*Glu Glu Asn Cys Glu Ser Leu* Ala Cys Arg Pro Pro Ser His Pro Cys
1140 1145 1150
Ala Asn Asn Thr Ser Val Cys Leu Pro Pro Asp Lys Leu Cys Asp Gly
1155 1160 1165
Asn Asp Asp Cys Gly Asp Gly Ser Asp Glu Gly Glu Leu Cys Asp Gln
1170 1175 1180
Cys Ser Leu Asn Asn Gly Gly Cys Ser His Asn Cys Ser Val Ala Pro
185 1190 1195 1200
Gly Glu Gly Ile Val Cys Ser Cys Pro Leu Gly Met Glu Leu Gly Pro
1205 1210 1215
Asp Asn His Thr Cys Gln Ile Gln Ser Tyr Cys Ala Lys His Leu Lys
1220 1225 1230
Cys Ser Gln Lys Cys Asp Gln Asn Lys Phe Ser Val Lys Cys Ser Cys
1235 1240 1245
Tyr Glu Gly Trp Val Leu Glu Pro Asp Gly Glu Ser Cys Arg Ser Leu
1250 1255 1260
Asp Pro Phe Lys Pro Phe Ile Ile Phe Ser Asn Arg His Glu Ile Arg
265 1270 1275 1280
Arg Ile Asp Leu His Lys Gly Asp Tyr Ser Val Leu Val Pro Gly Leu
1285 1290 1295

FIG.8B-3

Arg Asn Thr Ile Ala Leu Asp Phe His Leu Ser Gln Ser Ala Leu Tyr
1300 1305 1310
Trp Thr Asp Val Val Glu Asp Lys Ile Tyr Arg Gly Lys Leu Leu Asp
1315 1320 1325
Asn Gly Ala Leu Thr Ser Phe Glu Val Val Ile Gln Tyr Gly Leu Ala
1330 1335 1340
Thr Pro Glu Gly Leu Ala Val Asp Trp Ile Ala Gly Asn Ile Tyr Trp
345 1350 1355 1360
Val Glu Ser Asn Leu Asp Gln Ile Glu Val Ala Lys Leu Asp Gly Thr
1365 1370 1375
Leu Arg Thr Thr Leu Leu Ala Gly Asp Ile Glu His Pro Arg Ala Ile
1380 1385 1390
Ala Leu Asp Pro Arg Asp Gly Ile Leu Phe Trp Thr Asp Trp Asp Ala
1395 1400 1405
Ser Leu Pro Arg Ile Glu Ala Ala Ser Met Ser Gly Ala Gly Arg Arg
1410 1415 1420
Thr Val His Arg Glu Thr Gly Ser Gly Gly Trp Pro Asn Gly Leu Thr
425 1430 1435 1440
Val Asp Tyr Leu Glu Lys Arg Ile Leu Trp Ile Asp Ala Arg Ser Asp
1445 1450 1455
Ala Ile Tyr Ser Ala Arg Tyr Asp Gly Ser Gly His Met Glu Val Leu
1460 1465 1470
Arg Gly His Glu Phe Leu Ser His Pro Phe Ala Val Thr Leu Tyr Gly
1475 1480 1485
Gly Glu Val Tyr Trp Thr Asp Trp Arg Thr Asn Thr Leu Ala Lys Ala
1490 1495 1500
Asn Lys Trp Thr Gly His Asn Val Thr Val Val Gln Arg Thr Asn Thr
505 1510 1515 1520
Gln Pro Phe Asp Leu Gln Val Tyr His Pro Ser Arg Gln Pro Met Ala
1525 1530 1535
Pro Asn Pro Cys Glu Ala Asn Gly Gly Gln Gly Pro Cys Ser His Leu
1540 1545 1550
Cys Leu Ile Asn Tyr Asn Arg Thr Val Ser Cys Ala Cys Pro His Leu
1555 1560 1565
Met Lys Leu His Lys Asp Asn Thr Thr Cys Tyr Glu Phe Lys Lys Phe
1570 1575 1580
Leu Leu Tyr Ala Arg Gln Met Glu Ile Arg Gly Val Asp Leu Asp Ala
585 1590 1595 1600
Pro Tyr Tyr Asn Tyr Ile Ile Ser Phe Thr Val Pro Asp Ile Asp Asn
1605 1610 1615
Val Thr Val Leu Asp Tyr Asp Ala Arg Glu Gln Arg Val Tyr Trp Ser
1620 1625 1630
Asp Val Arg Thr Gln Ala Ile Lys Arg Ala Phe Ile Asn Gly Thr Gly
1635 1640 1645
Val Glu Thr Val Val Ser Ala Asp Leu Pro Asn Ala His Gly Leu Ala
1650 1655 1660
Val Asp Trp Val Ser Arg Asn Leu Phe Trp Thr Ser Tyr Asp Thr Asn
665 1670 1675 1680
Lys Lys Gln Ile Asn Val Ala Arg Leu Asp Gly Ser Phe Lys Asn Ala
1685 1690 1695
Val Val Gln Gly Leu Glu Gln Pro His Gly Leu Val Val His Pro Leu
1700 1705 1710

FIG.8B-4

Arg Gly Lys Leu Tyr Trp Thr Asp Gly Asp Asn Ile Ser Met Ala Asn
1715 1720 1725
Met Asp Gly Ser Asn Arg Thr Leu Leu Phe Ser Gly Gln Lys Gly Pro
1730 1735 1740
Val Gly Leu Ala Ile Asp Phe Pro Glu Ser Lys Leu Tyr Trp Ile Ser
745 1750 1755 1760
Ser Gly Asn His Thr Ile Asn Arg Cys Asn Leu Asp Gly Ser Gly Leu
1765 1770 1775
Glu Val Ile Asp Ala Met Arg Ser Gln Leu Gly Lys Ala Thr Ala Leu
1780 1785 1790
Ala Ile Met Gly Asp Lys Leu Trp Trp Ala Asp Gln Val Ser Glu Lys
1795 1800 1805
Met Gly Thr Cys Ser Lys Ala Asp Gly Ser Gly Ser Val Val Leu Arg
1810 1815 1820
Asn Ser Thr Thr Leu Val Met His Met Lys Val Tyr Asp Glu Ser Ile
825 1830 1835 1840
Gln Leu Asp His Lys Gly Thr Asn Pro Cys Ser Val Asn Asn Gly Asp
1845 1850 1855
Cys Ser Gln Leu Cys Leu Pro Thr Ser Glu Thr Thr Arg Ser Cys Met
1860 1865 1870
Cys Thr Ala Gly Tyr Ser Leu Arg Ser Gly Gln Gln Ala Cys Glu Gly
1875 1880 1885
Val Gly Ser Phe Leu Leu Tyr Ser Val His Glu Gly Ile Arg Gly Ile
1890 1895 1900
Pro Leu Asp Pro Asn Asp Lys Ser Asp Ala Leu Val Pro Val Ser Gly
905 1910 1915 1920
Thr Ser Leu Ala Val Gly Ile Asp Phe His Ala Glu Asn Asp Thr Ile
1925 1930 1935
Tyr Trp Val Asp Met Gly Leu Ser Thr Ile Ser Arg Ala Lys Arg Asp
1940 1945 1950
Gln Thr Trp Arg Glu Asp Val Val Thr Asn Gly Ile Gly Arg Val Glu
1955 1960 1965
Gly Ile Ala Val Asp Trp Ile Ala Gly Asn Ile Tyr Trp Thr Asp Gln
1970 1975 1980
Gly Phe Asp Val Ile Glu Val Ala Arg Leu Asn Gly Ser Phe Arg Tyr
985 1990 1995 2000
Val Val Ile Ser Gln Gly Leu Asp Lys Pro Arg Ala Ile Thr Val His
2005 2010 2015
Pro Glu Lys Gly Tyr Leu Phe Trp Thr Glu Trp Gly Gln Tyr Pro Arg
2020 2025 2030
Ile Glu Arg Ser Arg Leu Asp Gly Thr Glu Arg Val Val Leu Val Asn
2035 2040 2045
Val Ser Ile Ser Trp Pro Asn Gly Ile Ser Val Asp Tyr Gln Asp Gly
2050 2055 2060
Lys Leu Tyr Trp Cys Asp Ala Arg Thr Asp Lys Ile Glu Arg Ile Asp
065 2070 2075 2080
Leu Glu Thr Gly Glu Asn Arg Glu Val Val Leu Ser Ser Asn Asn Met
2085 2090 2095
Asp Met Phe Ser Val Ser Val Phe Glu Asp Phe Ile Tyr Trp Ser Asp
2100 2105 2110
Arg Thr His Ala Asn Gly Ser Ile Lys Arg Gly Ser Lys Asp Asn Ala
2115 2120 2125

FIG.8B-5

Thr Asp Ser Val Pro Leu Arg Thr Gly Ile Gly Val Gln Leu Lys Asp
2130 2135 2140
Ile Lys Val Phe Asn Arg Asp Arg Gln Lys Gly Thr Asn Val Cys Ala
145 2150 2155 2160
Val Ala Asn Gly Gly Cys Gln Gln Leu Cys Leu Tyr Arg Gly Arg Gly
2165 2170 2175
Gln Arg Ala Cys Ala Cys Ala His Gly Met Leu Ala Glu Asp Gly Ala
2180 2185 2190
Ser Cys Arg Glu Tyr Ala Gly Tyr Leu Leu Tyr Ser Glu Arg Thr Ile
2195 2200 2205
Leu Lys Ser Ile His Leu Ser Asp Glu Arg Asn Leu Asn Ala Pro Val
2210 2215 2220
Gln Pro Phe Glu Asp Pro Glu His Met Lys Asn Val Ile Ala Leu Ala
225 2230 2235 2240
Phe Asp Tyr Arg Ala Gly Thr Ser Pro Gly Thr Pro Asn Arg Ile Phe
2245 2250 2255
Phe Ser Asp Ile His Phe Gly Asn Ile Gln Gln Ile Asn Asp Asp Gly
2260 2265 2270
Ser Arg Arg Ile Thr Ile Val Glu Asn Val Gly Ser Val Glu Gly Leu
2275 2280 2285
Ala Tyr His Arg Gly Trp Asp Thr Leu Tyr Trp Thr Ser Tyr Thr Thr
2290 2295 2300
Ser Thr Ile Thr Arg His Thr Val Asp Gln Thr Arg Pro Gly Ala Phe
305 2310 2315 2320
Glu Arg Glu Thr Val Ile Thr Met Ser Gly Asp Asp His Pro Arg Ala
2325 2330 2335
Phe Val Leu Asp Glu Cys Gln Asn Leu Met Phe Trp Thr Asn Trp Asn
2340 2345 2350
Glu Gln His Pro Ser Ile Met Arg Ala Ala Leu Ser Gly Ala Asn Val
2355 2360 2365
Leu Thr Leu Ile Glu Lys Asp Ile Arg Thr Pro Asn Gly Leu Ala Ile
2370 2375 2380
Asp His Arg Ala Glu Lys Leu Tyr Phe Ser Asp Ala Thr Leu Asp Lys
385 2390 2395 2400
Ile Glu Arg Cys Glu Tyr Asp Gly Ser His Arg Tyr Val Ile Leu Lys
2405 2410 2415
Ser Glu Pro Val His Pro Phe Gly Leu Ala Val Tyr Gly Glu His Ile
2420 2425 2430
Phe Trp Thr Asp Trp Val Arg Arg Ala Val Gln Arg Ala Asn Lys His
2435 2440 2445
Val Gly Ser Asn Met Lys Leu Leu Arg Val Asp Ile Pro Gln Gln Pro
2450 2455 2460
Met Gly Ile Ile Ala Val Ala Asn Asp Thr Asn Ser Cys Glu Leu Ser
465 2470 2475 2480
Pro Cys Arg Ile Asn Asn Gly Gly Cys Gln Asp Leu Cys Leu Leu Thr
2485 2490 2495
His Gln Gly His Val Asn Cys Ser Cys Arg Gly Gly Arg Ile Leu Gln
2500 2505 2510
Asp Asp Leu Thr Cys Arg Ala Val Asn Ser Ser Cys Arg Ala Gln Asp
2515 2520 2525
Glu Phe Glu Cys Ala Asn Gly Glu Cys Ile Asn Phe Ser Leu Thr Cys
2530 2535 2540

FIG.8B-6

Asp Gly Val Pro His Cys Lys Asp Lys Ser Asp Glu Lys Pro Ser Tyr
545 2550 2555 2560
Cys Asn Ser Arg Arg Cys Lys Lys Thr Phe Arg Gln Cys Ser Asn Gly
2565 2570 2575
Arg Cys Val Ser Asn Met Leu Trp Cys Asn Gly Ala Asp Asp Cys Gly
2580 2585 2590
Asp Gly Ser Asp Glu Ile Pro Cys Asn Lys Thr Ala Cys Gly Val Gly
2595 2600 2605
Glu Phe Arg Cys Arg Asp Gly Thr Cys Ile Gly Asn Ser Ser Arg Cys
2610 2615 2620
Asn Gln Phe Val Asp Cys Glu Asp Ala Ser Asp Glu Met Asn Cys Ser
625 2630 2635 2640
Ala Thr Asp Cys Ser Ser Tyr Phe Arg Leu Gly Val Lys Gly Val Leu
2645 2650 2655
Phe Gln Pro Cys Glu Arg Thr Ser Leu Cys Tyr Ala Pro Ser Trp Val
2660 2665 2670
Cys Asp Gly Ala Asn Asp Cys Gly Asp Tyr Ser Asp Glu Arg Asp Cys
2675 2680 2685
Pro Gly Val Lys Arg Pro Arg Cys Pro Leu Asn Tyr Phe Ala Cys Pro
2690 2695 2700
Ser Gly Arg Cys Ile Pro Met Ser Trp Thr Cys Asp Lys Glu Asp Asp
705 2710 2715 2720
Cys Glu His Gly Glu Asp Glu Thr His Cys Asn Lys Phe Cys Ser Glu
2725 2730 2735
Ala Gln Phe Glu Cys Gln Asn His Arg Cys Ile Ser Lys Gln Trp Leu
2740 2745 2750
Cys Asp Gly Ser Asp Asp Cys Gly Asp Gly Ser Asp Glu Ala Ala His
2755 2760 2765
Cys Glu Gly Lys Thr Cys Gly Pro Ser Ser Phe Ser Cys Pro Gly Thr
2770 2775 2780
His Val Cys Val Pro Glu Arg Trp Leu Cys Asp Gly Asp Lys Asp Cys
785 2790 2795 2800
Ala Asp Gly Ala Asp Glu Ser Ile Ala Ala Gly Cys Leu Tyr Asn Ser
2805 2810 2815
Thr Cys Asp Asp Arg Glu Phe Met Cys Gln Asn Arg Gln Cys Ile Pro
2820 2825 2830
Lys His Phe Val Cys Asp His Asp Arg Asp Cys Ala Asp Gly Ser Asp
2835 2840 2845
Glu Ser Pro Glu Cys Glu Tyr Pro Thr Cys Gly Pro Ser Glu Phe Arg
2850 2855 2860
Cys Ala Asn Gly Arg Cys Leu Ser Ser Arg Gln Trp Glu Cys Asp Gly
865 2870 2875 2880
Glu Asn Asp Cys His Asp Gln Ser Asp Glu Ala Pro Lys Asn Pro His
2885 2890 2895
Cys Thr Ser Pro Glu His Lys Cys Asn Ala Ser Ser Gln Phe Leu Cys
2900 2905 2910
Ser Ser Gly Arg Cys Val Ala Glu Ala Leu Leu Cys Asn Gly Gln Asp
2915 2920 2925
Asp Cys Gly Asp Ser Ser Asp Glu Arg Gly Cys His Ile Asn Glu Cys
2930 2935 2940
Leu Ser Arg Lys Leu Ser Gly Cys Ser Gln Asp Cys Glu Asp Leu Lys
945 2950 2955 2960

FIG.8B-7

Ile Gly Phe Lys Cys Arg Cys Arg Pro Gly Phe Arg Leu Lys Asp Asp
2965 2970 2975
Gly Arg Thr Cys Ala Asp Val Asp Glu Cys Ser Thr Thr Phe Pro Cys
2980 2985 2990
Ser Gln Arg Cys Ile Asn Thr His Gly Ser Tyr Lys Cys Leu Cys Val
2995 3000 3005
Glu Gly Tyr Ala Pro Arg Gly Gly Asp Pro His Ser Cys Lys Ala Val
3010 3015 3020
Thr Asp Glu Glu Pro Phe Leu Ile Phe Ala Asn Arg Tyr Tyr Leu Arg
025 3030 3035 3040
Lys Leu Asn Leu Asp Gly Ser Asn Tyr Thr Leu Leu Lys Gln Gly Leu
3045 3050 3055
Asn Asn Ala Val Ala Leu Asp Phe Asp Tyr Arg Glu Gln Met Ile Tyr
3060 3065 3070
Trp Thr Asp Val Thr Thr Gln Gly Ser Met Ile Arg Arg Met His Leu
3075 3080 3085
Asn Gly Ser Asn Val Gln Val Leu His Arg Thr Gly Leu Ser Asn Pro
3090 3095 3100
Asp Gly Leu Ala Val Asp Trp Val Gly Gly Asn Leu Tyr Trp Cys Asp
105 3110 3115 3120
Lys Gly Arg Asp Thr Ile Glu Val Ser Lys Leu Asn Gly Ala Tyr Arg
3125 3130 3135
Thr Val Leu Val Ser Ser Gly Leu Arg Glu Pro Arg Ala Leu Val Val
3140 3145 3150
Asp Val Gln Asn Gly Tyr Leu Tyr Trp Thr Asp Trp Gly Asp His Ser
3155 3160 3165
Leu Ile Gly Arg Ile Gly Met Asp Gly Ser Ser Arg Ser Val Ile Val
3170 3175 3180
Asp Thr Lys Ile Thr Trp Pro Asn Gly Leu Thr Leu Asp Tyr Val Thr
185 3190 3195 3200
Glu Arg Ile Tyr Trp Ala Asp Ala Arg Glu Asp Tyr Ile Glu Phe Ala
3205 3210 3215
Ser Leu Asp Gly Ser Asn Arg His Val Val Leu Ser Gln Asp Ile Pro
3220 3225 3230
His Ile Phe Ala Leu Thr Leu Phe Glu Asp Tyr Val Tyr Trp Thr Asp
3235 3240 3245
Trp Glu Thr Lys Ser Ile Asn Arg Ala His Lys Thr Thr Gly Thr Asn
3250 3255 3260
Lys Thr Leu Leu Ile Ser Thr Leu His Arg Pro Met Asp Leu His Val
265 3270 3275 3280
Phe His Ala Leu Arg Gln Pro Asp Val Pro Asn His Pro Cys Lys Val
3285 3290 3295
Asn Asn Gly Gly Cys Ser Asn Leu Cys Leu Leu Ser Pro Gly Gly Gly
3300 3305 3310
His Lys Cys Ala Cys Pro Thr Asn Phe Tyr Leu Gly Ser Asp Gly Arg
3315 3320 3325
Thr Cys Val Ser Asn Cys Thr Ala Ser Gln Phe Val Cys Lys Asn Asp
3330 3335 3340
Lys Cys Ile Pro Phe Trp Trp Lys Cys Asp Thr Glu Asp Asp Cys Gly
345 3350 3355 3360
Asp His Ser Asp Glu Pro Pro Asp Cys Pro Glu Phe Lys Cys Arg Pro
3365 3370 3375

FIG.8B-8

```
Gly Gln Phe Gln Cys Ser Thr Gly Ile Cys Thr Asn Pro Ala Phe Ile
            3380                3385                3390
Cys Asp Gly Asp Asn Asp Cys Gln Asp Asn Ser Asp Glu Ala Asn Cys
        3395                3400                3405
Asp Ile His Val Cys Leu Pro Ser Gln Phe Lys Cys Thr Asn Thr Asn
    3410                3415                3420
Arg Cys Ile Pro Gly Ile Phe Arg Cys Asn Gly Gln Asp Asn Cys Gly
425                 3430                3435                3440
Asp Gly Glu Asp Glu Arg Asp Cys Pro Glu Val Thr Cys Ala Pro Asn
                3445                3450                3455
Gln Phe Gln Cys Ser Ile Thr Lys Arg Cys Ile Pro Arg Val Trp Val
            3460                3465                3470
Cys Asp Arg Asp Asn Asp Cys Val Asp Gly Ser Asp Glu Pro Ala Asn
        3475                3480                3485
Cys Thr Gln Met Thr Cys Gly Val Asp Glu Phe Arg Cys Lys Asp Ser
    3490                3495                3500
Gly Arg Cys Ile Pro Ala Arg Trp Lys Cys Asp Gly Glu Asp Asp Cys
505                 3510                3515                3520
Gly Asp Gly Ser Asp Glu Pro Lys Glu Glu Cys Asp Glu Arg Thr Cys
                3525                3530                3535
Glu Pro Tyr Gln Phe Arg Cys Lys Asn Asn Arg Cys Val Pro Gly Arg
            3540                3545                3550
Trp Gln Cys Asp Tyr Asp Asn Asp Cys Gly Asp Asn Ser Asp Glu Glu
        3555                3560                3565
Ser Cys Thr Pro Arg Pro Cys Ser Glu Ser Glu Phe Ser Cys Ala Asn
    3570                3575                3580
Gly Arg Cys Ile Ala Gly Arg Trp Lys Cys Asp Gly Asp His Asp Cys
585                 3590                3595                3600
Ala Asp Gly Ser Asp Glu Lys Asp Cys Thr Pro Arg Cys Asp Met Asp
                3605                3610                3615
Gln Phe Gln Cys Lys Ser Gly His Cys Ile Pro Leu Arg Trp Arg Cys
            3620                3625                3630
Asp Ala Asp Ala Asp Cys Met Asp Gly Ser Asp Glu Glu Ala Cys Gly
        3635                3640                3645
Thr Gly Val Arg Thr Cys Pro Leu Asp Glu Phe Gln Cys Asn Asn Thr
    3650                3655                3660
Leu Cys Lys Pro Leu Ala Trp Lys Cys Asp Gly Glu Asp Asp Cys Gly
665                 3670                3675                3680
Asp Asn Ser Asp Glu Asn Pro Glu Glu Cys Ala Arg Phe Val Cys Pro
                3685                3690                3695
Pro Asn Arg Pro Phe Arg Cys Lys Asn Asp Arg Val Cys Leu Trp Ile
            3700                3705                3710
Gly Arg Gln Cys Asp Gly Thr Asp Asn Cys Gly Asp Gly Thr Asp Glu
        3715                3720                3725
Glu Asp Cys Glu Pro Pro Thr Ala His Thr Thr His Cys Lys Asp Lys
    3730                3735                3740
Lys Glu Phe Leu Cys Arg Asn Gln Arg Cys Leu Ser Ser Ser Leu Arg
745                 3750                3755                3760
Cys Asn Met Phe Asp Asp Cys Gly Asp Gly Ser Asp Glu Glu Asp Cys
                3765                3770                3775
Ser Ile Asp Pro Lys Leu Thr Ser Cys Ala Thr Asn Ala Ser Ile Cys
            3780                3785                3790
```

FIG.8B-9

Gly Asp Glu Ala Arg Cys Val Arg Thr Glu Lys Ala Ala Tyr Cys Ala
3795 3800 3805
Cys Arg Ser Gly Phe His Thr Val Pro Gly Gln Pro Gly Cys Gln Asp
3810 3815 3820
Ile Asn Glu Cys Leu Arg Phe Gly Thr Cys Ser Gln Leu Cys Asn Asn
825 3830 3835 3840
Thr Lys Gly Gly His Leu Cys Ser Cys Ala Arg Asn Phe Met Lys Thr
3845 3850 3855
His Asn Thr Cys Lys Ala Glu Gly Ser Glu Tyr Gln Val Leu Tyr Ile
3860 3865 3870
Ala Asp Asp Asn Glu Ile Arg Ser Leu Phe Pro Gly His Pro His Ser
3875 3880 3885
Ala Tyr Glu Gln Ala Phe Gln Gly Asp Glu Ser Val Arg Ile Asp Ala
3890 3895 3900
Met Asp Val His Val Lys Ala Gly Arg Val Tyr Trp Thr Asn Trp His
905 3910 3915 3920
Thr Gly Thr Ile Ser Tyr Arg Ser Leu Pro Pro Ala Ala Pro Pro Thr
3925 3930 3935
Thr Ser Asn Arg His Arg Arg Gln Ile Asp Arg Gly Val Thr His Leu
3940 3945 3950
Asn Ile Ser Gly Leu Lys Met Pro Arg Gly Ile Ala Ile Asp Trp Val
3955 3960 3965
Ala Gly Asn Val Tyr Trp Thr Asp Ser Gly Arg Asp Val Ile Glu Val
3970 3975 3980
Ala Gln Met Lys Gly Glu Asn Arg Lys Thr Leu Ile Ser Gly Met Ile
985 3990 3995 4000
Asp Glu Pro His Ala Ile Val Val Asp Pro Leu Arg Gly Thr Met Tyr
4005 4010 4015
Trp Ser Asp Trp Gly Asn His Pro Lys Ile Glu Thr Ala Ala Met Asp
4020 4025 4030
Gly Thr Leu Arg Glu Thr Leu Val Gln Asp Asn Ile Gln Trp Pro Thr
4035 4040 4045
Gly Leu Ala Val Asp Tyr His Asn Glu Arg Leu Tyr Trp Ala Asp Ala
4050 4055 4060
Lys Leu Ser Val Ile Gly Ser Ile Arg Leu Asn Gly Thr Asp Pro Ile
065 4070 4075 4080
Val Ala Ala Asp Ser Lys Arg Gly Leu Ser His Pro Phe Ser Ile Asp
4085 4090 4095
Val Phe Glu Asp Tyr Ile Tyr Gly Val Thr Tyr Ile Asn Asn Arg Val
4100 4105 4110
Phe Lys Ile His Lys Phe Gly His Ser Pro Leu Val Asn Leu Thr Gly
4115 4120 4125
Gly Leu Ser His Ala Ser Asp Val Val Leu Tyr His Gln His Lys Gln
4130 4135 4140
Pro Glu Val Thr Asn Pro Cys Asp Arg Lys Lys Cys Glu Trp Leu Cys
145 4150 4155 4160
Leu Leu Ser Pro Ser Gly Pro Val Cys Thr Cys Pro Asn Gly Lys Arg
4165 4170 4175
Leu Asp Asn Gly Thr Cys Val Pro Val Pro Ser Pro Thr Pro Pro Pro
4180 4185 4190
Asp Ala Pro Arg Pro Gly Thr Cys Asn Leu Gln Cys Phe Asn Gly Gly
4195 4200 4205

FIG.8B-10

Ser Cys Phe Leu Asn Ala Arg Arg Gln Pro Lys Cys Arg Cys Gln Pro
4210 4215 4220
Arg Tyr Thr Gly Asp Lys Cys Glu Leu Asp Gln Cys Trp Glu His Cys
225 4230 4235 4240
Arg Asn Gly Gly Thr Cys Ala Ala Ser Pro Ser Gly Met Pro Thr Cys
4245 4250 4255
Arg Cys Pro Thr Gly Phe Thr Gly Pro Lys Cys Thr Gln Gln Val Cys
4260 4265 4270
Ala Gly Tyr Cys Ala Asn Asn Ser Thr Cys Thr Val Asn Gln Gly Asn
4275 4280 4285
Gln Pro Gln Cys Arg Cys Leu Pro Gly Phe Leu Gly Asp Arg Cys Gln
4290 4295 4300
Tyr Arg Gln Cys Ser Gly Tyr Cys Glu Asn Phe Gly Thr Cys Gln Met
305 4310 4315 4320
Ala Ala Asp Gly Ser Arg Gln Cys Arg Cys Thr Ala Tyr Phe Glu Gly
4325 4330 4335
Ser Arg Cys Glu Val Asn Lys Cys Ser Arg Cys Leu Glu Gly Ala Cys
4340 4345 4350
Val Val Asn Lys Gln Ser Gly Asp Val Thr Cys Asn Cys Thr Asp Gly
4355 4360 4365
Arg Val Ala Pro Ser Cys Leu Thr Cys Val Gly His Cys Ser Asn Gly
4370 4375 4380
Gly Ser Cys Thr Met Asn Ser Lys Met Met Pro Glu Cys Gln Cys Pro
385 4390 4395 4400
Pro His Met Thr Gly Pro Arg Cys Glu Glu His Val Phe Ser Gln Gln
4405 4410 4415
Gln Pro Gly His Ile Ala Ser Ile Leu Ile Pro Leu Leu Leu Leu Leu
4420 4425 4430
Leu Leu Val Leu Val Ala Gly Val Val Phe Trp Tyr Lys Arg Arg Val
4435 4440 4445
Gln Gly Ala Lys Gly Phe Gln His Gln Arg Met Thr Asn Gly Ala Met
4450 4455 4460
Asn Val Glu Ile Gly Asn Pro Thr Tyr Lys Met Tyr Glu Gly Gly Glu
465 4470 4475 4480
Pro Asp Asp Val Gly Gly Leu Leu Asp Ala Asp Phe Ala Leu Asp Pro
4485 4490 4495
Asp Lys Pro Thr Asn Phe Thr Asn Pro Val Tyr Ala Thr Leu Tyr Met
4500 4505 4510
Gly Gly His Gly Ser Arg His Ser Leu Ala Ser Thr Asp Glu Lys Arg
4515 4520 4525
Glu Leu Leu Gly Arg Gly Pro Glu Asp Glu Ile Gly Asp Pro Leu Ala
4530 4535 4540

FIG.8B-11

SEQUENCE LISTING

```
<160> NUMBER OF SEQ ID NOS: 59

<210> SEQ ID NO 1
<211> LENGTH: 14849
<212> TYPE: DNA
<213> ORGANISM: Mus musculus
```

-continued

<400> SEQUENCE: 1

```
cgctgctccc cgccagtgca ctgaggaggc ggaaacgggg gagcccctag tgctccatca     60
ggcccctacc aaggcacccc catcgggtcc acgcccccca ccccccaccc cgcctcctcc    120
caattgtgca tttttgcagc cggagtcggc tccgagatgg ggctgtgagc ttcgccctgg    180
gagggggaga ggagcgagga gtaaagcagg ggtgaagggt tcgaatttgg gggcaggggg    240
cgcacccgcg tcagcaggcc cttcccaggg ggctcggaac tgtaccattt cacctatgcc    300
cctggttcgc tttgcttaag gaaggataag atagaagagt cggggagagg aagataaagg    360
gggacccccc aattgggggg ggcgaggaca agaagtaaca ggaccagagg gtgggggctg    420
ctgtttgcat cggcccacac catgctgacc ccgccgttgc tgctgctcgt gccgctgctt    480
tcagctctgg tctccggggc cactatggat gcccctaaaa cttgcagccc taagcagttt    540
gcctgcagag accaaatcac ctgtatctca aagggctggc ggtgtgacgg tgaaagagat    600
tgccccgacg gctctgatga agcccctgag atctgtccac agagtaaagc ccagagatgc    660
ccgccaaatg agcacagttg tctggggact gagctatgtg tccccatgtc tcgtctctgc    720
aacgggatcc aggactgcat ggatggctca gacgagggtg ctcactgccg agagctccga    780
gccaactgtt ctcgaatggg ttgtcaacac cattgtgtac ctacacccag tgggcccacg    840
tgctactgta acagcagctt ccagctcgag gcagatggca agacgtgcaa agattttgac    900
gagtgttccg tgtatggcac ctgcagccag ctttgcacca acacagatgg ctccttcaca    960
tgtggctgtg ttgaaggcta cctgctgcaa ccggacaacc gctcctgcaa ggccaagaat   1020
gagccagtag atcggccgcc agtgctactg attgccaact ctcagaacat cctagctacg   1080
tacctgagtg ggcccaagt gtctaccatc acacccacca gcacccgaca aaccacggcc   1140
atggacttca gttatgccaa tgagaccgta tgctgggtgc acgttgggga cagtgctgcc   1200
cagacacagc tcaagtgtgc ccggatgcct ggcctgaagg gctttgtgga tgagcatacc   1260
atcaacatct ccctcagcct gcaccacgtg gagcagatgg caatcgactg gctgacggga   1320
aacttctact ttgtcgacga cattgacgac aggatctttg tctgtaaccg aaacggggac   1380
acctgtgtca ctctgctgga cctggaactc tacaacccca aaggcatcgc cttggacccc   1440
gccatgggga aggtgttctt cactgactac gggcagatcc caaaggtgga gcgctgtgac   1500
atggatggac agaaccgcac caagctggtg gatagcaaga tcgtgtttcc acacggcatc   1560
accctggacc tggtcagccg cctcgtctac tgggcggacg cctacctaga ctacatcgag   1620
gtggtagact acgaaggaa gggtcggcag accatcatcc aaggcatcct gatcgagcac   1680
ctgtacggcc tgaccgtgtt tgagaactat ctctacgcca ccaactcgga caatgccaac   1740
acgcagcaga agacgagcgt gatccgagtg aaccggttca acagtactga gtaccaggtc   1800
gtcacccgtg tggacaaggg tggtgccctg catatctacc accagcgacg ccagccccga   1860
gtgcggagtc acgcctgtga gaatgaccag tacgggaagc caggtggctg ctccgacatc   1920
tgcctcctgg ccaacagtca caaggcaagg acctgcaggt gcaggtctgg cttcagcctg   1980
ggaagtgatg ggaagtcttg taagaaacct gaacatgagc tgttcctcgt gtatggcaag   2040
ggccgaccag gcatcattag aggcatggac atgggggcca aggtcccaga tgagcacatg   2100
atccccatcg agaaccttat gaatccacgc gctctggact tccacgccga gaccggcttc   2160
atctactttg ctgacaccac cagctacctc attggccgcc agaaaattga tggcacggag   2220
agagagacta tcctgaagga tggcatccac aatgtggagg gcgtagccgt ggactggatg   2280
ggagacaatc tttactggac tgatgatggc cccaagaaga ccattagtgt ggccaggctg   2340
```

-continued

```
gagaaagccg ctcagacccg gaagactcta attgagggca agatgacaca ccccagggcc   2400
attgtagtgg atccactcaa tgggtggatg tactggacag actgggagga ggaccccaag   2460
gacagtcggc gagggcggct cgagagggct tggatggacg gctcacaccg agatatcttt   2520
gtcacctcca agacagtgct ttggcccaat gggctaagcc tggatatccc agccggacgc   2580
ctctactggg tggatgcctt ctatgaccga attgagacca tactgctcaa tggcacagac   2640
cggaagattg tatatgaggg tcctgaactg aatcatgcct tcggcctgtg tcaccatggc   2700
aactacctct tttggaccga gtaccggagc ggcagcgtct accgcttgga acggggcgtg   2760
gcaggcgcac cgcccactgt gacccttctg cgcagcgaga gaccgcctat ctttgagatc   2820
cgaatgtacg acgcgcacga gcagcaagtg ggtaccaaca aatgccgggt aaataacgga   2880
ggctgcagca gcctgtgcct cgccaccccc gggagccgcc agtgtgcctg tgccgaggac   2940
caggtgttgg acacagatgg tgtcacctgc ttggcgaacc catcctacgt gcccccaccc   3000
cagtgccagc cgggccagtt tgcctgtgcc aacaaccgct gcatccagga gcgctggaag   3060
tgtgacggag acaacgactg tctggacaac agcgatgagg ccccagcact gtgccatcaa   3120
cacacctgtc cctcggaccg attcaagtgt gagaacaacc ggtgtatccc caaccgctgg   3180
ctctgtgatg gggataatga ttgtggcaac agcgaggacg aatccaatgc cacgtgctca   3240
gcccgcacct gtccacccaa ccagttctcc tgtgccagtg gccgatgcat tcctatctca   3300
tggacctgtg atctggatga tgactgtggg gaccggtccg atgagtcagc ctcatgcgcc   3360
taccccacct gcttccccct gactcaattt acctgcaaca atggcagatg tattaacatc   3420
aactggcggt gtgacaacga caatgactgt ggggacaaca gcgacgaagc cggctgcagt   3480
cactcctgct ccagtaccca gttcaagtgc aacagtggca gatgcatccc cgagcactgg   3540
acgtgtgatg gggacaatga ttgtggggac tacagcgacg agacacacgc caactgtacc   3600
aaccaggcta caagacctcc tggtggctgc cactcggatg agttccagtg cccgctagat   3660
ggcctgtgca tcccccctgag gtggcgctgc gacggggaca ccgactgcat ggattccagc   3720
gatgagaaga gctgtgaggg cgtgacccat gtttgtgacc cgaatgtcaa gtttggctgc   3780
aaggactccg cccggtgcat cagcaaggcg tgggtgtgtg atggcgacag cgactgtgaa   3840
gataactccg acgaggagaa ctgtgaggcc ctggcctgca ggccaccctc ccatccctgc   3900
gccaacaaca cctctgtctg cctgcctcct gacaagctgt gcgacggcaa ggatgactgt   3960
ggagacggct cggatgaggg cgagctctgt gaccagtgtt ctctgaataa tggtggctgt   4020
agtcacaact gctcagtggc ccctggtgaa ggcatcgtgt gctcttgccc tctgggcatg   4080
gagctgggct ctgacaacca cacctgccag atccagagct actgtgccaa gcacctcaaa   4140
tgcagccaga agtgtgacca gaacaagttc agtgtgaagt gctcctgcta cgagggctgg   4200
gtcttggagc ctgacgggga aacgtgccgc agtctggatc ccttcaaact gttcatcatc   4260
ttctccaacc gccacgagat caggcgcatt gaccttcaca aggggggacta cagcgtccta   4320
gtgcctggcc tgcgcaacac tattgccctg gacttccacc tcagccagag tgccctctac   4380
tggaccgacg cggtagagga caagatctac cgtgggaaac tcctggacaa cggagccctg   4440
accagctttg aggtggtgat tcagtatggc ttggccacac cagagggcct ggctgtagat   4500
tggattgcag gcaacatcta ctgggtggag agcaacctgg accagatcga agtggccaag   4560
ctggacggaa ccctccgaac cactctgctg gcgggtgaca ttgagcaccc gagggccatc   4620
gctctggacc ctcgggatgg gattctgttt tggacagact gggatgccag cctgccacga   4680
atcgaggctg catccatgag tggagctggc cgccgaacca tccaccggga gacaggctct   4740
```

-continued

```
gggggctgcg ccaatgggct caccgtggat tacctggaga agcgcatcct ctggattgat   4800
gctaggtcag atgccatcta ttcagcccgg tatgacggct ccggccacat ggaggtgctt   4860
cggggacacg agttcctgtc acacccattt gccgtgacac tgtacggtgg ggaggtgtac   4920
tggaccgact ggcgaacaaa tacactggct aaggccaaca agtggactgg ccacaacgtc   4980
accgtggtac agaggaccaa cacccagccc ttcgacctgc aggtgtatca cccttcccgg   5040
cagcccatgg ctccaaaccc atgtgaggcc aatggcggcc ggggcccctg ttcccatctg   5100
tgcctcatca actacaaccg gaccgtctcc tgggcctgtc cccacctcat gaagctgcac   5160
aaggacaaca ccacctgcta tgagtttaag aagttcctgc tgtacgcacg tcagatggag   5220
atccggggcg tggacctgga tgccccgtac tacaattata tcatctcctt cacggtgcct   5280
gatatcgaca atgtcacggt gctggactat gatgcccgag agcagcgagt ttactggtct   5340
gatgtgcgga ctcaagccat caaaagggca tttatcaacg gcactggcgt ggagaccgtt   5400
gtctctgcag acttgcccaa cgcccacggg ctggctgtgg actgggtctc ccgaaatctg   5460
ttttggacaa gttacgacac caacaagaag cagattaacg tggcccggct ggacggctcc   5520
ttcaagaatg cggtggtgca gggcctggag cagccccacg gcctggtcgt ccacccgctt   5580
cgtggcaagc tctactggac tgatggggac aacatcagca tggccaacat ggatgggagc   5640
aaccacactc tgctcttcag tggccagaag ggccctgtgg ggttggccat tgacttccct   5700
gagagcaaac tctactggat cagctctggg aaccacacaa tcaaccgttg caatctggat   5760
gggagcgagc tggaggtcat cgacaccatg cggagccagc tgggcaaggc cactgccctg   5820
gccatcatgg gggacaagct gtggtgggca gatcaggtgt cagagaagat gggcacgtgc   5880
aacaaagccg atggctctgg gtccgtggtg ctgcggaaca gtaccacgtt ggttatgcac   5940
atgaaggtgt atgacgagag catccagcta gagcatgagg gcaccaaccc ctgcagtgtc   6000
aacaacggag actgttccca gctctgcctg ccaacatcag agacgactcg ctcctgtatg   6060
tgtacagccg gttacagcct ccggagcgga cagcaggcct gtgagggtgt gggctctttt   6120
ctcctgtact ctgtacatga gggaattcgg gggattccac tagatcccaa tgacaagtcg   6180
gatgccctgg tcccagtgtc cggaacttca ctggctgtcg gaatcgactt ccatgccgaa   6240
aatgacacta tttattgggt ggatatgggc ctaagcacca tcagcagggc caagcgtgac   6300
cagacatggc gagaggatgt ggtgaccaac ggtattggcc gtgtggaggg catcgccgtg   6360
gactggatcg caggcaacat atactggacg gaccagggct tcgatgtcat cgaggttgcc   6420
cggctcaatg gctcttttcg ttatgtggtc atttcccagg gtctggacaa gcctcgggcc   6480
atcactgtcc acccagagaa ggggtacttg ttctggaccg agtggggtca ttacccacgt   6540
attgagcggt ctcgccttga tggcacagag agagtggtgt tggttaatgt cagcatcagc   6600
tggcccaatg gcatctcagt agactatcag ggcggcaagc tctactggtg tgatgctcgg   6660
atggacaaga tcgagcgcat cgacctggaa acgggcgaga accgggaggt ggtcctgtcc   6720
agcaataaca tggatatgtt ctccgtgtcc gtgtttgagg acttcatcta ctggagtgac   6780
agaactcacg ccaatggctc catcaagcgc ggctgcaaag acaatgctac agactccgtg   6840
cctctgagga caggcattgg tgttcagctt aaagacatca aggtcttcaa cagggacagg   6900
cagaagggta ccaatgtgtg cgcggtagcc aacggcgggt gccagcagct ctgcttgtat   6960
cggggtggcg gacagcgagc ctgtgcctgt gcccacggga tgctggcaga agacggggcc   7020
tcatgccgag agtacgctgg ctacctgctc tactcagagc ggaccatcct caagagcatc   7080
cacctgtcgg atgagcgtaa cctcaacgca ccggtgcagc cctttgaaga ccccgagcac   7140
```

-continued

```
atgaaaaatg tcatcgccct ggcctttgac taccgagcag gcacctcccc ggggacccct   7200
aaccgcatct tcttcagtga catccacttt gggaacatcc agcagatcaa tgacgatggc   7260
tcgggcagga ccaccatcgt ggaaaatgtg ggctctgtgg aaggcctggc ctatcaccgt   7320
ggctgggaca cactgtactg gacaagctac accacatcca ccatcacccg ccacaccgtg   7380
gaccagactc gcccaggggc cttcgagagg gagacagtca tcaccatgtc cggagacgac   7440
cacccgagag cctttgtgct ggatgagtgc cagaacctga tgttctggac caattggaac   7500
gagctccatc caagcatcat gcgggcagcc ctatccggag ccaacgtcct gaccctcatt   7560
gagaaggaca tccgcacgcc caatgggttg gccatcgacc accgggcgga gaagctgtac   7620
ttctcggatg ccaccttgga caagatcgag cgctgcgagt acgacggctc ccaccgctat   7680
gtgatcctaa agtcggagcc cgtccacccc tttgggttgg cggtgtacgg agagcacatt   7740
ttctggactg actgggtgcg gcgggctgtg cagcgagcca acaagtatgt gggcagcgac   7800
atgaagctgc ttcgggtgga cattccccag caacccatgg gcatcatcgc cgtggccaat   7860
gacaccaaca gctgtgaact ctccccctgc cgtatcaaca atggaggctg ccaggatctg   7920
tgtctgctca cccaccaagg ccacgtcaac tgttcctgtc gagggggccg gatcctccag   7980
gaggacttca cctgccgggc tgtgaactcc tcttgtcggg cacaagatga gtttgagtgt   8040
gccaatgggg aatgtatcag cttcagcctc acctgtgatg gcgtctccca ctgcaaggac   8100
aagtccgatg agaagccctc ctactgcaac tcacgccgct gcaagaagac tttccgccag   8160
tgtaacaatg gccgctgtgt atccaacatg ctgtggtgca atggggtgga ttactgtggg   8220
gatggctctg atgagatacc ttgcaacaag actgcctgtg gtgtgggtga gttccgctgc   8280
cgggatgggt cctgcatcgg gaactccagt cgctgcaacc agtttgtgga ttgtgaggat   8340
gcctcggatg agatgaattg cagtgccaca gactgcagca gctatttccg cctgggcgtg   8400
aaaggtgtcc tcttccagcc gtgcgagcgg acatccctgt gctacgcacc tagctgggtg   8460
tgtgatggcg ccaacgactg tggagactac agcgatgaac gtgactgtcc aggtgtgaag   8520
cgccctaggt gcccgctcaa ttactttgcc tgccccagcg ggcgctgtat ccccatgagc   8580
tggacgtgtg acaaggagga tgactgtgag aacggcgagg atgagaccca ctgcaacaag   8640
ttctgctcag aggcacagtt cgagtgccag aaccaccggt gtatctccaa gcagtggctg   8700
tgtgacggta gcgatgattg cggggatggc tccgatgagg cagctcactg tgaaggcaag   8760
acatgtggcc cctcctcctt ctcctgtccc ggcacccacg tgtgtgtccc tgagcgctgg   8820
ctctgtgatg gcgacaagga ctgtaccgat ggcgcggatg agagtgtcac tgctggctgc   8880
ctgtacaaca gcacctgtga tgaccgtgag ttcatgtgcc agaaccgctt gtgtattccc   8940
aagcatttcg tgtgcgacca tgaccgtgac tgtgctgatg gctctgatga atcccctgag   9000
tgtgagtacc caacctgcgg gcccaatgaa ttccgctgtg ccaatgggcg ttgtctgagc   9060
tcccgtcagt gggaatgtga tggggagaat gactgtcacg accacagcga tgaggctccc   9120
aagaacccac actgcaccag cccagagcac aaatgcaatg cctcatcaca gttcctgtgc   9180
agcagcgggc gctgcgtggc tgaggcgttg ctctgcaacg gccaggacga ctgtggggac   9240
ggttcagacg aacgcgggtg ccatgtcaac gagtgtctca gccgcaagct cagtggctgc   9300
agtcaggact gcgaggacct caagataggc tttaagtgcc gctgtcgccc gggcttccgg   9360
ctaaaggacg atggcaggac ctgtgccgac ctggatgagt gcagcaccac cttcccctgc   9420
agccagctct gcatcaacac ccacggaagt tacaagtgtc tgtgtgtgga gggctatgca   9480
ccccgtggcg gtgaccccca cagctgcaaa gctgtgaccg atgaggagcc atttctcatc   9540
```

-continued

```
tttgccaacc ggtactacct gcggaagctc aacctggacg gctccaacta cacactgctt   9600
aagcagggcc tgaacaatgc ggtcgccttg gcatttgact accgagagca gatgatctac   9660
tggacgggcg tgaccaccca gggcagcatg attcgcagga tgcacctcaa cggcagcaac   9720
gtgcaggttc tgcaccggac gggccttagt aacccagatg ggctcgctgt ggactgggtg   9780
ggtggcaacc tgtactggtg tgacaagggc agagatacca ttgaggtgtc caagcttaac   9840
ggggcctatc ggacagtgct ggtcagctct ggcctccggg agcccagagc tctggtagtg   9900
gatgtacaga atgggtacct gtactggaca gactggggtg accactcact gatcggccgg   9960
attggcatgg atggatctgg ccgcagcatc atcgtggaca ctaagatcac atggcccaat  10020
ggcctgaccg tggactacgt cacggaacgc atctactggg ctgacgcccg tgaggactac  10080
atcgagttcg ccagcctgga tggctccaac cgtcacgttg tgctgagcca agacatccca  10140
cacatctttg cgctgaccct atttgaagac tacgtctact ggacagactg ggaaacgaag  10200
tccatcaacc gggcccacaa gaccacgggt gccaacaaaa cactcctcat cagcaccctg  10260
caccggccca tggacttaca tgtattccac gccctgcgcc agccagatgt gcccaatcac  10320
ccctgcaaag tcaacaatgg tggctgcagc aacctgtgcc tgctgtcccc tgggggtggt  10380
cacaagtgcg cctgccccac caacttctat ctgggtggcg atggccgtac ctgtgtgtcc  10440
aactgcacag caagccagtt tgtgtgcaaa aatgacaagt gcatcccctt ctggtggaag  10500
tgtgacacgg aggacgactg tggggatcac tcagacgagc ctccagactg tcccgagttc  10560
aagtgccgcc caggccagtt ccagtgctcc accggcatct gcaccaaccc tgccttcatc  10620
tgtgatgggg acaatgactg ccaagacaat agtgacgagg ccaattgcga cattcacgtc  10680
tgcttgccca gccaattcaa gtgcaccaac accaaccgct gcattcctgg catcttccgt  10740
tgcaatgggc aggacaactg cggggacggc gaggatgagc gggattgccc tgaggtgacc  10800
tgcgccccca accagttcca gtgctccatc accaagcgct gcatccctcg cgtctgggtc  10860
tgtgacaggg ataatcactg tgtggacggc agtgatgagc ctgccaactg tacccaaatg  10920
acctgtggag tggatgagtt ccgctgcaag gattctggcc gctgcatccc cgcgcgctgg  10980
aagtgtgacg gagaagatga ctgtggggat ggttcagatg agcccaagga agagtgtgat  11040
gagcgcacct gtgagccata ccagttccgc tgcaaaaaca accgctgtgt cccaggccgt  11100
tggcaatgtg actacgacaa cgactgcgga gataactcgg acgaggagag ctgcacacct  11160
cggccctgct ctgagagtga gtttttctgt gccaatggcc gctgcatcgc tgggcgctgg  11220
aagtgtgatg gggaccatga ctgtgccgac ggctcagacg agaaagactg caccccccgc  11280
tgtgatatgg accagttcca gtgcaagagt ggccactgca tcccccctgcg ctggccgtgt  11340
gacgcggatg ctgactgtat ggacggcagt gacgaggaag cctgtggcac tggggtgagg  11400
acctgcccat tggatgagtt tcaatgtaac aacaccttgt gcaagccgct ggcctggaag  11460
tgtgatggag aggacgactg tggggacaac tcagatgaga accccgagga atgcgcccgg  11520
ttcatctgcc ctcccaaccg gcctttccgc tgcaagaatg accgagtctg cctgtggatt  11580
gggcgccagt gtgatggcgt ggacaactgt ggagatggga ctgacgagga ggactgtgag  11640
ccccccacgg cccagaaccc ccactgcaaa gacaagaagg agttcctgtg ccgaaaccag  11700
cgctgtctat catcctccct gcgctgtaac atgttcgatg actgcggcga tggctccgat  11760
gaagaagatt gcagcatcga ccccaagctg accagctgtg ccaccaatgc cagcatgtgt  11820
ggggacgaag ctcgttgtgt gcgcactgag aaagctgcct actgtgcctg ccgctcgggc  11880
ttccatactg tgccgggcca gcccggatgc caggacatca acgagtgcct gcgctttggt  11940
```

-continued

```
acctgctctc agctctggaa caaacccaag ggaggccacc tctgcagctg tgcccgcaac  12000
ttcatgaaga cacacaacac ctgcaaagct gaaggctccg agtaccaggt gctatacatc  12060
gcggatgaca acgagatccg cagcttgttc ccgggccacc cccactcagc ctacgagcag  12120
acattccagg gcgatgagag tgtccgcata gatgccatgg atgtccatgt caaggccggc  12180
cgtgtctact ggactaactg gcacacgggc acaatctcct acaggagcct gccccctgcc  12240
gcccctccta ccacttccaa ccgccaccgg aggcagatcg accggggtgt cacccacctc  12300
aatatttcag ggctgaagat gccgaggggt atcgctatcg actgggtggc cgggaatgtg  12360
tactggaccg attccggccg agacgtgatt gaggtggcgc aaatgaaggg cgagaaccgc  12420
aagacgctca tctcgggcat gattgatgag ccccatgcca tcgtggtgga ccctctgagg  12480
ggcaccatgt actggtcaga ctgggggaac caccccaaga ttgaaacagc agcgatggat  12540
ggcacccttc gggagactct cgtgcaagac aacattcagt ggcctacagg gctggctgtg  12600
gactatcaca atgaacggct ctactgggca gatgccaagc tttcggtcat cggcagcatc  12660
cggctcaacg gcactgaccc cattgtggct gctgacagca aacgaggcct aagtcacccc  12720
ttcagcatcg atgtgtttga agactacatc tacggagtca cttacatcaa taatcgtgtc  12780
ttcaagatcc acaagtttgg acacagcccc ttgtacaacc taactggggg cctgagccat  12840
gcctctgatg tagtccttta ccatcaacac aagcagcctg aagtgaccaa cccctgtgac  12900
cgcaagaaat gcgaatggct gtgtctgctg agccccagcg ggcctgtctg cacctgtccc  12960
aatggaaaga ggctggataa tggcacctgt gtgcctgtgc cctctccaac acccccctcca  13020
gatgccccta ggcctggaac ctgcactctg cagtgcttca atggtggtag ttgtttcctc  13080
aacgctcgga ggcagcccaa gtgccgttgc cagccccgtt acacaggcga taagtgtgag  13140
ctggatcagt gctgggaata ctgtcacaac ggaggcacct gtgcggcttc cccatctggc  13200
atgcccacgt gccgctgtcc cactggcttc acgggcccca aatgcaccgc acaggtgtgt  13260
gcaggctact gctctaacaa cagcacctgc accgtcaacc agggcaacca gccccagtgc  13320
cgatgtctac ctggcttcct gggcgaccgt tgccagtacc ggcagtgctc tggcttctgt  13380
gagaactttg gcacctgtca gatggctgct gatggctccc gacaatgtcg ctgcaccgtc  13440
tactttgagg gaccaaggtg tgaggtgaac aagtgtagtc gctgtctcca aggcgcctgt  13500
gtggtcaata agcagaccgg agatgtcaca tgcaactgca ctgatggccg ggtagccccc  13560
agttgtctca cctgcatcga tcactgtagc aatggtggct cctgcaccat gaacagcaag  13620
atgatgcctg agtgccagtg cccgccccat atgacaggac cccggtgcca ggagcaggtt  13680
gttagtcagc aacagcctgg gcatatggcc tccatcctga tccctctgct gctgcttctc  13740
ctgctgcttc tggtggctgg cgtggtgttc tggtataagc ggcgagtccg aggggctaag  13800
ggcttccagc accagcggat gaccaatggg gccatgaatg tggaaattgg aaaccctacc  13860
tacaagatgt atgaaggtgg agagcccgat gatgtcgggg gcctactgga tgctgatttt  13920
gcccttgacc ctgacaagcc taccaacttc accaacccag tgtatgccac gctctacatg  13980
gggggccacg gcagccgcca ttccctggcc agcacggacg agaagcgaga actgctgggc  14040
cggggacctg aagacgagat aggagatccc ttggcatagg gccctgcccc gacggatgtc  14100
cccagaaagc cccctgccac atgagtcttt caatgaaccc cctccccagc cggcccttct  14160
ccggccctgc cgggtgtaca aatgtaaaaa tgaaggaatt actttttata tgtgagcgag  14220
caagcgagca agcacagtat tatctctttg catttccttc ctgcctgctc ctcagtatcc  14280
cccccatgct gccttgaggg ggcggggagg gctttgtggc tcaaaggtat gaaggagtcc  14340
```

-continued

```
acatgttccc taccgagcat acccctggaa gcctggcggc acggcctccc caccacgcct  14400

gtgcaagaca ctcaacgggg ctccgtgtcc cagctttcct ttccttggct ctctggggtt  14460

agttcagggg aggtggagtc ctctgctgac cctgtctgga agatttggct ctagctgagg  14520

aaggagtctt ttagttgagg gaagtcaccc caaaccccag ctcccacttt caggggcacc  14580

tctcagatgg ccatgctcag tatcccttcc agacaggccc tcccctctct agcgcccccct  14640

ctgtggctcc tagggctgaa cacattcttt ggtaactgtc cccaagcct cccatccccc  14700

tgagggccag gaagagtcgg ggcacaccaa ggaagggcaa gcgggcagcc ccattttggg  14760

gacgtgaacg ttttaataat ttttgctgaa ttcctttaca actaaataac acagatattg  14820

ttataaataa aattgtaaaa aaaaaaaaa                                    14849


<210> SEQ ID NO 2
<211> LENGTH: 4545
<212> TYPE: PRT
<213> ORGANISM: Mus musculus

<400> SEQUENCE: 2

Met Leu Thr Pro Pro Leu Leu Leu Leu Val Pro Leu Leu Ser Ala Leu
 1               5                  10                  15

Val Ser Gly Ala Thr Met Asp Ala Pro Lys Thr Cys Ser Pro Lys Gln
            20                  25                  30

Phe Ala Cys Arg Asp Gln Ile Thr Cys Ile Ser Lys Gly Trp Arg Cys
        35                  40                  45

Asp Gly Glu Arg Asp Cys Pro Asp Gly Ser Asp Glu Ala Pro Glu Ile
    50                  55                  60

Cys Pro Gln Ser Lys Ala Gln Arg Cys Pro Pro Asn Glu His Ser Cys
65                  70                  75                  80

Leu Gly Thr Glu Leu Cys Val Pro Met Ser Arg Leu Cys Asn Gly Ile
                85                  90                  95

Gln Asp Cys Met Asp Gly Ser Asp Glu Gly Ala His Cys Arg Glu Leu
            100                 105                 110

Arg Ala Asn Cys Ser Arg Met Gly Cys Gln His His Cys Val Pro Thr
        115                 120                 125

Pro Ser Gly Pro Thr Cys Tyr Cys Asn Ser Ser Phe Gln Leu Glu Ala
    130                 135                 140

Asp Gly Lys Thr Cys Lys Asp Phe Asp Glu Cys Ser Val Tyr Gly Thr
145                 150                 155                 160

Cys Ser Gln Leu Cys Thr Asn Thr Asp Gly Ser Phe Thr Cys Gly Cys
                165                 170                 175

Val Glu Gly Tyr Leu Leu Gln Pro Asp Asn Arg Ser Cys Lys Ala Lys
            180                 185                 190

Asn Glu Pro Val Asp Arg Pro Pro Val Leu Leu Ile Ala Asn Ser Gln
        195                 200                 205

Asn Ile Leu Ala Thr Tyr Leu Ser Gly Ala Gln Val Ser Thr Ile Thr
    210                 215                 220

Pro Thr Ser Thr Arg Gln Thr Thr Ala Met Asp Phe Ser Tyr Ala Asn
225                 230                 235                 240

Glu Thr Val Cys Trp Val His Val Gly Asp Ser Ala Ala Gln Thr Gln
                245                 250                 255

Leu Lys Cys Ala Arg Met Pro Gly Leu Lys Gly Phe Val Asp Glu His
            260                 265                 270

Thr Ile Asn Ile Ser Leu Ser Leu His His Val Glu Gln Met Ala Ile
        275                 280                 285
```

-continued

```
Asp Trp Leu Thr Gly Asn Phe Tyr Phe Val Asp Asp Ile Asp Asp Arg
    290                 295                 300

Ile Phe Val Cys Asn Arg Asn Gly Asp Thr Cys Val Thr Leu Leu Asp
305                 310                 315                 320

Leu Glu Leu Tyr Asn Pro Lys Gly Ile Ala Leu Asp Pro Ala Met Gly
                325                 330                 335

Lys Val Phe Phe Thr Asp Tyr Gly Gln Ile Pro Lys Val Glu Arg Cys
            340                 345                 350

Asp Met Asp Gly Gln Asn Arg Thr Lys Leu Val Asp Ser Lys Ile Val
        355                 360                 365

Phe Pro His Gly Ile Thr Leu Asp Leu Val Ser Arg Leu Val Tyr Trp
    370                 375                 380

Ala Asp Ala Tyr Leu Asp Tyr Ile Glu Val Val Asp Tyr Glu Gly Lys
385                 390                 395                 400

Gly Arg Gln Thr Ile Ile Gln Gly Ile Leu Ile Glu His Leu Tyr Gly
                405                 410                 415

Leu Thr Val Phe Glu Asn Tyr Leu Tyr Ala Thr Asn Ser Asp Asn Ala
            420                 425                 430

Asn Thr Gln Gln Lys Thr Ser Val Ile Arg Val Asn Arg Phe Asn Ser
        435                 440                 445

Thr Glu Tyr Gln Val Val Thr Arg Val Asp Lys Gly Gly Ala Leu His
    450                 455                 460

Ile Tyr His Gln Arg Arg Gln Pro Arg Val Arg Ser His Ala Cys Glu
465                 470                 475                 480

Asn Asp Gln Tyr Gly Lys Pro Gly Gly Cys Ser Asp Ile Cys Leu Leu
                485                 490                 495

Ala Asn Ser His Lys Ala Arg Thr Cys Arg Cys Arg Ser Gly Phe Ser
            500                 505                 510

Leu Gly Ser Asp Gly Lys Ser Cys Lys Lys Pro Glu His Glu Leu Phe
        515                 520                 525

Leu Val Tyr Gly Lys Gly Arg Pro Gly Ile Ile Arg Gly Met Asp Met
    530                 535                 540

Gly Ala Lys Val Pro Asp Glu His Met Ile Pro Ile Glu Asn Leu Met
545                 550                 555                 560

Asn Pro Arg Ala Leu Asp Phe His Ala Glu Thr Gly Phe Ile Tyr Phe
                565                 570                 575

Ala Asp Thr Thr Ser Tyr Leu Ile Gly Arg Gln Lys Ile Asp Gly Thr
            580                 585                 590

Glu Arg Glu Thr Ile Leu Lys Asp Gly Ile His Asn Val Glu Gly Val
        595                 600                 605

Ala Val Asp Trp Met Gly Asp Asn Leu Tyr Trp Thr Asp Asp Gly Pro
    610                 615                 620

Lys Lys Thr Ile Ser Val Ala Arg Leu Glu Lys Ala Ala Gln Thr Arg
625                 630                 635                 640

Lys Thr Leu Ile Glu Gly Lys Met Thr His Pro Arg Ala Ile Val Val
                645                 650                 655

Asp Pro Leu Asn Gly Trp Met Tyr Trp Thr Asp Trp Glu Glu Asp Pro
            660                 665                 670

Lys Asp Ser Arg Arg Gly Arg Leu Glu Arg Ala Trp Met Asp Gly Ser
        675                 680                 685

His Arg Asp Ile Phe Val Thr Ser Lys Thr Val Leu Trp Pro Asn Gly
    690                 695                 700
```

-continued

```
Leu Ser Leu Asp Ile Pro Ala Gly Arg Leu Tyr Trp Val Asp Ala Phe
705                 710                 715                 720

Tyr Asp Arg Ile Glu Thr Ile Leu Leu Asn Gly Thr Asp Arg Lys Ile
                725                 730                 735

Val Tyr Glu Gly Pro Glu Leu Asn His Ala Phe Gly Leu Cys His His
            740                 745                 750

Gly Asn Tyr Leu Phe Trp Thr Glu Tyr Arg Ser Gly Ser Val Tyr Arg
        755                 760                 765

Leu Glu Arg Gly Val Ala Gly Ala Pro Pro Thr Val Thr Leu Leu Arg
    770                 775                 780

Ser Glu Arg Pro Pro Ile Phe Glu Ile Arg Met Tyr Asp Ala His Glu
785                 790                 795                 800

Gln Gln Val Gly Thr Asn Lys Cys Arg Val Asn Asn Gly Gly Cys Ser
                805                 810                 815

Ser Leu Cys Leu Ala Thr Pro Gly Ser Arg Gln Cys Ala Cys Ala Glu
            820                 825                 830

Asp Gln Val Leu Asp Thr Asp Gly Val Thr Cys Leu Ala Asn Pro Ser
        835                 840                 845

Tyr Val Pro Pro Pro Gln Cys Gln Pro Gly Gln Phe Ala Cys Ala Asn
    850                 855                 860

Asn Arg Cys Ile Gln Glu Arg Trp Lys Cys Asp Gly Asp Asn Asp Cys
865                 870                 875                 880

Leu Asp Asn Ser Asp Glu Ala Pro Ala Leu Cys His Gln His Thr Cys
                885                 890                 895

Pro Ser Asp Arg Phe Lys Cys Glu Asn Asn Arg Cys Ile Pro Asn Arg
            900                 905                 910

Trp Leu Cys Asp Gly Asp Asn Asp Cys Gly Asn Ser Glu Asp Glu Ser
        915                 920                 925

Asn Ala Thr Cys Ser Ala Arg Thr Cys Pro Pro Asn Gln Phe Ser Cys
    930                 935                 940

Ala Ser Gly Arg Cys Ile Pro Ile Ser Trp Thr Cys Asp Leu Asp Asp
945                 950                 955                 960

Asp Cys Gly Asp Arg Ser Asp Glu Ser Ala Ser Cys Ala Tyr Pro Thr
                965                 970                 975

Cys Phe Pro Leu Thr Gln Phe Thr Cys Asn Asn Gly Arg Cys Ile Asn
            980                 985                 990

Ile Asn Trp Arg Cys Asp Asn Asp Asn Asp Cys Gly Asp Asn Ser Asp
        995                 1000                1005

Glu Ala Gly Cys Ser His Ser Cys Ser Ser Thr Gln Phe Lys Cys Asn
    1010                1015                1020

Ser Gly Arg Cys Ile Pro Glu His Trp Thr Cys Asp Gly Asp Asn Asp
1025                1030                1035                1040

Cys Gly Asp Tyr Ser Asp Glu Thr His Ala Asn Cys Thr Asn Gln Ala
                1045                1050                1055

Thr Arg Pro Pro Gly Gly Cys His Ser Asp Glu Phe Gln Cys Pro Leu
            1060                1065                1070

Asp Gly Leu Cys Ile Pro Leu Arg Trp Arg Cys Asp Gly Asp Thr Asp
        1075                1080                1085

Cys Met Asp Ser Ser Asp Glu Lys Ser Cys Glu Gly Val Thr His Val
    1090                1095                1100

Cys Asp Pro Asn Val Lys Phe Gly Cys Lys Asp Ser Ala Arg Cys Ile
1105                1110                1115                1120
```

-continued

```
Ser Lys Ala Trp Val Cys Asp Gly Asp Ser Asp Cys Glu Asp Asn Ser
                1125                1130                1135

Asp Glu Glu Asn Cys Glu Ala Leu Ala Cys Arg Pro Pro Ser His Pro
            1140                1145                1150

Cys Ala Asn Asn Thr Ser Val Cys Leu Pro Pro Asp Lys Leu Cys Asp
        1155                1160                1165

Gly Lys Asp Asp Cys Gly Asp Gly Ser Asp Glu Gly Glu Leu Cys Asp
    1170                1175                1180

Gln Cys Ser Leu Asn Asn Gly Gly Cys Ser His Asn Cys Ser Val Ala
1185                1190                1195                1200

Pro Gly Glu Gly Ile Val Cys Ser Cys Pro Leu Gly Met Glu Leu Gly
                1205                1210                1215

Ser Asp Asn His Thr Cys Gln Ile Gln Ser Tyr Cys Ala Lys His Leu
            1220                1225                1230

Lys Cys Ser Gln Lys Cys Asp Gln Asn Lys Phe Ser Val Lys Cys Ser
        1235                1240                1245

Cys Tyr Glu Gly Trp Val Leu Glu Pro Asp Gly Glu Thr Cys Arg Ser
    1250                1255                1260

Leu Asp Pro Phe Lys Leu Phe Ile Ile Phe Ser Asn Arg His Glu Ile
1265                1270                1275                1280

Arg Arg Ile Asp Leu His Lys Gly Asp Tyr Ser Val Leu Val Pro Gly
                1285                1290                1295

Leu Arg Asn Thr Ile Ala Leu Asp Phe His Leu Ser Gln Ser Ala Leu
            1300                1305                1310

Tyr Trp Thr Asp Ala Val Glu Asp Lys Ile Tyr Arg Gly Lys Leu Leu
        1315                1320                1325

Asp Asn Gly Ala Leu Thr Ser Phe Glu Val Val Ile Gln Tyr Gly Leu
    1330                1335                1340

Ala Thr Pro Glu Gly Leu Ala Val Asp Trp Ile Ala Gly Asn Ile Tyr
1345                1350                1355                1360

Trp Val Glu Ser Asn Leu Asp Gln Ile Glu Val Ala Lys Leu Asp Gly
                1365                1370                1375

Thr Leu Arg Thr Thr Leu Leu Ala Gly Asp Ile Glu His Pro Arg Ala
            1380                1385                1390

Ile Ala Leu Asp Pro Arg Asp Gly Ile Leu Phe Trp Thr Asp Trp Asp
        1395                1400                1405

Ala Ser Leu Pro Arg Ile Glu Ala Ala Ser Met Ser Gly Ala Gly Arg
    1410                1415                1420

Arg Thr Ile His Arg Glu Thr Gly Ser Gly Gly Cys Ala Asn Gly Leu
1425                1430                1435                1440

Thr Val Asp Tyr Leu Glu Lys Arg Ile Leu Trp Ile Asp Ala Arg Ser
                1445                1450                1455

Asp Ala Ile Tyr Ser Ala Arg Tyr Asp Gly Ser Gly His Met Glu Val
            1460                1465                1470

Leu Arg Gly His Glu Phe Leu Ser His Pro Phe Ala Val Thr Leu Tyr
        1475                1480                1485

Gly Gly Glu Val Tyr Trp Thr Asp Trp Arg Thr Asn Thr Leu Ala Lys
    1490                1495                1500

Ala Asn Lys Trp Thr Gly His Asn Val Thr Val Val Gln Arg Thr Asn
1505                1510                1515                1520

Thr Gln Pro Phe Asp Leu Gln Val Tyr His Pro Ser Arg Gln Pro Met
                1525                1530                1535
```

-continued

```
Ala Pro Asn Pro Cys Glu Ala Asn Gly Gly Arg Gly Pro Cys Ser His
            1540                1545                1550

Leu Cys Leu Ile Asn Tyr Asn Arg Thr Val Ser Trp Ala Cys Pro His
        1555                1560                1565

Leu Met Lys Leu His Lys Asp Asn Thr Thr Cys Tyr Glu Phe Lys Lys
    1570                1575                1580

Phe Leu Leu Tyr Ala Arg Gln Met Glu Ile Arg Gly Val Asp Leu Asp
1585                1590                1595                1600

Ala Pro Tyr Tyr Asn Tyr Ile Ile Ser Phe Thr Val Pro Asp Ile Asp
                1605                1610                1615

Asn Val Thr Val Leu Asp Tyr Asp Ala Arg Glu Gln Arg Val Tyr Trp
            1620                1625                1630

Ser Asp Val Arg Thr Gln Ala Ile Lys Arg Ala Phe Ile Asn Gly Thr
        1635                1640                1645

Gly Val Glu Thr Val Val Ser Ala Asp Leu Pro Asn Ala His Gly Leu
    1650                1655                1660

Ala Val Asp Trp Val Ser Arg Asn Leu Phe Trp Thr Ser Tyr Asp Thr
1665                1670                1675                1680

Asn Lys Lys Gln Ile Asn Val Ala Arg Leu Asp Gly Ser Phe Lys Asn
                1685                1690                1695

Ala Val Val Gln Gly Leu Glu Gln Pro His Gly Leu Val Val His Pro
            1700                1705                1710

Leu Arg Gly Lys Leu Tyr Trp Thr Asp Gly Asp Asn Ile Ser Met Ala
        1715                1720                1725

Asn Met Asp Gly Ser Asn His Thr Leu Leu Phe Ser Gly Gln Lys Gly
    1730                1735                1740

Pro Val Gly Leu Ala Ile Asp Phe Pro Glu Ser Lys Leu Tyr Trp Ile
1745                1750                1755                1760

Ser Ser Gly Asn His Thr Ile Asn Arg Cys Asn Leu Asp Gly Ser Glu
                1765                1770                1775

Leu Glu Val Ile Asp Thr Met Arg Ser Gln Leu Gly Lys Ala Thr Ala
            1780                1785                1790

Leu Ala Ile Met Gly Asp Lys Leu Trp Trp Ala Asp Gln Val Ser Glu
        1795                1800                1805

Lys Met Gly Thr Cys Asn Lys Ala Asp Gly Ser Gly Ser Val Val Leu
    1810                1815                1820

Arg Asn Ser Thr Thr Leu Val Met His Met Lys Val Tyr Asp Glu Ser
1825                1830                1835                1840

Ile Gln Leu Glu His Glu Gly Thr Asn Pro Cys Ser Val Asn Asn Gly
                1845                1850                1855

Asp Cys Ser Gln Leu Cys Leu Pro Thr Ser Glu Thr Thr Arg Ser Cys
            1860                1865                1870

Met Cys Thr Ala Gly Tyr Ser Leu Arg Ser Gly Gln Gln Ala Cys Glu
        1875                1880                1885

Gly Val Gly Ser Phe Leu Leu Tyr Ser Val His Glu Gly Ile Arg Gly
    1890                1895                1900

Ile Pro Leu Asp Pro Asn Asp Lys Ser Asp Ala Leu Val Pro Val Ser
1905                1910                1915                1920

Gly Thr Ser Leu Ala Val Gly Ile Asp Phe His Ala Glu Asn Asp Thr
                1925                1930                1935

Ile Tyr Trp Val Asp Met Gly Leu Ser Thr Ile Ser Arg Ala Lys Arg
            1940                1945                1950
```

-continued

```
Asp Gln Thr Trp Arg Glu Asp Val Val Thr Asn Gly Ile Gly Arg Val
        1955                1960                1965

Glu Gly Ile Ala Val Asp Trp Ile Ala Gly Asn Ile Tyr Trp Thr Asp
    1970                1975                1980

Gln Gly Phe Asp Val Ile Glu Val Ala Arg Leu Asn Gly Ser Phe Arg
1985                1990                1995                2000

Tyr Val Val Ile Ser Gln Gly Leu Asp Lys Pro Arg Ala Ile Thr Val
                2005                2010                2015

His Pro Glu Lys Gly Tyr Leu Phe Trp Thr Glu Trp Gly His Tyr Pro
            2020                2025                2030

Arg Ile Glu Arg Ser Arg Leu Asp Gly Thr Glu Arg Val Val Leu Val
        2035                2040                2045

Asn Val Ser Ile Ser Trp Pro Asn Gly Ile Ser Val Asp Tyr Gln Gly
    2050                2055                2060

Gly Lys Leu Tyr Trp Cys Asp Ala Arg Met Asp Lys Ile Glu Arg Ile
2065                2070                2075                2080

Asp Leu Glu Thr Gly Glu Asn Arg Glu Val Val Leu Ser Ser Asn Asn
                2085                2090                2095

Met Asp Met Phe Ser Val Ser Val Phe Glu Asp Phe Ile Tyr Trp Ser
            2100                2105                2110

Asp Arg Thr His Ala Asn Gly Ser Ile Lys Arg Gly Cys Lys Asp Asn
        2115                2120                2125

Ala Thr Asp Ser Val Pro Leu Arg Thr Gly Ile Gly Val Gln Leu Lys
    2130                2135                2140

Asp Ile Lys Val Phe Asn Arg Asp Arg Gln Lys Gly Thr Asn Val Cys
2145                2150                2155                2160

Ala Val Ala Asn Gly Gly Cys Gln Gln Leu Cys Leu Tyr Arg Gly Gly
                2165                2170                2175

Gly Gln Arg Ala Cys Ala Cys Ala His Gly Met Leu Ala Glu Asp Gly
            2180                2185                2190

Ala Ser Cys Arg Glu Tyr Ala Gly Tyr Leu Leu Tyr Ser Glu Arg Thr
        2195                2200                2205

Ile Leu Lys Ser Ile His Leu Ser Asp Glu Arg Asn Leu Asn Ala Pro
    2210                2215                2220

Val Gln Pro Phe Glu Asp Pro Glu His Met Lys Asn Val Ile Ala Leu
2225                2230                2235                2240

Ala Phe Asp Tyr Arg Ala Gly Thr Ser Pro Gly Thr Pro Asn Arg Ile
                2245                2250                2255

Phe Phe Ser Asp Ile His Phe Gly Asn Ile Gln Gln Ile Asn Asp Asp
            2260                2265                2270

Gly Ser Gly Arg Thr Thr Ile Val Glu Asn Val Gly Ser Val Glu Gly
        2275                2280                2285

Leu Ala Tyr His Arg Gly Trp Asp Thr Leu Tyr Trp Thr Ser Tyr Thr
    2290                2295                2300

Thr Ser Thr Ile Thr Arg His Thr Val Asp Gln Thr Arg Pro Gly Ala
2305                2310                2315                2320

Phe Glu Arg Glu Thr Val Ile Thr Met Ser Gly Asp Asp His Pro Arg
                2325                2330                2335

Ala Phe Val Leu Asp Glu Cys Gln Asn Leu Met Phe Trp Thr Asn Trp
            2340                2345                2350

Asn Glu Leu His Pro Ser Ile Met Arg Ala Ala Leu Ser Gly Ala Asn
        2355                2360                2365
```

-continued

```
Val Leu Thr Leu Ile Glu Lys Asp Ile Arg Thr Pro Asn Gly Leu Ala
    2370                2375                2380

Ile Asp His Arg Ala Glu Lys Leu Tyr Phe Ser Asp Ala Thr Leu Asp
2385                2390                2395                2400

Lys Ile Glu Arg Cys Glu Tyr Asp Gly Ser His Arg Tyr Val Ile Leu
                2405                2410                2415

Lys Ser Glu Pro Val His Pro Phe Gly Leu Ala Val Tyr Gly Glu His
            2420                2425                2430

Ile Phe Trp Thr Asp Trp Val Arg Arg Ala Val Gln Arg Ala Asn Lys
        2435                2440                2445

Tyr Val Gly Ser Asp Met Lys Leu Leu Arg Val Asp Ile Pro Gln Gln
    2450                2455                2460

Pro Met Gly Ile Ile Ala Val Ala Asn Asp Thr Asn Ser Cys Glu Leu
2465                2470                2475                2480

Ser Pro Cys Arg Ile Asn Asn Gly Gly Cys Gln Asp Leu Cys Leu Leu
                2485                2490                2495

Thr His Gln Gly His Val Asn Cys Ser Cys Arg Gly Gly Arg Ile Leu
            2500                2505                2510

Gln Glu Asp Phe Thr Cys Arg Ala Val Asn Ser Ser Cys Arg Ala Gln
        2515                2520                2525

Asp Glu Phe Glu Cys Ala Asn Gly Glu Cys Ile Ser Phe Ser Leu Thr
    2530                2535                2540

Cys Asp Gly Val Ser His Cys Lys Asp Lys Ser Asp Glu Lys Pro Ser
2545                2550                2555                2560

Tyr Cys Asn Ser Arg Arg Cys Lys Lys Thr Phe Arg Gln Cys Asn Asn
                2565                2570                2575

Gly Arg Cys Val Ser Asn Met Leu Trp Cys Asn Gly Val Asp Tyr Cys
            2580                2585                2590

Gly Asp Gly Ser Asp Glu Ile Pro Cys Asn Lys Thr Ala Cys Gly Val
        2595                2600                2605

Gly Glu Phe Arg Cys Arg Asp Gly Ser Cys Ile Gly Asn Ser Ser Arg
    2610                2615                2620

Cys Asn Gln Phe Val Asp Cys Glu Asp Ala Ser Asp Glu Met Asn Cys
2625                2630                2635                2640

Ser Ala Thr Asp Cys Ser Ser Tyr Phe Arg Leu Gly Val Lys Gly Val
                2645                2650                2655

Leu Phe Gln Pro Cys Glu Arg Thr Ser Leu Cys Tyr Ala Pro Ser Trp
            2660                2665                2670

Val Cys Asp Gly Ala Asn Asp Cys Gly Asp Tyr Ser Asp Glu Arg Asp
        2675                2680                2685

Cys Pro Gly Val Lys Arg Pro Arg Cys Pro Leu Asn Tyr Phe Ala Cys
    2690                2695                2700

Pro Ser Gly Arg Cys Ile Pro Met Ser Trp Thr Cys Asp Lys Glu Asp
2705                2710                2715                2720

Asp Cys Glu Asn Gly Glu Asp Glu Thr His Cys Asn Lys Phe Cys Ser
                2725                2730                2735

Glu Ala Gln Phe Glu Cys Gln Asn His Arg Cys Ile Ser Lys Gln Trp
            2740                2745                2750

Leu Cys Asp Gly Ser Asp Asp Cys Gly Asp Gly Ser Asp Glu Ala Ala
        2755                2760                2765

His Cys Glu Gly Lys Thr Cys Gly Pro Ser Ser Phe Ser Cys Pro Gly
    2770                2775                2780
```

-continued

```
Thr His Val Cys Val Pro Glu Arg Trp Leu Cys Asp Gly Asp Lys Asp
2785                2790                2795                2800

Cys Thr Asp Gly Ala Asp Glu Ser Val Thr Ala Gly Cys Leu Tyr Asn
                2805                2810                2815

Ser Thr Cys Asp Asp Arg Glu Phe Met Cys Gln Asn Arg Leu Cys Ile
            2820                2825                2830

Pro Lys His Phe Val Cys Asp His Asp Arg Asp Cys Ala Asp Gly Ser
        2835                2840                2845

Asp Glu Ser Pro Glu Cys Glu Tyr Pro Thr Cys Gly Pro Asn Glu Phe
    2850                2855                2860

Arg Cys Ala Asn Gly Arg Cys Leu Ser Ser Arg Gln Trp Glu Cys Asp
2865                2870                2875                2880

Gly Glu Asn Asp Cys His Asp His Ser Asp Glu Ala Pro Lys Asn Pro
                2885                2890                2895

His Cys Thr Ser Pro Glu His Lys Cys Asn Ala Ser Ser Gln Phe Leu
            2900                2905                2910

Cys Ser Ser Gly Arg Cys Val Ala Glu Ala Leu Leu Cys Asn Gly Gln
        2915                2920                2925

Asp Asp Cys Gly Asp Gly Ser Asp Glu Arg Gly Cys His Val Asn Glu
    2930                2935                2940

Cys Leu Ser Arg Lys Leu Ser Gly Cys Ser Gln Asp Cys Glu Asp Leu
2945                2950                2955                2960

Lys Ile Gly Phe Lys Cys Arg Cys Arg Pro Gly Phe Arg Leu Lys Asp
                2965                2970                2975

Asp Gly Arg Thr Cys Ala Asp Leu Asp Glu Cys Ser Thr Thr Phe Pro
            2980                2985                2990

Cys Ser Gln Leu Cys Ile Asn Thr His Gly Ser Tyr Lys Cys Leu Cys
        2995                3000                3005

Val Glu Gly Tyr Ala Pro Arg Gly Gly Asp Pro His Ser Cys Lys Ala
    3010                3015                3020

Val Thr Asp Glu Glu Pro Phe Leu Ile Phe Ala Asn Arg Tyr Tyr Leu
3025                3030                3035                3040

Arg Lys Leu Asn Leu Asp Gly Ser Asn Tyr Thr Leu Leu Lys Gln Gly
                3045                3050                3055

Leu Asn Asn Ala Val Ala Leu Ala Phe Asp Tyr Arg Glu Gln Met Ile
            3060                3065                3070

Tyr Trp Thr Gly Val Thr Thr Gln Gly Ser Met Ile Arg Arg Met His
        3075                3080                3085

Leu Asn Gly Ser Asn Val Gln Val Leu His Arg Thr Gly Leu Ser Asn
    3090                3095                3100

Pro Asp Gly Leu Ala Val Asp Trp Val Gly Gly Asn Leu Tyr Trp Cys
3105                3110                3115                3120

Asp Lys Gly Arg Asp Thr Ile Glu Val Ser Lys Leu Asn Gly Ala Tyr
                3125                3130                3135

Arg Thr Val Leu Val Ser Ser Gly Leu Arg Glu Pro Arg Ala Leu Val
            3140                3145                3150

Val Asp Val Gln Asn Gly Tyr Leu Tyr Trp Thr Asp Trp Gly Asp His
        3155                3160                3165

Ser Leu Ile Gly Arg Ile Gly Met Asp Gly Ser Gly Arg Ser Ile Ile
    3170                3175                3180

Val Asp Thr Lys Ile Thr Trp Pro Asn Gly Leu Thr Val Asp Tyr Val
3185                3190                3195                3200
```

-continued

```
Thr Glu Arg Ile Tyr Trp Ala Asp Ala Arg Glu Asp Tyr Ile Glu Phe
                3205                3210                3215

Ala Ser Leu Asp Gly Ser Asn Arg His Val Val Leu Ser Gln Asp Ile
            3220                3225                3230

Pro His Ile Phe Ala Leu Thr Leu Phe Glu Asp Tyr Val Tyr Trp Thr
        3235                3240                3245

Asp Trp Glu Thr Lys Ser Ile Asn Arg Ala His Lys Thr Thr Gly Ala
    3250                3255                3260

Asn Lys Thr Leu Leu Ile Ser Thr Leu His Arg Pro Met Asp Leu His
3265                3270                3275                3280

Val Phe His Ala Leu Arg Gln Pro Asp Val Pro Asn His Pro Cys Lys
                3285                3290                3295

Val Asn Asn Gly Gly Cys Ser Asn Leu Cys Leu Leu Ser Pro Gly Gly
            3300                3305                3310

Gly His Lys Cys Ala Cys Pro Thr Asn Phe Tyr Leu Gly Gly Asp Gly
        3315                3320                3325

Arg Thr Cys Val Ser Asn Cys Thr Ala Ser Gln Phe Val Cys Lys Asn
    3330                3335                3340

Asp Lys Cys Ile Pro Phe Trp Trp Lys Cys Asp Thr Glu Asp Asp Cys
3345                3350                3355                3360

Gly Asp His Ser Asp Glu Pro Pro Asp Cys Pro Glu Phe Lys Cys Arg
                3365                3370                3375

Pro Gly Gln Phe Gln Cys Ser Thr Gly Ile Cys Thr Asn Pro Ala Phe
            3380                3385                3390

Ile Cys Asp Gly Asp Asn Asp Cys Gln Asp Asn Ser Asp Glu Ala Asn
        3395                3400                3405

Cys Asp Ile His Val Cys Leu Pro Ser Gln Phe Lys Cys Thr Asn Thr
    3410                3415                3420

Asn Arg Cys Ile Pro Gly Ile Phe Arg Cys Asn Gly Gln Asp Asn Cys
3425                3430                3435                3440

Gly Asp Gly Glu Asp Glu Arg Asp Cys Pro Glu Val Thr Cys Ala Pro
                3445                3450                3455

Asn Gln Phe Gln Cys Ser Ile Thr Lys Arg Cys Ile Pro Arg Val Trp
            3460                3465                3470

Val Cys Asp Arg Asp Asn His Cys Val Asp Gly Ser Asp Glu Pro Ala
        3475                3480                3485

Asn Cys Thr Gln Met Thr Cys Gly Val Asp Glu Phe Arg Cys Lys Asp
    3490                3495                3500

Ser Gly Arg Cys Ile Pro Ala Arg Trp Lys Cys Asp Gly Glu Asp Asp
3505                3510                3515                3520

Cys Gly Asp Gly Ser Asp Glu Pro Lys Glu Glu Cys Asp Glu Arg Thr
                3525                3530                3535

Cys Glu Pro Tyr Gln Phe Arg Cys Lys Asn Asn Arg Cys Val Pro Gly
            3540                3545                3550

Arg Trp Gln Cys Asp Tyr Asp Asn Asp Cys Gly Asp Asn Ser Asp Glu
        3555                3560                3565

Glu Ser Cys Thr Pro Arg Pro Cys Ser Glu Ser Glu Phe Phe Cys Ala
    3570                3575                3580

Asn Gly Arg Cys Ile Ala Gly Arg Trp Lys Cys Asp Gly Asp His Asp
3585                3590                3595                3600

Cys Ala Asp Gly Ser Asp Glu Lys Asp Cys Thr Pro Arg Cys Asp Met
                3605                3610                3615
```

-continued

```
Asp Gln Phe Gln Cys Lys Ser Gly His Cys Ile Pro Leu Arg Trp Pro
            3620                3625                3630

Cys Asp Ala Asp Ala Asp Cys Met Asp Gly Ser Asp Glu Glu Ala Cys
        3635                3640                3645

Gly Thr Gly Val Arg Thr Cys Pro Leu Asp Glu Phe Gln Cys Asn Asn
    3650                3655                3660

Thr Leu Cys Lys Pro Leu Ala Trp Lys Cys Asp Gly Glu Asp Asp Cys
3665                3670                3675                3680

Gly Asp Asn Ser Asp Glu Asn Pro Glu Glu Cys Ala Arg Phe Ile Cys
                3685                3690                3695

Pro Pro Asn Arg Pro Phe Arg Cys Lys Asn Asp Arg Val Cys Leu Trp
            3700                3705                3710

Ile Gly Arg Gln Cys Asp Gly Val Asp Asn Cys Gly Asp Gly Thr Asp
        3715                3720                3725

Glu Glu Asp Cys Glu Pro Pro Thr Ala Gln Asn Pro His Cys Lys Asp
    3730                3735                3740

Lys Lys Glu Phe Leu Cys Arg Asn Gln Arg Cys Leu Ser Ser Ser Leu
3745                3750                3755                3760

Arg Cys Asn Met Phe Asp Asp Cys Gly Asp Gly Ser Asp Glu Glu Asp
                3765                3770                3775

Cys Ser Ile Asp Pro Lys Leu Thr Ser Cys Ala Thr Asn Ala Ser Met
            3780                3785                3790

Cys Gly Asp Glu Ala Arg Cys Val Arg Thr Glu Lys Ala Ala Tyr Cys
        3795                3800                3805

Ala Cys Arg Ser Gly Phe His Thr Val Pro Gly Gln Pro Gly Cys Gln
    3810                3815                3820

Asp Ile Asn Glu Cys Leu Arg Phe Gly Thr Cys Ser Gln Leu Trp Asn
3825                3830                3835                3840

Lys Pro Lys Gly Gly His Leu Cys Ser Cys Ala Arg Asn Phe Met Lys
                3845                3850                3855

Thr His Asn Thr Cys Lys Ala Glu Gly Ser Glu Tyr Gln Val Leu Tyr
            3860                3865                3870

Ile Ala Asp Asp Asn Glu Ile Arg Ser Leu Phe Pro Gly His Pro His
        3875                3880                3885

Ser Ala Tyr Glu Gln Thr Phe Gln Gly Asp Glu Ser Val Arg Ile Asp
    3890                3895                3900

Ala Met Asp Val His Val Lys Ala Gly Arg Val Tyr Trp Thr Asn Trp
3905                3910                3915                3920

His Thr Gly Thr Ile Ser Tyr Arg Ser Leu Pro Pro Ala Ala Pro Pro
                3925                3930                3935

Thr Thr Ser Asn Arg His Arg Arg Gln Ile Asp Arg Gly Val Thr His
            3940                3945                3950

Leu Asn Ile Ser Gly Leu Lys Met Pro Arg Gly Ile Ala Ile Asp Trp
        3955                3960                3965

Val Ala Gly Asn Val Tyr Trp Thr Asp Ser Gly Arg Asp Val Ile Glu
    3970                3975                3980

Val Ala Gln Met Lys Gly Glu Asn Arg Lys Thr Leu Ile Ser Gly Met
3985                3990                3995                4000

Ile Asp Glu Pro His Ala Ile Val Val Asp Pro Leu Arg Gly Thr Met
                4005                4010                4015

Tyr Trp Ser Asp Trp Gly Asn His Pro Lys Ile Glu Thr Ala Ala Met
            4020                4025                4030
```

-continued

```
Asp Gly Thr Leu Arg Glu Thr Leu Val Gln Asp Asn Ile Gln Trp Pro
        4035                4040                4045

Thr Gly Leu Ala Val Asp Tyr His Asn Glu Arg Leu Tyr Trp Ala Asp
    4050                4055                4060

Ala Lys Leu Ser Val Ile Gly Ser Ile Arg Leu Asn Gly Thr Asp Pro
4065                4070                4075                4080

Ile Val Ala Ala Asp Ser Lys Arg Gly Leu Ser His Pro Phe Ser Ile
                4085                4090                4095

Asp Val Phe Glu Asp Tyr Ile Tyr Gly Val Thr Tyr Ile Asn Asn Arg
            4100                4105                4110

Val Phe Lys Ile His Lys Phe Gly His Ser Pro Leu Tyr Asn Leu Thr
        4115                4120                4125

Gly Gly Leu Ser His Ala Ser Asp Val Val Leu Tyr His Gln His Lys
    4130                4135                4140

Gln Pro Glu Val Thr Asn Pro Cys Asp Arg Lys Lys Cys Glu Trp Leu
4145                4150                4155                4160

Cys Leu Leu Ser Pro Ser Gly Pro Val Cys Thr Cys Pro Asn Gly Lys
                4165                4170                4175

Arg Leu Asp Asn Gly Thr Cys Val Pro Val Pro Ser Pro Thr Pro Pro
            4180                4185                4190

Pro Asp Ala Pro Arg Pro Gly Thr Cys Thr Leu Gln Cys Phe Asn Gly
        4195                4200                4205

Gly Ser Cys Phe Leu Asn Ala Arg Arg Gln Pro Lys Cys Arg Cys Gln
    4210                4215                4220

Pro Arg Tyr Thr Gly Asp Lys Cys Glu Leu Asp Gln Cys Trp Glu Tyr
4225                4230                4235                4240

Cys His Asn Gly Gly Thr Cys Ala Ala Ser Pro Ser Gly Met Pro Thr
                4245                4250                4255

Cys Arg Cys Pro Thr Gly Phe Thr Gly Pro Lys Cys Thr Ala Gln Val
            4260                4265                4270

Cys Ala Gly Tyr Cys Ser Asn Asn Ser Thr Cys Thr Val Asn Gln Gly
        4275                4280                4285

Asn Gln Pro Gln Cys Arg Cys Leu Pro Gly Phe Leu Gly Asp Arg Cys
    4290                4295                4300

Gln Tyr Arg Gln Cys Ser Gly Phe Cys Glu Asn Phe Gly Thr Cys Gln
4305                4310                4315                4320

Met Ala Ala Asp Gly Ser Arg Gln Cys Arg Cys Thr Val Tyr Phe Glu
                4325                4330                4335

Gly Pro Arg Cys Glu Val Asn Lys Cys Ser Arg Cys Leu Gln Gly Ala
            4340                4345                4350

Cys Val Val Asn Lys Gln Thr Gly Asp Val Thr Cys Asn Cys Thr Asp
        4355                4360                4365

Gly Arg Val Ala Pro Ser Cys Leu Thr Cys Ile Asp His Cys Ser Asn
    4370                4375                4380

Gly Gly Ser Cys Thr Met Asn Ser Lys Met Met Pro Glu Cys Gln Cys
4385                4390                4395                4400

Pro Pro His Met Thr Gly Pro Arg Cys Gln Glu Gln Val Val Ser Gln
                4405                4410                4415

Gln Gln Pro Gly His Met Ala Ser Ile Leu Ile Pro Leu Leu Leu Leu
            4420                4425                4430

Leu Leu Leu Leu Leu Val Ala Gly Val Val Phe Trp Tyr Lys Arg Arg
        4435                4440                4445
```

-continued

```
Val Arg Gly Ala Lys Gly Phe Gln His Gln Arg Met Thr Asn Gly Ala
    4450                4455                4460

Met Asn Val Glu Ile Gly Asn Pro Thr Tyr Lys Met Tyr Glu Gly Gly
4465                4470                4475                4480

Glu Pro Asp Asp Val Gly Gly Leu Leu Asp Ala Asp Phe Ala Leu Asp
                4485                4490                4495

Pro Asp Lys Pro Thr Asn Phe Thr Asn Pro Val Tyr Ala Thr Leu Tyr
            4500                4505                4510

Met Gly Gly His Gly Ser Arg His Ser Leu Ala Ser Thr Asp Glu Lys
        4515                4520                4525

Arg Glu Leu Leu Gly Arg Gly Pro Glu Asp Glu Ile Gly Asp Pro Leu
    4530                4535                4540

Ala
4545
```

<210> SEQ ID NO 3
<211> LENGTH: 4577
<212> TYPE: DNA
<213> ORGANISM: Homo sapiens

<400> SEQUENCE: 3

```
gctacaatcc atctggtctc ctccagctcc ttctttctgc aacatgggga agaacaaact     60

ccttcatcca agtctggttc ttctcctctt ggtcctcctg cccacagacg cctcagtctc    120

tggaaaaccg cagtatatgg ttctggtccc ctccctgctc cacactgaga ccactgagaa    180

gggctgtgtc cttctgagct acctgaatga gacagtgact gtaagtgctt ccttggagtc    240

tgtcagggga aacaggagcc tcttcactga cctggaggcg gagaatgacg tactccactg    300

tgtcgccttc gctgtcccaa agtcttcatc caatgaggag gtaatgttcc tcactgtcca    360

agtgaaagga ccaacccaag aatttaagaa gcggaccaca gtgatggtta agaacgagga    420

cagtctggtc tttgtccaga cagacaaatc aatctacaaa ccagggcaga cagtgaaatt    480

tcgtgttgtc tccatggatg aaaactttca ccccctgaat gagttgattc cactagtata    540

cattcaggat cccaaaggaa atcgcatcgc acaatggcag agtttccagt tagagggtgg    600

cctcaagcaa ttttcttttc ccctctcatc agagcccttc cagggctcct acaaggtggt    660

ggtacagaag aaatcaggtg gaaggacaga gcaccctttc accgtggagg aatttgttct    720

tcccaagttt gaagtacaag taacagtgcc aaagataatc accatcttgg aagaagagat    780

gaatgtatca gtgtgtggcc tatacacata tgggaagcct gtccctggac atgtgactgt    840

gagcatttgc agaaagtata gtgacgcttc cgactgccac ggtgaagatt cacaggcttt    900

ctgtgagaaa ttcagtggac agctaaacag ccatggctgc ttctatcagc aagtaaaaac    960

caaggtcttc cagctgaaga ggaaggagta tgaaatgaaa cttcacactg aggcccagat   1020

ccaagaagaa ggaacagtgg tggaattgac tggaaggcag tccagtgaaa tcacaagaac   1080

cataaccaaa ctctcatttg tgaaagtgga ctcacacttt cgacagggaa ttcccttctt   1140

tgggcaggtg cgcctagtag atgggaaagg cgtccctata ccaaataaag tcatattcat   1200

cagaggaaat gaagcaaact attactccaa tgctaccacg gatgagcatg gccttgtaca   1260

gttctctatc aacaccacca acgttatggg tacctctctt actgttaggg tcaattacaa   1320

ggatcgtagt ccctgttacg gctaccagtg ggtgtcagaa gaacacgaag aggcacatca   1380

cactgcttat cttgtgttct ccccaagcaa gagctttgtc caccttgagc ccatgtctca   1440

tgaactaccc tgtggccata ctcagacagt ccaggcacat tatattctga atggaggcac   1500
```

-continued

```
cctgctgggg ctgaagaagc tctcctttta ttatctgata atggcaaagg gaggcattgt   1560
ccgaactggg actcatggac tgcttgtgaa gcaggaagac atgaagggcc atttttccat   1620
ctcaatccct gtgaagtcag acattgctcc tgtcgctcgg ttgctcatct atgctgtttt   1680
acctaccggg gacgtgattg gggattctgc aaaatatgat gttgaaaatt gtctggccaa   1740
caaggtggat ttgagcttca gcccatcaca aagtctccca gcctcacacg cccacctgcg   1800
agtcacagcg gctcctcagt ccgtctgcgc cctccgtgct gtggaccaaa gcgtgctgct   1860
catgaagcct gatgctgagc tctcggcgtc ctcggtttac aacctgctac cagaaaagga   1920
cctcactggc ttccctgggc ctttgaatga ccaggacgat gaagactgca tcaatcgtca   1980
taatgtctat attaatggaa tcacatatac tccagtatca agtacaaatg aaaaggatat   2040
gtacagcttc ctagaggaca tgggcttaaa ggcattcacc aactcaaaga ttcgtaaacc   2100
caaaatgtgt ccacagcttc aacagtatga aatgcatgga cctgaaggtc tacgtgtagg   2160
tttttatgag tcagatgtaa tgggaagagg ccatgcacgc ctggtgcatg ttgaagagcc   2220
tcacacggag accgtacgaa agtacttccc tgagacatgg atctgggatt tggtggtggt   2280
aaactcagca ggggtggctg aggtaggagt aacagtccct gacaccatca ccgagtggaa   2340
ggcaggggcc ttctgcctgt ctgaagatgc tggacttggt atctcttcca ctgcctctct   2400
ccgagccttc cagcccttct ttgtggagct tacaatgcct tactctgtga ttcgtggaga   2460
ggccttcaca ctcaaggcca cggtcctaaa ctaccttccc aaatgcatcc gggtcagtgt   2520
gcagctggaa gcctctcccg ccttccttgc tgtcccagtg gagaaggaac aagcgcctca   2580
ctgcatctgt gcaaacgggc ggcaaactgt gtcctgggca gtaaccccaa agtcattagg   2640
aaatgtgaat ttcactgtga gcgcagaggc actagagtct caagagctgt gtgggactga   2700
ggtgccttca gttcctgaac acggaaggaa agacacagtc atcaagcctc tgttggttga   2760
acctgaagga ctagagaagg aaacaacatt caactcccta ctttgtccat caggtggtga   2820
ggtttctgaa gaattatccc tgaaactgcc accaaatgtg gtagaagaat ctgcccgagc   2880
ttctgtctca gttttgggag acatattagg ctctgccatg caaaacacac aaaatcttct   2940
ccagatgccc tatggctgtg gagagcagaa tatggtcctc tttgctccta acatctatgt   3000
actggattat ctaaatgaaa cacagcagct tactccagag gtcaagtcca aggccattgg   3060
ctatctcaac actggttacc agagacagtt gaactacaaa cactatgatg gctcctacag   3120
cacctttggg gagcgatatg gcaggaacca gggcaacacc tggctcacag cctttgttct   3180
gaagactttt gcccaagctc gagcctacat cttcatcgat gaagcacaca ttacccaagc   3240
cctcatatgg ctctcccaga ggcagaagga caatggctgt ttcaggagct ctgggtcact   3300
gctcaacaat gccataaagg gaggagtaga agatgaagtg accctctccg cctatatcac   3360
catcgccctt ctggagattc ctctcacagt cactcaccct gttgtccgca atgccctgtt   3420
ttgcctggag tcagcctgga agacagcaca agaaggggac catggcagcc atgtatatac   3480
caaagcactg ctggcctatg cttttgccct ggcaggtaac caggacaaga ggaaggaagt   3540
actcaagtca cttaatgagg aagctgtgaa gaaagacaac tctgtccatt gggagcgccc   3600
tcagaaaccc aaggcaccag tggggcattt ttacgaaccc caggctccct ctgctgaggt   3660
ggagatgaca tcctatgtgc tcctcgctta tctcacggcc cagccagccc caacctcgga   3720
ggacctgacc tctgcaacca acatcgtgaa gtggatcacg aagcagcaga atgcccaggg   3780
cggtttctcc tccacccagg acacagtggt ggctctccat gctctgtcca aatatggagc   3840
cgccacattt accaggactg ggaaggctgc acaggtgact atccagtctt cagggacatt   3900
```

-continued

```
ttccagcaaa ttccaagtgg acaacaacaa tcgcctgtta ctgcagcagg tctcattgcc   3960

agagctgcct ggggaataca gcatgaaagt gacaggagaa ggatgtgtct acctccagac   4020

ctccttgaaa tacaatattc tcccagaaaa ggaagagttc ccctttgctt taggagtgca   4080

gactctgcct caaacttgtg atgaacccaa agcccacacc agcttccaaa tctccctaag   4140

tgtcagttac acagggagcc gctctgcctc caacatggcg atcgttgatg tgaagatggt   4200

ctctggcttc attcccctga agccaacagt gaaaatgctt gaaagatcta accatgtgag   4260

ccggacagaa gtcagcagca accatgtctt gatttacctt gataaggtgt caaatcagac   4320

actgagcttg ttcttcacgg ttctgcaaga tgtcccagta agagatctca aaccagccat   4380

agtgaaagtc tatgattact acgagacgga tgagtttgca atcgctgagt acaatgctcc   4440

ttgcagcaaa gatcttggaa atgcttgaag accacaaggc tgaaaagtgc tttgctggag   4500

tcctgttctc tgagctccac agaagacacg tgtttttgta tctttaaaga cttgatgaat   4560

aaacactttt tctggtc                                                  4577
```

<210> SEQ ID NO 4
<211> LENGTH: 4422
<212> TYPE: DNA
<213> ORGANISM: Homo sapiens

<400> SEQUENCE: 4

```
atggggaaga acaaactcct tcatccaagt ctggttcttc tcctcttggt cctcctgccc     60

acagacgcct cagtctctgg aaaaccgcag tatatggttc tggtcccctc cctgctccac    120

actgagacca ctgagaaggg ctgtgtcctt ctgagctacc tgaatgagac agtgactgta    180

agtgcttcct tggagtctgt caggggaaac aggagcctct tcactgacct ggaggcggag    240

aatgacgtac tccactgtgt cgccttcgct gtcccaaagt cttcatccaa tgaggaggta    300

atgttcctca ctgtccaagt gaaaggacca acccaagaat ttaagaagcg gaccacagtg    360

atggttaaga acgaggacag tctggtcttt gtccagacag acaaatcaat ctacaaacca    420

gggcagacag tgaaatttcg tgttgtctcc atggatgaaa actttcaccc cctgaatgag    480

ttgattccac tagtatacat tcaggatccc aaaggaaatc gcatcgcaca atggcagagt    540

ttccagttag agggtggcct caagcaattt tcttttcccc tctcatcaga gcccttccag    600

ggctcctaca aggtggtggt acagaagaaa tcaggtggaa ggacagagca ccctttcacc    660

gtggaggaat ttgttcttcc caagtttgaa gtacaagtaa cagtgccaaa gataatcacc    720

atcttggaag aagagatgaa tgtatcagtg tgtggcctat acacatatgg gaagcctgtc    780

cctggacatg tgactgtgag catttgcaga aagtatagtg acgcttccga ctgccacggt    840

gaagattcac aggctttctg tgagaaattc agtggacagc taaacagcca tggctgcttc    900

tatcagcaag taaaaaccaa ggtcttccag ctgaagagga aggagtatga aatgaaactt    960

cacactgagg cccagatcca agaagaagga acagtggtgg aattgactgg aaggcagtcc   1020

agtgaaatca caagaaccat aaccaaactc tcatttgtga aagtggactc acactttcga   1080

cagggaattc ccttctttgg gcaggtgcgc ctagtagatg ggaaaggcgt ccctatacca   1140

aataaagtca tattcatcag aggaaatgaa gcaaactatt actccaatgc taccacggat   1200

gagcatggcc ttgtacagtt ctctatcaac accaccaacg ttatgggtac ctctcttact   1260

gttagggtca attacaagga tcgtagtccc tgttacggct accagtgggt gtcagaagaa   1320

cacgaagagg cacatcacac tgcttatctt gtgttctccc caagcaagag ctttgtccac   1380

cttgagccca tgtctcatga actaccctgt ggccatactc agacagtcca ggcacattat   1440
```

-continued

```
attctgaatg gaggcaccct gctggggctg aagaagctct ccttttatta tctgataatg   1500
gcaaagggag gcattgtccg aactgggact catggactgc ttgtgaagca ggaagacatg   1560
aagggccatt tttccatctc aatccctgtg aagtcagaca ttgctcctgt cgctcggttg   1620
ctcatctatg ctgttttacc taccggggac gtgattgggg attctgcaaa atatgatgtt   1680
gaaaattgtc tggccaacaa ggtggatttg agcttcagcc catcacaaag tctcccagcc   1740
tcacacgccc acctgcgagt cacagcggct cctcagtccg tctgcgccct ccgtgctgtg   1800
gaccaaagcg tgctgctcat gaagcctgat gctgagctct cggcgtcctc ggtttacaac   1860
ctgctaccag aaaaggacct cactggcttc cctgggcctt tgaatgacca ggacgatgaa   1920
gactgcatca atcgtcataa tgtctatatt aatggaatca catatactcc agtatcaagt   1980
acaaatgaaa aggatatgta cagcttccta gaggacatgg gcttaaaggc attcaccaac   2040
tcaaagattc gtaaacccaa aatgtgtcca cagcttcaac agtatgaaat gcatggacct   2100
gaaggtctac gtgtaggttt ttatgagtca gatgtaatgg gaagaggcca tgcacgcctg   2160
gtgcatgttg aagagcctca cacggagacc gtacgaaagt acttccctga gacatggatc   2220
tgggatttgg tggtggtaaa ctcagcaggg gtggctgagg taggagtaac agtccctgac   2280
accatcaccg agtggaaggc aggggccttc tgcctgtctg aagatgctgg acttggtatc   2340
tcttccactg cctctctccg agccttccag cccttctttg tggagcttac aatgccttac   2400
tctgtgattc gtggagaggc cttcacactc aaggccacgg tcctaaacta ccttcccaaa   2460
tgcatccggg tcagtgtgca gctggaagcc tctcccgcct tccttgctgt cccagtggag   2520
aaggaacaag cgcctcactg catctgtgca aacgggcggc aaactgtgtc ctgggcagta   2580
accccaaagt cattaggaaa tgtgaatttc actgtgagcg cagaggcact agagtctcaa   2640
gagctgtgtg ggactgaggt gccttcagtt cctgaacacg gaaggaaaga cacagtcatc   2700
aagcctctgt tggttgaacc tgaaggacta gagaaggaaa caacattcaa ctccctactt   2760
tgtccatcag gtggtgaggt ttctgaagaa ttatccctga aactgccacc aaatgtggta   2820
gaagaatctg cccgagcttc tgtctcagtt ttgggagaca tattaggctc tgccatgcaa   2880
aacacacaaa atcttctcca gatgccctat ggctgtggag agcagaatat ggtcctcttt   2940
gctcctaaca tctatgtact ggattatcta aatgaaacac agcagcttac tccagaggtc   3000
aagtccaagg ccattggcta tctcaacact ggttaccaga gacagttgaa ctacaaacac   3060
tatgatggct cctacagcac ctttggggag cgatatggca ggaaccaggg caacacctgg   3120
ctcacagcct ttgttctgaa gacttttgcc caagctcgag cctacatctt catcgatgaa   3180
gcacacatta cccaagccct catatggctc tcccagaggc agaaggacaa tggctgtttc   3240
aggagctctg ggtcactgct caacaatgcc ataaagggag gagtagaaga tgaagtgacc   3300
ctctccgcct atatcaccat cgcccttctg gagattcctc tcacagtcac tcaccctgtt   3360
gtccgcaatg ccctgttttg cctggagtca gcctggaaga cagcacaaga aggggaccat   3420
ggcagccatg tatataccaa agcactgctg gcctatgctt ttgccctggc aggtaaccag   3480
gacaagagga aggaagtact caagtcactt aatgaggaag ctgtgaagaa agacaactct   3540
gtccattggg agcgccctca gaaacccaag gcaccagtgg ggcattttta cgaaccccag   3600
gctccctctg ctgaggtgga gatgacatcc tatgtgctcc tcgcttatct cacggcccag   3660
ccagccccaa cctcggagga cctgacctct gcaaccaaca tcgtgaagtg gatcacgaag   3720
cagcagaatg cccagggcgg tttctcctcc acccaggaca cagtggtggc tctccatgct   3780
ctgtccaaat atggagccgc cacatttacc aggactggga aggctgcaca ggtgactatc   3840
```

-continued

```
cagtcttcag ggacattttc cagcaaattc caagtggaca acaacaatcg cctgttactg   3900

cagcaggtct cattgccaga gctgcctggg gaatacagca tgaaagtgac aggagaagga   3960

tgtgtctacc tccagacctc cttgaaatac aatattctcc cagaaaagga agagttcccc   4020

tttgctttag gagtgcagac tctgcctcaa acttgtgatg aacccaaagc ccacaccagc   4080

ttccaaatct ccctaagtgt cagttacaca gggagccgct ctgcctccaa catggcgatc   4140

gttgatgtga agatggtctc tggcttcatt cccctgaagc caacagtgaa aatgcttgaa   4200

agatctaacc atgtgagccg gacagaagtc agcagcaacc atgtcttgat ttaccttgat   4260

aaggtgtcaa atcagacact gagcttgttc ttcacggttc tgcaagatgt cccagtaaga   4320

gatctcaaac cagccatagt gaaagtctat gattactacg agacggatga gtttgcaatc   4380

gctgagtaca atgctccttg cagcaaagat cttggaaatg ct                      4422
```

<210> SEQ ID NO 5
<211> LENGTH: 1474
<212> TYPE: PRT
<213> ORGANISM: Homo sapiens

<400> SEQUENCE: 5

```
Met Gly Lys Asn Lys Leu Leu His Pro Ser Leu Val Leu Leu Leu Leu
 1               5                  10                  15

Val Leu Leu Pro Thr Asp Ala Ser Val Ser Gly Lys Pro Gln Tyr Met
            20                  25                  30

Val Leu Val Pro Ser Leu Leu His Thr Glu Thr Thr Glu Lys Gly Cys
        35                  40                  45

Val Leu Leu Ser Tyr Leu Asn Glu Thr Val Thr Val Ser Ala Ser Leu
    50                  55                  60

Glu Ser Val Arg Gly Asn Arg Ser Leu Phe Thr Asp Leu Glu Ala Glu
65                  70                  75                  80

Asn Asp Val Leu His Cys Val Ala Phe Ala Val Pro Lys Ser Ser Ser
                85                  90                  95

Asn Glu Glu Val Met Phe Leu Thr Val Gln Val Lys Gly Pro Thr Gln
            100                 105                 110

Glu Phe Lys Lys Arg Thr Thr Val Met Val Lys Asn Glu Asp Ser Leu
        115                 120                 125

Val Phe Val Gln Thr Asp Lys Ser Ile Tyr Lys Pro Gly Gln Thr Val
    130                 135                 140

Lys Phe Arg Val Val Ser Met Asp Glu Asn Phe His Pro Leu Asn Glu
145                 150                 155                 160

Leu Ile Pro Leu Val Tyr Ile Gln Asp Pro Lys Gly Asn Arg Ile Ala
                165                 170                 175

Gln Trp Gln Ser Phe Gln Leu Glu Gly Gly Leu Lys Gln Phe Ser Phe
            180                 185                 190

Pro Leu Ser Ser Glu Pro Phe Gln Gly Ser Tyr Lys Val Val Val Gln
        195                 200                 205

Lys Lys Ser Gly Gly Arg Thr Glu His Pro Phe Thr Val Glu Glu Phe
    210                 215                 220

Val Leu Pro Lys Phe Glu Val Gln Val Thr Val Pro Lys Ile Ile Thr
225                 230                 235                 240

Ile Leu Glu Glu Glu Met Asn Val Ser Val Cys Gly Leu Tyr Thr Tyr
                245                 250                 255

Gly Lys Pro Val Pro Gly His Val Thr Val Ser Ile Cys Arg Lys Tyr
            260                 265                 270
```

-continued

```
Ser Asp Ala Ser Asp Cys His Gly Glu Asp Ser Gln Ala Phe Cys Glu
        275                 280                 285

Lys Phe Ser Gly Gln Leu Asn Ser His Gly Cys Phe Tyr Gln Gln Val
    290                 295                 300

Lys Thr Lys Val Phe Gln Leu Lys Arg Lys Glu Tyr Glu Met Lys Leu
305                 310                 315                 320

His Thr Glu Ala Gln Ile Gln Glu Glu Gly Thr Val Val Glu Leu Thr
                325                 330                 335

Gly Arg Gln Ser Ser Glu Ile Thr Arg Thr Ile Thr Lys Leu Ser Phe
            340                 345                 350

Val Lys Val Asp Ser His Phe Arg Gln Gly Ile Pro Phe Phe Gly Gln
        355                 360                 365

Val Arg Leu Val Asp Gly Lys Gly Val Pro Ile Pro Asn Lys Val Ile
    370                 375                 380

Phe Ile Arg Gly Asn Glu Ala Asn Tyr Tyr Ser Asn Ala Thr Thr Asp
385                 390                 395                 400

Glu His Gly Leu Val Gln Phe Ser Ile Asn Thr Thr Asn Val Met Gly
                405                 410                 415

Thr Ser Leu Thr Val Arg Val Asn Tyr Lys Asp Arg Ser Pro Cys Tyr
            420                 425                 430

Gly Tyr Gln Trp Val Ser Glu Glu His Glu Glu Ala His His Thr Ala
        435                 440                 445

Tyr Leu Val Phe Ser Pro Ser Lys Ser Phe Val His Leu Glu Pro Met
    450                 455                 460

Ser His Glu Leu Pro Cys Gly His Thr Gln Thr Val Gln Ala His Tyr
465                 470                 475                 480

Ile Leu Asn Gly Gly Thr Leu Leu Gly Leu Lys Lys Leu Ser Phe Tyr
                485                 490                 495

Tyr Leu Ile Met Ala Lys Gly Gly Ile Val Arg Thr Gly Thr His Gly
            500                 505                 510

Leu Leu Val Lys Gln Glu Asp Met Lys Gly His Phe Ser Ile Ser Ile
        515                 520                 525

Pro Val Lys Ser Asp Ile Ala Pro Val Ala Arg Leu Leu Ile Tyr Ala
    530                 535                 540

Val Leu Pro Thr Gly Asp Val Ile Gly Asp Ser Ala Lys Tyr Asp Val
545                 550                 555                 560

Glu Asn Cys Leu Ala Asn Lys Val Asp Leu Ser Phe Ser Pro Ser Gln
                565                 570                 575

Ser Leu Pro Ala Ser His Ala His Leu Arg Val Thr Ala Ala Pro Gln
            580                 585                 590

Ser Val Cys Ala Leu Arg Ala Val Asp Gln Ser Val Leu Leu Met Lys
        595                 600                 605

Pro Asp Ala Glu Leu Ser Ala Ser Ser Val Tyr Asn Leu Leu Pro Glu
    610                 615                 620

Lys Asp Leu Thr Gly Phe Pro Gly Pro Leu Asn Asp Gln Asp Asp Glu
625                 630                 635                 640

Asp Cys Ile Asn Arg His Asn Val Tyr Ile Asn Gly Ile Thr Tyr Thr
                645                 650                 655

Pro Val Ser Ser Thr Asn Glu Lys Asp Met Tyr Ser Phe Leu Glu Asp
            660                 665                 670

Met Gly Leu Lys Ala Phe Thr Asn Ser Lys Ile Arg Lys Pro Lys Met
        675                 680                 685
```

-continued

```
Cys Pro Gln Leu Gln Gln Tyr Glu Met His Gly Pro Glu Gly Leu Arg
    690                 695                 700

Val Gly Phe Tyr Glu Ser Asp Val Met Gly Arg Gly His Ala Arg Leu
705                 710                 715                 720

Val His Val Glu Glu Pro His Thr Glu Thr Val Arg Lys Tyr Phe Pro
                725                 730                 735

Glu Thr Trp Ile Trp Asp Leu Val Val Val Asn Ser Ala Gly Val Ala
            740                 745                 750

Glu Val Gly Val Thr Val Pro Asp Thr Ile Thr Glu Trp Lys Ala Gly
        755                 760                 765

Ala Phe Cys Leu Ser Glu Asp Ala Gly Leu Gly Ile Ser Ser Thr Ala
    770                 775                 780

Ser Leu Arg Ala Phe Gln Pro Phe Phe Val Glu Leu Thr Met Pro Tyr
785                 790                 795                 800

Ser Val Ile Arg Gly Glu Ala Phe Thr Leu Lys Ala Thr Val Leu Asn
                805                 810                 815

Tyr Leu Pro Lys Cys Ile Arg Val Ser Val Gln Leu Glu Ala Ser Pro
            820                 825                 830

Ala Phe Leu Ala Val Pro Val Glu Lys Glu Gln Ala Pro His Cys Ile
        835                 840                 845

Cys Ala Asn Gly Arg Gln Thr Val Ser Trp Ala Val Thr Pro Lys Ser
    850                 855                 860

Leu Gly Asn Val Asn Phe Thr Val Ser Ala Glu Ala Leu Glu Ser Gln
865                 870                 875                 880

Glu Leu Cys Gly Thr Glu Val Pro Ser Val Pro Glu His Gly Arg Lys
                885                 890                 895

Asp Thr Val Ile Lys Pro Leu Leu Val Glu Pro Glu Gly Leu Glu Lys
            900                 905                 910

Glu Thr Thr Phe Asn Ser Leu Leu Cys Pro Ser Gly Gly Glu Val Ser
        915                 920                 925

Glu Glu Leu Ser Leu Lys Leu Pro Pro Asn Val Val Glu Glu Ser Ala
    930                 935                 940

Arg Ala Ser Val Ser Val Leu Gly Asp Ile Leu Gly Ser Ala Met Gln
945                 950                 955                 960

Asn Thr Gln Asn Leu Leu Gln Met Pro Tyr Gly Cys Gly Glu Gln Asn
                965                 970                 975

Met Val Leu Phe Ala Pro Asn Ile Tyr Val Leu Asp Tyr Leu Asn Glu
            980                 985                 990

Thr Gln Gln Leu Thr Pro Glu Val Lys Ser Lys Ala Ile Gly Tyr Leu
        995                 1000                1005

Asn Thr Gly Tyr Gln Arg Gln Leu Asn Tyr Lys His Tyr Asp Gly Ser
    1010                1015                1020

Tyr Ser Thr Phe Gly Glu Arg Tyr Gly Arg Asn Gln Gly Asn Thr Trp
1025                1030                1035                1040

Leu Thr Ala Phe Val Leu Lys Thr Phe Ala Gln Ala Arg Ala Tyr Ile
                1045                1050                1055

Phe Ile Asp Glu Ala His Ile Thr Gln Ala Leu Ile Trp Leu Ser Gln
            1060                1065                1070

Arg Gln Lys Asp Asn Gly Cys Phe Arg Ser Ser Gly Ser Leu Leu Asn
        1075                1080                1085

Asn Ala Ile Lys Gly Gly Val Glu Asp Glu Val Thr Leu Ser Ala Tyr
    1090                1095                1100
```

-continued

```
Ile Thr Ile Ala Leu Leu Glu Ile Pro Leu Thr Val Thr His Pro Val
1105                1110                1115                1120

Val Arg Asn Ala Leu Phe Cys Leu Glu Ser Ala Trp Lys Thr Ala Gln
                1125                1130                1135

Glu Gly Asp His Gly Ser His Val Tyr Thr Lys Ala Leu Leu Ala Tyr
            1140                1145                1150

Ala Phe Ala Leu Ala Gly Asn Gln Asp Lys Arg Lys Glu Val Leu Lys
        1155                1160                1165

Ser Leu Asn Glu Glu Ala Val Lys Lys Asp Asn Ser Val His Trp Glu
    1170                1175                1180

Arg Pro Gln Lys Pro Lys Ala Pro Val Gly His Phe Tyr Glu Pro Gln
1185                1190                1195                1200

Ala Pro Ser Ala Glu Val Glu Met Thr Ser Tyr Val Leu Leu Ala Tyr
                1205                1210                1215

Leu Thr Ala Gln Pro Ala Pro Thr Ser Glu Asp Leu Thr Ser Ala Thr
            1220                1225                1230

Asn Ile Val Lys Trp Ile Thr Lys Gln Gln Asn Ala Gln Gly Gly Phe
        1235                1240                1245

Ser Ser Thr Gln Asp Thr Val Val Ala Leu His Ala Leu Ser Lys Tyr
    1250                1255                1260

Gly Ala Ala Thr Phe Thr Arg Thr Gly Lys Ala Ala Gln Val Thr Ile
1265                1270                1275                1280

Gln Ser Ser Gly Thr Phe Ser Ser Lys Phe Gln Val Asp Asn Asn Asn
                1285                1290                1295

Arg Leu Leu Leu Gln Gln Val Ser Leu Pro Glu Leu Pro Gly Glu Tyr
            1300                1305                1310

Ser Met Lys Val Thr Gly Glu Gly Cys Val Tyr Leu Gln Thr Ser Leu
        1315                1320                1325

Lys Tyr Asn Ile Leu Pro Glu Lys Glu Glu Phe Pro Phe Ala Leu Gly
    1330                1335                1340

Val Gln Thr Leu Pro Gln Thr Cys Asp Glu Pro Lys Ala His Thr Ser
1345                1350                1355                1360

Phe Gln Ile Ser Leu Ser Val Ser Tyr Thr Gly Ser Arg Ser Ala Ser
                1365                1370                1375

Asn Met Ala Ile Val Asp Val Lys Met Val Ser Gly Phe Ile Pro Leu
            1380                1385                1390

Lys Pro Thr Val Lys Met Leu Glu Arg Ser Asn His Val Ser Arg Thr
        1395                1400                1405

Glu Val Ser Ser Asn His Val Leu Ile Tyr Leu Asp Lys Val Ser Asn
    1410                1415                1420

Gln Thr Leu Ser Leu Phe Phe Thr Val Leu Gln Asp Val Pro Val Arg
1425                1430                1435                1440

Asp Leu Lys Pro Ala Ile Val Lys Val Tyr Asp Tyr Tyr Glu Thr Asp
                1445                1450                1455

Glu Phe Ala Ile Ala Glu Tyr Asn Ala Pro Cys Ser Lys Asp Leu Gly
            1460                1465                1470

Asn Ala
```

<210> SEQ ID NO 6
<211> LENGTH: 14896
<212> TYPE: DNA
<213> ORGANISM: Homo sapiens -continued

<400> SEQUENCE: 6

```
cagcggtgcg agctccaggc ccatgcactg aggaggcgga aacaagggga gcccccagag     60
ctccatcaag ccccctccaa aggctcccct acccggtcca cgccccccac cccccctccc    120
cgcctcctcc caattgtgca tttttgcagc cggaggcggc tccgagatgg ggctgtgagc    180
ttcgcccggg gaggggggaaa gagcagcgag gagtgaagcg ggggggtggg gtgaagggtt    240
tggatttcgg ggcagggggc gcacccccgt cagcaggccc tccccaaggg gctcggaact    300
ctacctcttc acccacgccc ctggtgcgct ttgccgaagg aaagaataag aacagagaag    360
gaggaggggg aaaggaggaa aagggggacc ccccaactgg ggggggtgaa ggagagaagt    420
agcaggacca gaggggaagg ggctgctgct tgcatcagcc cacaccatgc tgaccccgcc    480
gttgctcctg ctgctgcccc tgctctcagc tctggtcgcg gcggctatcg acgcccctaa    540
gacttgcagc cccaagcagt ttgcctgcag agatcaaata acctgtatct caaagggctg    600
gcggtgcgac ggtgagaggg actgcccaga cggatctgac gaggcccctg agatttgtcc    660
acagagtaag gcccagcgat gccagccaaa cgagcataac tgcctgggta ctgagctgtg    720
tgttcccatg tcccgcctct gcaatggggt ccaggactgc atggacggct cagatgaggg    780
gccccactgc cgagagctcc aaggcaactg ctctcgcctg ggctgccagc accattgtgt    840
ccccacactc gatgggccca cctgctactg caacagcagc tttcagcttc aggcagatgg    900
caagacctgc aaagattttg atgagtgctc agtgtacggc acctgcagcc agctatgcac    960
caacacagac ggctccttca tatgtggctg tgttgaagga tacctcctgc agccggataa   1020
ccgctcctgc aaggccaaga acgagccagt agaccggccc cctgtgctgt tgatagccaa   1080
ctcccagaac atcttggcca cgtacctgag tggggcccag gtgtctacca tcacacctac   1140
gagcacgcgg cagaccacag ccatggactt cagctatgcc aacgagaccg tatgctgggt   1200
gcatgttggg gacagtgctg ctcagacgca gctcaagtgt gcccgcatgc ctggcctaaa   1260
gggcttcgtg gatgagcaca ccatcaacat ctccctcagt ctgcaccacg tggaacagat   1320
ggccatcgac tggctgacag gcaacttcta ctttgtggat gacatcgatg ataggatctt   1380
tgtctgcaac agaaatgggg acacatgtgt cacattgcta gacctggaac tctacaaccc   1440
caagggcatt gccctggacc ctgccatggg gaaggtgttt ttcactgact atgggcagat   1500
cccaaaggtg gaacgctgtg acatggatgg gcagaaccgc accaagctcg tcgacagcaa   1560
gattgtgttt cctcatggca tcacgctgga cctggtcagc cgccttgtct actgggcaga   1620
tgcctatctg gactatattg aagtggtgga ctatgagggc aagggccgcc agaccatcat   1680
ccagggcatc ctgattgagc acctgtacgg cctgactgtg tttgagaatt atctctatgc   1740
caccaactcg gacaatgcca atgcccagca gaagacgagt gtgatccgtg tgaaccgctt   1800
taacagcacc gagtaccagg ttgtcacccg ggtggacaag ggtggtgccc tccacatcta   1860
ccaccagagg cgtcagcccc gagtgaggag ccatgcctgt gaaaacgacc agtatgggaa   1920
gccgggtggc tgctctgaca tctgcctgct ggccaacagc cacaaggcgc ggacctgccg   1980
ctgccgttcc ggcttcagcc tgggcagtga cgggaagtca tgcaagaagc cggagcatga   2040
gctgttcctc gtgtatggca agggccggcc aggcatcatc cggggcatgg atatgggggc   2100
caaggtcccg gatgagcaca tgatccccat tgaaaacctc atgaaccccc gagccctgga   2160
cttccacgct gagaccggct tcatctactt tgccgacacc accagctacc tcattggccg   2220
ccagaagatt gatggcactg agcgggagac catcctgaag gacggcatcc acaatgtgga   2280
gggtgtggcc gtggactgga tgggagacaa tctgtactgg acggacgatg ggcccaaaaa   2340
```

-continued

```
gacaatcagc gtggccaggc tggagaaagc tgctcagacc cgcaagactt taatcgaggg   2400
caaaatgaca caccccaggg ctattgtggt ggatccactc aatgggtgga tgtactggac   2460
agactgggag gaggacccca aggacagtcg gcgtgggcgg ctggagaggg cgtggatgga   2520
tggctcacac cgagacatct ttgtcacctc caagacagtg ctttggccca atgggctaag   2580
cctggacatc ccggctgggc gcctctactg ggtggatgcc ttctacgacc gcatcgagac   2640
gatactgctc aatggcacag accggaagat tgtgtatgaa ggtcctgagc tgaaccacgc   2700
ctttggcctg tgtcaccatg gcaactacct cttctggact gagtatcgga gtggcagtgt   2760
ctaccgcttg gaacggggtg taggaggcgc acccccccact gtgacccttc tgcgcagtga   2820
gcggcccccc atctttgaga tccgaatgta tgatgcccag cagcagcaag ttggcaccaa   2880
caaatgccgg gtgaacaatg gcggctgcag cagcctgtgc ttggccaccc ctgggagccg   2940
ccagtgcgcc tgtgctgagg accaggtgtt ggacgcagac ggcgtcactt gcttggcgaa   3000
cccatcctac gtgcctccac cccagtgcca gccaggcgag tttgcctgtg ccaacagccg   3060
ctgcatccag gagcgctgga agtgtgacgg agacaacgat tgcctggaca acagtgatga   3120
ggccccagcc ctctgccatc agcacacctg cccctcggac cgattcaagt gcgagaacaa   3180
ccggtgcatc cccaaccgct ggctctgcga cggggacaat gactgtggga acagtgaaga   3240
tgagtccaat gccacttgtt cagcccgcac ctgccccccc aaccagttct cctgtgccag   3300
tggccgctgc atccccatct cctggacgtg tgatctggat gacgactgtg gggaccgctc   3360
tgatgagtct gcttcgtgtg cctatcccac ctgcttcccc ctgactcagt ttacctgcaa   3420
caatggcaga tgtatcaaca tcaactggag atgcgacaat gacaatgact gtggggacaa   3480
cagtgacgaa gccggctgca gccactcctg ttctagcacc cagttcaagt gcaacagcgg   3540
gcgttgcatc cccgagcact ggacctgcga tggggacaat gactgcggag actacagtga   3600
tgagacacac gccaactgca ccaaccaggc cacgaggccc cctggtggct gccacactga   3660
tgagttccag tgccggctgg atggactatg catccccctg cggtggcgct gcgatgggga   3720
cactgactgc atggactcca gcgatgagaa gagctgtgag ggagtgaccc acgtctgcga   3780
tcccagtgtc aagtttggct gcaaggactc agctcggtgc atcagcaaag cgtgggtgtg   3840
tgatggcgac aatgactgtg aggataactc ggacgaggag aactgcgagt ccctggcctg   3900
caggccaccc tcgcaccctt gtgccaacaa cacctcagtc tgcctgcccc ctgacaagct   3960
gtgtgatggc aacgacgact gtggcgacgg ctcagatgag ggcgagctct gcgaccagtg   4020
ctctctgaat aacggtggct gcagccacaa ctgctcagtg gcacctggcg aaggcattgt   4080
gtgttcctgc cctctgggca tggagctggg gcccgacaac cacacctgcc agatccagag   4140
ctactgtgcc aagcatctca aatgcagcca aaagtgcgac cagaacaagt tcagcgtgaa   4200
gtgctcctgc tacgagggct gggtcctgga acctgacggc gagagctgcc gcagcctgga   4260
ccccttcaag ccgttcatca ttttctccaa ccgccatgaa atccggcgca tcgatcttca   4320
caaaggagac tacagcgtcc tggtgcccgg cctgcgcaac accatcgccc tggacttcca   4380
cctcagccag agcgccctct actggaccga cgtggtggag gacaagatct accgcgggaa   4440
gctgctggac aacggagccc tgactagttt cgaggtggtg attcagtatg gcctggccac   4500
acccgagggc ctggctgtag actggattgc aggcaacatc tactgggtgg agagtaacct   4560
ggatcagatc gaggtggcca agctggatgg gaccctccgg accaccctgc tggccggtga   4620
cattgagcac cccaagggca tcgcactgga tccccgggat gggatcctgt tttggacaga   4680
ctgggatgcc agcctgcccc gcattgaggc agcctccatg agtggggctg ggcgccgcac   4740
```

-continued

```
cgtgcaccgg gagaccggct ctgggggctg gcccaacggg ctcaccgtgg actacctgga   4800

gaagcgcatc ctttggattg acgccaggtc agatgccatt tactcagccc gttacgacgg   4860

ctctggccac atggaggtgc ttcggggaca cgagttcctg tcgcacccgt ttgcagtgac   4920

gctgtacggg ggggaggtct actggactga ctggcgaaca aacacactgg ctaaggccaa   4980

caagtggacc ggccacaatg tcaccgtggt acagaggacc aacacccagc cctttgacct   5040

gcaggtgtac cacccctccc gccagcccat ggctcccaat ccctgtgagg ccaatggggg   5100

ccagggcccc tgctcccacc tgtgtctcat caactacaac cggaccgtgt cctgcgcctg   5160

cccccacctc atgaagctcc acaaggacaa caccacctgc tatgagttta agaagttcct   5220

gctgtacgca cgtcagatgg agatccgagg tgtggacctg gatgctccct actacaacta   5280

catcatctcc ttcacggtgc ccgacatcga caacgtcaca gtgctagact acgatgcccg   5340

cgagcagcgt gtgtactggt ctgacgtgcg gacacaggcc atcaagcggg ccttcatcaa   5400

cggcacaggc gtggagacag tcgtctctgc agacttgcca aatgcccacg ggctggctgt   5460

ggactgggtc tcccgaaacc tgttctggac aagctatgac accaataaga agcagatcaa   5520

tgtggcccgg ctggatggct ccttcaagaa cgcagtggtg cagggcctgg agcagcccca   5580

tggccttgtc gtccaccctc tgcgtgggaa gctctactgg accgatggtg acaacatcag   5640

catggccaac atggatggca gcaatcgcac cctgctcttc agtggccaga agggccccgt   5700

gggcctggct attgacttcc ctgaaagcaa actctactgg atcagctccg ggaaccatac   5760

catcaaccgc tgcaacctgg atgggagtgg gctggaggtc atcgatgcca tgcggagcca   5820

gctgggcaag gccaccgccc tggccatcat gggggacaag ctgtggtggg ctgatcaggt   5880

gtcggaaaag atgggcacat gcagcaaggc tgacggctcg ggctccgtgg tccttcggaa   5940

cagcaccacc ctggtgatgc acatgaaggt ctatgacgag agcatccagc tggaccataa   6000

gggcaccaac ccctgcagtg tcaacaacgg tgactgctcc cagctctgcc tgcccacgtc   6060

agagacgacc cgctcctgca tgtgcacagc cggctatagc ctccggagtg gccagcaggc   6120

ctgcgagggc gtaggttcct ttctcctgta ctctgtgcat gagggaatca ggggaattcc   6180

cctggatccc aatgacaagt cagatgccct ggtcccagtg tccgggacct cgctggctgt   6240

cggcatcgac ttccacgctg aaaatgacac catctactgg gtggacatgg gcctgagcac   6300

gatcagccgg gccaagcggg accagacgtg gcgtgaagac gtggtgacca atggcattgg   6360

ccgtgtggag ggcattgcag tggactggat cgcaggcaac atctactgga cagaccaggg   6420

ctttgatgtc atcgaggtcg cccggctcaa tggctccttc cgctacgtgg tgatctccca   6480

gggtctagac aagccccggg ccatcaccgt ccacccggag aaagggtact tgttctggac   6540

tgagtggggt cagtatccgc gtattgagcg gtctcggcta gatggcacgg agcgtgtggt   6600

gctggtcaac gtcagcatca gctggcccaa cggcatctca gtggactacc aggatgggaa   6660

gctgtactgg tgcgatgcac ggacagacaa gattgaacgg atcgacctgg agacaggtga   6720

gaaccgcgag gtggttctgt ccagcaacaa catggacatg ttttcagtgt ctgtgtttga   6780

ggatttcatc tactggagtg acaggactca tgccaacggc tctatcaagc gcgggagcaa   6840

agacaatgcc acagactccg tgcccctgcg aaccggcatc ggcgtccagc ttaaagacat   6900

caaagtcttc aaccgggacc ggcagaaagg caccaacgtg tgcgcggtgg ccaatggcgg   6960

gtgccagcag ctgtgcctgt accggggccg tgggcagcgg gcctgcgcct gtgcccacgg   7020

gatgctggct gaagacggag catcgtgccg cgagtatgcc ggctacctgc tctactcaga   7080

gcgcaccatt ctcaagagta tccacctgtc ggatgagcgc aacctcaatg cgcccgtgca   7140
```

-continued

```
gcccttcgag gaccctgagc acatgaagaa cgtcatcgcc ctggcctttg actaccgggc   7200
aggcacctct ccgggcaccc ccaatcgcat cttcttcagc gacatccact ttgggaacat   7260
ccaacagatc aacgacgatg gctccaggag gatcaccatt gtggaaaacg tgggctccgt   7320
ggaaggcctg gcctatcacc gtggctggga cactctctat tggacaagct acacgacatc   7380
caccatcacg cgccacacag tggaccagac ccgcccaggg gccttcgagc gtgagaccgt   7440
catcactatg tctggagatg accacccacg ggccttcgtt ttggacgagt gccagaacct   7500
catgttctgg accaactgga atgagcagca tcccagcatc atgcgggcgg cgctctcggg   7560
agccaatgtc ctgaccctta tcgagaagga catccgtacc cccaatggcc tggccatcga   7620
ccaccgtgcc gagaagctct acttctctga cgccaccctg gacaagatcg agcggtgcga   7680
gtatgacggc tcccaccgct atgtgatcct aaagtcagag cctgtccacc ccttcgggct   7740
ggccgtgtat ggggagcaca ttttctggac tgactgggtg cggcgggcag tgcagcgggc   7800
caacaagcac gtgggcagca acatgaagct gctgcgcgtg gacatccccc agcagcccat   7860
gggcatcatc gccgtggcca acgacaccaa cagctgtgaa ctctctccat gccgaatcaa   7920
caacggtggc tgccaggacc tgtgtctgct cactcaccag ggccatgtca actgctcatg   7980
ccgagggggc cgaatcctcc aggatgacct cacctgccga gcggtgaatt cctcttgccg   8040
agcacaagat gagtttgagt gtgccaatgg cgagtgcatc aacttcagcc tgacctgcga   8100
cggcgtcccc cactgcaagg acaagtccga tgagaagcca tcctactgca actcccgccg   8160
ctgcaagaag actttccggc agtgcagcaa tgggcgctgt gtgtccaaca tgctgtggtg   8220
caacggggcc gacgactgtg gggatggctc tgacgagatc ccttgcaaca agacagcctg   8280
tggtgtgggc gagttccgct gccgggacgg gacctgcatc gggaactcca gccgctgcaa   8340
ccagtttgtg gattgtgagg acgcctcaga tgagatgaac tgcagtgcca ccgactgcag   8400
cagctacttc cgcctgggcg tgaagggcgt gctcttccag ccctgcgagc ggacctcact   8460
ctgctacgca cccagctggg tgtgtgatgg cgccaatgac tgtggggact acagtgatga   8520
gcgcgactgc ccaggtgtga aacgccccag atgccctctg aattacttcg cctgccctag   8580
tgggcgctgc atccccatga gctggacgtg tgacaaagag gatgactgtg aacatggcga   8640
ggacgagacc cactgcaaca agttctgctc agaggcccag tttgagtgcc agaaccatcg   8700
ctgcatctcc aagcagtggc tgtgtgacgg cagcgatgac tgtgggggatg gctcagacga   8760
ggctgctcac tgtgaaggca agacgtgcgg cccctcctcc ttctcctgcc ctggcaccca   8820
cgtgtgcgtc cccgagcgct ggctctgtga cggtgacaaa gactgtgctg atggtgcaga   8880
cgagagcatc gcagctggtt gcttgtacaa cagcacttgt gacgaccgtg agttcatgtg   8940
ccagaaccgc cagtgcatcc ccaagcactt cgtgtgtgac cacgaccgtg actgtgcaga   9000
tggctctgat gagtcccccg agtgtgagta cccgacctgc ggccccagtg agttccgctg   9060
tgccaatggg cgctgtctga gctcccgcca gtgggagtgt gatggcgaga atgactgcca   9120
cgaccagagt gacgaggctc ccaagaaccc acactgcacc agcccagagc acaagtgcaa   9180
tgcctcgtca cagttcctgt gcagcagtgg gcgctgtgtg gctgaggcac tgctctgcaa   9240
cggccaggat gactgtggcg acagctcgga cgagcgtggc tgccacatca atgagtgtct   9300
cagccgcaag ctcagtggct gcagccagga ctgtgaggac ctcaagatcg gcttcaagtg   9360
ccgctgtcgc cctggcttcc ggctgaagga tgacggccgg acgtgtgctg atgtggacga   9420
gtgcagcacc accttcccct gcagccagcg ctgcatcaac acccatggca gctataagtg   9480
tctgtgtgtg gagggctatg caccccgcgg cggcgacccc cacagctgca aggctgtgac   9540
```

-continued

```
tgacgaggaa ccgtttctga tcttcgccaa ccggtactac ctgcgcaagc tcaacctgga   9600
cgggtccaac tacacgttac ttaagcaggg cctgaacaac gccgttgcct tggattttga   9660
ctaccgagag cagatgatct actggacaga tgtgaccacc cagggcagca tgatccgaag   9720
gatgcacctt aacgggagca atgtgcaggt cctacaccgt acaggcctca gcaaccccga   9780
tgggctggct gtggactggg tgggtggcaa cctgtactgg tgcgacaaag gccgggacac   9840
catcgaggtg tccaagctca atggggccta tcggacggtg ctggtcagct ctggcctccg   9900
tgagcccagg gctctggtgg tggatgtgca gaatgggtac ctgtactgga cagactgggg   9960
tgaccattca ctgatcggcc gcatcggcat ggatgggtcc agccgcagcg tcatcgtgga  10020
caccaagatc acatggccca atggcctgac gctggactat gtcactgagc gcatctactg  10080
ggccgacgcc cgcgaggact acattgaatt tgccagcctg gatggctcca atcgccacgt  10140
tgtgctgagc caggacatcc cgcacatctt tgcactgacc ctgtttgagg actacgtcta  10200
ctggaccgac tgggaaacaa agtccattaa ccgagcccac aagaccacgg gcaccaacaa  10260
aacgctcctc atcagcacgc tgcaccggcc catggacctg catgtcttcc atgccctgcg  10320
ccagccagac gtgcccaatc accccctgcaa ggtcaacaat ggtggctgca gcaacctgtg  10380
cctgctgtcc cccgggggag ggcacaaatg tgcctgcccc accaacttct acctgggcag  10440
cgatgggcgc acctgtgtgt ccaactgcac ggctagccag tttgtatgca agaacgacaa  10500
gtgcatcccc ttctggtgga agtgtgacac cgaggacgac tgcggggacc actcagacga  10560
gcccccggac tgccctgagt tcaagtgccg gcccggacag ttccagtgct ccacaggtat  10620
ctgcacaaac cctgccttca tctgcgatgg cgacaatgac tgccaggaca acagtgacga  10680
ggccaactgt gacatccacg tctgcttgcc cagtcagttc aaatgcacca acaccaaccg  10740
ctgtattccc ggcatcttcc gctgcaatgg gcaggacaac tgcggagatg gggaggatga  10800
gagggactgc cccgaggtga cctgcgcccc caaccagttc cagtgctcca ttaccaaacg  10860
gtgcatcccc cgggtctggg tctgcgaccg ggacaatgac tgtgtggatg gcagtgatga  10920
gcccgccaac tgcacccaga tgacctgtgg tgtggacgag ttccgctgca aggattcggg  10980
ccgctgcatc ccagcgcgtt ggaagtgtga cggagaggat gactgtgggg atggctcgga  11040
tgagcccaag gaagagtgtg atgaacgcac ctgtgagcca taccagttcc gctgcaagaa  11100
caaccgctgc gtgcccggcc gctggcagtg cgactacgac aacgattgcg gtgacaactc  11160
cgatgaagag agctgcaccc ctcggccctg ctccgagagt gagttctcct gtgccaacgg  11220
ccgctgcatc gcggggcgct ggaaatgcga tggagaccac gactgcgcgg acggctcgga  11280
cgagaaagac tgcacccccc gctgtgacat ggaccagttc cagtgcaaga gcggccactg  11340
catccccctg cgctggcgct gtgacgcaga cgccgactgc atggacggca gcgacgagga  11400
ggcctgcggc actggcgtgc ggacctgccc cctggacgag ttccagtgca acaacacctt  11460
gtgcaagccg ctggcctgga agtgcgatgg cgaggatgac tgtggggaca actcagatga  11520
gaaccccgag gagtgtgccc ggttcgtgtg ccctcccaac cggcccttcc gttgcaagaa  11580
tgaccgcgtc tgtctgtgga tcgggcgcca atgcgatggc acggacaact gtggggatgg  11640
gactgatgaa gaggactgtg agccccccac agcccacacc acccactgca aagacaagaa  11700
ggagtttctg tgccggaacc agcgctgcct ctcctcctcc ctgcgctgca acatgttcga  11760
tgactgcggg gacggctctg acgaggagga ctgcagcatc gaccccaagc tgaccagctg  11820
cgccaccaat gccagcatct gtggggacga ggcacgctgc gtgcgcaccg agaaagcggc  11880
ctactgtgcc tgccgctcgg gcttccacac cgtgcccggc cagcccggat gccaagacat  11940
```

-continued

```
caacgagtgc ctgcgcttcg gcacctgctc ccagctctgc aacaacacca agggcggcca  12000
cctctgcagc tgcgctcgga acttcatgaa gacgcacaac acctgcaagg ccgaaggctc  12060
tgagtaccag gtcctgtaca tcgctgatga caatgagatc cgcagcctgt tccccggcca  12120
cccccattcg gcttacgagc aggcattcca gggtgacgag agtgtccgca ttgatgctat  12180
ggatgtccat gtcaaggctg gccgtgtcta ttggaccaac tggcacacgg gcaccatctc  12240
ctaccgcagc ctgccacctg ctgcgcctcc taccacttcc aaccgccacc ggcgacagat  12300
tgaccggggt gtcacccacc tcaacatttc agggctgaag atgcccagag gcatcgccat  12360
cgactgggtg gccggaaacg tgtactggac cgactcgggc cgagatgtga ttgaggtggc  12420
gcagatgaag ggcgagaacc gcaagacgct catctcgggc atgattgacg agccccacgc  12480
cattgtggtg gacccactga gggggaccat gtactggtca gactggggca accaccccaa  12540
gattgagacg gcagcgatgg atgggacgct tcgggagaca ctggtgcagg acaacattca  12600
gtggcccaca ggcctggccg tggattatca caatgagcgg ctgtactggg cagacgccaa  12660
gctttcagtc atcggcagca tccggctcaa tggcacggac cccattgtgg ctgctgacag  12720
caaacgaggc ctaagtcacc ccttcagcat cgacgtcttt gaggattaca tctatggtgt  12780
cacctacatc aataatcgtg tcttcaagat ccataagttt ggccacagcc ccttggtcaa  12840
cctgacaggg ggcctgagcc acgcctctga cgtggtcctt taccatcagc acaagcagcc  12900
cgaagtgacc aacccatgtg accgcaagaa atgcgagtgg ctctgcctgc tgagccccag  12960
tgggcctgtc tgcacctgtc ccaatgggaa gcggctggac aacggcacat gcgtgcctgt  13020
gccctctcca acgccccccc cagatgctcc ccggcctgga acctgtaacc tgcagtgctt  13080
caacggtggc agctgtttcc tcaatgcacg gaggcagccc aagtgccgct gccaaccccg  13140
ctacacgggt gacaagtgtg aactggacca gtgctgggag cactgtcgca atgggggcac  13200
ctgtgctgcc tccccctctg gcatgcccac gtgccggtgc cccacgggct tcacgggccc  13260
caaatgcacc cagcaggtgt gtgcgggcta ctgtgccaac aacagcacct gcactgtcaa  13320
ccagggcaac cagccccagt gccgatgcct acccggcttc ctgggcgacc gctgccagta  13380
ccggcagtgc tctggctact gtgagaactt tggcacatgc cagatggctg ctgatggctc  13440
ccgacaatgc cgctgcactg cctactttga gggatcgagg tgtgaggtga acaagtgcag  13500
ccgctgtctc gaaggggcct gtgtggtcaa caagcagagt ggggatgtca cctgcaactg  13560
cacggatggc cgggtggccc ccagctgtct gacctgcgtc ggccactgca gcaatggcgg  13620
ctcctgtacc atgaacagca aaatgatgcc tgagtgccag tgcccacccc acatgacagg  13680
gccccggtgt gaggagcacg tcttcagcca gcagcagcca ggacatatag cctccatcct  13740
aatccctctg ctgttgctgc tgctgctggt tctggtggcc ggagtggtat tctggtataa  13800
gcggcgagtc caaggggcta agggcttcca gcaccaacgg atgaccaacg gggccatgaa  13860
cgtggagatt ggaaacccca cctacaagat gtacgaaggc ggagagcctg atgatgtggg  13920
aggcctactg gacgctgact ttgccctgga ccctgacaag cccaccaact tcaccaaccc  13980
cgtgtatgcc acactctaca tgggggggcca tggcagtcgc cactccctgg ccagcacgga  14040
cgagaagcga gaactcctgg gccggggccc tgaggacgag ataggggacc ccttggcata  14100
gggccctgcc ccgtcggact gcccccagaa agcctcctgc cccctgccgg tgaagtcctt  14160
cagtgagccc ctccccagcc agcccttccc tggccccgcc ggatgtataa atgtaaaaat  14220
gaaggaatta cattttatat gtgagcgagc aagccggcaa gcgagcacag tattatttct  14280
ccatcccctc cctgcctgct ccttggcacc cccatgctgc cttcagggag acaggcaggg  14340
```

-continued

```
agggcttggg gctgcacctc ctaccctccc accagaacgc accccactgg gagagctggt  14400

ggtgcagcct tcccctccct gtataagaca ctttgccaag gctctcccct ctcgccccat  14460

ccctgcttgc ccgctcccac agcttcctga gggctaattc tgggaaggga gagttctttg  14520

ctgcccctgt ctggaagacg tggctctggg tgaggtaggc gggaaaggat ggagtgtttt  14580

agttcttggg ggaggccacc ccaaacccca gccccaactc caggggcacc tatgagatgg  14640

ccatgctcaa ccccctccc agacaggccc tccctgtctc cagggccccc accgaggttc  14700

ccagggctgg agacttcctc tggtaaacat tcctccagcc tcccctcccc tggggacgcc  14760

aaggaggtgg gccacaccca ggaagggaaa gcgggcagcc ccgttttggg gacgtgaacg  14820

ttttaataat ttttgctgaa ttctttacaa ctaaataaca cagatattct tataaataaa  14880

attgtaaaaa aaaaaa                                                  14896
```

```
<210> SEQ ID NO 7
<211> LENGTH: 126
<212> TYPE: PRT
<213> ORGANISM: Homo sapiens

<400> SEQUENCE: 7

Ile Ala Leu Asp Phe His Leu Ser Gln Ser Ala Leu Tyr Trp Thr Asp
 1               5                  10                  15

Val Val Glu Asp Lys Ile Tyr Arg Gly Lys Leu Leu Asp Asn Gly Ala
            20                  25                  30

Leu Thr Ser Phe Glu Val Val Ile Gln Tyr Gly Leu Ala Thr Pro Glu
        35                  40                  45

Gly Leu Ala Val Asp Trp Ile Ala Gly Asn Ile Tyr Trp Val Glu Ser
    50                  55                  60

Asn Leu Asp Gln Ile Glu Val Ala Lys Leu Asp Gly Thr Leu Arg Thr
65                  70                  75                  80

Thr Leu Leu Ala Gly Asp Ile Glu His Pro Arg Ala Ile Ala Leu Asp
                85                  90                  95

Pro Arg Asp Gly Ile Leu Phe Trp Thr Asp Trp Asp Ala Ser Leu Pro
            100                 105                 110

Arg Ile Glu Ala Ala Ser Met Ser Gly Ala Gly Arg Arg Thr
        115                 120                 125


<210> SEQ ID NO 8
<211> LENGTH: 153
<212> TYPE: PRT
<213> ORGANISM: Homo sapiens

<400> SEQUENCE: 8

Leu Leu Gln Gln Val Ser Leu Pro Glu Leu Pro Gly Glu Tyr Ser Met
 1               5                  10                  15

Lys Val Thr Gly Glu Gly Cys Val Tyr Leu Gln Thr Ser Leu Lys Tyr
            20                  25                  30

Asn Ile Leu Pro Glu Lys Glu Glu Phe Pro Phe Ala Leu Gly Val Gln
        35                  40                  45

Thr Leu Pro Gln Thr Cys Asp Glu Pro Lys Ala His Thr Ser Phe Gln
    50                  55                  60

Ile Ser Leu Ser Val Ser Tyr Thr Gly Ser Arg Ser Ala Ser Asn Met
65                  70                  75                  80

Ala Ile Val Asp Val Lys Met Val Ser Gly Phe Ile Pro Leu Lys Pro
                85                  90                  95
```

-continued

```
Thr Val Lys Met Leu Glu Arg Ser Asn His Val Ser Arg Thr Glu Val
            100                 105                 110

Ser Ser Asn His Val Leu Ile Tyr Leu Asp Lys Val Ser Asn Gln Thr
        115                 120                 125

Leu Ser Leu Phe Phe Thr Val Leu Gln Asp Val Pro Val Arg Asp Leu
    130                 135                 140

Lys Pro Ala Ile Val Lys Val Tyr Asp
145                 150


<210> SEQ ID NO 9
<211> LENGTH: 138
<212> TYPE: PRT
<213> ORGANISM: Homo sapiens

<400> SEQUENCE: 9

Met Lys Val Thr Gly Glu Gly Cys Val Tyr Leu Gln Thr Ser Leu Lys
 1               5                  10                  15

Tyr Asn Ile Leu Pro Glu Lys Glu Glu Phe Pro Phe Ala Leu Gly Val
            20                  25                  30

Gln Thr Leu Pro Gln Thr Cys Asp Glu Pro Lys Ala His Thr Ser Phe
        35                  40                  45

Gln Ile Ser Leu Ser Val Ser Tyr Thr Gly Ser Arg Ser Ala Ser Asn
    50                  55                  60

Met Ala Ile Val Asp Val Lys Met Val Ser Gly Phe Ile Pro Leu Lys
65                  70                  75                  80

Pro Thr Val Lys Met Leu Glu Arg Ser Asn His Val Ser Arg Thr Glu
                85                  90                  95

Val Ser Ser Asn His Val Leu Ile Tyr Leu Asp Lys Val Ser Asn Gln
            100                 105                 110

Thr Leu Ser Leu Phe Phe Thr Val Leu Gln Asp Val Pro Val Arg Asp
        115                 120                 125

Leu Lys Pro Ala Ile Val Lys Val Tyr Asp
    130                 135


<210> SEQ ID NO 10
<211> LENGTH: 27
<212> TYPE: PRT
<213> ORGANISM: Homo sapiens

<400> SEQUENCE: 10

Ser Val Ser Tyr Thr Gly Ser Arg Ser Ala Ser Asn Met Ala Ile Val
 1               5                  10                  15

Asp Val Lys Met Val Ser Gly Phe Ile Pro Leu
            20                  25


<210> SEQ ID NO 11
<211> LENGTH: 126
<212> TYPE: PRT
<213> ORGANISM: Homo sapiens

<400> SEQUENCE: 11

Leu Gln Gln Val Ser Leu Pro Glu Leu Pro Gly Glu Tyr Ser Met Lys
 1               5                  10                  15

Val Thr Gly Glu Gly Cys Val Tyr Leu Gln Thr Ser Leu Lys Tyr Asn
            20                  25                  30

Ile Leu Pro Glu Lys Glu Glu Phe Pro Phe Ala Leu Gly Val Gln Thr
        35                  40                  45
```

-continued

```
Leu Pro Gln Thr Cys Asp Glu Pro Lys Ala His Thr Ser Phe Gln Ile
    50                  55                  60

Ser Leu Ser Val Ser Tyr Thr Gly Ser Arg Ser Ala Ser Asn Met Ala
65                  70                  75                  80

Ile Val Asp Val Lys Met Val Ser Gly Phe Ile Pro Leu Lys Pro Thr
                85                  90                  95

Val Lys Met Leu Glu Arg Ser Asn His Val Ser Arg Thr Glu Val Ser
            100                 105                 110

Ser Asn His Val Leu Ile Tyr Leu Asp Lys Val Ser Asn Gln
        115                 120                 125


<210> SEQ ID NO 12
<211> LENGTH: 111
<212> TYPE: PRT
<213> ORGANISM: Homo sapiens

<400> SEQUENCE: 12

Leu Gln Gln Val Ser Leu Pro Glu Leu Pro Gly Glu Tyr Ser Met Lys
 1               5                  10                  15

Val Thr Gly Glu Gly Cys Val Tyr Leu Gln Thr Ser Leu Lys Tyr Asn
            20                  25                  30

Ile Leu Pro Glu Lys Glu Glu Phe Pro Phe Ala Leu Gly Val Gln Thr
        35                  40                  45

Leu Pro Gln Thr Cys Asp Glu Pro Lys Ala His Thr Ser Phe Gln Ile
    50                  55                  60

Ser Leu Ser Val Ser Tyr Thr Gly Ser Arg Ser Ala Ser Asn Met Ala
65                  70                  75                  80

Ile Val Asp Val Lys Met Val Ser Gly Phe Ile Pro Leu Lys Pro Thr
                85                  90                  95

Val Lys Met Leu Glu Arg Ser Asn His Val Ser Arg Thr Glu Val
            100                 105                 110


<210> SEQ ID NO 13
<211> LENGTH: 81
<212> TYPE: PRT
<213> ORGANISM: Homo sapiens

<400> SEQUENCE: 13

Leu Gln Gln Val Ser Leu Pro Glu Leu Pro Gly Glu Tyr Ser Met Lys
 1               5                  10                  15

Val Thr Gly Glu Gly Cys Val Tyr Leu Gln Thr Ser Leu Lys Tyr Asn
            20                  25                  30

Ile Leu Pro Glu Lys Glu Glu Phe Pro Phe Ala Leu Gly Val Gln Thr
        35                  40                  45

Leu Pro Gln Thr Cys Asp Glu Pro Lys Ala His Thr Ser Phe Gln Ile
    50                  55                  60

Ser Leu Ser Val Ser Tyr Thr Gly Ser Arg Ser Ala Ser Asn Met Ala
65                  70                  75                  80

Ile


<210> SEQ ID NO 14
<211> LENGTH: 101
<212> TYPE: PRT
<213> ORGANISM: Homo sapiens
```

<400> SEQUENCE: 14

```
Gln Thr Ser Leu Lys Tyr Asn Ile Leu Pro Glu Lys Glu Glu Phe Pro
 1               5                  10                  15

Phe Ala Leu Gly Val Gln Thr Leu Pro Gln Thr Cys Asp Glu Pro Lys
            20                  25                  30

Ala His Thr Ser Phe Gln Ile Ser Leu Ser Val Ser Tyr Thr Gly Ser
        35                  40                  45

Arg Ser Ala Ser Asn Met Ala Ile Val Asp Val Lys Met Val Ser Gly
    50                  55                  60

Phe Ile Pro Leu Lys Pro Thr Val Lys Met Leu Glu Arg Ser Asn His
65                  70                  75                  80

Val Ser Arg Thr Glu Val Ser Ser Asn His Val Leu Ile Tyr Leu Asp
                85                  90                  95

Lys Val Ser Asn Gln
            100
```

<210> SEQ ID NO 15
<211> LENGTH: 76
<212> TYPE: PRT
<213> ORGANISM: Homo sapiens

<400> SEQUENCE: 15

```
Gln Thr Ser Leu Lys Tyr Asn Ile Leu Pro Glu Lys Glu Glu Phe Pro
 1               5                  10                  15

Phe Ala Leu Gly Val Gln Thr Leu Pro Gln Thr Cys Asp Glu Pro Lys
            20                  25                  30

Ala His Thr Ser Phe Gln Ile Ser Leu Ser Val Ser Tyr Thr Gly Ser
        35                  40                  45

Arg Ser Ala Ser Asn Met Ala Ile Val Asp Val Lys Met Val Ser Gly
    50                  55                  60

Phe Ile Pro Leu Lys Pro Thr Val Lys Met Leu Glu
65                  70                  75
```

<210> SEQ ID NO 16
<211> LENGTH: 56
<212> TYPE: PRT
<213> ORGANISM: Homo sapiens

<400> SEQUENCE: 16

```
Gln Thr Ser Leu Lys Tyr Asn Ile Leu Pro Glu Lys Glu Glu Phe Pro
 1               5                  10                  15

Phe Ala Leu Gly Val Gln Thr Leu Pro Gln Thr Cys Asp Glu Pro Lys
            20                  25                  30

Ala His Thr Ser Phe Gln Ile Ser Leu Ser Val Ser Tyr Thr Gly Ser
        35                  40                  45

Arg Ser Ala Ser Asn Met Ala Ile
    50                  55
```

<210> SEQ ID NO 17
<211> LENGTH: 76
<212> TYPE: PRT
<213> ORGANISM: Homo sapiens

<400> SEQUENCE: 17

```
Gln Thr Cys Asp Glu Pro Lys Ala His Thr Ser Phe Gln Ile Ser Leu
 1               5                  10                  15

Ser Val Ser Tyr Thr Gly Ser Arg Ser Ala Ser Asn Met Ala Ile Val
            20                  25                  30
```

-continued

```
Asp Val Lys Met Val Ser Gly Phe Ile Pro Leu Lys Pro Thr Val Lys
        35                  40                  45

Met Leu Glu Arg Ser Asn His Val Ser Arg Thr Glu Val Ser Ser Asn
    50                  55                  60

His Val Leu Ile Tyr Leu Asp Lys Val Ser Asn Gln
65                  70                  75


<210> SEQ ID NO 18
<211> LENGTH: 76
<212> TYPE: PRT
<213> ORGANISM: Homo sapiens

<400> SEQUENCE: 18

Gln Thr Cys Asp Glu Pro Lys Ala His Thr Ser Phe Gln Ile Ser Leu
 1               5                  10                  15

Ser Val Ser Tyr Thr Gly Ser Arg Ser Ala Ser Asn Met Ala Ile Val
            20                  25                  30

Asp Val Lys Met Val Ser Gly Phe Ile Pro Leu Lys Pro Thr Val Lys
        35                  40                  45

Met Leu Glu Arg Ser Asn His Val Ser Arg Thr Glu Val Ser Ser Asn
    50                  55                  60

His Val Leu Ile Tyr Leu Asp Lys Val Ser Asn Gln
65                  70                  75


<210> SEQ ID NO 19
<211> LENGTH: 31
<212> TYPE: PRT
<213> ORGANISM: Homo sapiens

<400> SEQUENCE: 19

Gln Thr Cys Asp Glu Pro Lys Ala His Thr Ser Phe Gln Ile Ser Leu
 1               5                  10                  15

Ser Val Ser Tyr Thr Gly Ser Arg Ser Ala Ser Asn Met Ala Ile
            20                  25                  30


<210> SEQ ID NO 20
<211> LENGTH: 44
<212> TYPE: PRT
<213> ORGANISM: Homo sapiens

<400> SEQUENCE: 20

Lys Thr Cys Ser Pro Lys Gln Phe Ala Cys Arg Asp Gln Ile Thr Cys
 1               5                  10                  15

Ile Ser Lys Gly Trp Arg Cys Asp Gly Glu Arg Asp Cys Pro Asp Gly
            20                  25                  30

Ser Asp Glu Ala Pro Glu Ile Cys Pro Gln Ser Lys
        35                  40


<210> SEQ ID NO 21
<211> LENGTH: 86
<212> TYPE: PRT
<213> ORGANISM: Homo sapiens

<400> SEQUENCE: 21

Lys Thr Cys Ser Pro Lys Gln Phe Ala Cys Arg Asp Gln Ile Thr Cys
 1               5                  10                  15

Ile Ser Lys Gly Trp Arg Cys Asp Gly Glu Arg Asp Cys Pro Asp Gly
            20                  25                  30

Ser Asp Glu Ala Pro Glu Ile Cys Pro Gln Ser Lys Ala Gln Arg Cys
        35                  40                  45
```

-continued

Gln Pro Asn Glu His Asn Cys Leu Gly Thr Glu Leu Cys Val Pro Met
50 55 60

Ser Arg Leu Cys Asn Gly Val Gln Asp Cys Met Asp Gly Ser Asp Glu
65 70 75 80

Gly Pro His Cys Arg Glu
85

<210> SEQ ID NO 22
<211> LENGTH: 43
<212> TYPE: PRT
<213> ORGANISM: Homo sapiens

<400> SEQUENCE: 22

Lys Ala Gln Arg Cys Gln Pro Asn Glu His Asn Cys Leu Gly Thr Glu
1 5 10 15

Leu Cys Val Pro Met Ser Arg Leu Cys Asn Gly Val Gln Asp Cys Met
20 25 30

Asp Gly Ser Asp Glu Gly Pro His Cys Arg Glu
35 40

<210> SEQ ID NO 23
<211> LENGTH: 42
<212> TYPE: PRT
<213> ORGANISM: Homo sapiens

<400> SEQUENCE: 23

Gln Cys Gln Pro Gly Glu Phe Ala Cys Ala Asn Ser Arg Cys Ile Gln
1 5 10 15

Glu Arg Trp Lys Cys Asp Gly Asp Asn Asp Cys Leu Asp Asn Ser Asp
20 25 30

Glu Ala Pro Ala Leu Cys His Gln His Thr
35 40

<210> SEQ ID NO 24
<211> LENGTH: 82
<212> TYPE: PRT
<213> ORGANISM: Homo sapiens

<400> SEQUENCE: 24

Gln Cys Gln Pro Gly Glu Phe Ala Cys Ala Asn Ser Arg Cys Ile Gln
1 5 10 15

Glu Arg Trp Lys Cys Asp Gly Asp Asn Asp Cys Leu Asp Asn Ser Asp
20 25 30

Glu Ala Pro Ala Leu Cys His Gln His Thr Cys Pro Ser Asp Arg Phe
35 40 45

Lys Cys Glu Asn Asn Arg Cys Ile Pro Asn Arg Trp Leu Cys Asp Gly
50 55 60

Asp Asn Asp Cys Gly Asn Ser Glu Asp Glu Ser Asn Ala Thr Cys Ser
65 70 75 80

Ala Arg

<210> SEQ ID NO 25
<211> LENGTH: 122
<212> TYPE: PRT
<213> ORGANISM: Homo sapiens -continued

<400> SEQUENCE: 25

Gln Cys Gln Pro Gly Glu Phe Ala Cys Ala Asn Ser Arg Cys Ile Gln
1 5 10 15

Glu Arg Trp Lys Cys Asp Gly Asp Asn Asp Cys Leu Asp Asn Ser Asp
20 25 30

Glu Ala Pro Ala Leu Cys His Gln His Thr Cys Pro Ser Asp Arg Phe
35 40 45

Lys Cys Glu Asn Asn Arg Cys Ile Pro Asn Arg Trp Leu Cys Asp Gly
50 55 60

Asp Asn Asp Cys Gly Asn Ser Glu Asp Glu Ser Asn Ala Thr Cys Ser
65 70 75 80

Ala Arg Thr Cys Pro Pro Asn Gln Phe Ser Cys Ala Ser Gly Arg Cys
85 90 95

Ile Pro Ile Ser Trp Thr Cys Asp Leu Asp Asp Asp Cys Gly Asp Arg
100 105 110

Ser Asp Glu Ser Ala Ser Cys Ala Tyr Pro
115 120

<210> SEQ ID NO 26
<211> LENGTH: 161
<212> TYPE: PRT
<213> ORGANISM: Homo sapiens

<400> SEQUENCE: 26

Gln Cys Gln Pro Gly Glu Phe Ala Cys Ala Asn Ser Arg Cys Ile Gln
1 5 10 15

Glu Arg Trp Lys Cys Asp Gly Asp Asn Asp Cys Leu Asp Asn Ser Asp
20 25 30

Glu Ala Pro Ala Leu Cys His Gln His Thr Cys Pro Ser Asp Arg Phe
35 40 45

Lys Cys Glu Asn Asn Arg Cys Ile Pro Asn Arg Trp Leu Cys Asp Gly
50 55 60

Asp Asn Asp Cys Gly Asn Ser Glu Asp Glu Ser Asn Ala Thr Cys Ser
65 70 75 80

Ala Arg Thr Cys Pro Pro Asn Gln Phe Ser Cys Ala Ser Gly Arg Cys
85 90 95

Ile Pro Ile Ser Trp Thr Cys Asp Leu Asp Asp Asp Cys Gly Asp Arg
100 105 110

Ser Asp Glu Ser Ala Ser Cys Ala Tyr Pro Thr Cys Phe Pro Leu Thr
115 120 125

Gln Phe Thr Cys Asn Asn Gly Arg Cys Ile Asn Ile Asn Trp Arg Cys
130 135 140

Asp Asn Asp Asn Asp Cys Gly Asp Asn Ser Asp Glu Ala Gly Cys Ser
145 150 155 160

His

<210> SEQ ID NO 27
<211> LENGTH: 208
<212> TYPE: PRT
<213> ORGANISM: Homo sapiens

<400> SEQUENCE: 27

Gln Cys Gln Pro Gly Glu Phe Ala Cys Ala Asn Ser Arg Cys Ile Gln
1 5 10 15

Glu Arg Trp Lys Cys Asp Gly Asp Asn Asp Cys Leu Asp Asn Ser Asp
20 25 30

-continued

```
Glu Ala Pro Ala Leu Cys His Gln His Thr Cys Pro Ser Asp Arg Phe
        35                  40                  45

Lys Cys Glu Asn Asn Arg Cys Ile Pro Asn Arg Trp Leu Cys Asp Gly
    50                  55                  60

Asp Asn Asp Cys Gly Asn Ser Glu Asp Glu Ser Asn Ala Thr Cys Ser
65                  70                  75                  80

Ala Arg Thr Cys Pro Pro Asn Gln Phe Ser Cys Ala Ser Gly Arg Cys
                85                  90                  95

Ile Pro Ile Ser Trp Thr Cys Asp Leu Asp Asp Asp Cys Gly Asp Arg
            100                 105                 110

Ser Asp Glu Ser Ala Ser Cys Ala Tyr Pro Thr Cys Phe Pro Leu Thr
        115                 120                 125

Gln Phe Thr Cys Asn Asn Gly Arg Cys Ile Asn Ile Asn Trp Arg Cys
    130                 135                 140

Asp Asn Asp Asn Asp Cys Gly Asp Asn Ser Asp Glu Ala Gly Cys Ser
145                 150                 155                 160

His Ser Cys Ser Ser Thr Gln Phe Lys Cys Asn Ser Gly Arg Cys Ile
                165                 170                 175

Pro Glu His Trp Thr Cys Asp Gly Asp Asn Asp Cys Gly Asp Tyr Ser
            180                 185                 190

Asp Glu Thr His Ala Asn Cys Thr Asn Gln Ala Thr Arg Pro Pro Gly
        195                 200                 205


<210> SEQ ID NO 28
<211> LENGTH: 150
<212> TYPE: PRT
<213> ORGANISM: Homo sapiens

<400> SEQUENCE: 28

Gln Cys Gln Pro Gly Glu Phe Ala Cys Ala Asn Ser Arg Cys Ile Gln
 1               5                  10                  15

Glu Arg Trp Lys Cys Asp Gly Asp Asn Asp Cys Leu Asp Asn Ser Asp
            20                  25                  30

Glu Ala Pro Ala Leu Cys His Gln His Thr Cys Pro Ser Asp Arg Phe
        35                  40                  45

Lys Cys Glu Asn Asn Arg Cys Ile Pro Asn Arg Trp Leu Cys Asp Gly
    50                  55                  60

Asp Asn Asp Cys Gly Asn Ser Glu Asp Glu Ser Asn Ala Thr Cys Ser
65                  70                  75                  80

Ala Arg Thr Cys Pro Pro Asn Gln Phe Ser Cys Ala Ser Gly Arg Cys
                85                  90                  95

Ile Pro Ile Ser Trp Thr Cys Asp Leu Asp Asp Asp Cys Gly Asp Arg
            100                 105                 110

Ser Asp Glu Ser Ala Ser Cys Ala Tyr Pro Thr Cys Phe Pro Leu Thr
        115                 120                 125

Gln Phe Thr Cys Asn Asn Gly Arg Cys Ile Asn Ile Asn Trp Arg Cys
    130                 135                 140

Asp Asn Asp Asn Asp Cys
145                 150


<210> SEQ ID NO 29
<211> LENGTH: 231
<212> TYPE: PRT
<213> ORGANISM: Homo sapiens
```

-continued

<400> SEQUENCE: 29

```
Gln Cys Gln Pro Gly Glu Phe Ala Cys Ala Asn Ser Arg Cys Ile Gln
 1              5                   10                  15

Glu Arg Trp Lys Cys Asp Gly Asp Asn Asp Cys Leu Asp Asn Ser Asp
            20                  25                  30

Glu Ala Pro Ala Leu Cys His Gln His Thr Cys Pro Ser Asp Arg Phe
        35                  40                  45

Lys Cys Glu Asn Asn Arg Cys Ile Pro Asn Arg Trp Leu Cys Asp Gly
    50                  55                  60

Asp Asn Asp Cys Gly Asn Ser Glu Asp Glu Ser Asn Ala Thr Cys Ser
65                  70                  75                  80

Ala Arg Thr Cys Pro Pro Asn Gln Phe Ser Cys Ala Ser Gly Arg Cys
                85                  90                  95

Ile Pro Ile Ser Trp Thr Cys Asp Leu Asp Asp Asp Cys Gly Asp Arg
            100                 105                 110

Ser Asp Glu Ser Ala Ser Cys Ala Tyr Pro Thr Cys Phe Pro Leu Thr
        115                 120                 125

Gln Phe Thr Cys Asn Asn Gly Arg Cys Ile Asn Ile Asn Trp Arg Cys
    130                 135                 140

Asp Asn Asp Asn Asp Cys Gly Asp Asn Ser Asp Glu Ala Gly Cys Ser
145                 150                 155                 160

His Ser Cys Ser Ser Thr Gln Phe Lys Cys Asn Ser Gly Arg Cys Ile
                165                 170                 175

Pro Glu His Trp Thr Cys Asp Gly Asp Asn Asp Cys Gly Asp Tyr Ser
            180                 185                 190

Asp Glu Thr His Ala Asn Cys Thr Asn Gln Ala Thr Arg Pro Pro Gly
        195                 200                 205

Gly Cys His Thr Asp Glu Phe Gln Cys Arg Leu Asp Gly Leu Cys Ile
    210                 215                 220

Pro Leu Arg Trp Arg Cys Asp
225                 230
```

<210> SEQ ID NO 30
<211> LENGTH: 40
<212> TYPE: PRT
<213> ORGANISM: Homo sapiens

<400> SEQUENCE: 30

```
Cys Pro Ser Asp Arg Phe Lys Cys Glu Asn Asn Arg Cys Ile Pro Asn
 1              5                   10                  15

Arg Trp Leu Cys Asp Gly Asp Asn Asp Cys Gly Asn Ser Glu Asp Glu
            20                  25                  30

Ser Asn Ala Thr Cys Ser Ala Arg
        35                  40
```

<210> SEQ ID NO 31
<211> LENGTH: 80
<212> TYPE: PRT
<213> ORGANISM: Homo sapiens

<400> SEQUENCE: 31

```
Cys Pro Ser Asp Arg Phe Lys Cys Glu Asn Asn Arg Cys Ile Pro Asn
 1              5                   10                  15

Arg Trp Leu Cys Asp Gly Asp Asn Asp Cys Gly Asn Ser Glu Asp Glu
            20                  25                  30
```

-continued

```
Ser Asn Ala Thr Cys Ser Ala Arg Thr Cys Pro Pro Asn Gln Phe Ser
        35                  40                  45

Cys Ala Ser Gly Arg Cys Ile Pro Ile Ser Trp Thr Cys Asp Leu Asp
    50                  55                  60

Asp Asp Cys Gly Asp Arg Ser Asp Glu Ser Ala Ser Cys Ala Tyr Pro
65                  70                  75                  80


<210> SEQ ID NO 32
<211> LENGTH: 119
<212> TYPE: PRT
<213> ORGANISM: Homo sapiens

<400> SEQUENCE: 32

Cys Pro Ser Asp Arg Phe Lys Cys Glu Asn Asn Arg Cys Ile Pro Asn
 1               5                  10                  15

Arg Trp Leu Cys Asp Gly Asp Asn Asp Cys Gly Asn Ser Glu Asp Glu
            20                  25                  30

Ser Asn Ala Thr Cys Ser Ala Arg Thr Cys Pro Pro Asn Gln Phe Ser
        35                  40                  45

Cys Ala Ser Gly Arg Cys Ile Pro Ile Ser Trp Thr Cys Asp Leu Asp
    50                  55                  60

Asp Asp Cys Gly Asp Arg Ser Asp Glu Ser Ala Ser Cys Ala Tyr Pro
65                  70                  75                  80

Thr Cys Phe Pro Leu Thr Gln Phe Thr Cys Asn Asn Gly Arg Cys Ile
                85                  90                  95

Asn Ile Asn Trp Arg Cys Asp Asn Asp Asn Asp Cys Gly Asp Asn Ser
            100                 105                 110

Asp Glu Ala Gly Cys Ser His
        115


<210> SEQ ID NO 33
<211> LENGTH: 166
<212> TYPE: PRT
<213> ORGANISM: Homo sapiens

<400> SEQUENCE: 33

Cys Pro Ser Asp Arg Phe Lys Cys Glu Asn Asn Arg Cys Ile Pro Asn
 1               5                  10                  15

Arg Trp Leu Cys Asp Gly Asp Asn Asp Cys Gly Asn Ser Glu Asp Glu
            20                  25                  30

Ser Asn Ala Thr Cys Ser Ala Arg Thr Cys Pro Pro Asn Gln Phe Ser
        35                  40                  45

Cys Ala Ser Gly Arg Cys Ile Pro Ile Ser Trp Thr Cys Asp Leu Asp
    50                  55                  60

Asp Asp Cys Gly Asp Arg Ser Asp Glu Ser Ala Ser Cys Ala Tyr Pro
65                  70                  75                  80

Thr Cys Phe Pro Leu Thr Gln Phe Thr Cys Asn Asn Gly Arg Cys Ile
                85                  90                  95

Asn Ile Asn Trp Arg Cys Asp Asn Asp Asn Asp Cys Gly Asp Asn Ser
            100                 105                 110

Asp Glu Ala Gly Cys Ser His Ser Cys Ser Ser Thr Gln Phe Lys Cys
        115                 120                 125

Asn Ser Gly Arg Cys Ile Pro Glu His Trp Thr Cys Asp Gly Asp Asn
    130                 135                 140
```

-continued

Asp Cys Gly Asp Tyr Ser Asp Glu Thr His Ala Asn Cys Thr Asn Gln
145 150 155 160

Ala Thr Arg Pro Pro Gly
165

<210> SEQ ID NO 34
<211> LENGTH: 108
<212> TYPE: PRT
<213> ORGANISM: Homo sapiens

<400> SEQUENCE: 34

Cys Pro Ser Asp Arg Phe Lys Cys Glu Asn Asn Arg Cys Ile Pro Asn
1 5 10 15

Arg Trp Leu Cys Asp Gly Asp Asn Asp Cys Gly Asn Ser Glu Asp Glu
20 25 30

Ser Asn Ala Thr Cys Ser Ala Arg Thr Cys Pro Pro Asn Gln Phe Ser
35 40 45

Cys Ala Ser Gly Arg Cys Ile Pro Ile Ser Trp Thr Cys Asp Leu Asp
50 55 60

Asp Asp Cys Gly Asp Arg Ser Asp Glu Ser Ala Ser Cys Ala Tyr Pro
65 70 75 80

Thr Cys Phe Pro Leu Thr Gln Phe Thr Cys Asn Asn Gly Arg Cys Ile
85 90 95

Asn Ile Asn Trp Arg Cys Asp Asn Asp Asn Asp Cys
100 105

<210> SEQ ID NO 35
<211> LENGTH: 289
<212> TYPE: PRT
<213> ORGANISM: Homo sapiens

<400> SEQUENCE: 35

Cys Pro Ser Asp Arg Phe Lys Cys Glu Asn Asn Arg Cys Ile Pro Asn
1 5 10 15

Arg Trp Leu Cys Asp Gly Asp Asn Asp Cys Gly Asn Ser Glu Asp Glu
20 25 30

Ser Asn Ala Thr Cys Ser Ala Arg Thr Cys Pro Pro Asn Gln Phe Ser
35 40 45

Cys Ala Ser Gly Arg Cys Ile Pro Ile Ser Trp Thr Cys Asp Leu Asp
50 55 60

Asp Asp Cys Gly Asp Arg Ser Asp Glu Ser Ala Ser Cys Ala Tyr Pro
65 70 75 80

Thr Cys Phe Pro Leu Thr Gln Phe Thr Cys Asn Asn Gly Arg Cys Ile
85 90 95

Asn Ile Asn Trp Arg Cys Asp Asn Asp Asn Asp Cys Gly Asp Asn Ser
100 105 110

Asp Glu Ala Gly Cys Ser His Ser Cys Ser Ser Thr Gln Phe Lys Cys
115 120 125

Asn Ser Gly Arg Cys Ile Pro Glu His Trp Thr Cys Asp Gly Asp Asn
130 135 140

Asp Cys Gly Asp Tyr Ser Asp Glu Thr His Ala Asn Cys Thr Asn Gln
145 150 155 160

Ala Thr Arg Pro Pro Gly Gly Cys His Thr Asp Glu Phe Gln Cys Arg
165 170 175

Leu Asp Gly Leu Cys Ile Pro Leu Arg Trp Arg Cys Asp Gly Asp Thr
180 185 190

-continued

```
Asp Cys Met Asp Ser Ser Asp Glu Lys Ser Cys Glu Gly Val Thr His
        195                 200                 205

Val Cys Asp Pro Ser Val Lys Phe Gly Cys Lys Asp Ser Ala Arg Cys
    210                 215                 220

Ile Ser Lys Ala Trp Val Cys Asp Gly Asp Asn Asp Cys Glu Asp Asn
225                 230                 235                 240

Ser Asp Glu Glu Asn Cys Glu Ser Leu Ala Cys Arg Pro Pro Ser His
                245                 250                 255

Pro Cys Ala Asn Asn Thr Ser Val Cys Leu Pro Pro Asp Lys Leu Cys
            260                 265                 270

Asp Gly Asn Asp Asp Cys Gly Asp Gly Ser Asp Glu Gly Glu Leu Cys
        275                 280                 285

Asp


<210> SEQ ID NO 36
<211> LENGTH: 40
<212> TYPE: PRT
<213> ORGANISM: Homo sapiens

<400> SEQUENCE: 36

Thr Cys Pro Pro Asn Gln Phe Ser Cys Ala Ser Gly Arg Cys Ile Pro
 1               5                  10                  15

Ile Ser Trp Thr Cys Asp Leu Asp Asp Asp Cys Gly Asp Arg Ser Asp
            20                  25                  30

Glu Ser Ala Ser Cys Ala Tyr Pro
        35                  40


<210> SEQ ID NO 37
<211> LENGTH: 79
<212> TYPE: PRT
<213> ORGANISM: Homo sapiens

<400> SEQUENCE: 37

Thr Cys Pro Pro Asn Gln Phe Ser Cys Ala Ser Gly Arg Cys Ile Pro
 1               5                  10                  15

Ile Ser Trp Thr Cys Asp Leu Asp Asp Asp Cys Gly Asp Arg Ser Asp
            20                  25                  30

Glu Ser Ala Ser Cys Ala Tyr Pro Thr Cys Phe Pro Leu Thr Gln Phe
        35                  40                  45

Thr Cys Asn Asn Gly Arg Cys Ile Asn Ile Asn Trp Arg Cys Asp Asn
    50                  55                  60

Asp Asn Asp Cys Gly Asp Asn Ser Asp Glu Ala Gly Cys Ser His
65                  70                  75


<210> SEQ ID NO 38
<211> LENGTH: 126
<212> TYPE: PRT
<213> ORGANISM: Homo sapiens

<400> SEQUENCE: 38

Thr Cys Pro Pro Asn Gln Phe Ser Cys Ala Ser Gly Arg Cys Ile Pro
 1               5                  10                  15

Ile Ser Trp Thr Cys Asp Leu Asp Asp Asp Cys Gly Asp Arg Ser Asp
            20                  25                  30

Glu Ser Ala Ser Cys Ala Tyr Pro Thr Cys Phe Pro Leu Thr Gln Phe
        35                  40                  45

Thr Cys Asn Asn Gly Arg Cys Ile Asn Ile Asn Trp Arg Cys Asp Asn
    50                  55                  60
```

-continued

```
Asp Asn Asp Cys Gly Asp Asn Ser Asp Glu Ala Gly Cys Ser His Ser
65                  70                  75                  80

Cys Ser Ser Thr Gln Phe Lys Cys Asn Ser Gly Arg Cys Ile Pro Glu
                85                  90                  95

His Trp Thr Cys Asp Gly Asp Asn Asp Cys Gly Asp Tyr Ser Asp Glu
            100                 105                 110

Thr His Ala Asn Cys Thr Asn Gln Ala Thr Arg Pro Pro Gly
        115                 120                 125


<210> SEQ ID NO 39
<211> LENGTH: 68
<212> TYPE: PRT
<213> ORGANISM: Homo sapiens

<400> SEQUENCE: 39

Thr Cys Pro Pro Asn Gln Phe Ser Cys Ala Ser Gly Arg Cys Ile Pro
 1               5                  10                  15

Ile Ser Trp Thr Cys Asp Leu Asp Asp Asp Cys Gly Asp Arg Ser Asp
            20                  25                  30

Glu Ser Ala Ser Cys Ala Tyr Pro Thr Cys Phe Pro Leu Thr Gln Phe
        35                  40                  45

Thr Cys Asn Asn Gly Arg Cys Ile Asn Ile Asn Trp Arg Cys Asp Asn
    50                  55                  60

Asp Asn Asp Cys
65


<210> SEQ ID NO 40
<211> LENGTH: 248
<212> TYPE: PRT
<213> ORGANISM: Homo sapiens

<400> SEQUENCE: 40

Cys Pro Pro Asn Gln Phe Ser Cys Ala Ser Gly Arg Cys Ile Pro Ile
 1               5                  10                  15

Ser Trp Thr Cys Asp Leu Asp Asp Asp Cys Gly Asp Arg Ser Asp Glu
            20                  25                  30

Ser Ala Ser Cys Ala Tyr Pro Thr Cys Phe Pro Leu Thr Gln Phe Thr
        35                  40                  45

Cys Asn Asn Gly Arg Cys Ile Asn Ile Asn Trp Arg Cys Asp Asn Asp
    50                  55                  60

Asn Asp Cys Gly Asp Asn Ser Asp Glu Ala Gly Cys Ser His Ser Cys
65                  70                  75                  80

Ser Ser Thr Gln Phe Lys Cys Asn Ser Gly Arg Cys Ile Pro Glu His
                85                  90                  95

Trp Thr Cys Asp Gly Asp Asn Asp Cys Gly Asp Tyr Ser Asp Glu Thr
            100                 105                 110

His Ala Asn Cys Thr Asn Gln Ala Thr Arg Pro Pro Gly Gly Cys His
        115                 120                 125

Thr Asp Glu Phe Gln Cys Arg Leu Asp Gly Leu Cys Ile Pro Leu Arg
    130                 135                 140

Trp Arg Cys Asp Gly Asp Thr Asp Cys Met Asp Ser Ser Asp Glu Lys
145                 150                 155                 160

Ser Cys Glu Gly Val Thr His Val Cys Asp Pro Ser Val Lys Phe Gly
                165                 170                 175

Cys Lys Asp Ser Ala Arg Cys Ile Ser Lys Ala Trp Val Cys Asp Gly
            180                 185                 190
```

-continued

```
Asp Asn Asp Cys Glu Asp Asn Ser Asp Glu Glu Asn Cys Glu Ser Leu
        195                 200                 205

Ala Cys Arg Pro Pro Ser His Pro Cys Ala Asn Asn Thr Ser Val Cys
    210                 215                 220

Leu Pro Pro Asp Lys Leu Cys Asp Gly Asn Asp Asp Cys Gly Asp Gly
225                 230                 235                 240

Ser Asp Glu Gly Glu Leu Cys Asp
                245


<210> SEQ ID NO 41
<211> LENGTH: 39
<212> TYPE: PRT
<213> ORGANISM: Homo sapiens

<400> SEQUENCE: 41

Thr Cys Phe Pro Leu Thr Gln Phe Thr Cys Asn Asn Gly Arg Cys Ile
 1               5                  10                  15

Asn Ile Asn Trp Arg Cys Asp Asn Asp Asn Asp Cys Gly Asp Asn Ser
            20                  25                  30

Asp Glu Ala Gly Cys Ser His
        35


<210> SEQ ID NO 42
<211> LENGTH: 86
<212> TYPE: PRT
<213> ORGANISM: Homo sapiens

<400> SEQUENCE: 42

Thr Cys Phe Pro Leu Thr Gln Phe Thr Cys Asn Asn Gly Arg Cys Ile
 1               5                  10                  15

Asn Ile Asn Trp Arg Cys Asp Asn Asp Asn Asp Cys Gly Asp Asn Ser
            20                  25                  30

Asp Glu Ala Gly Cys Ser His Ser Cys Ser Ser Thr Gln Phe Lys Cys
        35                  40                  45

Asn Ser Gly Arg Cys Ile Pro Glu His Trp Thr Cys Asp Gly Asp Asn
    50                  55                  60

Asp Cys Gly Asp Tyr Ser Asp Glu Thr His Ala Asn Cys Thr Asn Gln
65                  70                  75                  80

Ala Thr Arg Pro Pro Gly
                85


<210> SEQ ID NO 43
<211> LENGTH: 169
<212> TYPE: PRT
<213> ORGANISM: Homo sapiens

<400> SEQUENCE: 43

Thr Cys Phe Pro Leu Thr Gln Phe Thr Cys Asn Asn Gly Arg Cys Ile
 1               5                  10                  15

Asn Ile Asn Trp Arg Cys Asp Asn Asp Asn Asp Cys Gly Asp Asn Ser
            20                  25                  30

Asp Glu Ala Gly Cys Ser His Ser Cys Ser Ser Thr Gln Phe Lys Cys
        35                  40                  45

Asn Ser Gly Arg Cys Ile Pro Glu His Trp Thr Cys Asp Gly Asp Asn
    50                  55                  60

Asp Cys Gly Asp Tyr Ser Asp Glu Thr His Ala Asn Cys Thr Asn Gln
65                  70                  75                  80
```

-continued

```
Ala Thr Arg Pro Pro Gly Gly Cys His Thr Asp Glu Phe Gln Cys Arg
                85                  90                  95

Leu Asp Gly Leu Cys Ile Pro Leu Arg Trp Arg Cys Asp Gly Asp Thr
            100                 105                 110

Asp Cys Met Asp Ser Ser Asp Glu Lys Ser Cys Glu Gly Val Thr His
        115                 120                 125

Val Cys Asp Pro Ser Val Lys Phe Gly Cys Lys Asp Ser Ala Arg Cys
    130                 135                 140

Ile Ser Lys Ala Trp Val Cys Asp Gly Asp Asn Asp Cys Glu Asp Asn
145                 150                 155                 160

Ser Asp Glu Glu Asn Cys Glu Ser Leu
                165


<210> SEQ ID NO 44
<211> LENGTH: 209
<212> TYPE: PRT
<213> ORGANISM: Homo sapiens

<400> SEQUENCE: 44

Thr Cys Phe Pro Leu Thr Gln Phe Thr Cys Asn Asn Gly Arg Cys Ile
 1               5                  10                  15

Asn Ile Asn Trp Arg Cys Asp Asn Asp Asn Asp Cys Gly Asp Asn Ser
            20                  25                  30

Asp Glu Ala Gly Cys Ser His Ser Cys Ser Ser Thr Gln Phe Lys Cys
        35                  40                  45

Asn Ser Gly Arg Cys Ile Pro Glu His Trp Thr Cys Asp Gly Asp Asn
    50                  55                  60

Asp Cys Gly Asp Tyr Ser Asp Glu Thr His Ala Asn Cys Thr Asn Gln
65                  70                  75                  80

Ala Thr Arg Pro Pro Gly Gly Cys His Thr Asp Glu Phe Gln Cys Arg
                85                  90                  95

Leu Asp Gly Leu Cys Ile Pro Leu Arg Trp Arg Cys Asp Gly Asp Thr
            100                 105                 110

Asp Cys Met Asp Ser Ser Asp Glu Lys Ser Cys Glu Gly Val Thr His
        115                 120                 125

Val Cys Asp Pro Ser Val Lys Phe Gly Cys Lys Asp Ser Ala Arg Cys
    130                 135                 140

Ile Ser Lys Ala Trp Val Cys Asp Gly Asp Asn Asp Cys Glu Asp Asn
145                 150                 155                 160

Ser Asp Glu Glu Asn Cys Glu Ser Leu Ala Cys Arg Pro Pro Ser His
                165                 170                 175

Pro Cys Ala Asn Asn Thr Ser Val Cys Leu Pro Pro Asp Lys Leu Cys
            180                 185                 190

Asp Gly Asn Asp Asp Cys Gly Asp Gly Ser Asp Glu Gly Glu Leu Cys
        195                 200                 205

Asp


<210> SEQ ID NO 45
<211> LENGTH: 47
<212> TYPE: PRT
<213> ORGANISM: Homo sapiens
```

-continued

<400> SEQUENCE: 45

```
Ser Cys Ser Ser Thr Gln Phe Lys Cys Asn Ser Gly Arg Cys Ile Pro
 1               5                  10                  15

Glu His Trp Thr Cys Asp Gly Asp Asn Asp Cys Gly Asp Tyr Ser Asp
            20                  25                  30

Glu Thr His Ala Asn Cys Thr Asn Gln Ala Thr Arg Pro Pro Gly
        35                  40                  45
```

<210> SEQ ID NO 46
<211> LENGTH: 89
<212> TYPE: PRT
<213> ORGANISM: Homo sapiens

<400> SEQUENCE: 46

```
Ser Cys Ser Ser Thr Gln Phe Lys Cys Asn Ser Gly Arg Cys Ile Pro
 1               5                  10                  15

Glu His Trp Thr Cys Asp Gly Asp Asn Asp Cys Gly Asp Tyr Ser Asp
            20                  25                  30

Glu Thr His Ala Asn Cys Thr Asn Gln Ala Thr Arg Pro Pro Gly Gly
        35                  40                  45

Cys His Thr Asp Glu Phe Gln Cys Arg Leu Asp Gly Leu Cys Ile Pro
    50                  55                  60

Leu Arg Trp Arg Cys Asp Gly Asp Thr Asp Cys Met Asp Ser Ser Asp
65                  70                  75                  80

Glu Lys Ser Cys Glu Gly Val Thr His
                85
```

<210> SEQ ID NO 47
<211> LENGTH: 170
<212> TYPE: PRT
<213> ORGANISM: Homo sapiens

<400> SEQUENCE: 47

```
Ser Cys Ser Ser Thr Gln Phe Lys Cys Asn Ser Gly Arg Cys Ile Pro
 1               5                  10                  15

Glu His Trp Thr Cys Asp Gly Asp Asn Asp Cys Gly Asp Tyr Ser Asp
            20                  25                  30

Glu Thr His Ala Asn Cys Thr Asn Gln Ala Thr Arg Pro Pro Gly Gly
        35                  40                  45

Cys His Thr Asp Glu Phe Gln Cys Arg Leu Asp Gly Leu Cys Ile Pro
    50                  55                  60

Leu Arg Trp Arg Cys Asp Gly Asp Thr Asp Cys Met Asp Ser Ser Asp
65                  70                  75                  80

Glu Lys Ser Cys Glu Gly Val Thr His Val Cys Asp Pro Ser Val Lys
                85                  90                  95

Phe Gly Cys Lys Asp Ser Ala Arg Cys Ile Ser Lys Ala Trp Val Cys
            100                 105                 110

Asp Gly Asp Asn Asp Cys Glu Asp Asn Ser Asp Glu Glu Asn Cys Glu
        115                 120                 125

Ser Leu Ala Cys Arg Pro Pro Ser His Pro Cys Ala Asn Asn Thr Ser
    130                 135                 140

Val Cys Leu Pro Pro Asp Lys Leu Cys Asp Gly Asn Asp Asp Cys Gly
145                 150                 155                 160

Asp Gly Ser Asp Glu Gly Glu Leu Cys Asp
                165                 170
```

-continued

<210> SEQ ID NO 48
<211> LENGTH: 42
<212> TYPE: PRT
<213> ORGANISM: Homo sapiens

<400> SEQUENCE: 48

```
Gly Cys His Thr Asp Glu Phe Gln Cys Arg Leu Asp Gly Leu Cys Ile
 1              5                   10                  15

Pro Leu Arg Trp Arg Cys Asp Gly Asp Thr Asp Cys Met Asp Ser Ser
            20                  25                  30

Asp Glu Lys Ser Cys Glu Gly Val Thr His
        35                  40
```

<210> SEQ ID NO 49
<211> LENGTH: 83
<212> TYPE: PRT
<213> ORGANISM: Homo sapiens

<400> SEQUENCE: 49

```
Gly Cys His Thr Asp Glu Phe Gln Cys Arg Leu Asp Gly Leu Cys Ile
 1              5                   10                  15

Pro Leu Arg Trp Arg Cys Asp Gly Asp Thr Asp Cys Met Asp Ser Ser
            20                  25                  30

Asp Glu Lys Ser Cys Glu Gly Val Thr His Val Cys Asp Pro Ser Val
        35                  40                  45

Lys Phe Gly Cys Lys Asp Ser Ala Arg Cys Ile Ser Lys Ala Trp Val
    50                  55                  60

Cys Asp Gly Asp Asn Asp Cys Glu Asp Asn Ser Asp Glu Glu Asn Cys
65                  70                  75                  80

Glu Ser Leu
```

<210> SEQ ID NO 50
<211> LENGTH: 123
<212> TYPE: PRT
<213> ORGANISM: Homo sapiens

<400> SEQUENCE: 50

```
Gly Cys His Thr Asp Glu Phe Gln Cys Arg Leu Asp Gly Leu Cys Ile
 1              5                   10                  15

Pro Leu Arg Trp Arg Cys Asp Gly Asp Thr Asp Cys Met Asp Ser Ser
            20                  25                  30

Asp Glu Lys Ser Cys Glu Gly Val Thr His Val Cys Asp Pro Ser Val
        35                  40                  45

Lys Phe Gly Cys Lys Asp Ser Ala Arg Cys Ile Ser Lys Ala Trp Val
    50                  55                  60

Cys Asp Gly Asp Asn Asp Cys Glu Asp Asn Ser Asp Glu Glu Asn Cys
65                  70                  75                  80

Glu Ser Leu Ala Cys Arg Pro Pro Ser His Pro Cys Ala Asn Asn Thr
                85                  90                  95

Ser Val Cys Leu Pro Pro Asp Lys Leu Cys Asp Gly Asn Asp Asp Cys
            100                 105                 110

Gly Asp Gly Ser Asp Glu Gly Glu Leu Cys Asp
        115                 120
```

<210> SEQ ID NO 51
<211> LENGTH: 41
<212> TYPE: PRT
<213> ORGANISM: Homo sapiens -continued

<400> SEQUENCE: 51

Val Cys Asp Pro Ser Val Lys Phe Gly Cys Lys Asp Ser Ala Arg Cys
1 5 10 15

Ile Ser Lys Ala Trp Val Cys Asp Gly Asp Asn Asp Cys Glu Asp Asn
20 25 30

Ser Asp Glu Glu Asn Cys Glu Ser Leu
35 40

<210> SEQ ID NO 52
<211> LENGTH: 81
<212> TYPE: PRT
<213> ORGANISM: Homo sapiens

<400> SEQUENCE: 52

Val Cys Asp Pro Ser Val Lys Phe Gly Cys Lys Asp Ser Ala Arg Cys
1 5 10 15

Ile Ser Lys Ala Trp Val Cys Asp Gly Asp Asn Asp Cys Glu Asp Asn
20 25 30

Ser Asp Glu Glu Asn Cys Glu Ser Leu Ala Cys Arg Pro Pro Ser His
35 40 45

Pro Cys Ala Asn Asn Thr Ser Val Cys Leu Pro Pro Asp Lys Leu Cys
50 55 60

Asp Gly Asn Asp Asp Cys Gly Asp Gly Ser Asp Glu Gly Glu Leu Cys
65 70 75 80

Asp

<210> SEQ ID NO 53
<211> LENGTH: 40
<212> TYPE: PRT
<213> ORGANISM: Homo sapiens

<400> SEQUENCE: 53

Ala Cys Arg Pro Pro Ser His Pro Cys Ala Asn Asn Thr Ser Val Cys
1 5 10 15

Leu Pro Pro Asp Lys Leu Cys Asp Gly Asn Asp Asp Cys Gly Asp Gly
20 25 30

Ser Asp Glu Gly Glu Leu Cys Asp
35 40

<210> SEQ ID NO 54
<211> LENGTH: 10
<212> TYPE: PRT
<213> ORGANISM: Homo sapiens

<400> SEQUENCE: 54

Ser Gly Phe Ser Leu Gly Ser Asp Gly Lys
1 5 10

<210> SEQ ID NO 55
<211> LENGTH: 10
<212> TYPE: PRT
<213> ORGANISM: Homo sapiens

<400> SEQUENCE: 55

Gly Ile Ala Leu Asp Pro Ala Met Gly Lys
1 5 10

-continued

```
<210> SEQ ID NO 56
<211> LENGTH: 10
<212> TYPE: PRT
<213> ORGANISM: Homo sapiens

<400> SEQUENCE: 56

Gly Gly Ala Leu His Ile Tyr His Gln Arg
 1               5                  10


<210> SEQ ID NO 57
<211> LENGTH: 11
<212> TYPE: PRT
<213> ORGANISM: Homo sapiens

<400> SEQUENCE: 57

Val Phe Phe Thr Asp Tyr Gly Gln Ile Pro Lys
 1               5                  10


<210> SEQ ID NO 58
<211> LENGTH: 9
<212> TYPE: PRT
<213> ORGANISM: Homo sapiens

<400> SEQUENCE: 58

Gly Ala Leu His Ile Tyr His Gln Arg
 1               5


<210> SEQ ID NO 59
<211> LENGTH: 19
<212> TYPE: PRT
<213> ORGANISM: Homo sapiens

<400> SEQUENCE: 59

Arg Val Thr Tyr His Ser Pro Ser Tyr Val Tyr His Gln Phe Glu Arg
 1               5                  10                  15

Arg Ala Lys
```

ALPHA(2) MACROGLOBULIN RECEPTOR AS A HEAT SHOCK PROTEIN RECEPTOR AND USES THEREOF

This application claims priority under 35 U.S.C. § 119(e) to provisional application No. 60/209,095, filed Jun. 2, 2000, which is incorporated by reference herein in its entirety.

The invention was made with government support under grant number CA64394 awarded by the National Institutes of Health. The government has certain rights in the invention.

1. INTRODUCTION

The present invention relates to the use of alpha (2) macroglobulin ("α2M") receptor as a heat shock protein receptor, cells that express the α2M receptor bound to an HSP, and antibodies and other molecules that bind the α2M receptor-HSP complex. The invention also relates to screening assays to identify compounds that modulate the interaction of an HSP with the α2M receptor, and methods for using compositions comprising α2M-receptor sequences for the diagnosis and treatment of immune disorders, proliferative disorders, and infectious diseases.

2. BACKGROUND OF THE INVENTION

2.1. Heat Shock Proteins

Heat shock proteins (HSPs), also referred to as stress proteins, were first identified as proteins synthesized by cells in response to heat shock. Hsps have classified into five families, based on molecular weight, Hsp100, Hsp90, Hsp70, Hsp60, and smHsp. Many members of these families were found subsequently to be induced in response to other stressful stimuli including nutrient deprivation, metabolic disruption, oxygen radicals, and infection with intracellular pathogens (see Welch, May 1993, Scientific American 56–64; Young, 1990, Annu. Rev. Immunol. 8:401–420; Craig, 1993, Science 260:1902–1903; Gething et al., 1992, Nature 355:33–45; and Lindquist et al., 1988, Annu. Rev. Genetics 22:631–677).

Heat shock proteins are among the most highly conserved proteins in existence. For example, DnaK, the Hsp70 from *E. coli* has about 50% amino acid sequence identity with Hsp70 proteins from excoriates (Bardwell et al., 1984, Proc. Natl. Acad. Sci. 81:848–852). The Hsp60 and Hsp90 families also show similarly high levels of intra-family conservation (Hickey et al., 1989, Mol. Cell. Biol. 9:2615–2626; Jindal, 1989, Mol. Cell. Biol. 9:2279–2283). In addition, it has been discovered that the Hsp60, Hsp70 and Hsp90 families are composed of proteins that are related to the stress proteins in sequence, for example, having greater than 35% amino acid identity, but whose expression levels are not altered by stress.

Studies on the cellular response to heat shock and other physiological stresses revealed that the HSPs are involved not only in cellular protection against these adverse conditions, but also in essential biochemical and immunological processes in unstressed cells. HSPs accomplish different kinds of chaperoning functions. For example, members of the Hsp70 family, located in the cell cytoplasm, nucleus, mitochondria, or endoplasmic reticulum (Lindquist et al., 1988, Ann. Rev. Genetics 22:631–677), are involved in the presentation of antigens to the cells of the immune system, and are also involved in the transfer, folding and assembly of proteins in normal cells. HSPs are capable of binding proteins or peptides, and releasing the bound proteins or peptides in the presence of adenosine triphosphate (ATP) or low pH.

2.2. Immunogenicity of HSP-Peptide Complexes

Srivastava et al. demonstrated immune response to methylcholanthrene-induced sarcomas of inbred mice (1988, Immunol. Today 9:78–83). In these studies, it was found that the molecules responsible for the individually distinct immunogenicity of these tumors were glycoproteins of 96 kDa (gp96) and intracellular proteins of 84 to 86 kDa (Srivastava et al., 1986, Proc. Natl. Acad. Sci. USA 83:3407–3411; Ullrich et al., 1986, Proc. Natl. Acad. Sci. USA 83:3121–3125). Immunization of mice with gp96 or p84/86 isolated from a particular tumor rendered the mice immune to that particular tumor, but not to antigenically distinct tumors. Isolation and characterization of genes encoding gp96 and p84/86 revealed significant homology between them, and showed that gp96 and p84/86 were, respectively, the endoplasmic reticular and cytosolic counterparts of the same heat shock proteins (Srivastava et al., 1988, Immunogenetics 28:205–207; Srivastava et al, 1991, Curr. Top. Microbiol. Immunol. 167:109–123). Further, Hsp70 was shown to elicit immunity to the tumor from which it was isolated but not to antigenically distinct tumors. However, Hsp70 depleted of peptides was found to lose its immunogenic activity (Udono and Srivastava, 1993, J. Exp. Med. 178:1391–1396). These observations suggested that the heat shock proteins are not immunogenic per se, but form noncovalent complexes with antigenic peptides, and the complexes can elicit specific immunity to the antigenic peptides (Srivastava, 1993, Adv. Cancer Res. 62:153–177; Udono et al., 1994, J. Immunol., 152:5398–5403; Suto et al., 1995, Science, 269:1585–1588).

Noncovalent complexes of HSPs and peptide, purified from cancer cells, can be used for the treatment and prevention of cancer and have been described in PCT publications WO 96/10411, dated Apr. 11, 1996, and WO 97/10001, dated Mar. 20, 1997 (U.S. Pat. No. 5,750,119 issued Apr. 12, 1998, and U.S. Pat. No. 5,837,251 issued Nov. 17, 1998, respectively, each of which is incorporated by reference herein in its entirety). The isolation and purification of stress protein-peptide complexes has been described, for example, from pathogen-infected cells, and can be used for the treatment and prevention of infection caused by the pathogen, such as viruses, and other intracellular pathogens, including bacteria, protozoa, fungi and parasites (see, for example, PCT Publication WO 95/24923, dated Sep. 21, 1995). Immunogenic stress protein-peptide complexes can also be prepared by in vitro complexing of stress protein and antigenic peptides, and the uses of such complexes for the treatment and prevention of cancer and infectious diseases has been described in PCT publication WO 97/10000, dated Mar. 20, 1997 (U.S. Pat. No. 6,030,618 issued Feb. 29, 2000. The use of stress protein-peptide complexes for sensitizing antigen presenting cells in vitro for use in adoptive immunotherapy is described in PCT publication WO 97/10002, dated Mar. 20, 1997 (see also U.S. Pat. No. 5,985,270 issued Nov. 16, 1999).

2.3. Alpha (2) Macroglobulin Receptor

The alpha (2) macroglobulin receptor ("α2MR"), also known as LDL (low-density lipoprotein) receptor-Related Protein ("LRP") or CD91, is primarily expressed in liver, brain and placenta. The α2MR is a member of the low density lipoprotein receptor family. The extracellular domain of the human receptor comprises six 50-amino acid EGF repeats and 31 complement repeats of approximately 40–42 amino acids. The complement repeats are organized, from the amino to the carboxy-terminus, into clusters of 2, 8, 10 and 11 repeats, called Cluster I, II, III and IV (Herz et al., 1988, EMBO J. 7:4119–4127). One study points to Cluster II (C1-II), which contains complement repeats 3–10 (CR3–10), as the major ligand binding portion of the receptor (Horn et al., 1997, J. Biol. Chem. 272:13608–13613). The α2M receptor plays a role in endocytosis of a diversity of ligands. In addition to α2M, other ligands of α2MR include lipoprotein complexes, lactoferrin, tissue-type plasminogen activator (tPA), urokinase-type plasminogen activator (uPA), and exotoxins. Thus, the α2M receptor plays roles in a variety of cellular processes, including endocytosis, antigen presentation, cholesterol regulation, ApoE-containing lipoprotein clearance, and chylomicron remnant removal.

Human α2M is synthesized as a 1474 amino acid precursor, the first 23 of which function as a signal sequence that is cleaved to yield a 1451 amino acid mature protein (Kan et al., 1985, Proc. Natl. Acad. Sci. U.S.A. 82:2282–2286). In experiments with recombinant protein, the carboxy-terminal 138 amino acids of α2M (representing amino acids 1314–1451 of the mature protein) was found to bind the receptor. This domain has been called the RBD (receptor-binding domain; Salvesent et al., 1992, FEBS Lett. 313: 198–202; Holtet et al., 1994, FEBS Lett. 344:242–246). An RBD variant (RBDv), a proteolytic fragment of α2M comprising an additional 15 amino terminal residues (representing amino acids 1314–1451 of the mature protein) binds to the receptor with almost the same affinity as α2M-proteinase (Holtet et al., 1994, FEBS Lett. 344:242–246).

Alignment of α2MR ligands identifies a conserved domain present in the RBDs of α macroglobulins. The conserved sequence spans amino acids 1366–1392 of human α2M. Conserved residues within this domain are $Phe_{1366}$, $Leu_{1369}$, $Lys_{1370}$, $Val_{1373}$, $Lys_{1374}$, $Glu_{1377}$, $Val_{1382}$, $Arg_{1384}$ (Nielsen et al., 1996, J. Biol. Chem. 271:12909–12912). Of these, $Lys_{1370}$ and $Lys_{1374}$ were shown to be critical for receptor binding (Nielsen et al., 1996, J. Biol. Chem. 271: 12909–12912).

Binding of ligands, including the binding to α2M, to α2MR is inhibited by α2MR-associated protein (RAP). RAP is a 39 kDa folding chaperone that resides in the endoplasmic reticulum and is required for the normal processing of α2MR. RAP has the ability to competitively inhibit the binding of all α2MR to all α2MR ligands tested. One study shows RAP to bind to complement repeats $C5–C_7$ in cluster II (C1-II) of α2MR (Horn et al., 1997, J. Biol. Chem. 272:13608–13613); another shows RAP to bind to all two complement repeat-modules in C1-II except the C9–C10 module (Andersen et al., J. Biol. Chem., Mar. 24, 2000, PMID: 10747921; published electronically ahead of print). Three structural domains, 1, 2 and 3, have been identified in RAP, consisting of amino acid residues 18–112, 113–218 and 219–323, respectively. Ligand competition titration of recombinant RAP domains indicates that determinants for the inhibition of test ligands reside in the C-terminal regions of domains 1 and 3 (Ellgaard et al., 1997, Eur. J. Biochem. 244:544–51).

2.4. Antigen Presentation

Major histocompatibility complex (MHC) molecules present antigens on the cell surface of antigen-presenting cells. Cytotoxic T lymphocytes (CTLs) then recognize MHC molecules and their associated peptides and kill the target cell. Antigens are processed by two distinct antigen processing routes depending upon whether their origin is intracellular or extracellular. Intracellular or endogenous protein antigens, i.e., antigens synthesized within the antigen-presenting cell, are presented by MHC class I (MHC I) molecules to CD8+ cytotoxic T lymphocytes. On the other hand, extracellular or exogenously synthesized antigenic determinants are presented on the cell surface of "specialized" or "professional" APCs (macrophages, for example) by MHC class II molecules to CD4+ T cells (see, generally, Fundamental Immunology, W. E. Paul (ed.), New York: Raven Press, 1984). This compartmental segregation of antigen processing routes is important to prevent tissue destruction that could otherwise occur during an immune response as a result of shedding of neighboring cell MHC I antigens.

The heat shock protein gp96 chaperones a wide array of peptides, depending upon the source from which gp96 is isolated (for review, see Srivastava et al., 1998, Immunity 8: 657–665). Tumor-derived gp96 carries tumor-antigenic peptides (Ishii et al., 1999, J. Immunology 162:1303–1309); gp96 preparations from virus-infected cells carry viral epitopes (Suto and Srivastava, 1995, Science 269:1585–1588; Nieland et al., 1998, Proc. Natl. Acad. Sci. USA 95:1800–1805), and gp96 preparations from cells transfected with model antigens such as ovalbumin or β-galactosidase are associated with the corresponding epitopes (Arnold et al., 1995, J. Exp. Med. 182:885–889; Breloer et al., 1998, Eur. J. Immunol. 28:1016–1021). The association of gp96 with peptides occurs in vivo (Menoret and Srivastava, 1999, Biochem. Biophys. Research Commun. 262: 813–818). Gp96-peptide complexes, whether isolated from cells (Tamura et al., 1997, Science 278:117–120), or reconstituted in vitro (Blachere et al., 1997, J. Exp. Med. 186: 1183–1406) are excellent immunogens and have been used extensively to elicit CD8+ T cell responses specific for the gp96-chaperoned antigenic peptides.

The capacity of gp96-peptide complexes to elicit an immune response is dependent upon the transfer of the peptide to MHC class I molecules of antigen-presenting cells (Suto and Srivastava, 1995, supra). Endogenously synthesized antigens chaperoned by gp96 in the endoplasmic reticulum [ER] can prime antigen-specific CD8+ T cells (or MHC I-restricted CTLs) in vivo; this priming of CD8+ T cells requires macrophages. However, the process whereby exogenously introduced gp96-peptide complexes elicit the antigen-specific CD8+ T cell response is not completely understood since there is no established pathway for the translocation of extracellular antigens into the class I presentation machinery. Yet antigenic peptides of extracellular origin associated with HSPs are somehow salvaged by macrophages, channeled into the endogenous pathway, and presented by MHC I molecules to be recognized by CD8+ lymphocytes (Suto and Srivastava, 1995, supra; Blachere et al., 1997, J. Exp. Med. 186:1315–22).

Several models have been proposed to explain the delivery of extracellular peptides for antigen presentation. One proposal, known as the "direct transfer" model, suggests that HSP-chaperoned peptides are transferred to MHC I molecules on the cell surface of macrophages for presentation to CD8+ T lymphocytes. Another suggestion is that soluble extracellular proteins can be trafficked to the cytosol via constitutive macropinocytosis in bone marrow-derived macrophages and dendritic cells (Norbury et al., 1997, Eur. J. Immunol. 27:280–288). Yet another proposed mechanism is that HSPs are taken up by the MHC class I molecules of the macrophage, which stimulate the appropriate T cells (Srivastava et al., 1994, Immunogenetics 39:93–98. Others have suggested that a novel intracellular trafficking pathway may be involved for the transport of peptides from the extracellular medium into the lumen of ER (Day et al., 1997, Proc. Natl. Acad. Sci. 94:8064–8069; Nicchitta, 1998, Curr. Opin. in Immunol. 10:103–109). Further suggestions include the involvement of phagocytes which (a) possess an ill-defined pathway to shunt protein from the phagosome into the cytosol where it would enter the normal class I pathway; (b) digest ingested material in lysosomes and regurgitate peptides for loading on the surface to class I molecules (Bevan, 1995, J. Exp. Med. 182:639–41).

Still others have proposed a receptor-mediated pathway for the delivery of extracellular peptides to the cell surface of APCs for antigen presentation. In view of the extremely small quantity of gp96-chaperoned antigenic peptides required for immunization (Blachere et al., 1997, supra), and the strict dependence of immunogenicity of gp96-peptide complexes on functional antigen presenting cells (APCs) (Udono et al., 1994, Proc. Natl. Acad. Sci. U.S.A. 91:3077–3081), APCs had been proposed to possess receptors for gp96 (Srivastava et al., 1994, Immunogenetics 39:93–98). Preliminary microscopic evidence consistent with such receptors has been recently obtained (Binder et al., 1998, Cell Stress & Chaperones 3 (Supp. 1):2.; Amold-Schild et al., 1999, J. Immunol. 162: 3757–3760; and Wassenberg et al., 1999, J. Cell Sci. 1:12). One hypothesis is that the mannose receptor is used in the uptake of gp96, but no mechanism has been proposed for the non-glycosylated HSPs, such as Hsp70 (Ciupitu et al., 1998, J. Exp. Med., 187:685–691).

The identification and characterization of specific molecules involved in HSP-mediated antigen presentation of peptides could provide useful reagents and techniques for eliciting specific immunity by HSP and HSP-peptide complexes, and for developing novel diagnostic and therapeutic methods.

Citation or discussion of a reference herein shall not be construed as an admission that such is prior art to the present invention.

3. SUMMARY OF THE INVENTION

The present invention relates to compositions and methods for the use of the alpha (2) macroglobulin ("α2M") receptor as a heat shock protein receptor. The invention is based, in part, on the Applicant's discovery that the α2M receptor is a cell surface receptor for heat shock proteins. In particular, the Applicant has shown that the heat shock protein gp96 binds directly to the α2M receptor, and that α2M inhibits re-presentation of gp96-chaperoned antigenic peptides by macrophages. Because no precedent exists for receptors that recognize abundant and intracellular proteins like HSPs, the discovery of an HSP cell surface receptor was highly unexpected.

The present invention provides compositions comprising complexes of HSPs and the α2M receptor, and antibodies and other molecules that bind the HSP-α2M receptor complex. The invention also encompasses methods for the use of the α2M receptor as a heat shock protein receptor, including methods for screening for compounds that modulate the interaction of HSP and the α2M receptor, and methods for treatment and detection of HSP-α2M receptor-mediated processes and HSP-α2M receptor-related disorders and conditions, such as autoimmune disorders, proliferative disorders and infectious diseases.

The invention provides a method for identifying a compound that modulates an HSP-α2M receptor-mediated process, comprising: (a) contacting a test compound with a heat shock protein and an alpha (2) macroglobulin receptor; and (b) measuring the level of alpha (2) macroglobulin receptor activity or expression, such that if the level of activity or expression measured in (b) differs from the level of alpha (2) macroglobulin receptor activity in the absence of the test compound, then a compound that modulates an HSP-α2M receptor-mediated process is identified. In one embodiment of this method the compound identified is an antagonist which interferes with the interaction of the heat shock protein with the alpha (2) macroglobulin receptor, further comprising the step of: (c) determining whether the level interferes with the interaction of the heat shock protein and the alpha (2) macroglobulin receptor. In another embodiment, the test compound is an antibody specific for the alpha (2) macroglobulin receptor. In another embodiment, the test compound is an antibody specific for alpha (2) macroglobulin. In another embodiment, test compound is an antibody specific for a heat shock protein. In another embodiment, the test compound is a small molecule. In another yet embodiment, the test compound is a peptide. In another embodiment, the peptide comprises at least 5 consecutive amino acids of the alpha (2) macroglobulin receptor. In yet another embodiment, the peptide comprises at least 5 consecutive amino acids of alpha (2) macroglobulin. In yet another embodiment, the peptide comprises at least 5 consecutive amino acids of a heat shock protein sequence. In another embodiment, the compound is an agonist which enhances the interaction of the heat shock protein with the alpha (2) macroglobulin receptor. In another embodiment, which the HSP-α2M receptor-mediated process affects an autoimmune disorder, a disease or disorder involving disruption of antigen presentation or endocytosis, a disease or disorder involving cytokine clearance or inflammation, a proliferative disorder, a viral disorder or other infectious disease, hypercholesterolemia, Alzheimer's disease, diabetes, or osteoporosis.

The invention also provides a method for identifying a compound that modulates an HSP-α2M receptor-mediated process, comprising: (a) contacting a test compound with a heat shock protein and an alpha (2) macroglobulin receptor-expressing cell; and (b) measuring the level of alpha (2) macroglobulin receptor activity or expression in the cell, such that if the level of activity or expression measured in (b) differs from the level of alpha (2) macroglobulin receptor activity in the absence of the test compound, then a compound that modulates an HSP-α2M receptor-mediated process is identified. In yet another embodiment, wherein the alpha (2) macroglobulin receptor activity measured is the ability to interact with a heat shock protein.

The invention also encompasses a method for identifying a compound that modulates the binding of a heat shock protein to the α2M receptor, comprising: (a) contacting a heat shock protein with an alpha (2) macroglobulin receptor, or fragment, or analog, derivative or mimetic thereof, in the presence of a test compound; and (b) measuring the amount of heat shock protein bound to the alpha (2) macroglobulin receptor, or fragment, analog, derivative or mimetic thereof, such that if the amount of bound heat shock protein measured in (b) differs from the amount of bound heat shock protein measured in the absence of the test compound, then a compound that modulates the binding of an HSP to the α2M receptor is identified. In another embodiment, alpha (2) macroglobulin receptor contacted in step (a) is on a cell surface. In another embodiment, the alpha (2) macroglobulin receptor is immobilized to a solid surface. In another embodiment, the solid surface is a microtiter dish. In another embodiment, the amount of bound heat shock protein is measured by contacting the cell with a heat shock protein-specific antibody. In yet another embodiment, the heat shock protein is labeled and the amount of bound heat shock protein is measured by detecting the label. In another embodiment, the heat shock protein is labeled with a fluorescent label.

The invention further provides a method for identifying a compound that modulates heat shock protein-mediated antigen presentation by alpha (2) macroglobulin receptor-expressing cells comprising: (a) adding a test compound to a mixture of alpha (2) macroglobulin receptor-expressing cells and a complex consisting essentially of a heat shock protein noncovalently associated with an antigenic molecule, under conditions conducive to alpha (2) macroglobulin receptor-mediated endocytosis; (b) measuring the level of antigen-specific stimulation of cytotoxic T cells by alpha (2) macroglobulin receptor-expressing cells, such that if the level measured in (b) differs from the level of said stimulation in the absence of the test compound, then a compound that modulates heat shock protein-mediated antigen presentation by alpha (2) macroglobulin receptor-expressing cells is identified. In one embodiment of this method, the step of measuring the level of the antigenic molecule presented on the cell surface of step (b) comprises: (i) adding the alpha (2) macroglobulin receptor-expressing cells formed in step (a) to T cells under conditions conducive to the activation of the T cells; and (ii) comparing the level of activation of said cytotoxic T cells with the level of activation of T cells by an alpha (2) macroglobulin receptor-expressing cell formed in the absence of the test compound, wherein an increase of decrease in level of T cell activation indicates that a compound that modulates heat shock protein-mediated antigen presentation by alpha (2) macroglobulin receptor-expressing cells is identified.

In various embodiments, the heat shock protein used in the methods of the invention is gp96.

In another embodiment, the invention provides a method for detecting a heat shock protein-alpha (2) macroglobulin receptor-related disorder in a mammal comprising measuring the level of an HSP-alpha (2) macroglobulin receptor-mediated process in a patient sample, such that if the measured level differs from the level found in clinically normal individuals, then a heat shock protein-alpha (2) macroglobulin receptor-related disorder is detected.

The invention also encompasses kits comprising compositions of the invention. In one embodiment, a kit is provided, packaged in one or more containers, comprising: (a) a purified heat shock protein, nucleic acid encoding a heat shock protein, or cell expressing a heat shock protein; and (b) an alpha (2) macroglobulin receptor polypeptide, nucleic acid encoding an alpha (2) macroglobulin receptor polypeptide, or cell expressing an alpha (2) macroglobulin receptor polypeptide. In one embodiment, the kit the alpha (2) macroglobulin receptor polypeptide, nucleic acid encoding an alpha (2) macroglobulin receptor polypeptide, or cell expressing an alpha (2) macroglobulin receptor polypeptide is purified. In another embodiment, the kit further comprises instructions for use in treating an autoimmune disorder, an infectious disease, or a proliferative disorder.

The invention also provides a method for modulating an immune response comprising administering to a mammal a purified compound that modulates the interaction of a heat shock protein with the alpha (2) macroglobulin receptor. In one embodiment, the compound is an agonist which enhances the interaction of the heat shock protein and the alpha (2) macroglobulin receptor. In another embodiment of this method the compound in an antagonist that interferes with the interaction between the heat shock protein and the α2M receptor.

The invention further provides a method for treating an autoimmune disorder comprising administering to a mammal in need of such treatment a purified compound that interferes with the interaction of a heat shock protein with the alpha (2) macroglobulin receptor. In one embodiment of this method the compound in an antagonist that interferes with the interaction between the heat shock protein and the α2M receptor. In one embodiment, the antagonist is an antibody specific for alpha (2) macroglobulin receptor. In another embodiment, the antagonist is an antibody specific for a heat shock protein. In another embodiment, the antagonist is a small molecule. In another embodiment, the antagonist is a peptide. In another embodiment, the peptide comprises at least 5 consecutive amino acids of alpha (2) macroglobulin receptor. In another embodiment, the peptide comprises at least 5 consecutive amino acids of alpha (2) macroglobulin. In another embodiment, the peptide comprises at least 5 consecutive amino acids of a heat shock protein sequence.

The invention further provides a method for increasing the immunopotency of a cancer cell or an infected cell comprising transforming said cell with a nucleic acid comprising a nucleotide sequence that (i) is operably linked to a promoter, and (ii) encodes an alpha (2) macroglobulin receptor polypeptide.

Still further, the invention provides a method for increasing the immunopotency of a cancer cell or an infected cell comprising: (a) transforming said cell with a nucleic acid comprising a nucleotide sequence that (i) is operably linked to a promoter, and (ii) encodes an alpha (2) macroglobulin receptor polypeptide, and (b) administering said cell to an individual in need of treatment, so as to obtain an elevated immune response.

The invention also provides a recombinant cancer cell transformed with a nucleic acid comprising a nucleotide sequence that (i) is operably linked to a promoter, and (ii) encodes an alpha (2) macroglobulin receptor polypeptide. In one embodiment, the recombinant cell is a human cell.

In yet another embodiment, the invention provides a recombinant infected cell transformed with a nucleic acid comprising a nucleotide sequence that (i) is operably linked to a promoter, and (ii) encodes an alpha (2) macroglobulin receptor polypeptide. In one embodiment, the recombinant cell is a human cell.

The term "HSP-α2M receptor-mediated process" as used herein refers to a process dependent and/or responsive, either directly or indirectly, to the interaction of HSP with the α2M receptor. Such processes include processes that result from an aberrant level of expression, synthesis and/or activity of α2M receptor, such as endocytic activities relating to the binding of the various α2M ligands, including but not limited to HSP, α2M, lipoprotein complexes, lactoferrin, tissue-type plasminogen activator (tPA), urokinase-type plasminogen activator (uPA), and exotoxins. Such processes include, but are not limited to, endocytosis, antigen presentation, cholesterol regulation, apoE-containing lipoprotein clearance, and chylomicron remnant removal.

The terms "HSP-α2M receptor-related disorder" and "HSP-α2M receptor-related condition", as used herein, refers to a disorder and a condition, respectively, involving a HSP-α2M receptor interaction. Such disorders and conditions may result, for example, from an aberrant ability of the α2M receptor to interact with HSP, perhaps due to aberrant levels of HSP and/or α2M receptor expression, synthesis and/or activity relative to levels found in normal, unaffected, unimpaired individuals, levels found in clinically normal individuals, and/or levels found in a population whose levels represent a baseline, average HSP and/or α2M receptor levels. Such disorders include, but are not limited to, autoimmune disorders, diseases and disorders involving disruption of antigen presentation and/or endocytosis, diseases and disorders involving cytokine clearance and/or inflammation, proliferative disorders, viral disorders and other infectious diseases, hypercholesterolemia, Alzheimer's disease, diabetes, and osteoporosis.

4. BRIEF DESCRIPTION OF THE FIGURES

Figure 1B:
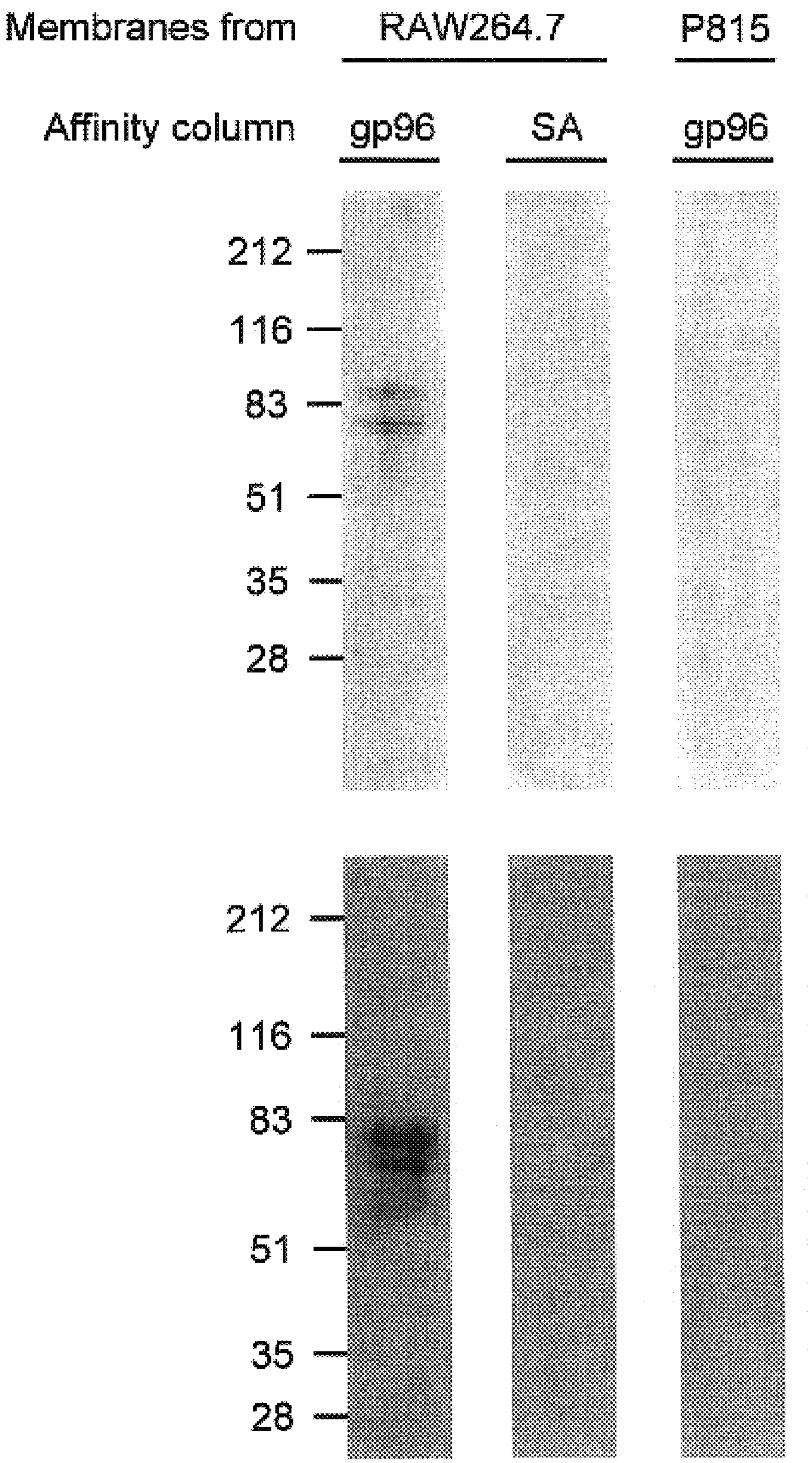
Figure 1C:
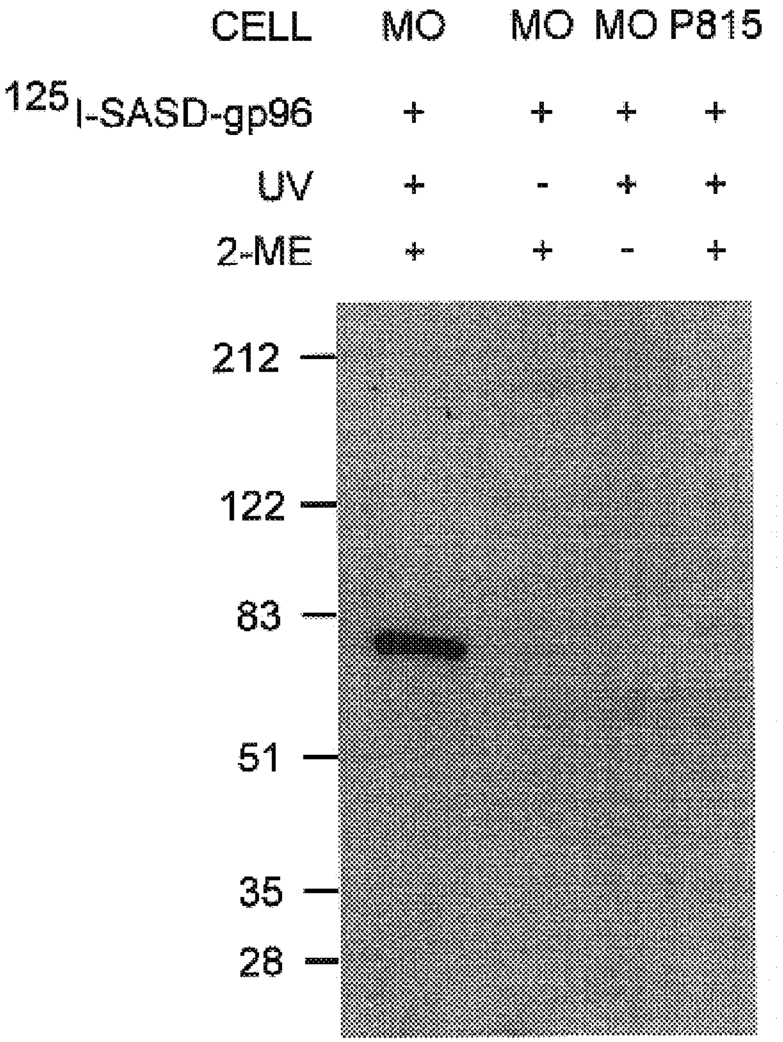

FIGS. 1A–C. Identification of an 80 kDa polypeptide as a putative gp96 receptor. A. Confocal microscopy of re-presentation-competent RAW264.7 cells stained with gp96-FITC (left panel) and with albumin-FITC (right panel). B. SDS-PAGE analysis of detergent extracts of plasma membranes from surface biotinylated RAW264.7 (re-presentation-competent) or P815 cells (representation-incompetent) eluted from gp96 or albumin-Sepharose (SA) columns and stained with silver stain (top) or avidin-peroxidase (bottom). C. gp96-SASD-$I^{125}$ was cross-linked to live peritoneal macrophages (MO) or P815 cells, and the cell lysates examined by SDS-PAGE and autoradiography. Various components were omitted as controls, as indicated.

Figure 2A:
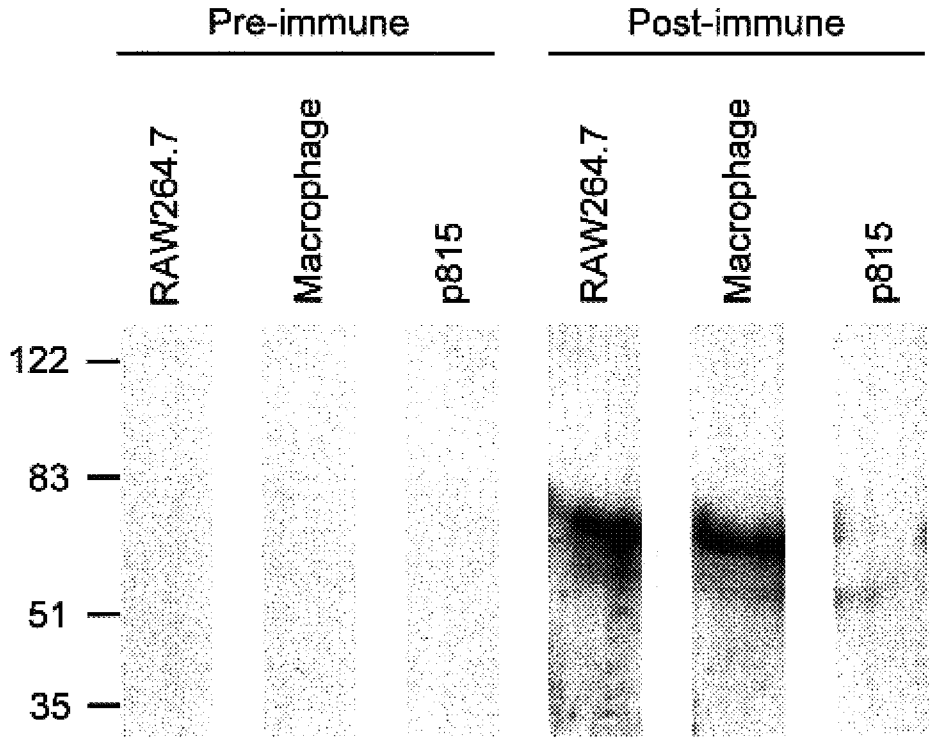
Figure 2B:
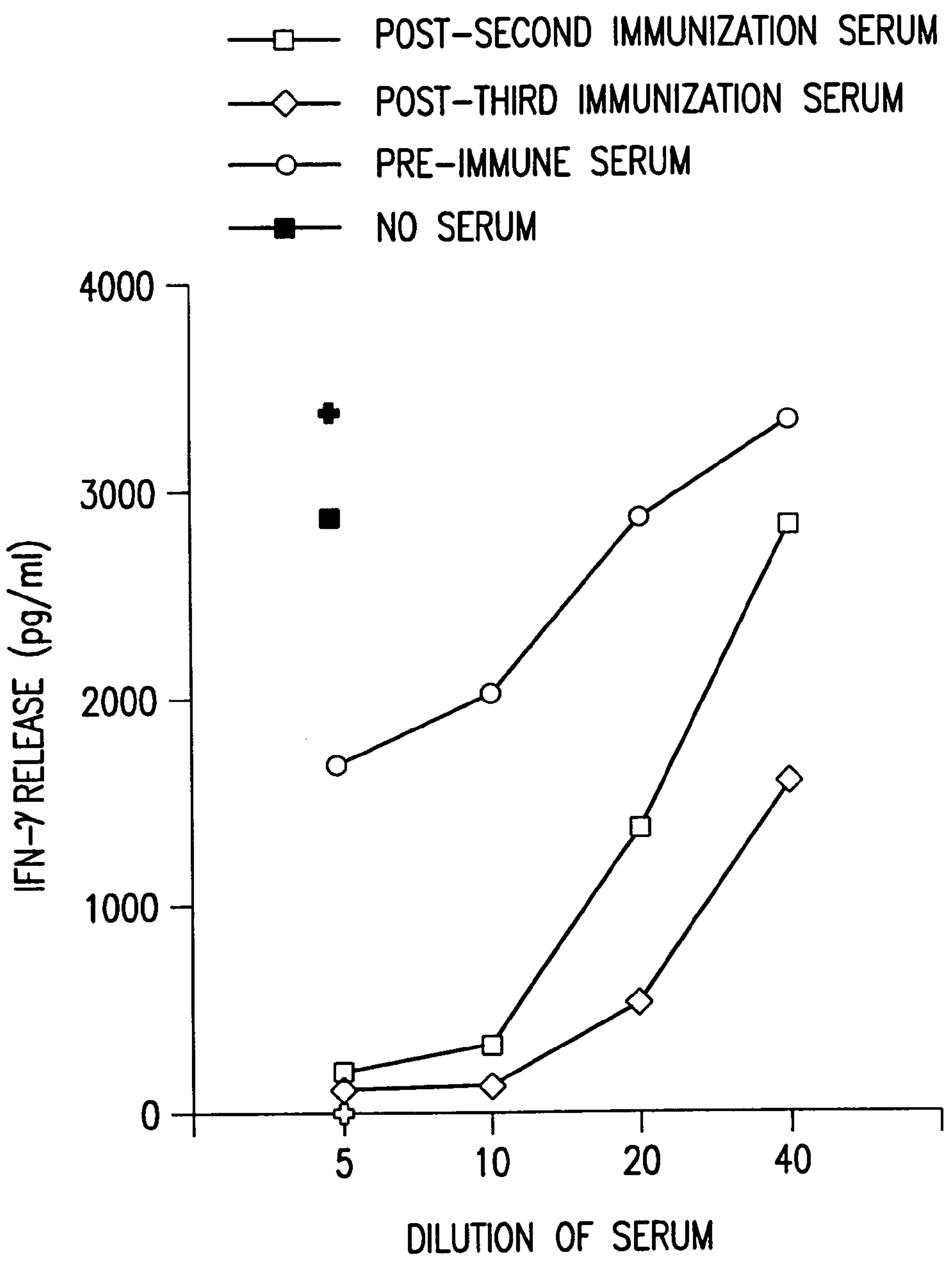

FIGS. 2A–B. Anti-p80 antiserum detects an 80 kDa molecule and inhibits re-presentation of gp96-chaperoned AH1 peptide by macrophage. A. Pre-immune and immune sera were used to probe blots of plasma membrane extracts of RAW264.7, peritoneal macrophages (both cell types re-presentation-competent), or P815 cells. B. Re-presentation of gp96-chaperoned peptide AH1. Sera were added at the final dilution indicated. The solid cross indicates the level of T cell stimulation when the APCs were pulsed directly with the AH1 peptide. The open cross indicates the corresponding value with unpulsed APCs.

Figure 3B:
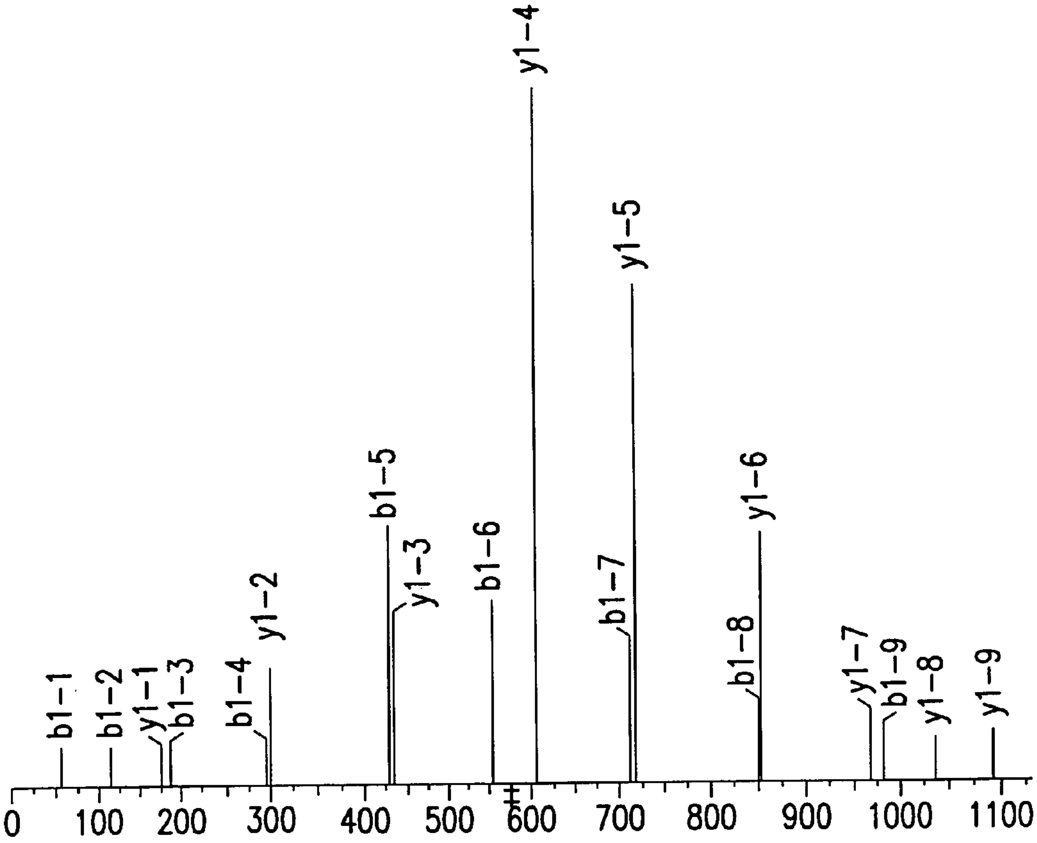

FIGS. 3A–C. Protein microsequencing of the 80 kDa protein. A. Analysis of a single tryptic (GALHIYHQR) peptide (SEQ ID NO:58) by tandem-mass spectrometry. All possible b- and y-ion series together with identified b-ion series (red) and y-ion series (blue) are shown. B. Collision-induced dissociation (CID) spectrum of this peptide is shown. C. Four identified peptides from the α2M receptor, peptide mass, and sequence are shown.

Figure 4:
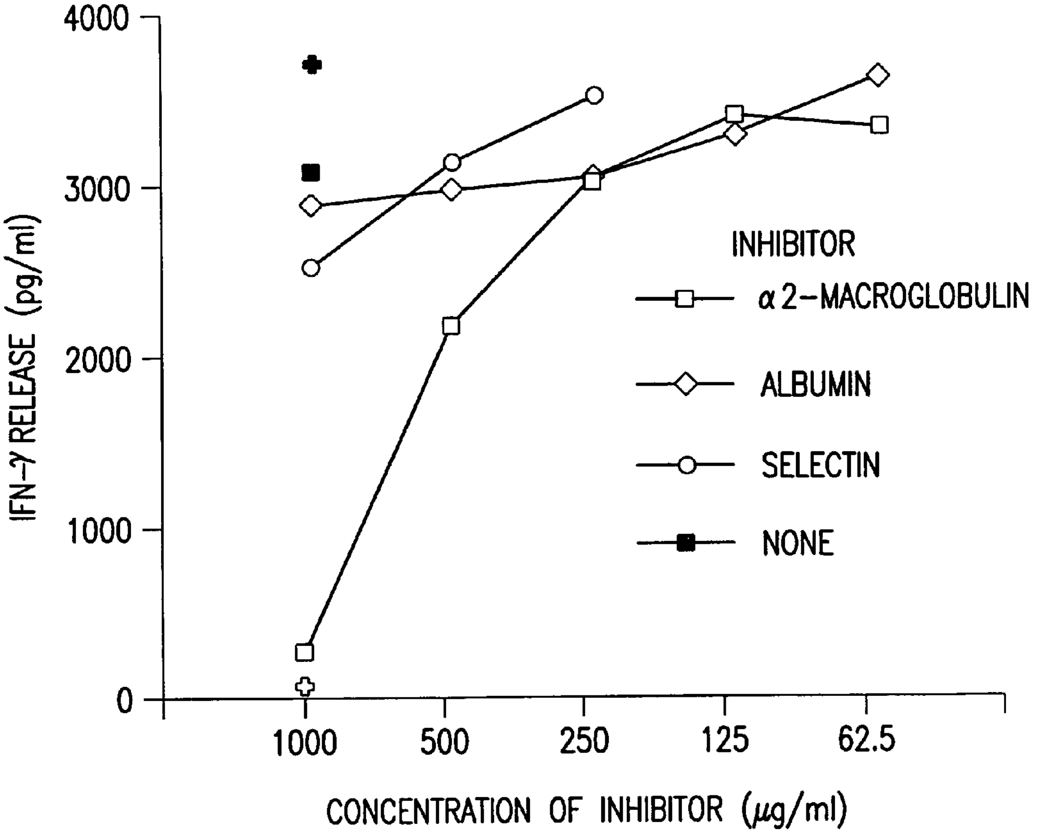

FIG. 4. α2-Macroglobulin inhibits re-presentation of gp96-chaperoned AH1 peptide by macrophage. The solid cross indicates the level of T cell stimulation when the APCs were pulsed directly with the AH1 peptide. The open cross indicates the corresponding value with unpulsed APCs.

Figure 5:
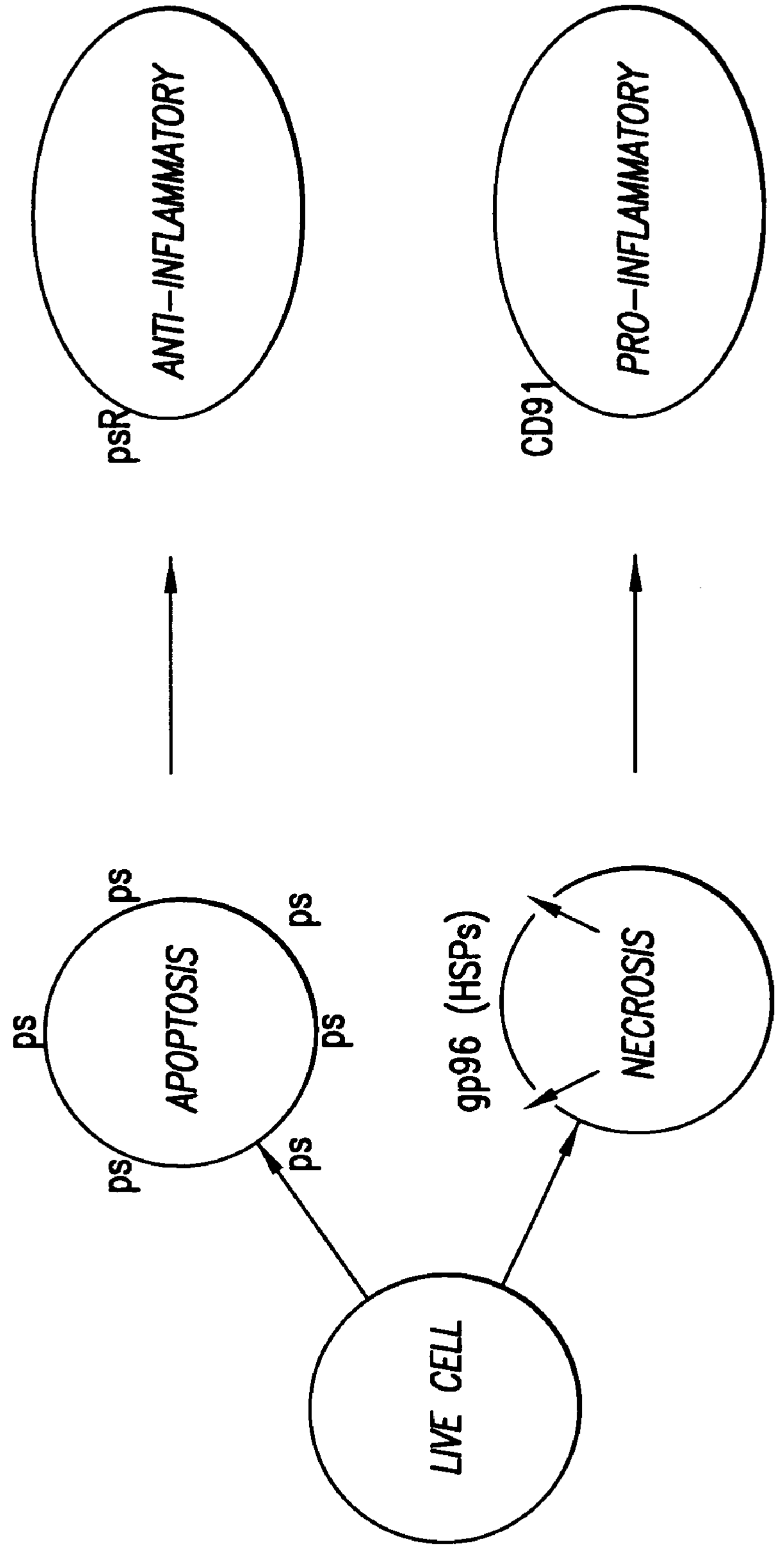

FIG. 5. α2M receptor is a sensor of necrotic cell death due to its ability to detect extracellular gp96. Conversely, receptors (psR) for phosphatidyl serine (ps) detect apoptotic cell death.

FIG. 6A. The mouse α2MR cDNA (SEQ ID NO:1) and predicted open reading frame of murine α2MR protein (Genbank accession no. CAA47817). B. The murine α2M protein (SEQ ID NO:2), with residues identified by microsequencing an 80 kDa, gp96-interacting fragment of the receptor highlighted in bold.

FIG. 7A. The human α2M cDNA (SEQ ID NO:3) and predicted open reading frame of α2M protein (SEQ ID NO:4)(Genbank accession no. M11313). B. The sequence of the mature human α2M protein (SEQ ID NO:5), following cleavage of the N-terminal 23 amino acid signal sequence. Highlighted residues represent the 138 amino acid α2MR-binding domain (RBD). Underlined residues represent an extension of the RBD that is present in a α2MR-binding, proteolytic fragment of α2M (RBDv). Bolded residues have been shown to be important for α2MR binding. Italicized residues represent a domain that is conserved among ligands of α2MR.

FIG. 8A. The human α2MR cDNA (SEQ ID NO:6) and predicted open reading frame of human α2MR protein (Genbank accession no. NP_002323). B. Primary amino acid sequence of human α2MR (SEQ ID NO:7). The approximate locations of complement repeat clusters I and II are highlighted in grey. Individual complement repeats of C1-II are indicated as follows: amino acids of CR3, 5, 7 and 9 are in italics, and amino acids of CR4, 6, 8, and 10 are underlined. Amino acids highlighted in bold were present in an 80 kDa peptide fragment of the mouse α2MR that bound to gp96. The double underlined residues represent the predicted signal peptide. For the locations of other features of the receptor, such as the EGF repeats, see the article by (Herz et al., 1988, EMBO J. 7:4119–4127).

5. DETAILED DESCRIPTION OF THE INVENTION

The present invention relates to compositions and methods for the use of the alpha (2) macroglobulin ("α2M") receptor as a heat shock protein receptor. In particular, the present invention provides compositions comprising isolated HSP-α2M receptor complexes, including isolated and/or recombinant cells, and antibodies, molecules and compounds that modulate the interaction of an HSP with the α2M receptor. The invention further encompasses methods for the use of the α2M receptor as a heat shock protein receptor, including screening assays to identify compounds that modulate the interaction of an HSP with the α2M receptor, and methods for the use of these molecules and complexes for the diagnosis and treatment of immune disorders, proliferative disorders, and infectious diseases.

A heat shock protein, or "HSP", useful in the practice of the invention may be selected from among any cellular protein that satisfies any one of the following criteria: the intracellular concentration of an HSP increases when a cell is exposed to a stressful stimulus; an HSP can bind other proteins or peptides, and can release the bound proteins or peptides in the presence of adenosine triphosphate (ATP) or low pH; or an HSP possesses at least 35% homology with any cellular protein having any of the above properties. Preferably, the HSP used in the compositions and methods of the present invention includes, but are not limited to, HSP90, gp96, BiP, Hsp70, DnaK, Hsc70, PhoE calreticulin, PDI, or an shsp, alone or in combination.

In a preferred embodiment, an HSP is a mammalian (e.g., mouse, rat, primate, domestic animal such as dog, cat, cow, horse), and is most preferably, human.

Hsps useful in the practice of the invention include, but are not limited to, members of the HSP60 family, HSP70 family, HSP90 family, HSP 100 family, sHSP family, calreticulin, PDI, and other proteins in the endoplasmic reticulum that contain thioredoxin-like domain(s), such as, but not limited to, ERp72 and ERp61.

HSP analogs, muteins, derivatives, and fragments can also be used in place of HSPs according to the invention. An HSP peptide-binding "fragment" for use in the invention refers to a polypeptide comprising a HSP peptide-binding domain that is capable of becoming non-covalently associated with a peptide to form a complex that is capable of eliciting an immune response. In one embodiment, an HSP peptide-binding fragment is a polypeptide comprising an HSP peptide-binding domain of approximately 100 to 200 amino acids.

Databases can also be searched to identify sequences with various degrees of similarities to a query sequence using programs, such as FASTA and BLAST, which rank the similar sequences by alignment scores and statistics. Such nucleotide sequences of non-limiting examples of HSPs that can be used for preparation of the HSPs used in the methods of the invention are as follows: human Hsp70, Genbank Accession No. NM_005345, Sargent et al., 1989, Proc. Natl. Acad. Sci. U.S.A., 86:1968–1972; human Hsp90, Genbank Accession No. X15183, Yamazaki et al., Nucl. Acids Res. 17:7108; human gp96: Genbank Accession No. X15187, Maki et al., 1990, Proc. Natl. Acad. Sci., 87: 5658–5562; human BiP: Genbank Accession No. M19645; Ting et al., 1988, DNA 7: 275–286; human Hsp27, Genbank Accession No. M24743; Hickey et al., 1986, Nucleic Acids Res. 14:4127–45; mouse Hsp70: Genbank Accession No. M35021, Hunt et al., 1990, Gene, 87:199–204; mouse gp96: Genbank Accession No. M16370, Srivastava et al., 1987, Proc. Natl. Acad. Sci., 85:3807–3811; and mouse BiP: Genbank Accession No. U16277, Haas et al., 1988, Proc. Natl. Acad. Sci. U.S.A., 85: 2250–2254. Due to the degeneracy of the genetic code, the term "HSP sequence", as used herein, refers not only to the naturally occurring amino acid and nucleotide sequence but also encompasses all the other degenerate sequences that encode the HSP.

The aforementioned HSP families also contain proteins that are related to HSPs in sequence, for example, having greater than 35% amino acid identity, but whose expression levels are not altered by stress. Therefore, it is contemplated that the definition of heat shock or stress protein, as used herein, embraces other proteins, mutants, analogs, and variants thereof having at least 35% to 55%, preferably 55% to 75%, and most preferably 75% to 85% amino acid identity with members of these families whose expression levels in a cell are enhanced in response to a stressful stimulus. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264–2268, modified as in Karlin and Altschul, 1993, Proc. Natl. Acad. Sci. USA 90:5873–5877. Such an algorithm is incorporated into the NBLAST and XBLAST programs of Altschul, et al., 1990, J. Mol. Biol. 215: 403–410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al., 1997, Nucleic Acids Res. 25:3389–3402. Alternatively, PSI-Blast can be used to perform an iterated search which detects distant relationships between molecules (Altschul et al., 1997, supra). When utilizing BLAST, Gapped BLAST, and PSI-Blast programs, the default parameters of the respective programs (e.g., XBLAST and NBLAST) can be used (see http://www.ncbi.nlm.nih.gov). Another preferred, non-limiting example of a mathematical algorithm utilized for the comparison of sequences is the algorithm of Myers and Miller, 1988, CABIOS 4:11–17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The immunogenic HSP-peptide complexes of the invention may include any complex containing an HSP and a peptide that is capable of inducing an immune response in a mammal. The peptides are preferably noncovalently associated with the HSP. Preferred complexes may include, but are not limited to, gp96-peptide complexes, HSP90-peptide complexes, HSP70-peptide complexes, HSP60-peptide complexes, HSP100-peptide complexes, calreticulin-peptide complexes, and sHSP-peptide complexes. For example, the HSP gp96 which is present in the endoplasmic reticulum of eukaryotic cells and is related to the cytoplasmic HSP90's can be used to generate an effective vaccine containing a gp96-peptide complex.

The HSPs, α2M receptor, and/or antigenic molecules for use in the invention can be purified from natural sources, chemically synthesized, or recombinantly produced. Although the HSPs may be allogeneic to the patient, in a preferred embodiment, the HSPs are autologous to the patient to whom they are administered.

5.1 Compositions of the Invention

The present invention provides compositions that increase or decrease the interaction between an HSP and the α2M receptor which can be used to elicit an immune response. Such compositions also include antibodies that specifically recognize HSP-α2M receptor complexes, isolated cells that express HSP-α2M receptor complexes, and isolated and recombinant cells that contain recombinant α2M receptor and HSP sequences. In addition, in various methods of the invention, sequences encoding the α2M receptor, an HSP, and α2M are used for immunotherapy. Such compositions can be used, for example, in immunotherapy against proliferative disorders, infectious diseases, and other HSP-α2M receptor-related disorders. Methods for the synthesis and production of such compositions are described herein.

5.1.1 Recombinant Expression

In various embodiments of the invention, sequences encoding the α2M receptor, an HSP, or α2M are inserted into an expression vector for propagation and expression in recombinant cells. Thus, in one embodiment, the α2M receptor, HSP, or α2M coding region is linked to a non-native promoter for expression in recombinant cells.

The amino acid sequence of the portion of the α2M receptor that recognizes and binds to HSPs is shown in FIG. 6B (SEQ ID NO:2). Based on the discovery by the Applicant, this portion of the α2M receptor is responsible for recognizing and binding to HSPs and HSP-antigenic peptide complexes. After binding HSPs, the α2M receptor facilitates transport of the HSP-antigenic peptide complex into the cell, where the peptide antigens associate with MHC class I molecules and are then presented on the cell surface of the cell, and become available to stimulate an immune response. Based on this invention, compositions comprising agonists and antagonists of the α2M receptor and HSPs interactions can be used to modulate the immune response. Thus, recombinant α2M receptor polypeptides, complexes of α2M receptor and an HSP or HSP-antigenic peptide complexes, and recombinant cells expressing the α2M receptor or the α2M receptor and antigenic peptides can be used in methods for immunotherapy and diagnostic methods described herein.

In various embodiments of the invention, sequences encoding the α2M receptor, and/or a heat shock protein or α2M, or fragments thereof, are inserted into an expression vector for propagation and expression in recombinant cells. An expression construct, as used herein, refers to a nucleotide sequence encoding a particular gene product, such as the α2M receptor, HSP or α2M, operably associated with one or more regulatory regions which allows expression of the encoded gene product in an appropriate host cell. "Operably-associated" refers to an association in which the regulatory regions and the nucleotide sequence encoding the gene product to be expressed are joined and positioned in such a way as to permit transcription, and ultimately, translation.

The DNA may be obtained from known sequences derived from sequence databases by standard procedures known in the art by DNA amplification or molecular cloning directly from a tissue, cell culture, or cloned DNA (e.g., a DNA "library"). Any eukaryotic cell may serve as the nucleic acid source for obtaining the coding region of an hsp gene. Nucleic acid sequences encoding HSPs can be isolated from vertebrate, mammalian, as well as primate sources, including humans. Clones derived from genomic DNA may contain regulatory and intron DNA regions in addition to coding regions; clones derived from cDNA will contain only exon sequences. Whatever the source, the hsp gene should be cloned into a suitable vector for propagation of the gene.

Vectors based on *E. coli* are the most popular and versatile systems for high level expression of foreign proteins (Makrides, 1996, Microbiol Rev, 60:512–538). Non-limiting examples of regulatory regions that can be used for expression in *E. coli* may include but not limited to lac, trp, lpp, phoA, recA, tac, $\lambda P_L$, and phage T3 and T7 promoters (Makrides, 1996, Microbiol Rev, 60:512–538). Non-limiting examples of prokaryotic expression vectors may include the λgt vector series such as λgt11 (Huynh et al., 1984 in "DNA Cloning Techniques", Vol. I: A Practical Approach (D. Glover, ed.), pp. 49–78, IRL Press, Oxford), and the pET vector series (Studier et al., 1990, Methods Enzymol., 185: 60–89). However, a potential drawback of a prokaryotic host-vector system is the inability to perform many of the post-translational processing events of mammalian cells. Thus, an eukaryotic host-vector system is preferred, a mammalian host-vector system is more preferred, and a human host-vector system is the most preferred.

The regulatory regions necessary for transcription of the oα2M receptor sequence, for example, can be provided by the expression vector. A translation initiation codon (ATG) may also be provided to express a nucleotide sequence encoding an α2M receptor that lacks an initiation codon. In a compatible host-construct system, cellular proteins required for transcription, such as RNA polymerase and transcription factors, will bind to the regulatory regions on the expression construct to effect transcription of the α2M receptor sequence in the host organism. The precise nature of the regulatory regions needed for gene expression may vary from host cell to host cell. Generally, a promoter is required which is capable of binding RNA polymerase to initiate the transcription of an operably-associated nucleic acid sequence. Such regulatory regions may include those 5'-non-coding sequences involved with initiation of transcription and translation, such as the TATA box, the cap site, a CAAT box, and the like. The non-coding region 3' to the coding sequence may contain transcriptional termination regulatory sequences, such as terminators and polyadenylation sites.

Both constitutive and inducible regulatory regions may be used for expression of the α2M receptor, HSP, or α2M. It may be desirable to use inducible promoters when the conditions optimal for growth of the recombinant cells and the conditions for high level expression of the gene product are different. Examples of useful regulatory regions are provided in the next section below.

For expression of the α2M receptor, HSP, or α2M gene product in mammalian host cells, a variety of regulatory regions can be used, for example, the SV40 early and late promoters, the cytomegalovirus (CMV) immediate early promoter, and the Rous sarcoma virus long terminal repeat (RSV-LTR) promoter. Inducible promoters that may be useful in mammalian cells include but are not limited to those associated with the metallothionein II gene, mouse mammary tumor virus glucocorticoid responsive long terminal repeats (MMTV-LTR), the β-interferon gene, and the Hsp70 gene (Williams et al., 1989, Cancer Res. 49:2735–42; Taylor et al., 1990, Mol. Cell Biol., 10:165–75). It may be advantageous to use heat shock promoters or stress promoters to drive expression of the α2M receptor in recombinant host cells.

The following animal regulatory regions, which exhibit tissue specificity and have been utilized in transgenic animals, can also be used in tumor cells of a particular tissue type: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315: 338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

The efficiency of expression of the α2M receptor in a host cell may be enhanced by the inclusion of appropriate transcription enhancer elements in the expression vector, such as those found in SV40 virus, Hepatitis B virus, cytomegalovirus, immunoglobulin genes, metallothionein, β-actin (see Bittner et al., 1987, Methods in Enzymol. 153:516–544; Gorman, 1990, Curr. Op. in Biotechnol. 1:36–47).

The expression vector may also contain sequences that permit maintenance and replication of the vector in more than one type of host cell, or integration of the vector into the host chromosome. Such sequences may include but are not limited to replication origins, autonomously replicating sequences (ARS), centromere DNA, and telomere DNA. It may also be advantageous to use shuttle vectors that can be replicated and maintained in at least two types of host cells.

In addition, the expression vector may contain selectable or screenable marker genes for initially isolating or identifying host cells that contain DNA encoding an α2M receptor. For long term, high yield production of α2M receptor, stable expression in mammalian cells is preferred. A number of selection systems may be used for mammalian cells, including, but not limited, to the Herpes simplex virus thymidine kinase (Wigler et al., 1977, Cell 11:223), hypoxanthine-guanine phosphoribosyltransferase (Szybalski and Szybalski, 1962, Proc. Natl. Acad. Sci. USA 48:2026), and adenine phosphoribosyltransferase (Lowy et al., 1980, Cell 22:817) genes can be employed in $tk^-$, $hgprt^-$ or $aprt^-$ cells, respectively. Also, antimetabolite resistance can be used as the basis of selection for dihydrofolate reductase (dhfr), which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neomycin phosphotransferase (neo), which confers resistance to the aminoglycoside G-418 (Colberre-Garapin et al., 1981, J. Mol. Biol. 150:1); and hygromycin phosphotransferase (hyg), which confers resistance to hygromycin (Santerre et al., 1984, Gene 30:147). Other selectable markers, such as but not limited to histidinol and Zeocin™ can also be used.

In order to insert the α2M receptor, HSP, or α2M DNA sequence into the cloning site of a vector, DNA sequences with regulatory functions, such as promoters, must be attached to DNA sequences encoding the α2M receptor, HSP, or α2M, respectively. To do this, linkers or adapters providing the appropriate compatible restriction sites may be ligated to the ends of cDNA or synthetic DNA encoding an α2M receptor, by techniques well known in the art (Wu et al., 1987, Methods in Enzymol 152:343–349). Cleavage with a restriction enzyme can be followed by modification to create blunt ends by digesting back or filling in single-stranded DNA termini before ligation. Alternatively, a desired restriction enzyme site can be introduced into a fragment of DNA by amplification of the DNA by use of PCR with primers containing the desired restriction enzyme site.

In one embodiment, an expression construct comprising an α2M receptor sequence operably associated with regulatory regions can be directly introduced into appropriate host cells for expression and production of α2M receptor without further cloning (see, for example, U.S. Pat. No. 5,580,859). The expression constructs may also contain DNA sequences that facilitate integration of the α2M receptor sequence into the genome of the host cell, e.g., via homologous recombination. In this instance, it is not necessary to employ an expression vector comprising a replication origin suitable for appropriate host cells in order to propagate and express the α2M receptor in the host cells.

Expression constructs containing cloned nucleotide sequence encoding the α2M receptor, an HSP, or α2M can be introduced into the host cell by a variety of techniques known in the art, including but not limited to, for prokaryotic cells, bacterial transformation (Hanahan, 1985, in DNA Cloning, A Practical Approach, 1:109–136), and for eukaryotic cells, calcium phosphate mediated transfection (Wigler et al., 1977, Cell 11:223–232), liposome-mediated transfection (Schaefer-Ridder et al., 1982, Science 215:166–168), electroporation (Wolff et al., 1987, Proc Natl Acad Sci 84:3344), and microinjection (Cappechi, 1980, Cell 22:479–488).

For long term, high yield production of properly processed α2M receptor, HSP, or α2M, stable expression in mammalian cells is preferred. Cell lines that stably express the α2M receptor, HSP, α2M, or α2M receptor-peptide complexes may be engineered by using a vector that contains a selectable marker. By way of example but not limitation, following the introduction of the expression constructs, engineered cells may be allowed to grow for 1–2 days in an enriched media, and then are switched to a selective media. The selectable marker in the expression construct confers resistance to the selection and optimally allows cells to stably integrate the expression construct into their chromosomes and to grow in culture and to be expanded into cell lines. Such cells can be cultured for a long period of time while the desired gene product is expressed continuously.

The recombinant cells may be cultured under standard conditions of temperature, incubation time, optical density, and media composition. Alternatively, recombinant antigenic cells may be cultured under conditions emulating the nutritional and physiological requirements of the cancer cell or infected cell. However, conditions for growth of recombinant cells may be different from those for expression of the α2M receptor, HSPs, α2M, or antigenic proteins.

5.1.2 Peptide Synthesis

An alternative to producing HSP, α2M receptor, or α2M peptides and polypeptides by recombinant techniques is peptide synthesis. For example, a peptide corresponding to a portion of an HSP or an α2M peptide comprising the receptor-binding domain, which can be used as an antagonist in the therapeutic methods described herein, can be synthesized by use of a peptide synthesizer. Synthetic peptides corresponding to α2M receptor sequences useful for therapeutic methods described herein can also be produced synthetically. Conventional peptide synthesis may be used or other synthetic protocols well known in the art.

For example, peptides having the amino acid sequence of the α2M receptor, an HSP or α2M, or an analog, mutein, fragment, or derivative thereof, may be synthesized by solid-phase peptide synthesis using procedures similar to those described by Merrifield, 1963, J. Am. Chem. Soc., 85:2149. During synthesis, N-α-protected amino acids having protected side chains are added stepwise to a growing polypeptide chain linked by its C-terminal and to an insoluble polymeric support i.e., polystyrene beads. The peptides are synthesized by linking an amino group of an N-α-deprotected amino acid to an α-carboxyl group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc which is acid labile and Fmoc which is base labile. Details of appropriate chemistries, resins, protecting groups, protected amino acids and reagents are well known in the art and so are not discussed in detail herein (See, Atherton, et al., 1989, Solid Phase Peptide Synthesis: A Practical Approach, IRL Press, and Bodanszky, 1993, Peptide Chemistry, A Practical Textbook, 2nd Ed., Springer-Verlag).

Purification of the resulting α2M receptor, HSP, or α2M peptides is accomplished using conventional procedures, such as preparative HPLC using gel permeation, partition and/or ion exchange chromatography. The choice of appropriate matrices and buffers are well known in the art and so are not described in detail herein.

In addition, analogs and derivatives of α2M receptor, HSP, or α2M protein can be chemically synthesized. Furthermore, if desired, nonclassical amino acids or chemical amino acid analogs can be introduced as a substitution or addition into the α2M receptor, HSP, or α2M sequence. Non-classical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Na-methyl amino acids, and amino acid analogs in general.

5.1.3 Antibodies Specific for α2M Receptor-HSP Complexes

Described herein are methods for the production of antibodies capable of specifically recognizing α2M receptor epitopes, HSP-α2M receptor complex epitopes or epitopes of conserved variants or peptide fragments of the receptor or receptor complexes. Such antibodies are useful for therapeutic and diagnostic methods of the invention.

Such antibodies may include, but are not limited to, polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above. Such antibodies may be used, for example, in the detection of an α2M receptor or HSP-α2M receptor complex in an biological sample. Such antibodies may also be utilized in conjunction with, for example, compound screening schemes, as described below, in Section 5.2, for the evaluation of the effect of test compounds on the interaction between HSPs and the α2M receptor.

Anti-α2M receptor complex antibodies may additionally be used as a method for the inhibition of abnormal receptor product activity. Thus, such antibodies may, be utilized as part of treatment methods for HSP-α2M receptor related disorders, e.g., autoimmune disorders.

For the production of antibodies against α2M receptor or receptor complexes, various host animals may be immunized by injection with an α2M receptor or HSP-α2M receptor complex, or a portion thereof. An antigenic portion of α2M receptor or HSP-α2M receptor complex can be readily predicted by algorithms known in the art.

Host animals may include, but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

Polyclonal antibodies are heterogeneous populations of antibody molecules derived from the sera of animals immunized with an antigen, such as an α2M receptor or HSP-α2M receptor complex, or an antigenic functional derivative thereof. For the production of polyclonal antibodies, host animals such as those described above, may be immunized by injection with α2M receptor or HSP-α2M receptor complex, or portion thereof, supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to, the hybridoma technique of Kohler and Milstein, (1975, Nature 256, 495–497; and U.S. Pat. No. 4,376,110), the human B-cell hybridoma technique (Kosbor et al., 1983, Immunology Today 4: 72; Cole et al., 1983, Proc. Natl. Acad. Sci. USA 80, 2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison, et al., 1984, Proc. Natl. Acad. Sci., 81: 6851–6855; Neuberger, et al., 1984, Nature 312: 604–608; Takeda, et al., 1985, Nature, 314: 452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region (see, e.g., Cabilly et al., U.S. Pat. No. 4,816,567; and Boss et al., U.S. Pat. No. 4,816,397, which are incorporated herein by reference in their entirety).

In an additional embodiment of the invention, monoclonal antibodies can be produced in germ-free animals (see PCT International Publication No. WO 89/12690, published Dec. 12, 1989). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). Techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule specific for an α2M receptor-HSP complex together with genes from a human antibody molecule of appropriate biological activity can also be used; such antibodies are within the scope of this invention.

Humanized antibodies are also provided (see U.S. Pat. No. 5,225,539 by Winter). An immunoglobuin light or heavy chain variable region consists of a "framework" region interrupted by three hypervariable regions, referred to as coniplementarity determining regions (CDRs). The extent of the framework region and CDRs have been precisely defined (see, "Sequences of Proteins of Immunological Interest", Kabat, E. et al., U.S. Department of Health and Human Services (1983). Briefly, humanized antibodies are antibody molecules from non-human species having one or more CDRs from the non-human species and a framework region from a human immunoglobulin molecule. Such CDRS-grafted antibodies have been successfully constructed against various antigens, for example, antibodies against IL-2 receptor as described in Queen et al., 1989, Proc. Natl. Acad. Sci. USA 86:10029; antibodies against the cell surface receptor CAMPATH as described in Riechmann et al., 1988, Nature 332:323; antibodies against hepatitis B in Co et al., 1991, Proc. Natl. Acad. Sci. USA 88:2869; as well as against viral antigens of the respiratory syncytial virus in Tempest et al., 1991, Bio-Technology 9:267. Humanized antibodies are most preferred for therapeutic use in humans.

Alternatively, techniques described for the production of single chain antibodies (U.S. Pat. No. 4,946,778; Bird, 1988, Science 242: 423–426; Huston et al., 1988, Proc. Natl. Acad.

Sci. USA 85: 5879–5883; and Ward et al., 1989, Nature 334: 544–546) can be adapted to produce single chain antibodies against α2M receptor or HSP-α2M receptor complexes, or portions thereof. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the $F(ab')_2$ fragments, which can be produced by pepsin digestion of the antibody molecule and the Fab fragments, which can be generated by reducing the disulfide bridges of the $F(ab')_2$ fragments. Alternatively, Fab expression libraries may be constructed (Huse et al., 1989, Science, 246: 1275–1281) to allow rapid and easy identification of monoclonal Fab fragments with the desired specificity.

Antibodies to the α2M receptor can, in turn, be utilized to generate anti-idiotype antibodies that "mimic" the α2M receptor, using techniques well known to those skilled in the art (see, e.g., Greenspan & Bona, 1993, FASEB J 7(5): 437–444; and Nissinoff, 1991, J. Immunol. 147(8):2429–2438). For example antibodies which bind to the α2M receptor ECD and competitively inhibit the binding of HSPs to the α2M receptor can be used to generate anti-idiotypes that "mimic" the ECD and, therefore, bind and neutralize HSPs. Such neutralizing anti-idiotypes or Fab fragments of such anti-idiotypes can be used in therapeutic regimens to neutralize the native ligand and treat HSP-α2M receptor-related disorders, such as immunological disorders, proliferative disorders, and infectious diseases.

Alternatively, antibodies to the α2M receptor that can act as agonists of the α2M receptor activity can be generated. Such antibodies will bind to the α2M receptor and activate the signal transducing activity of the receptor. In addition, antibodies that act as antagonist of the α2M receptor activity, i.e. inhibit the activation of the α2M receptor would be particularly useful for treating autoimmune disorders, proliferative disorders, such as cancer, and infectious diseases. Methods for assaying for such agonists and antagonists are described in detail in Section 5.2, below.

5.2 Assays for the Identification of Compounds that Modulate HSP-α2M Receptor Interactions The present invention is based on the discovery that the α2M receptor recognizes HSP-antigenic peptide complexes and transports them within the cell for the purpose of presenting such antigenic molecules to cells of the immune system and eliciting an immune response. Thus, methods for identifying a molecule that enhances or blocks the function of the receptor are included in the invention. The present invention provides in vitro and in vivo assay systems, described in the subsections below, which can be used to identify compounds or compositions that modulate the activity of the α2M receptor and its interaction with HSPs or HSP-peptide complexes. The invention provides screening methodologies useful in the identification of small molecules, proteins and other compounds which modulate the interaction of HSPs with the α2M receptor. Such compounds may bind the α2M receptor genes or gene products with differing affinities, and may serve as regulators of receptor activity in vivo with useful therapeutic applications in modulating the immune response. For example, certain compounds that inhibit receptor function may be used in patients to downregulate destructive immune responses which are caused by cellular release of HSPs.

Methods to screen potential agents for their ability to modulate α2M receptor expression and activity can be designed based on the inventor's discovery of the receptor and its role in HSP or HSP-peptide complex binding and recognition. α2M receptor protein, nucleic acids, and derivatives can be used in screening assays to detect molecules that specifically bind to HSP proteins, derivatives, or nucleic acids, and thus have potential use as agonists or antagonists of the α2M receptor, to modulate the immune response. In a preferred embodiment, such assays are performed to screen for molecules with potential utility as anti-autoimmune disease, anti-cancer and anti-infective drugs (such as anti-viral drugs and antibiotic drugs), or lead compounds for drug development. For example, recombinant cells expressing α2M receptor nucleic acids can be used to recombinantly produce α2M receptor in these assays, to screen for molecules that interfere with the binding of HSPs to the α2M receptor. Similar methods can be used to screen for molecules that bind to the α2M receptor derivatives or nucleic acids. Methods that can be used to carry out the foregoing are commonly known in the art.

In one embodiment, an assay for identifying a compound that modulates an HSP-α2M receptor-mediated process is disclosed. This assay comprises: (a) contacting a test compound with an HSP and an α2M receptor; and (b) measuring the level of α2M receptor activity or expression, such that if the level of activity or expression measured in (b) differs from the level of α2M receptor activity in the absence of the test compound, then a compound that modulates an HSP-α2M receptor-mediated process is identified. In another embodiment, in which the compound identified is an antagonist which interferes with the interaction of the HSP with the α2M receptor, the method further comprises the step of determining whether the level interferes with the interaction of the HSP and the α2M receptor.

In another embodiment, a cell-based method for identifying a compound that modulates an HSP-α2M receptor-mediated process is described. This method comprises the following steps: (a) contacting a test compound with a heat shock protein and an α2M receptor-expressing cell; and (b) measuring the level of α2M receptor activity or expression in the cell, such that if the level of activity or expression measured in (b) differs from the level of α2M receptor activity in the absence of the test compound, then a compound that modulates an HSP-α2M receptor-mediated process is identified.

In another embodiment, a receptor-ligand binding assay for identifying a compound that modulates the binding of an HSP to the α2M receptor, comprises: (a) contacting an HSP with an α2M receptor, or fragment, or analog, derivative or mimetic thereof, in the presence of a test compound; and (b) measuring the amount of heat shock protein bound to the α2M receptor, or fragment, analog, derivative or mimetic thereof, such that if the amount of bound heat shock protein measured in (b) differs from the amount of bound heat shock protein measured in the absence of the test compound, then a compound that modulates the binding of an HSP to the α2M receptor is identified.

In another embodiment, a method for identifying a compound that modulates heat shock protein-mediated antigen presentation by alpha (2) macroglobulin receptor-expressing cells comprises: (a) adding a test compound to a mixture of alpha (2) macroglobulin receptor-expressing cells and a complex consisting essentially of a heat shock protein noncovalently associated with an antigenic molecule, under conditions conducive to alpha (2) macroglobulin receptor-mediated endocytosis; (b) measuring the level of stimulation of antigen-specific cytotoxic T cells by the alpha (2) macroglobulin receptor-expressing cells, such that if the level measured in (b) differs from the level of said stimulation in the absence of the test compound, then a compound that modulates heat shock protein-mediated antigen presentation by alpha (2) macroglobulin receptor-expressing cells is identified.

The assays of the present invention may be first optimized on a small scale (i.e., in test tubes), and then scaled up for high-throughput assays. In various embodiments, the in vitro screening assays of the present invention may be performed using purified components or cell lysates. In other embodiments, the screening assays may be carried out in intact cells in culture and in animal models. In accordance with the present invention, test compounds which are shown to modulate the activity of the α2M receptor as described herein in vitro, will further be assayed in vivo, including cultured cells and animal models to determine if the test compound has the similar effects in vivo and to determine the effects of the test compound on antigen presentation, cytokine release, intracellular $Ca^{++}$ release, T-cell cytotoxicity, tumor progression, the accumulation or degradation of positive and negative regulators, cellular proliferation, etc.

5.2.1 α2M Receptor-Ligand Binding Assays

The screening assays, described herein, can be used to identify compounds and compositions, including peptides and organic, non-protein molecules that modulate the interaction between HSPs and the α2M receptor. Recombinant, synthetic, and otherwise exogenous compounds may have binding capacity and, therefore, may be candidates for pharmaceutical agents. Alternatively, the proteins and compounds include endogenous cellular components which interact with the identified genes and proteins in vivo. Such endogenous components may provide new targets for pharmaceutical and therapeutic interventions.

Thus, in a preferred embodiment, both naturally occurring and/or synthetic compounds (e.g., libraries of small molecules or peptides), may be screened for modulating α2M receptor activity. In another series of embodiments, cell lysates or tissue homogenates may be screened for proteins or other compounds which bind to one of the normal or mutant α2M receptor genes and α2M receptor polypeptides.

The screening assays described herein may be used to identify small molecules, peptides or proteins, or derivatives, analogs and fragments thereof, that modulate the interaction of HSPs and the α2M receptor. Such compounds may be used as agonists or antagonists of the uptake of HSPs and HSP complexes by the cell surface receptor. For example, compounds that modulate the HSP-α2M receptor interaction include, but are not limited to, compounds that bind to the α2M receptor, thereby either inhibiting (antagonists) or enhancing (agonists) the binding of HSPs and HSP complexes to the receptor, as well as compounds that bind to HSPs, thereby preventing or enhancing binding of HSPs to the receptor. Compounds that affect α2M gene activity (by affecting α2M gene expression, including molecules, e.g., proteins or small organic molecules, that affect transcription or interfere with splicing events so that expression of the full length or truncated forms of α2M can be modulated) can also be identified in the screens of the invention. Further, it should be noted that the assays described can also identify compounds that modulate HSP uptake by α2M receptor (e.g., compounds which affect downstream signaling in the α2M receptor signal transduction pathway). The identification and use of such compounds which affect signaling events downstream of the α2M receptor and thus modulate effects of the receptor on the immune response are within the scope of the invention.

Compounds that affect the α2M receptor gene activity (by affecting the α2M receptor gene expression, including molecules, e.g., proteins or small organic molecules, that affect transcription or interfere with splicing events so that expression of the full length or the truncated form of the α2M receptor can be modulated) can also be identified in the screens of the invention. However, it should be noted that the assays described can also identify compounds that modulate the α2M receptor signal transduction (e.g., compounds which affect downstream signaling events, such as inhibitors or enhancers of endocytic activity which is activated by ligand binding to the α2M receptor). The identification and use of such compounds which affect signaling events downstream of the α2M receptor and thus modulate effects of the α2M receptor on the allergenic response are within the scope of the invention.

The screening assays described herein are designed to detect compounds that modulate, i.e. interfere with or enhance, HSP-α2M receptor interactions. As described in detail below, such assays are functional assays, such as binding assays, that can be adapted to a high-throughput screening methodologies.

Binding assays can be used to identify compounds that modulate the interaction between HSPs and the α2M receptor. In one aspect of the invention the screens may be designed to identify compounds that disrupt the interaction between the α2M receptor and an HSP, such as, for example, peptides derived from an HSP, α2M, or another α2M receptor ligand. Such compounds will be useful as lead compounds for antagonists of HSP-α2M receptor-related disorders and conditions, such as immune disorders, proliferative disorders, and infectious diseases.

Binding assays may be performed either as direct binding assays or as competition binding assays. In a direct binding assay, a test compound is tested for binding either to the α2M receptor or to an HSP. Then, in a second step, the test compound is tested for its ability to modulate the HSP-α2M receptor interaction. Competition binding assays, on the other hand, assess the ability of a test compound to compete with an HSP for binding to the α2M receptor.

In a direct binding assay, either the HSP and/or the α2M receptor is contacted with a test compound under conditions that allow binding of the test compound to the ligand or the receptor. The binding may take place in solution or on a solid surface. Preferably, the test compound is previously labeled for detection. Any detectable compound may be used for labeling, such as but not limited to, a luminescent, fluorescent, or radioactive isotope or group containing same, or a nonisotopic label, such as an enzyme or dye. After a period of incubation sufficient for binding to take place, the reaction is exposed to conditions and manipulations that remove excess or non-specifically bound test compound. Typically, it involves washing with an appropriate buffer. Finally, the presence of an HSPs-test compound or a the α2M receptor-test compound complex is detected.

In a competition binding assay, test compounds are assayed for their ability to disrupt or enhance the binding of the HSP to the α2M receptor. Labeled HSP may be mixed with the α2M receptor or fragment or derivative thereof, and placed under conditions in which the interaction between them would normally occur, with and without the addition of the test compound. The amount of labeled HSP that binds the α2M receptor may be compared to the amount bound in the presence or absence of test compound.

In a preferred embodiment, to facilitate complex formation and detection, the binding assay is carried out with one or more components immoblilized on a solid surface. In various embodiments, the solid support could be, but is not restricted to, polycarbonate, polystyrene, polypropylene, polyethlene, glass, nitrocellulose, dextran, nylon, polyacrylamide and agarose. The support configuration can include beads, membranes, microparticles, the interior surface of a reaction vessel such as a microtiter plate, test tube or other reaction vessel. The immobilization of the α2M receptor, or other component, can be achieved through covalent or non-covalent attachments. In one embodiment, the attachment may be indirect, i.e. through an attached antibody. In another embodiment, the α2M receptor and negative controls are tagged with an epitope, such as glutathione S-transferase (GST) so that the attachment to the solid surface can be mediated by a commercially available antibody such as anti-GST (Santa Cruz Biotechnology).

For example, such an affinity binding assay may be performed using a the α2M receptor which is immobilized to a solid support. Typically, the non-mobilized component of the binding reaction, in this case either HSP or the test compound, is labeled to enable detection. A variety of labeling methods are available and may be used, such as luminescent, chromophore, fluorescent, or radioactive isotope or group containing same, and nonisotopic labels, such as enzymes or dyes. In a preferred embodiment, the test compound is labeled with a fluorophore such as fluorescein isothiocyanate (FITC, available from Sigma Chemicals, St. Louis).

The labeled test compounds, or HSP plus test compounds, are then allowed to contact with the solid support, under conditions that allow specific binding to occur. After the binding reaction has taken place, unbound and non-specifically bound test compounds are separated by means of washing the surface. Attachment of the binding partner to the solid phase can be accomplished in various ways known to those skilled in the art, including but not limited to chemical cross-linking, non-specific adhesion to a plastic surface, interaction with an antibody attached to the solid phase, interaction between a ligand attached to the binding partner (such as biotin) and a ligand-binding protein (such as avidin or streptavidin) attached to the solid phase, and so on.

Finally, the label remaining on the solid surface may be detected by any detection method known in the art. For example, if the test compound is labeled with a fluorophore, a fluorimeter may be used to detect complexes.

Preferably, the α2M receptor is added to binding assays in the form of intact cells that express the α2M receptor, or isolated membranes containing the α2M receptor. Thus, direct binding to the α2M receptor or the ability of a test compound to modulate an HSP-α2M receptor complex may be assayed in intact cells in culture or in animal models in the presence and absence of the test compound. A labeled HSP may be mixed with cells that express the α2M receptor, or to crude extracts obtained from such cells, and the test compound may be added. Isolated membranes may be used to identify compounds that interact with the α2M receptor. For example, in a typical experiment using isolated membranes, cells may be genetically engineered to express the α2M receptor. Membranes can be harvested by standard techniques and used in an in vitro binding assay. Labeled ligand (e.g., $^{125}$I-labeled HSP) is bound to the membranes and assayed for specific activity; specific binding is determined by comparison with binding assays performed in the presence of excess unlabeled (cold) ligand. Alternatively, soluble α2M receptor may be recombinantly expressed and utilized in non-cell based assays to identify compounds that bind to the α2M receptor. The recombinantly expressed α2M receptor polypeptides or fusion proteins containing the extracellular domain (ECD) of the α2M receptor, or one or more subdomains thereof, can be used in the non-cell based screening assays. Alternatively, peptides corresponding to one or more of the CDs of the α2M receptor, or fusion proteins containing one or more of the CDs of the α2M receptor can be used in non-cell based assay systems to identify compounds that bind to the cytoplasmic portion of the α2M receptor; such compounds may be useful to modulate the signal transduction pathway of the α2M receptor. In non-cell based assays the recombinantly expressed the α2M receptor is attached to a solid substrate such as a test tube, microtiter well or a column, by means well known to those in the art (see Ausubel et al., supra). The test compounds are then assayed for their ability to bind to the α2M receptor.

Alternatively, the binding reaction may be carried out in solution. In this assay, the labeled component is allowed to interact with its binding partner(s) in solution. If the size differences between the labeled component and its binding partner(s) permit such a separation, the separation can be achieved by passing the products of the binding reaction through an ultrafilter whose pores allow passage of unbound labeled component but not of its binding partner(s) or of labeled component bound to its partner(s). Separation can also be achieved using any reagent capable of capturing a binding partner of the labeled component from solution, such as an antibody against the binding partner, a ligand-binding protein which can interact with a ligand previously attached to the binding partner, and so on.

In a one embodiment, for example, a phage library can be screened by passing phage from a continuous phage display library through a column containing purified α2M receptor, or derivative, analog, fragment, or domain, thereof, linked to a solid phase, such as plastic beads. By altering the stringency of the washing buffer, it is possible to enrich for phage that express peptides with high affinity for the α2M receptor. Phage isolated from the column can be cloned and the affinities of the short peptides can be measured directly. Sequences for more than one oligonucleotide can be combined to test for even higher affinity binding to the α2M receptor. Knowing which amino acid sequences confer the strongest binding to the α2M receptor, computer models can be used to identify the molecular contacts between the α2M receptor and the test compound. This will allow the design of non-protein compounds which mimic those contacts. Such a compound may have the same activity of the peptide and can be used therapeutically, having the advantage of being efficient and less costly to produce.

In another specific embodiment of this aspect of the invention, the solid support is membranes containing the α2M receptor attached to a microtiter dish. Test compounds, for example, cells that express library members are cultivated under conditions that allow expression of the library members in the microtiter dish. Library members that bind to the protein (or nucleic acid or derivative) are harvested. Such methods, are described by way of example in Parmley and Smith, 1988, Gene 73:305–318; Fowlkes et al., 1992, BioTechniques 13:422–427; PCT Publication No. WO 94/18318; and in references cited hereinabove.

In another embodiment of the present invention, interactions between the α2M receptor or HSP and a test compound may be assayed in vitro. Known or unknown molecules are assayed for specific binding to the α2M receptor nucleic acids, proteins, or derivatives under conditions conducive to binding, and then molecules that specifically bind to the α2M receptor are identified. The two components can be measured in a variety of ways. One approach is to label one of the components with an easily detectable label, place it together with a test component(s) under conditions that allow binding to occur, perform a separation step which separates bound labeled component from unbound labeled component, and then measure the amount of bound component. In one embodiment, the α2M receptor can be labeled and added to a test agent, using conditions that allow binding to occur. Binding of the test agent can be determined using polyacrylamide gel analysis to compare complexes formed in the presence and absence of the test agent.

In yet another embodiment, binding of HSP to the α2M receptor may be assayed in intact cells in animal models. A labeled HSP may be administered directly to an animal, with and without a test compound. Uptake of the HSP may be measured in the presence and the absence of test compound. For these assays, host cells to which the test compound is added may be genetically engineered to express the α2M receptor and/or HSP, which may be transient, induced or constitutive, or stable. For the purposes of the screening methods of the present invention, a wide variety of host cells may be used including, but not limited to, tissue culture cells, mammalian cells, yeast cells, and bacteria. Mammalian cells such as macrophages or other cells that express the α2M receptor, i.e., cells of the monocytic lineage, liver parenchymal cells, fibroblasts, keratinocytes, neuronal cells, and placental syncytiotrophoblasts, may be a preferred cell type in which to carry out the assays of the present invention. Bacteria and yeast are relatively easy to cultivate but process proteins differently than mammalian cells.

5.2.2 α2M Receptor Activity Assays

After identification of a test compound that modulates the interaction of HSP with the α2M receptor, the test compound can be further characterized to measure its effect on α2M receptor activity and the HSP-α2M receptor endocytic signaling pathway. For example, the test compound may be characterized by testing its effect on HSP/α2M cellular activity in vivo. Such assays include downstream signaling assays, antigen presentation assays, assays for antigen-specific activation of cytotoxic T cells, and the like.

In various embodiments, a candidate compound identified in a primary assay may be tested for its effect on innate α2M receptor signaling activity. For example, downstream signaling effects of α2M receptor activation which can be assayed include, but are not limited to: enhanced locomotion and chemotaxis of macrophages (Forrester et al., 1983, Immunology 50: 251–259), down regulation of proteinase synthesis, and elevation of intracellular calcium, inositol phosphates and cyclic AMP (Misra et al., 1993, Biochem. J., 290:885–891). Other innate immune responses that can be tested are release of cytokines (i.e., IL-12, IL1β, GMCSF, and TNFα). Thus, as secondary assays, any identified candidate compound can be tested for changes in such activities in the presence and absence.

For example, in one embodiment, a chemotaxis assay can be used to further characterize a candidate identified by a primary screening assay. It is known that α2M modified by protease interaction can induce directional migration of cells towards their ligand. A number of techniques can be used to test chemotactic migration in vitro (see, e.g., Leonard et al., 1995, "Measurement of α and β Chemokines", in Current Protocols in Immunology, 6.12.1–6.12.28, Ed. Coligan et al., John Wiley & Sons, Inc. 1995). For example, in one embodiment, a candidate compound can be tested for its ability to modulate the ability of alpha (2) macroglobulin receptor to induce migration of cells that express the receptor using a chemokine gradient in a multiwell Boyden chemotaxis chamber. In a specific example of this method, a serial dilution of an HSP/alpha (2) macroglobulin receptor antagonist or agonist test compound identified in the primary screen is placed in the bottom wells of the Boyden chemotaxis chamber. A constant amount of HSP is also added to the dilution series. As a control, at least one aliquot contains only HSP. The contribution of the antagonist or agonist compound to the chemotactic activity of alpha (2) macroglobulin receptor is measured by comparing number of migrating cells on the lower surface of the membrane filter of the aliquots containing only HSP, with the number of cells in aliquots containing test compound and HSP. If addition of the test compound to the HSP solution results in a decrease in the number of cells detected the membrane relative to the number of cells detected using a solution containing only HSP, then an antagonist of HSP induction of chemotactic activity of alpha (2) macroglobulin receptor-expressing cells is identified.

Elevation in intracellular ionized calcium concentration ($[Ca^{2+}]_1$) is also an indicator of α2M receptor activation (Misra et al., 1993, supra). Thus, in another embodiment, calcium flux assays can be used as secondary screens to further characterize modulators of HSP/α2M receptor interactions. Intracellular calcium ion concentration can be measured in cells that express the α2M receptor in the presence of the HSP, in the presence and the absence of a test compound. For example, calcium mobilization can be detected and measured by flow cytometry, by labeling with fluorescent dyes that are trapped intracellularly A fluorescent dye such as Indo-1 exhibits a change in emission spectrum upon binding calcium, the ratio of fluorescence produced by the calcium-bound dye to that produce by the unbound dye may be used to estimate the intracellular calcium concentration. In a specific embodiment, cells are incubated in a cuvette in media containing Indo-1 at 37° C. and are excited, and fluorescence is measured using a fluorimeter (Photon Technology Corporation, International). HSP is added at a specific time point, in the presence and the absence of a test compound, EGTA is added to the cuvette to release and chelate total calcium, and the response is measured. Binding of HSP ligand results in increased intracellular $Ca^{2+}$ concentration in cells that express alpha (2) macroglobulin receptor. An agonist results in a relative increased intracellular $Ca^{2+}$ concentration, whereas an antagonist results in a relative decreased intracellular $Ca^{2+}$ concentration In other embodiments, antigen-specific response assays may be used to detect the effect of a candidate compound on presentation of antigenic molecule by HSP. For example, an antigen presentation assay may be performed to determine the effect of a compound in vivo on the uptake of HSP-antigenic molecules by cells expressing the α2M receptor. Such re-presentation assays are known in the art, and have been described previously (Suto and Srivastava, 1995, Science 269:1585–1588). For example, in one embodiment, antigen presenting cells, such as a macrophage cell line (e.g., RAW264.7), are mixed with antigen-specific T cells in media, using approximately 10,000 cells of each type at approximately a 1:1 ratio. Complexes of HSP (10 μg/ml) and a peptide antigen, as well as test compound, is added to the cells and the culture is incubated for approximately 20 hours. Stimulation of T cells may then be measured in the presence and absence of test compound.

In another embodiment, antigen-specific T cell stimulation may be assayed. In one embodiment an IFN-γ release assay may be used. After washing, cells are fixed, permeabilized, and reacted with dye-labeled antibodies reactive with human IFN-γ (PE- anti-IFN-γ). Samples are analyzed by flow cytometry using standard techniques. Alternatively, a filter immunoassay, ELISA (enzyme linked immunosorbent assay), or enzyme-linked immunospot assay (ELISPOT) assay, may be used to detect specific cytokines produced by an activated T cell. In one embodiment, for example, a nitrocellulose-backed microtiter plate is coated with a purified cytokine-specific primary antibody, i.e., anti-IFN-γ, and the plate is blocked to avoid background due to nonspecific binding of other proteins. A sample of APC cells stimulated with antigen is diluted onto the wells of the microtiter plate. A labeled, e.g., biotin-labeled, secondary anti-cytokine antibody is added. The antibody cytokine complex can then be detected, i.e., by enzyme-conjugated streptavidin—cytokine-secreting cells will appear as "spots" by visual, microscopic, or electronic detection methods. In another embodiment, "tetramer staining" assay (Altman et al., 1996, Science 274: 94–96) may be used to identify antigen-specific T-cells. For example, an MHC molecule containing a specific peptide antigen, such as a tumor-specific antigen, is multimerized to make soluble peptide tetramers and labeled, for example, by complexing to streptavidin. The MHC-peptide antigen complex is then mixed with a population of stimulated T cells. Biotin is then used to stain T cells which recognize and bind to the MHC-antigen complex.

5.2.3 Compounds that can be Screened in Accordance with the Invention

The screening assays described herein may be used to identify small molecules, peptides or proteins, or derivatives, analogs and fragments thereof, that modulate the interaction of the HSP with the α2M receptor. The compounds which may be screened in accordance with the invention include, but are not limited to small molecules, peptides, antibodies and fragments thereof, and other organic compounds (e.g., peptidomimetics) that bind to the ECD of the α2M receptor and either inhibit the activity triggered by the natural ligand (i.e., antagonists) or mimic the activity triggered by the natural ligand (i.e., agonists), as well as small molecules, peptides, antibodies or fragments thereof, and other organic compounds. In one embodiment, such compounds include sequences of the α2M receptor, such as the ECD of the α2M receptor (or a portion thereof), which can bind to and "neutralize" natural ligands, such as HSPs, α2M, LDL, etc. In another embodiment, such compounds include ligand sequences, such as HSP sequences and/or α2M sequences, which can bind to the active site of the α2M receptor, and block its activity.

Compounds that may be used for screening include, but are not limited to, peptides such as, for example, soluble peptides, including but not limited to members of random peptide libraries; (see, e.g., Lam et al., 1991, Nature 354: 82–84; Houghten et al., 1991, Nature 354:84–86), and combinatorial chemistry-derived molecular library made of D- and/or L-configuration amino acids, phosphopeptides (including, but not limited to, members of random or partially degenerate, directed phosphopeptide libraries; see, e.g., Songyang et al., 1993, Cell 72:767–778), antibodies (including, but not limited to, polyclonal, monoclonal, humanized, anti-idiotypic, chimeric or single chain antibodies, and FAb, $F(ab')_2$ and FAb expression library fragments, and epitope-binding fragments thereof), and small organic or inorganic molecules.

In one embodiment of the present invention, peptide libraries may be used as a source of test compounds that can be used to screen for modulators of HSP-α2M receptor interactions. Diversity libraries, such as random or combinatorial peptide or nonpeptide libraries can be screened for molecules that specifically bind to the α2M receptor. Many libraries are known in the art that can be used, e.g., chemically synthesized libraries, recombinant (e.g., phage display libraries), and in vitro translation-based libraries.

Examples of chemically synthesized libraries are described in Fodor et al., 1991, Science 251:767–773; Houghten et al., 1991, Nature 354:84–86; Lam et al., 1991, Nature 354:82–84; Medynski, 1994, Bio/Technology 12:709–710; Gallop et al., 1994, J. Medicinal Chemistry 37(9):1233-$^{125}$I; Ohlmeyer et al., 1993, Proc. Natl. Acad. Sci. USA 90:10922–10926; Erb et al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; Salmon et al., 1993, Proc. Natl. Acad. Sci. USA 90:11708–11712; PCT Publication No. WO 93/20242; and Brenner and Lerner, 1992, Proc. Natl. Acad. Sci. USA 89:5381–5383.

Examples of phage display libraries are described in Scott & Smith, 1990, Science 249:386–390; Devlin et al., 1990, Science, 249:404–406; Christian et al., 1992, J. Mol. Biol. 227:711–718; Lenstra, 1992, J. Immunol. Meth. 152:149–157; Kay et al., 1993, Gene 128:59–65; and PCT Publication No. WO 94/18318 dated Aug. 18, 1994.

By way of examples of nonpeptide libraries, a benzodiazepine library (see e.g., Bunin et al., 1994, Proc. Natl. Acad. Sci. USA 91:4708–4712) can be adapted for use. Peptoid libraries (Simon et al, 1992, Proc. Natl. Acad. Sci. USA 89:9367–9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138–11142).

Screening the libraries can be accomplished by any of a variety of commonly known methods. See, e.g., the following references, which disclose screening of peptide libraries: Parmley & Smith, 1989, Adv. Exp. Med. Biol. 251:215–218; Scott & Smith, 1990, Science 249:386–390; Fowlkes et al., 1992; BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. No. 5,096,815, U.S. Pat. No. 5,223,409, and U.S. Pat. No. 5,198,346, all to Ladner et al.; Rebar & Pabo, 1993, Science 263:671–673; and PCT Publication No. WO 94/18318.

In another embodiment of the present invention, the screening may be performed by adding the labeled HSP to in vitro translation systems such as a rabbit reticulocyte lysate (RRL) system and then proceeding with in vitro priming reaction. In vitro translation-based libraries include but are not limited to those described in PCT Publication No. WO 91/05058 dated Apr. 18, 1991; and Mattheakis et al., 1994, Proc. Natl. Acad. Sci. USA 91:9022–9026.

Compounds that can be tested and identified methods described herein can include, but are not limited to, compounds obtained from any commercial source, including Aldrich (Milwaukee, Wis. 53233), Sigma Chemical (St. Louis, Mo.), Fluka Chemie AG (Buchs, Switzerland) Fluka Chemical Corp. (Ronkonkoma, N.Y.;), Eastman Chemical Company, Fine Chemicals (Kingsport, Tenn.), Boehringer Mannheim GmbH (Mannheim, Germany), Takasago (Rockleigh, N.J.), SST Corporation (Clifton, N.J.), Ferro (Zachary, La. 70791), Riedel-deHaen Aktiengesellschaft (Seelze, Germany), PPG Industries Inc., Fine Chemicals (Pittsburgh, Pa.

15272). Further any kind of natural products may be screened using the methods of the invention, including microbial, fungal, plant or animal extracts.

Furthermore, diversity libraries of test compounds, including small molecule test compounds, may be utilized. For example, libraries may be commercially obtained from Specs and BioSpecs B.V. (Rijswijk, The Netherlands), Chembridge Corporation (San Diego, Calif.), Contract Service Company (Dolgoprudny, Moscow Region, Russia), Comgenex USA Inc. (Princeton, N.J.), Maybridge Chemicals Ltd. (Cornwall PL34 OHW, United Kingdom), and Asinex (Moscow, Russia).

Still further, combinatorial library methods known in the art, can be utilize, including, but not limited to: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145). Combinatorial libraries of test compounds, including small molecule test compounds, can be utilized, and may, for example, be generated as disclosed in Eichler & Houghten, 1995, Mol. Med. Today 1:174–180; Dolle, 1997, Mol. Divers. 2:223–236; and Lam, 1997, Anticancer Drug Des. 12:145–167.

Examples of methods for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented in solution (e.g., Houghten, 1992, BioTechniques 13:412–421), or on beads (Lam, 1991, Nature 354:82–84), chips (Fodor, 1993, Nature 364:555–556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865–1869) or phage (Scott and Smith, 1990, Science 249:386–390; Devlin, 1990, Science 249:404–406; Cwirla et al., 1990, Proc. Natl. Acad. Sci. USA 87:6378–6382; and Felici, 1991, J. Mol. Biol. 222:301–310).

Screening the libraries can be accomplished by any of a variety of commonly known methods. See, e.g., the following references, which disclose screening of peptide libraries: Parmley & Smith, 1989, Adv. Exp. Med. Biol. 251:215–218; Scott & Smith, 1990, Science 249:386–390; Fowlkes et al., 1992; BioTechniques 13:422–427; Oldenburg et al., 1992, Proc. Natl. Acad. Sci. USA 89:5393–5397; Yu et al., 1994, Cell 76:933–945; Staudt et al., 1988, Science 241:577–580; Bock et al., 1992, Nature 355:564–566; Tuerk et al., 1992, Proc. Natl. Acad. Sci. USA 89:6988–6992; Ellington et al., 1992, Nature 355:850–852; U.S. Pat. No. 5,096,815, U.S. Pat. No. 5,223,409, and U.S. Pat. No. 5,198,346, all to Ladner et al.; Rebar & Pabo, 1993, Science 263:671–673; and PCT Publication No. WO 94/18318.

5.3 Identification of Fragments of the α2M Receptor and/or HSPs Useful for Immunotherapy The invention also encompasses methods for identifying HSP-binding α2M receptor fragments ("HSP-binding domains"), and analogs, muteins, or derivatives thereof, which are capable of binding to, and uptake of, HSP-antigenic peptide complexes. Such HSP-binding domains can then be tested for activity in vivo and in vitro using the α2M receptor/ligand binding assays, described in Section 5.2.1, above. In one embodiment, such a method for identifying an α2M receptor fragment capable of binding a heat shock protein comprises the steps of: (a) contacting a heat shock protein with one or more alpha (2) macroglobulin receptor fragments; and (b) identifying an α2M receptor polypeptide fragment which specifically binds to the heat shock protein.

HSP-binding domains of the alpha (2) macroglobulin receptor capable of binding HSP-antigenic peptide complexes, and can be further tested for activity using either in vivo binding assays, re-presentation assays, or CTL assays, such as those described in Section 5.2.2, above. For example, one such method for identifying an α2M receptor fragment capable of inducing an HSP-α2M receptor-mediated process comprises the steps of: (a) contacting a heat shock protein with cell expressing α2M receptor fragment; and (b) measuring the level of alpha (2) macroglobulin receptor activity in the cell, such that if the level of the HSP-α2M receptor-mediated process or activity measured in (b) is greater than the level of alpha (2) macroglobulin receptor activity in the absence of the α2M receptor fragment, then an α2M receptor fragment capable of inducing an HSP-α2M receptor-mediated process is identified. Depending on their behavior in such assays, such molecules can be used to either enhance or, alternatively, block the function of the receptor when administered or expressed in vivo. For example, these assays can be used to identify α2M receptor HSP-binding domains which can bind HSP-antigen complexes and negatively interfere with their uptake by antigen presenting cells. These antagonists could be used to down-regulate immune responses which are caused by cellular release of HSPs. Alternatively, certain α2M receptor HSP-binding domains may be used to enhance HSP-antigen complex uptake and signaling. Such agonists could be administered or expressed in subjects to elicit an immune response against an antigen of interest.

In another embodiment, the invention encompasses methods for identifying HSP fragments which are capable of binding and being taken up by the α2M receptor ("α2M receptor-binding domains"), and analogs, muteins, or derivatives thereof. As described for assays for α2M receptor-related polypeptides described above, such α2M receptor-binding domains can then be tested for activity in vivo and in vitro using the binding assays described in Section 5.2.1, above. For example, one such method for identifying a heat shock protein fragment capable of binding an α2M receptor comprises: (a) contacting an α2M receptor with one or more heat shock protein fragments; and (b) identifying a heat shock protein fragment which specifically binds to the α2M receptor.

HSP fragments of interest may be further tested in cells, using in vivo binding assays, re-presentation assays, or CTL assays, such as those described in Section 5.2.2, above. For example, in one embodiment, such a method for identifying a heat shock protein fragment capable of inducing an HSP-α2M receptor-mediated process comprises: a) contacting an α2M receptor fragment with a cell expressing a heat shock protein; and b) measuring the level of alpha (2) macroglobulin receptor activity in the cell, such that if the level of the HSP-α2M receptor-mediated process or activity measured in (b) is greater than the level of alpha (2) macroglobulin receptor activity in the absence of said heat shock protein fragment. Alternatively, α2M receptor-binding domains which decrease uptake of HSPs could be used to block HSP uptake by the α2M receptor. In one embodiment, such HSP fragments comprising α2M receptor-binding domain sequences could be used to construct recombinant fusion proteins, comprised of a heat shock protein α2M receptor-binding domain and an antigenic peptide sequence. Such recombinant fusion proteins may be used to elicit an immune response and to treat or prevent immune diseases and disorders (Suzue et al., 1997, Proc. Natl. Acad. Sci. U.S.A. 94: 13146–51).

The α2M receptor fragments, analogs, muteins, and derivatives and/or HSP fragments, analogs, muteins, and derivatives of the invention may be produced by recombinant DNA techniques, synthetic methods, or by enzymatic or chemical cleavage of native α2M receptor and/or HSPs.

Any eukaryotic cell may serve as the nucleic acid source for obtaining the coding region of an α2M receptor or HSP gene. Nucleic acid sequences encoding HSPs and or the α2M receptor can be isolated from vertebrate, mammalian, as well as primate sources, including humans. Amino acid sequences and nucleotide sequences of naturally occurring HSPs and α2M receptor are generally available in sequence databases, such as Genbank.

The DNA may be obtained by standard procedures known in the art by DNA amplification or molecular cloning directly from a tissue, cell culture, or cloned DNA (e.g., a DNA “library”). Clones derived from genomic DNA may contain regulatory and intron DNA regions in addition to coding regions; clones derived from cDNA will contain only exon sequences. In a preferred embodiment, DNA can be amplified from genomic or cDNA by polymerase chain reaction (PCR) amplification using primers designed from the known sequence of an HSP or α2M receptor. The polymerase chain reaction (PCR) is commonly used for obtaining genes or gene fragments of interest. For example, a nucleotide sequence encoding a fragment of any desired length can be generated using PCR primers that flank the nucleotide sequence encoding the peptide-binding domain. Alternatively, an HSP or α2M receptor gene sequence can be cleaved at appropriate sites with restriction endonuclease(s) if such sites are available, releasing a fragment of DNA encoding the peptide-binding domain. If convenient restriction sites are not available, they may be created in the appropriate positions by site-directed mutagenesis and/or DNA amplification methods known in the art (see, for example, Shankarappa et al., 1992, PCR Method Appl. 1:277–278). The DNA fragment that encodes a fragment of the HSP or α2M receptor gene is then isolated, and ligated into an appropriate expression vector, care being taken to ensure that the proper translation reading frame is maintained. Alternatives to isolating the genomic DNA include, but are not limited to, chemically synthesizing the gene sequence itself from a known sequence or making cDNA to the mRNA which encodes the HSP and/or α2M receptor.

Any technique for mutagenesis known in the art can be used to modify individual nucleotides in a DNA sequence, for purpose of making amino acid substitution(s) in the expressed peptide sequence, or for creating/deleting restriction sites to facilitate further manipulations. Such techniques include but are not limited to, chemical mutagenesis, in vitro site-directed mutagenesis (Hutchinson, C., et al., 1978, J. Biol. Chem 253:6551), oligonucleotide-directed mutagenesis (Smith, 1985, Ann. Rev. Genet. 19:423–463; Hill et al., 1987, Methods Enzymol. 155:558–568), PCR-based overlap extension (Ho et al., 1989, Gene 77:51–59), PCR-based megaprimer mutagenesis (Sarkar et al., 1990, Biotechniques, 8:404–407), etc. Modifications can be confirmed by double stranded dideoxy DNA sequencing.

An alternative to producing HSP and/or α2M receptor fragments by recombinant techniques is peptide synthesis. For example, a peptide corresponding to a portion of an HSP and/or α2M receptor comprising the substrate-binding domain, or which binds peptides in vitro, can be synthesized by use of a peptide synthesizer. Conventional peptide synthesis may be used or other synthetic protocols well known in the art.

In addition, analogs and derivatives of HSP and/or α2M receptor can be chemically synthesized. Furthermore, if desired, nonclassical amino acids or chemical amino acid analogs can be introduced as a substitution or addition into the HSP and/or α2M receptor sequence. Non-classical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Ca-methyl amino acids, Na-methyl amino acids, and amino acid analogs in general.

HSP and/or α2M receptor peptides, or a mutant or derivative thereof, may be synthesized by solid-phase peptide synthesis using procedures similar to those described by Merrifield, 1963, J. Am. Chem. Soc., 85:2149. During synthesis, N-α-protected amino acids having protected side chains are added stepwise to a growing polypeptide chain linked by its C-terminal and to an insoluble polymeric support i.e., polystyrene beads. The peptides are synthesized by linking an amino group of an N-α-deprotected amino acid to an α-carboxyl group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc which is acid labile and Fmoc which is base labile. Details of appropriate chemistries, resins, protecting groups, protected amino acids and reagents are well known in the art and so are not discussed in detail herein (See, Atherton, et al., 1989, Solid Phase Peptide Synthesis: A Practical Approach, IRL Press, and Bodanszky, 1993, Peptide Chemistry, A Practical Textbook, 2nd Ed., Springer-Verlag).

Purification of the resulting fragment is accomplished using conventional procedures, such as preparative HPLC using gel permeation, partition and/or ion exchange chromatography. The choice of appropriate matrices and buffers are well known in the art and so are not described in detail herein.

In an alternative embodiment, fragments of an HSP or the α2M receptor may be obtained by chemical or enzymatic cleavage of native or recombinant HSP and/or α2M receptor molecules. Specific chemical cleavage can be performed by cyanogen bromide, $NaBH_4$, acetylation, formylation, oxidation, reduction, metabolic synthesis in the presence of tunicamycin, etc. Endoproteases that cleave at specific sites can also be used. Such proteases are known in the art, including, but not limited to, trypsin, α-chymotrypsin, V8 protease, papain, and proteinase K (see Ausubel et al., (eds.), in “Current Protocols in Molecular Biology”, Greene Publishing Associates and Wiley Interscience, New York, 17.4.6–17.4.8). The HSP and/or α2M receptor amino acid sequence of interest can be examined for the recognition sites of these proteases. An enzyme is chosen which can release a peptide-binding domain or peptide-binding fragment. The HSP and/or α2M receptor molecule is then incubated with the protease, under conditions that allow digestion by the protease and release of the specifically designated peptide-binding fragments. Alternatively, such protease digestions can be carried out blindly, i.e., not knowing which digestion product will contain the peptide-binding domain, using specific or general specificity proteases, such as proteinase K or pronase.

Once a fragment is prepared, the digestion products may be purified as described above, and subsequently tested for the ability to bind peptide or for immunogenicity. Methods for determining the immunogenicity of HSP complexes by cytotoxicity tests are described in Section 5.2.2.

5.4 Drug Design

Upon identification of a compound that modulates the interaction of the HSP with the α2M receptor, such a compound can be further investigated to test for an ability to alter the immune response. In particular, for example, the compounds identified via the present methods can be further tested in vivo in accepted animal models of HSP-α2M receptor-mediated processes and HSP-α2M receptor related disorders, such as, e.g., immune disorders, proliferative disorders, and infectious diseases.

Computer modeling and searching technologies permit identification of compounds, or the improvement of already identified compounds, which can modulate the interaction of an HSP with the α2M receptor. Having identified such a compound or composition, the active sites or regions are identified. Such active sites might typically be ligand binding sites. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential the α2M receptor-modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites of either the α2M receptor or the HSP, and related ligands and their analogs, will be apparent to those of skill in the art.

Examples of molecular modeling systems are the CHARMm and QUANTA programs (Polygen Corporation, Waltham, Mass.). CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen et al.) 1988, Acta Pharmaceutical Fennica 97:159–166); Ripka (1988 New Scientist 54–57); McKinaly and Rossmann (1989, Annu. Rev. Pharmacol. Toxiciol. 29:111–122); Perry and Davies, OSAR: Quantitative Structure-Activity Relationships in Drug Design pp. 189–193 Alan R. Liss, Inc. 1989; Lewis and Dean (1989, Proc. R. Soc. Lond. 236: 125–140 and 141–162); and, with respect to a model receptor for nucleic acid components, Askew et al. (1989, J. Am. Chem. Soc. 111:1082–1090). Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

5.5 Diagnostic Uses

The α2M receptor is a cell surface protein present on many tissues and cell types (Herz et al., 1988, EMBO J. 7:4119–27; Moestrup et al., 1992, Cell Tissue Res. 269: 375–82), that appears to be involved in the specific uptake and re-presentation of HSPs and HSP-peptide complexes. The α2M receptor was initially identified as a heat shock protein receptor due to its interaction with gp96, which is exclusively intracellular and is released as a result of necrotic but not apoptotic cell death. Thus, gp96 uptake by the α2M receptor may act as a sensor of necrotic cell death.

As such, HSP-α2M receptor complexes may be used to detect and diagnose proliferative disorders, such as cancer, autoimmune disorders and infectious disease. Therefore, α2M receptor proteins, analogues, derivatives, and subsequences thereof, α2M receptor nucleic acids (and sequences complementary thereto), and anti-α2M receptor antibodies, have uses in detecting and diagnosing such disorders.

The α2M receptor and α2M receptor nucleic acids can be used in assays to detect, prognose, or diagnose immune system disorders that may result in tumorigenesis, carcinomas, adenomas etc, and viral disease.

The molecules of the present invention can be used in assays, such as immunoassays, to detect, prognose, diagnose, or monitor various conditions, diseases, and disorders affecting α2M receptor expression, or monitor the treatment thereof. In particular, such an immunoassay is carried out by a method comprising contacting a sample derived from a patient with an HSP-α2M receptor specific antibody under conditions such that immunospecific binding can occur, and detecting or measuring the amount of any immunospecific binding by the antibody. In a specific aspect, such binding of antibody, in tissue sections, can be used to detect aberrant α2M receptor localization or aberrant (e.g., low or absent) levels of α2M receptor. In a specific embodiment, antibody to the α2M receptor can be used to assay a patient tissue or serum sample for the presence of the α2M receptor where an aberrant level of α2M receptor is an indication of a diseased condition. By "aberrant levels," is meant increased or decreased levels relative to that present, or a standard level representing that present, in an analogous sample from a portion of the body or from a subject not having the disorder.

The immunoassays which can be used include but are not limited to competitive and non-competitive assay systems using techniques such as western blots, immunohisto-chemistry radioimmunoassays, ELISA, "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

α2M receptor genes and related nucleic acid sequences and subsequences, including complementary sequences, can also be used in hybridization assays. α2M receptor nucleic acid sequences, or subsequences thereof, comprising about at least 8 nucleotides, can be used as hybridization probes. Hybridization assays can be used to detect, prognose, diagnose, or monitor conditions, disorders, or disease states associated with aberrant changes in α2M receptor expression and/or activity as described supra. In particular, such a hybridization assay is carried out by a method comprising contacting a sample containing nucleic acid with a nucleic acid probe capable of hybridizing to α2M receptor DNA or RNA, under conditions such that hybridization can occur, and detecting or measuring any resulting hybridization.

In specific embodiments, diseases and disorders involving decreased immune responsiveness during an infection or malignant disorder can be diagnosed, or their suspected presence can be screened for, or a predisposition to develop such disorders can be detected, by detecting decreased levels of α2M receptor protein, α2M receptor RNA, or the α2M receptor functional activity (e.g., binding to HSP, antibody-binding activity etc.), or by detecting mutations in α2M receptor RNA, DNA or α2M receptor protein (e.g., translocations in the α2M receptor nucleic acids, truncations in the α2M receptor gene or protein, changes in nucleotide or amino acid sequence relative to wild-type α2M receptor) that cause decreased expression or activity of α2M receptor. Such diseases and disorders include but are not limited to those described in Sections 5.7, 5.8, and 5.9. By way of example, levels of the α2M receptor protein can be detected by immunoassay, levels of α2M receptor RNA can be detected by hybridization assays (e.g., Northern blots, in situ-hybridization), α2M receptor activity can be assayed by measuring binding activities in vivo or in vitro. Translocations, deletions, and point mutations in α2M receptor nucleic acids can be detected by Southern blotting, FISH, RFLP analysis, SSCP, PCR using primers, preferably primers that generate a fragment spanning at least most of the α2M receptor gene, sequencing of α2M receptor genomic DNA or cDNA obtained from the patient, etc.

In a preferred embodiment, levels of α2M receptor mRNA or protein in a patient sample are detected or measured relative to the levels present in an analogous sample from a subject not having the malignancy or hyperproliferative disorder. Decreased levels indicate that the subject may develop, or have a predisposition to developing, viral infection, malignancy, or hyperproliferative disorder.

In another specific embodiment, diseases and disorders involving a deficient immune responsiveness resulting in cell proliferation or in which cell proliferation is desirable for treatment, are diagnosed, or their suspected presence can be screened for, or a predisposition to develop such disorders can be detected, by detecting increased levels of the α2M receptor protein, α2M receptor RNA, or the α2M receptor functional activity (e.g., HSP binding or α2M receptor antibody, etc.), or by detecting mutations in α2M receptor RNA, DNA or protein (e.g., translocations in α2M receptor nucleic acids, truncations in the gene or protein, changes in nucleotide or amino acid sequence relative to wild-type α2M receptor) that cause increased expression or activity of the α2M receptor. Such diseases and disorders include, but are not limited to, those described in Sections 5.7, 5.8, and 5.9. By way of example, levels of the α2M receptor protein, levels of α2M receptor RNA, α2M receptor binding activity, and the presence of translocations or point mutations can be determined as described above.

In a specific embodiment, levels of α2M receptor mRNA or protein in a patient sample are detected or measured, relative to the levels present in an analogous sample from a subject not having the disorder, in which increased levels indicate that the subject has, or has a predisposition to, an autoimmune disorder.

Kits for diagnostic use are also provided, that comprise in one or more containers an anti-α2M receptor antibody, and, optionally, a labeled binding partner to the antibody. Alternatively, the anti-α2M receptor antibody can be labeled (with a detectable marker, e.g., a chemiluminescent, enzymatic, fluorescent, or radioactive moiety). A kit is also provided that comprises in one or more containers a nucleic acid probe capable of hybridizing to α2M receptor RNA. In a specific embodiment, a kit can comprise in one or more containers a pair of primers (e.g., each in the size range of 6–30 nucleotides) that are capable of priming amplification [e.g., by polymerase chain reaction (see e.g., Innis et al., 1990, PCR Protocols, Academic Press, Inc., San Diego, Calif.), ligase chain reaction (see EP 320,308) use of Qβ replicase, cyclic probe reaction, or other methods known in the art] under appropriate reaction conditions of at least a portion of an α2M receptor nucleic acid. A kit can optionally further comprise in a container a predetermined amount of a purified α2M receptor protein or nucleic acid, e.g., for use as a standard or control.

5.6 Therapeutic Uses

The invention further encompasses methods for modulating the immune response. The α2M receptor recognizes and transports HSP-antigenic peptide complexes for the purpose of presenting such antigenic molecules to cells of the immune system and eliciting an immune response. Thus, the compositions and methods of the invention may be used for therapeutic treatment of HSP-α2M receptor-related disorders and conditions, such as autoimmune diseases, cancer and infectious diseases. In particular, as described in detail hereinbelow, recombinant cells comprising HSP-α2M receptor complexes, antibodies and other compounds that modulate the interaction between HSPs and the α2M receptor, as well as other compounds that modulate HSP-α2M receptor-mediated processes may be used to elicit, or block, an immune response to treat such HSP-α2M receptor-related disorders and conditions.

5.6.1 Therapeutic Use of Identified Agonists and Antagonists

Compounds, such as those identified by screening methods provided herein, that modulate the interaction between HSPs and the α2M receptor can be useful as therapeutics. Such compounds, include, but are not limited to, agonists, antagonists, such as antibodies, antisense RNAs and ribozymes Compounds which interfere with HSP-α2M receptor 1 interaction can be used to block an immune response, and can be used to treat autoimmune responses and conditions. Other antibodies, agonists, antagonists, antisense RNAs and ribozymes may upregulate HSP-α2M receptor interaction, activity, or expression, and would enhance the uptake of HSP-antigen complexes, and therefore be useful in stimulating the host's immune system prior to, or concurrent with, the administration of a vaccine. Described below are methods and compositions for the use of such compounds in the treatment of HSP-α2M receptor-related disorders, such as immune disorders, proliferative disorders, and infectious diseases.

In one embodiment an antagonist of HSP-α2M receptor interaction is used to block the immune response. Such antagonists include compounds that interfere with binding of an HSP to the receptor by competing for binding to the α2M receptor, the HSP, or the HSP-α2M receptor complex.

In one embodiment, the antagonist is an antibody specific for the α2M receptor, or a fragment thereof which contains the HSP ligand binding site. In another embodiment the antagonist is an antibody specific for an HSP, which interferes with binding of the HSP to the receptor.

In another embodiment, the antagonist is an peptide which comprises at least contiguous 10 amino acids of an HSP sequence. Such a peptide can bind to the ligand binding site of the α2M receptor a block the interaction of an HSP or HSP complex. In another embodiment, the antagonist is a peptide which comprises at least contiguous 10 amino acids of α2M sequence, which, like an HSP, can bind to the α2M receptor and interfere with the binding and uptake of HSP-antigen complexes. In yet another embodiment, the antagonist is a peptide which comprises at least contiguous 10 amino acids of α2M receptor sequence, in particular the ECD of the α2M receptor (or a portion thereof), which can bind to and "neutralize" natural ligands, such as HSPs, α2M, LDL, etc.

Such peptides may be produced synthetically or by using standard molecular biology techniques. Amino acid sequences and nucleotide sequences of naturally occurring α2M and HSPs are generally available in sequence databases, such as GenBank. Computer programs, such as Entrez, can be used to browse the database, and retrieve any amino acid sequence and genetic sequence data of interest by accession number. Methods for recombinant and synthetic production of such peptides are described in Sections 5.1.1 and 5.1.2.

Additionally, compounds, such as those identified via techniques such as those described hereinabove, in Section 5.2, that are capable of modulating α2M receptor gene product activity can be administered using standard techniques that are well known to those of skill in the art.

5.6.1.1 Competitive Antagonists of HSP-α2MR

In one embodiment an antagonist of HSP-α2M receptor interaction is used to block the immune response to an HSP-antigen complex, e.g., to treat an auto-immune disorder. Such antagonists include molecules that interfere with binding by binding to the α2M receptor (α2MR), thereby interfering with binding of an HSP to the receptor. An example of this type of competitive inhibitor is an antibody to α2MR, or a fragment of α2MR which contains an HSP ligand binding site. Another example of a competitive antagonist is α2M, or a receptor-binding fragment thereof, which itself binds to α2M receptor, thereby blocking the binding and uptake of HSP-antigen complexes by the cell.

An HSP-α2M competitive inhibitor can be any type of molecule, including but not limited to a protein, nucleic acid or drug. In a preferred embodiment, the HSP-α2M competitive inhibitor is an α2MR-binding or an HSP-binding peptide. Examples of such peptides are provided below.

5.6.1.1.1 α2MR-Binding Peptides

αMacroglobulin peptides

In one embodiment of the present invention, an HSP-α2MR competitive antagonist is an a macroglobulin, preferably α2M, or α2MR-binding portion thereof.

Functional expression of α2M or α2MR-binding portions thereof (including recombinant expression as a FX fusion protein, processing, purification and refolding) is preferably carried out as described by Holtet et al., 1994, FEBS Lett. 344:242–246.

In a specific mode of the embodiment, an α2MR-binding portion of α2M consists of or comprises a fragment of the α2M RBD consisting of at least 10 (continuous) amino acids. In other modes of the embodiment, the fragment consists of at least 20, 30, 40, 50, 75 or 100 amino acids of the RBD. In specific modes of the embodiment, such fragments are not larger than 27, 138 or 153 amino acids. Most preferred peptides comprise one or both of amino acids $Lysl_{370}$ and $Lysl_{374}$. Such peptides include those consisting of amino acids 1299–1451 (vRBD in FIG. 7B) (SEQ ID NO:8), 1314–1451 (SEQ ID NO:9) (RBD in FIG. 7B) or 1366–1392 (SEQ ID NO:10) of the mature α2M protein. Other preferred peptides include but are not limited to those consisting of amino acids 1300–1425 (SEQ ID NO:11), 1300–1400 (SEQ ID NO:12), 1300–1380 (SEQ ID NO:13), 1325–1425 (SEQ ID NO:14), 1325–1400 (SEQ ID NO:15), 1325–1380 (SEQ ID NO:16), 1350–1425 (SEQ ID NO:17), 1350–1400 (SEQ ID NO:18), or 1350–1380 (SEQ ID NO:19) of the mature human α2M protein.

Derivatives or analogs of α2M or α2MR-binding portions of α2M are also contemplated as competitive antagonists of HSP-α2MR complexes. Such derivative or analogs include but are not limited to those molecules comprising regions that are substantially homologous to α2M, the α2M RBD or fragments thereof (e.g. in various embodiments, at least 60% or 70% or 80% or 90% or 95% identity over an amino acid sequence of identical size or when compared to an aligned sequence in which the alignment is done by a computer homology program known in the art) or whose encoding nucleic acid is capable of hybridizing to a coding α2M RBD sequence, under stringent, moderately stringent, or nonstringent conditions. In certain specific embodiments, an α2M derivative is a chimeric or fusion protein comprising an α2M protein or α2MR-binding portion thereof (preferably consisting of at least 10 amino acids of the α2M RBD comprising $Lys_{1370}$ and $Lys_{1374}$) joined at its amino- or carboxy-terminus via a peptide bond to an amino acid sequence of a different protein.

In particular, α2M derivatives can be made by altering α2M coding sequences by substitutions, additions or deletions that provide for functionally equivalent molecules. Due to the degeneracy of nucleotide coding sequences, other DNA sequences which encode substantially the same amino acid sequence as a α2M gene may be used in the practice of the present invention. These include but are not limited to nucleotide sequences comprising all or α2MR-binding portions of α2M genes which are altered by the substitution of different codons that encode a functionally equivalent amino acid residue within the sequence, thus producing a silent change. Likewise, the α2M derivatives of the invention include, but are not limited to, those containing, as a primary amino acid sequence, all or an α2MR-binding portion of the amino acid sequence of an α2M protein, including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The α2M derivatives and analogs of the invention can be produced by various methods known in the art. The manipulations which result in their production can occur at the gene or protein level. For example, the cloned α2M gene sequence can be modified by any of numerous strategies known in the art (Maniatis, T., 1990, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of α2M, care should be taken to ensure that the modified gene remains within the same translational reading frame as α2M, uninterrupted by translational stop signals, in the gene region where the desired α2M activity is encoded.

Manipulations of the α2M sequence may also be made at the protein level. Included within the scope of the invention are α2M protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

In addition, analogs and derivatives of α2M can be chemically synthesized. For example, an α2MR-binding portion of α2M can be synthesized by use of a peptide synthesizer. Furthermore, if desired, nonclassical amino acids or chemical amino acid analogs can be introduced as a substitution or addition into the α2M sequence. Non-classical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In other specific modes of the embodiment, an HSP-α2MR competitive antagonist is another a macroglobulin or α2MR-binding portion thereof, for example an a macroglobulin RBD domain selected from Nielsen et al., supra, FIG. 3, Group A.

RAP

In one embodiment of the present invention, an HSP-α2MR competitive antagonist is α2MR-associated protein (RAP) (Genbank accession no. A39875) or an α2MR-binding portion thereof. In a specific mode of the embodiment, an α2MR-binding portion of RAP consists of or comprises a fragment of the RAP RBD consisting of at least 10 (continuous) amino acids. In other modes of the embodiment, the fragment consists of at least 20, 30, 40, 50, 75 or 100 amino acids of the RBD. In specific modes of the embodiment, such fragments are not larger than 28, 50 or 100 amino acids. In other specific modes of the embodiment, an α2MR-binding portion of RAP comprises an α2MR-binding portion of domain 1 or 3, e.g. as depicted in Nielsen et al., supra, FIG. 3, Group D or E. Expression of recombinant RAP or an α2MR-binding portion thereof, e.g. domain 1 or 3, is preferably achieved as described by Andersen et al., supra).

5.6.1.1.2 HSP-Binding Peptides

α2MR peptides

In one embodiment of the present invention, an HSP-α2MR competitive antagonist is α2MR peptide, preferably a soluble peptide, that can bind to HSPs and therefore competitively inhibit HSP binding to the native receptor.

Functional expression of HSP-binding portions of α2MR is preferably carried out as described for the CR8 domain by Huang et al., 1999, J. Biol. Chem 274:14130–14136. Briefly, to maintain proper folding, the protein is expressed as a GST fusion, expressed recombinantly, the GST portion cleaved, uncleaved protein removed on GSH-Sepharose, and cleaved protein refolded. Since the complement repeats bind to calcium, proper folding is assayed by measuring the binding of the refolded protein to calcium.

In a specific mode of the embodiment, an HSP-binding portion of α2MR consists of or comprises at least one complement repeat, most preferably selected from CR3—CR10. In another specific mode of the embodiment, an HSP-binding portion of α2MR comprises a cluster of complement repeats, most preferably C1-II. In other modes of the embodiment, the HSP-binding portion consists of at least 10, more preferably at least 20, yet more preferably at least 30, yet more preferably at least 40, and most preferably at least 80 (continuous) amino acids. In specific modes of the embodiment, such fragments are not larger than 40–45 amino acids. In other specific modes of the embodiment, such fragments are not larger than 80–90 amino acids. Exemplary preferred peptides include but are not limited to those consisting of amino acids 25–68 (SEQ ID NO:20), 25–110 (SEQ ID NO:21), 68–110 (SEQ ID NO:22), 853–894 (SEQ ID NO:23), 853–934 (SEQ ID NO:24), 853–974 (SEQ ID NO:25), 853–1013 (SEQ ID NO:26), 853–1060 (SEQ ID NO:27), 853–1102 (SEQ ID NO:28), 853–1183 (SEQ ID NO:29), 895–934 (SEQ ID NO:30), 895–974 (SEQ ID NO:31), 895–1013 (SEQ ID NO:32), 895–1060 (SEQ ID NO:33), 895–1102 (SEQ ID NO:34), 895–1183 (SEQ ID NO:35), 935–974 (SEQ ID NO:36), 935–1013 (SEQ ID NO:37), 935–1060 (SEQ ID NO:38), 935–1102 (SEQ ID NO:39), 935–1183 (SEQ ID NO:40), 975–1013 (SEQ ID NO:41), 975–1060 (SEQ ID NO:42), 975–1143 (SEQ ID NO:43), 975–1183 (SEQ ID NO:44), 1014–1060 (SEQ ID NO:45), 1014–1102 (SEQ ID NO:46), 1014–1183 (SEQ ID NO:47), 1061–1102 (SEQ ID NO:48), 1061–1143 (SEQ ID NO:49), 1061–1183 (SEQ ID NO:50), 1103–1143 (SEQ ID NO:51), 1103–1183 (SEQ ID NO:52), or 1144–1183 (SEQ ID NO:53) of human α2MR.

Derivatives or analogs of HSP-binding portions α2MR also contemplated as competitive antagonists of HSP-α2MR complexes. Such derivative or analogs include but are not limited to those molecules comprising regions that are substantially homologous to the extracellular domain of α2MR or fragments thereof (e.g., in various embodiments, at least 60% or 70% or 80% or 90% or 95% identity over an amino acid sequence of identical size or when compared to an aligned sequence in which the alignment is done by a computer homology program known in the art) or whose encoding nucleic acid is capable of hybridizing to a sequence encoding an α2MR HSP-binding sequence, under stringent, moderately stringent, or nonstringent conditions. In certain specific embodiments, an α2MR derivative is a chimeric or fusion protein comprising an HSP-binding portion of α2MR, preferably consisting of at least one complement repeat of C1-II) joined at its amino- or carboxy-terminus via a peptide bond to an amino acid sequence of a different protein. Such a chimeric protein can be produced recombinantly as described above, by omitting the cleavage repurification steps.

Other HSP-binding α2MR derivatives can be made by altering α2MR coding sequences by substitutions, additions or deletions that provide for functionally equivalent molecules. Due to the degeneracy of nucleotide coding sequences, other DNA sequences which encode substantially the same amino acid sequence as an HSP-binding α2MR gene or gene fragment may be used in the practice of the present invention. Selection of suitable alterations and production of HSP-binding α2MR derivatives can be made applying the same principles described above for α2M derivatives and using the general methods described in Sections 5.1.1 and 5.1.2.

HSP Peptides

In another mode of the embodiment, the antagonist is an peptide which comprises at least contiguous 10 amino acids of an HSP sequence. Such a peptide can bind to the ligand binding site of the α2M receptor a block the interaction of an HSP or HSP complex.

Such peptides may be produced synthetically or by using standard molecular biology techniques. Amino acid sequences and nucleotide sequences of naturally occurring HSPs are generally available in sequence databases, such as GenBank. Computer programs, such as Entrez, can be used to browse the database, and retrieve any amino acid sequence and genetic sequence data of interest by accession number. Methods for recombinant and synthetic production of such peptides are described in Sections 5.1.1 and 5.1.2.

Additionally, compounds, such as those identified via techniques such as those described hereinabove, in Section 5.2, that are capable of modulating α2M receptor gene product activity can be administered using standard techniques that are well known to those of skill in the art.

5.6.2 Therapeutic Use of the α2M Receptor Against Cancer and Infectious Diseases In another embodiment, symptoms of certain α2M receptor gene disorders, such as autoimmune disorders, or proliferative or differentiative disorders causing tumorigenesis or cancer, may be ameliorated by modulating the level of α2M receptor gene expression and/or α2M receptor gene product activity. In one embodiment, for example, a decrease in α2M receptor gene expression may be useful to decrease α2M receptor activity, and ameliorate the symptoms of an autoimmune disorder. In this case, the level of α2M receptor gene expression may be decreased by using α2M receptor gene sequences in conjunction with well-known antisense, gene "knock-out," ribozyme and/or triple helix methods. In another embodiment, an increase in α2M receptor gene expression may be desired to compensate for a mutant or impaired gene in an HSP-α2M receptor-mediated pathway, and to ameliorate the symptoms of an HSP-α2M receptor-related disorder.

Among the compounds that may exhibit the ability to modulate the activity, expression or synthesis of the α2M receptor gene, including the ability to ameliorate the symptoms of an HSP-α2M receptor related disorder are antisense, ribozyme, and triple helix molecules. Such molecules may be designed to reduce or inhibit either unimpaired, or if appropriate, mutant target gene activity. Techniques for the production and use of such molecules are well known to those of skill in the art.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarity, although preferred, is not required.

A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the 2M receptor gene could be used in an antisense approach to inhibit translation of endogenous α2M receptor mRNA. Antisense nucleic acids should be at least six nucleotides in length, and are preferably oligonucleotides ranging from 6 to about 50 nucleotides in length.

In specific aspects the oligonucleotide is at least 10 nucleotides, at least 17 nucleotides, at least 25 nucleotides or at least 50 nucleotides.

In an embodiment of the present invention, oligonucleotides complementary to the nucleic acids encoding the HSP receptor ligand binding domain are used.

Regardless of the choice of target sequence, it is preferred that in vitro studies are first performed to quantitate the ability of the antisense oligonucleotide to inhibit gene expression.

It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86, 6553–6556; Lemaitre et al., 1987, Proc. Natl. Acad. Sci. 84, 648–652; PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, BioTechniques 6, 958–976) or intercalating agents (see, e.g., Zon, 1988, Pharm. Res. 5, 539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 31-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate (S-ODNs), a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15, 6625–6641). The oligonucleotide is a 2'-0-methylribonucleotide (Inoue et al., 1987, Nucl. Acids Res. 15, 6131–6148), or a chimeric RNA-DNA analogue (Inoue et al., 1987, FEBS Lett. 215, 327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16, 3209), methylphosphonate oligonucleotides can be prepared by use of controlled pore glass polymer supports (Sarin et al., 1988, Proc. Natl. Acad. Sci. U.S.A. 85, 7448–7451), etc.

While antisense nucleotides complementary to the target gene coding region sequence could be used, those complementary to the transcribed, untranslated region are most preferred.

In one embodiment of the present invention, gene expression downregulation is achieved because specific target mRNAs are digested by RNAse H after they have hybridized with the antisense phosphorothioate oligonucleotides (S-ODNs). Since no rules exist to predict which antisense S-ODNs will be more successful, the best strategy is completely empirical and consists of trying several antisense S-ODNs. Antisense phosphorothioate oligonucleotides (S-ODNs) will be designed to target specific regions of mRNAs of interest.

Control S-ODNs consisting of scrambled sequences of the antisense S-ODNs will also be designed to assure identical nucleotide content and minimize differences potentially attributable to nucleic acid content. All S-ODNs can be synthesized by Oligos Etc. (Wilsonville, Oreg.). In order to test the effectiveness of the antisense molecules when applied to cells in culture, such as assays for research purposes or ex vivo gene therapy protocols, cells will be grown to 60–80% confluence on 100 mm tissue culture plates, rinsed with PBS and overlaid with lipofection mix consisting of 8 ml Opti-MEM, 52.8 μl Lipofectin, and a final concentration of 200 nM S-ODNs. Lipofections will be carried out using Lipofectin Reagent and Opti-MEM (Gibco BRL). Cells will be incubated in the presence of the lipofection mix for 5 hours. Following incubation the medium will be replaced with complete DMEM. Cells will be harvested at different time points post-lipofection and protein levels will be analyzed by Western blot.

Antisense molecules should be targeted to cells that express the target gene, either directly to the subject in vivo or to cells in culture, such as in ex vivo gene therapy protocols. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290, 304–310), the promoter contained in the 3' long terminal repeat of Rous sarcoma virus (Yamamoto et al., 1980, Cell 22, 787–797), the herpes thymidine kinase promoter (Wagner et al., 1981, Proc. Natl. Acad. Sci. U.S.A. 78, 1441–1445), the regulatory sequences of the metallothionein gene (Brinster et al., 1982, Nature 296, 39–42), etc. Any type of plasmid, cosmid, YAC or viral vector can be used to prepare the recombinant DNA construct which can be introduced directly into the tissue site. Alternatively, viral vectors can be used that selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product. (See, e.g., PCT International Publication WO90/11364, published Oct. 4, 1990; Sarver et al., 1990, Science 247, 1222–1225). In an embodiment of the present invention, oligonucleotides which hybridize to the HSP receptor gene are designed to be complementary to the nucleic acids encoding the HSP receptor ligand binding domain.

Ribozymes are enzymatic RNA molecules capable of catalyzing the specific cleavage of RNA. (For a review, see Rossi, 1994, Current Biology 4, 469–471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers, 1995, Molecular Biology and Biotechnology: A Comprehensive Desk Reference, VCH Publishers, New York, (see especially FIG. 4, p. 833) and in Haseloff & Gerlach, 1988, Nature, 334, 585–591, which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in Tetrahymena thermophila (known as the IVS, or L-19 IVS RNA) and that has been extensively described by Thomas Cech and collaborators (Zaug et al., 1984, Science, 224, 574–578; Zaug and Cech, 1986, Science, 231, 470–475; Zaug et al., 1986, Nature, 324, 429–433; published International patent application No. WO 88/04300 by University Patents Inc.; Been & Cech, 1986, Cell, 47, 207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes unlike antisense molecules, are catalytic, a lower intracellular concentration is required for efficiency.

Endogenous target gene expression can also be reduced by inactivating or "knocking out" the target gene or its promoter using targeted homologous recombination (e.g., see Smithies et al., 1985, Nature 317, 230–234; Thomas & Capecchi, 1987, Cell 51, 503–512; Thompson et al., 1989, Cell 5, 313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited modifications to ES (embryonic stem) cells can be used to generate animal offspring with an inactive target gene (e.g., see Thomas & Capecchi, 1987 and Thompson, 1989, supra). However this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, 1991, Anticancer Drug Des., 6(6), 569–584; Helene et al., 1992, Ann. N.Y. Acad. Sci., 660, 27–36; and Maher, 1992, Bioassays 14(12), 807–815).

Nucleic acid molecules to be used in triple helix formation for the inhibition of transcription should be single stranded and composed of deoxyribonucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC+triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods such as those described, below, in Section 5.6.3 that do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Anti-sense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

5.6.3 Gene Replacement Therapy

With respect to an increase in the level of normal α2M receptor gene expression and/or α2M receptor gene product activity, α2M receptor gene nucleic acid sequences can, for example, be utilized for the treatment of immune disorders resulting in proliferative disorders such as cancer. Such treatment can be administered, for example, in the form of gene replacement therapy. Specifically, one or more copies of a normal α2M receptor gene or a portion of the α2M receptor gene that directs the production of an α2M receptor gene product exhibiting normal α2M receptor gene function, may be inserted into the appropriate cells within a patient, using vectors that include, but are not limited to adenovirus, adeno-associated virus, and retrovirus vectors, in addition to other particles that introduce DNA into cells, such as liposomes.

Gene replacement therapy techniques should be capable of delivering α2M receptor gene sequences to cell types that express the HSP receptor within patients. Thus, in one embodiment, techniques that are well known to those of skill in the art (see, e.g., PCT Publication No. WO89/10134, published Apr. 25, 1988) can be used to enable α2M receptor gene sequences to be delivered to developing cells of the myeloid lineage, for example, to the bone marrow. In another specific embodiment, gene replacement can be accomplished using macrophages in vitro, and delivered to a patient using the techniques of adoptive immunotherapy.

In another embodiment, techniques for delivery involve direct administration of such α2M receptor gene sequences to the site of the cells in which the α2M receptor gene sequences are to be expressed, e.g., directly at the site of the tumor.

Additional methods that may be utilized to increase the overall level of α2M receptor gene expression and/or α2M receptor gene product activity include the introduction of appropriate α2M receptor-expressing cells, preferably autologous cells, into a patient at positions and in numbers that are sufficient to ameliorate the symptoms of an α2M receptor disorder. Such cells may be either recombinant or non-recombinant.

Among the cells that can be administered to increase the overall level of α2M receptor gene expression in a patient are cells that normally express the α2M receptor gene.

Alternatively, cells, preferably autologous cells, can be engineered to express α2M receptor gene sequences, and may then be introduced into a patient in positions appropriate for the amelioration of the symptoms of an α2M receptor disorder or a proliferative or viral disease, e.g., cancer and tumorigenesis. Alternately, cells that express an unimpaired α2M receptor gene and that are from a MHC matched individual can be utilized, and may include, for example, brain cells. The expression of the α2M receptor gene sequences is controlled by the appropriate gene regulatory sequences to allow such expression in the necessary cell types. Such gene regulatory sequences are well known to the skilled artisan. Such cell-based gene therapy techniques are well known to those skilled in the art, see, e.g., Anderson, U.S. Pat. No. 5,399,349.

When the cells to be administered are non-autologous cells, they can be administered using well known techniques that prevent a host immune response against the introduced cells from developing. For example, the cells may be introduced in an encapsulated form which, while allowing for an exchange of components with the immediate extracellular environment, does not allow the introduced cells to be recognized by the host immune system.

5.6.4 Delivery of Soluble α2M Receptor Polypeptides

Genetically engineered cells that express soluble α2M receptor ECDs or fusion proteins, e.g., fusion Ig molecules can be administered in vivo where they may function as "bioreactors" that deliver a supply of the soluble molecules. Such soluble α2M receptor polypeptides and fusion proteins, when expressed at appropriate concentrations, should neutralize or "mop up" HSPs or other native ligand for the α2M receptor, and thus act as inhibitors of α2M receptor activity and may therefore be used to treat HSP-α2M receptor-related disorders and diseases, such as autoimmune disorders, proliferative disorders, and infectious diseases.

5.6.5 Delivery of Dominant Negative Mutants

In another embodiment of the invention, dominant negative mutants ("dominant negatives") may be used therapeutically to block the immune response to an HSP-antigen complex, e.g., to treat an auto-immune disorder. In general, such dominant-negatives are mutants which, when expressed, interact with ligand (i.e., HSP-antigenic molecule complex), but lack one or more functions, i.e. endocytotic functions and/or signaling functions, of normal α2MR. Such mutants interfere with the function of normal α2MR in the same cell or in a different cell, e.g. by titration of HSP-peptide complexes from the wild type receptor. Such a mutation, for example, can be one or more point mutation(s), a deletion, insertion, or other mutation in either the extracellular of the 515 kDa subunit, or the extracellular, transmembrane or intracellular domains of the 85 kDa subunit of the alpha (2) macroglobulin receptor (see Krieger and Herz, 1994, Annu. Rev. Biochem 63:601–637 for α2MR subunit configuration). However, in construction of dominant negative mutations in the either subunit, care should be taken to ensure that the cleavage domain (signaling cleavage between aas 3525 and 3526 of the precursor of α2MR) remains intact so that the 515 kDa subunit is processed and presented on the cell surface. Additionally, care should be taken to ensure that the domains by which the two subunits associate should also remain functional. For example, in a specific embodiment, the C-terminal intracellular domain of the 85 kDa subunit is truncated. In another embodiment, a point mutation on the N-terminal 515 kDa subunit blocks endocytosis but not ligand binding. In another embodiment, the N-terminal 515 kDa subunit is expressed as a fusion protein, wherein the C-terminus of said fusion protein is the transmembrane domain and optionally the intracellular domain, of another Type I single transmembrane receptor.

Expression of a such a dominant negative mutation in cell can block uptake of ligand by normal functional receptors in the same or neighboring cells by titrating out the amount of available ligand. Thus, a recombinant antigen presenting cell expressing such a dominant negative can be used to titrate out HSP-antigenic molecule complexes when administered to a patient in need of treatment for an autoimmune disorder.

5.7 Target Autoimmune Diseases

Autoimmune diseases that can be treated by the methods of the present invention include, but are not limited to, insulin dependent diabetes mellitus (i.e., IDDM, or autoimmune diabetes), multiple sclerosis, systemic lupus erythematosus, Sjogren's syndrome, scleroderma, polymyositis, chronic active hepatitis, mixed connective tissue disease, primary biliary cirrhosis, pernicious anemia, autoimmune thyroiditis, idiopathic Addison's disease, vitiligo, gluten-sensitive enteropathy, Graves' disease, myasthenia gravis, autoimmune neutropenia, idiopathic thrombocytopenia purpura, rheumatoid arthritis, cirrhosis, pemphigus vulgaris, autoimmune infertility, Goodpasture's disease, bullous pemphigoid, discoid lupus, ulcerative colitis, and dense deposit disease. The diseases set forth above, as referred to herein, include those exhibited by animal models for such diseases, such as, for example non-obese diabetic (NOD) mice for IDDM and experimental autoimmune encephalomyelitis (EAE) mice for multiple sclerosis.

The methods of the present invention can be used to treat such autoimmune diseases by reducing or eliminating the immune response to the patient's own (self) tissue, or, alternatively, by reducing or eliminating a pre-existing autoimmune response directed at tissues or organs transplanted to replace self tissues or organs damaged by the autoimmune response.

5.8 Target Infectious Diseases

The infectious diseases that can be treated or prevented using the methods and compositions of the present invention include those caused by intracellular pathogens such as viruses, bacteria, protozoans, and intracellular parasites. Viruses include, but are not limited to viral diseases such as those caused by hepatitis type B virus, parvoviruses, such as adeno-associated virus and cytomegalovirus, papovaviruses such as papilloma virus, polyoma viruses, and SV40, adenoviruses, herpes viruses such as herpes simplex type I (HSV-I), herpes simplex type II (HSV-II), and Epstein-Barr virus, poxviruses, such as variola (smallpox) and vaccinia virus, RNA viruses, including but not limited to human immunodeficiency virus type I (HIV-I), human immunodeficiency virus type II (HIV-II), human T-cell lymphotropic virus type I (HTLV-I), and human T-cell lymphotropic virus type II (HTLV-II); influenza virus, measles virus, rabies virus, Sendai virus, picomaviruses such as poliomyelitis virus, coxsackieviruses, rhinoviruses, reoviruses, togaviruses such as rubella virus (German measles) and Semliki forest virus, arboviruses, and hepatitis type A virus.

In another embodiment, bacterial infections can be treated or prevented such as, but not limited to disorders caused by pathogenic bacteria including, but not limited to, *Streptococcus pyogenes, Streptococcus pneumoniae, Neisseria gonorrhoea, Neisseria meningitidis, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromotis, Staphylococcus aureus, Vibrio cholerae, Escherichia coli, Pseudomonas aeruginosa, Campylobacter* (Vibrio)*fetus, Campylobacter jejuni, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhiimurium, Salmonella typhii, Treponema pallidum, Treponema pertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella abortus, Brucella suis, Brucella melitensis, Mycoplasma spp., Rickettsia prowazeki, Rickettsia tsutsugumushi, Chlamydia* spp., and *Helicobacter pylori.*

In another preferred embodiment, the methods can be used to treat or prevent infections caused by pathogenic protozoans such as, but not limited to, *Entomoeba histolytica, Trichomonas tenas, Trichomonas hominis, Trichomonas vaginalis, Trypanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasm odium falciparum*, and *Plasmodium malaria.*

5.9 Target Proliferative Cell Disorders

With respect to specific proliferative and oncogenic disease associated with HSP-α2M receptor activity, the diseases that can be treated or prevented by the methods of the present invention include, but are not limited to: human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

Diseases and disorders involving a deficiency in cell proliferation or in which cell proliferation is desired for treatment or prevention, and that can be treated or prevented by inhibiting the α2M receptor function, include but are not limited to degenerative disorders, growth deficiencies, hypoproliferative disorders, physical trauma, lesions, and wounds; for example, to promote wound healing, or to promote regeneration in degenerated, lesioned or injured tissues, etc.

5.10 Pharmaceutical Preparations and Methods of Administration

The compounds that are determined to affect α2M receptor gene expression or gene product activity can be administered to a patient at therapeutically effective doses to treat or ameliorate a cell proliferative disorder. A therapeutically effective dose refers to that amount of the compound sufficient to result in amelioration of symptoms of such a disorder.

5.10.1 Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

5.10.2 Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

6. EXAMPLE

Identification of α2M Receptor as an HSP Receptor

6.1 Introduction

The Example presented herein describes the successful identification of an interaction between gp96 and the α2M receptor present in macrophages and dendritic cells. The experiments presented herein form the basis for isolating α2M receptor polypeptides and for the screening, diagnostic, and therapeutic methods of the present invention.

The Applicant of the present invention noted that certain observations were inconsistent with a "direct transfer" model of HSP-chaperoned peptide antigen presentation. First, the immunogenicity of HSP preparations is dependent on the presence of functional phagocytic cells but not B cells or other nonprofessional antigen-presenting cells, (Udono and Srivastava, 1993, supra; Suto and Srivastava, 1995, supra), whereas free peptides can sensitize all cell types. Second, extremely small quantities of HSP-peptide complexes were effective in eliciting specific immunity, i.e., gp96-chaperoned peptides are several hundred times as effective as free peptides in sensitizing macrophages for CTL recognition, suggesting the possibility of a specific uptake mechanism. Third, gp96-chaperoned peptides elicited an MHC I response that was not limited by the size of peptide. Finally, the processing of gp96-peptide complexes in macrophage was found to be sensitive to Brefeldin A (BFA), which blocks transport through the Golgi apparatus, suggesting that processing occurred through an intercellular mechanism. These observations led to the hypothesis that HSP-chaperoned peptides may be processed internally and re-presented by MHC class I molecules on the cell surfaces of macrophages (Suto and Srivastava, 1995, supra). There is also the hypothesis that the mannose receptor is used in the uptake of gp96 but no mechanism has been proposed for the non-glycosylated HSPs, such as HSP70 (Ciupitu et al., 1998, J. Exp. Med., 187: 685–691). Others suggested that a novel intracellular trafficking pathway may be involved for the transport of peptides from the extracellular medium into the lumen of ER) Day et al., 1997, Proc. Natl. Acad. Sci. 94:8065–8069; Nicchitta, 1998, Curr. Opin. in Immunol. 10: 103–109). Further suggestions include the involvement of phagocytes which (a) possess an ill-defined pathway to shunt protein from the phagosome into thecytosol where it would enter the normal class I pathway; (b) digest ingested material in lysosomes and regurgitate peptides for loading on the surface to class I molecules (Bevan, 1995, J. Exp. Med. 192:639–41). The discovery of a receptor for heat shock protein as disclosed herein helps to resolve the paradox of how extracellular antigenic peptides complexed to HSPs can be presented by MHC class I molecules on antigen presenting cells.

6.2 Materials and Methods

Affinity chromatography. Proteins (1 mg) in 2 ml volume were incubated with 2 ml of equilibrated AminoLink beads in PBS with a reductant ($NaCNBH_3$) for 1 hour. Uncoupled protein was removed by extensive washing of the column and unreactive groups quenched. Immobilization yields were typically>92% of the starting amount of protein. Columns were stored at 4° C. until used. Such columns were made with gp96 (purified as described in Srivastava et al., 1986, Proc. Natl. Acad. Sci., U.S.A. 83:3407–3411) and albumin. For membrane purification, cells were lysed by dounce homogenization in hypotonic buffer containing PMSF. Unlyzed cells and nuclei were removed by centrifugation at 1000 g for 5 mm. The postnuclear supernatant was centrifuged at 100,000 g for 90 mins. The pellet contains total membranes and was fractionated by aqueous two-phase partition with a dextran/polyethylene glycol biphase. Briefly membranes were resuspended in PEG (33% wt/wt in 0.22 M sodium phosphate buffer, pH 6.5) and underlaid gently with dextran (20% wt/wt in 0.22M sodium phosphate buffer, pH 6.5). The two phases were mixed gently and centrifuged at 2000 g for 15 mins. The white material at the interphase was enriched for plasma membranes, whose proteins were extracted by 2 hr incubation in 20 mM Tris buffer (pH8, containing 0.08% octylglucoside) at 4° C.

Photo cross-linking of gp96 to putative receptor. The cross-linker (SASD, (Pierce) was labeled with 1125 using iodobeads (Pierce). Radiolabeled SASD was covalently attached to gp96 by incubation at room temperature for 1 hr. Free SASD and $I^{125}$ were removed by size exclusion column (KwikSep columns, Pierce). For cross-linking studies, $I^{125}$-SASD-gp96 (50 μg gp96) was incubated with purified $CD11b^+$ cells. Unbound protein was removed by washing. All procedures to this point were carried out in very dim light. Proteins were cross-linked with UV light. Cells were lysed with lysis buffer (0.5% NP4O, 10 mM Tris, 1 mMEDTA, 150 mM NaCl) and treated with 100 mM 2-mercaptoethanol to cleave the cross-linker. Cell lysates were analyzed by SDS-PAGE and autoradiography.

Re-presentation assays. Re-presentation assays were carried out as described (Suto and Srivastava, 1995, Science 269:1585–1588). Antigen presenting cells (RAW264.7 macrophage cell line) were plated at a 1:1 ratio with AH I-specific T cells in complete RPMI. Approximately 10,000 cells of each type were used. Gp96 (10 μg/ml) chaperoning the AH1-20 mer peptide (RVTYHSPSYVYHQFERRAK) (SEQ ID NO:59) was added to the cells and the entire culture was incubated for 20 hrs. Stimulation of T cells was measured by quantifying the amount of IFN-γ released into the supernatants by ELISA (Endogen).

Protein Microsequencing. Proteins identified by affinity chromatography were analyzed on SDS-PAGE and stained with coomasie blue or transferred onto PVDF membrane and stained with coomasie blue, all of it under keratin-free conditions. Protein bands were excised with a razor from the gel or membrane. Tryptic peptides from an 80 kDa faint coomassie band were extracted by 50% acetonitrile, 5% formic acid, dried, and loaded onto a 75 m 10 cm, reverse-phase C18, microcapillary column (3 μl vol) and tryptic peptides were separated by on-line microcapillary liquid chromatography-tendem mass spectrometry followed by database searching using the SEQUEST program as previously described. (Gatlin et al., 2000, Anal. Chem. 72:757–63; Link et al., 1999, Nat. Biotechnol. 17:676–82). The analysis was carried out in a data-dependent auto-MS/MS fashion using a Finnigan LCQ iontrap Mass Spectrometer.

6.3 Results

Identification of an 80 kDa protein as a potential gp96 receptor. Homogenous preparations of gp96 were coupled to FITC and the gp96-FITC was used to stain RAW264.7 cells, shown to be functionally capable of re-presenting gp96-chaperoned peptides. Gp96-FITC but not control albumin-FITC preparations stained the cell surface of RAW264.7 cells (FIG. 1A). Plasma membrane preparations of cell surface-biotinylated RAW264.7 cells were solubilized in 0.08% octyl-glucoside and the soluble extract was applied to a gp96-Sepharose column. The bound proteins were eluted with 3M sodium chloride. SDS-PAGE analysis of the eluate showed 2 major bands of ~75–80 kDa size (FIG. 1B, top left). Blotting of this gel with avidin-peroxidase showed that both bands were biotinylated, indicating their surface localization (FIG. 1B, bottom left). Affinity purification of membrane extracts of RAW264.7 cells over control serum albumin affinity columns did not result in isolation of any proteins, nor did probing of immunoblots of such gels with avidin peroxidase detect any albumin-binding surface proteins (FIG. 1B, top and bottom center lanes). As an additional control, chromatography of membrane extracts of P815 cells which do not bind gp96-FITC and which do not re-present gp96-chaperoned peptides, on gp96 affinity columns did not result in elution of any gp96-binding proteins (FIG. 1B, top and bottom right lanes).

In parallel experiments, gp96 molecules were coupled to the radio-iodinated linker sulfosuccinimidyl(4-azidosalicylamido)hexanoate (SASD) which contains a photo cross-linkable group. Gp96-SASD-$I^{125}$ was pulsed onto peritoneal macrophages, which have been shown previously to re-present gp96-chaperoned peptides (Suto and Srivastava, 1995, Science 269:1585–1588). Excess gp96-SASD was removed by multiple rounds of washing of the cells and photoactivation was carried out by exposure of cells to UV light for 10 mm. Cell lysates were reduced in order to transfer the $I^{125}$ group to the putative gp96 ligand and were analyzed by SDS—PAGE followed by autoradiography. The gp96 molecule was observed to cross-link to an 80 kDa band specifically present in re-presentation-competent macrophage but not in the re-presentation-incompetent P815 cells (FIG. 1C). This band appears to correspond in size to the larger of the two bands seen in eluates of gp96 affinity columns (FIG. 1D). No band corresponding to the lower band in that preparation is seen in the photo cross-linked preparation. The observation of a specific binding of gp96 to an 80 kDa protein in two different re-presentation-competent cell types, but not in a re-presentation-incompetent cell line, and by two independent assays supported the candidacy of the 80 kDa molecule for the gp96 receptor.

Antiserum against the 80 kDa protein inhibits re-presentation of a gp96-chaperoned antigenic peptide. The eluates containing the 75–80 kDa proteins were used to immunize a New Zealand white rabbit, and pre-immune and immune sera were used to probe blots of plasma membrane extracts of the re-presentation-competent RAW264.7 and primary peritoneal macrophages and the re-presentation-incompetent P815 cells. The immune but not the pre-immune serum detected the 80 kDa band (and a faint lower 75 kDa band) in plasma membrane extracts of primary macrophage and the RAW264.7 membranes but not of P815 cells (FIG. 2A). The pre-immune and immune sera were tested in a functional assay for their ability to block re-presentation of gp96-chaperoned peptides. The Ld-restricted epitope AH1 derived from the gp70 antigen of murine colon carcinoma CT26 (Huang et al., 1996, Proc. Natl. Acad. Sci. U.S.A. 93:9730–9735) was used as the model system. Complexes of gp96 with an AH1 precursor (used to inhibit direct presentation) were pulsed onto RAW264.7 cells which were used to stimulate a Ld/AH1-specific CD8+ T cell clone. Release of interferon-γ by the clones was measured as a marker of their activation. RAW264.7 cells were able to re-present gp96-chaperoned AH1 precursor effectively in this assay. It was observed that at the highest concentration, the immune sera inhibited re-presentation completely (FIG. 2B). Although the pre-immune serum was ineffective in inhibiting representation as compared to the immune sera, it did inhibit re-presentation significantly at higher concentrations. The significance of this observation became clear later when we determined the identity of the gp96 receptor. Repeated immunizations with the affinity-purified gp96-binding proteins did not result in corresponding increase in antibody titers.

Identification of the 80 kDa protein as an amino terminal fragment of the heavy chain of the α2M receptor. The 80 kDa protein eluted from the gp96 affinity column was resolved on SDS-PAGE and visualized by staining with Coomassie Brilliant Blue. The protein band was subjected to in-gel trypsin digestion and mass spectrometry-based protein microsequencing as described in the methods in Section 6.2. Four independent tryptic peptides corresponding to N-terminal region of the a2-macroglobulin (α2M) receptor, designated by immunologists as CD91, were identified (FIG. 3C).

α2M inhibits re-presentation of a gp96-chaperoned antigenic peptide by RA W264.7. α2M receptor is one of the known natural ligands for the α2M receptor. Its ability to inhibit re-presentation of gp96-chaperoned antigenic peptide AH1 was tested in the assay described in FIG. 2. α2M but not control proteins selectin (CD62) or serum albumin was observed to inhibit re-presentation completely and titratably (FIG. 4). This observation was also consistent with the result in FIG. 2 that while the pre-immune serum did not detect an 80 kDa band in plasma membranes of RAW264.7 cells, it did inhibit re-presentation to some degree at high concentrations. Thus, by structural as well as functional criteria, the α2M receptor was determined to fulfill the criteria essential for a receptor for gp96.

6.4 Discussion

The α2M receptor, which is also designated CD91, was initially identified as a protein related to the low density lipoprotein (LDL) receptor Related Protein (LRP) (Strickland et al., 1990, J. Biol. Chem. 265:17401–17404; Kristensen et al., 1990, FEBS Lett. 276:151–155). The protein consists of an ~420 kDa β subunit, an 85 kDa p subunit and a 39 kDa tightly associated molecule (RAP). The α and β subunits are encoded by a single transcript of 15 Kb in size (Van Leuven et al., 1993, Biochim. Biophys. Acta. 1173: 71–74. The receptor has been shown to be present in cells of the monocytic lineage and in hepatocytes, fibroblasts and keratinocytes. CD91 has been shown previously to bind the activated form of the plasma glycoprotein α2M, which binds to and inhibits a wide variety of endoproteinases. α2M receptor also binds to other ligands such as transforming growth factor β (O'Connor-McCourt et al., 1987, J. Biol. Chem. 262:14090–14099), platelet-derived growth factor (Huang et al., 1984, Proc. Natl. Acad. Sci. U.S.A. 81:342–346), and fibroblast growth factor (Dennis et al., 1989, J. Biol. Chem. 264:7210–7216). α2M is thus believed to regulate, and specifically diminish, the activities of its various ligands. Complexed with these various ligands, α2M binds cc2M receptor on the cell surface and is internalized through receptor-mediated endocytosis. Uptake of α2M-complexed ligands has been assumed thus far to be the primary function of the α2M receptor, although a role for it in lipid metabolism is also assumed. α2M receptor ligands other than α2M, such as tissue-specific plasminogen activator-inhibitor complex (Orth et al., 1992, Proc. Natl. Acad. Sci. U.S.A. 89:7422–7426) and urokinase-PAI1 complex (Nykjaer et al., 1992, J. Biol. Chem. 267:14543–14546), have been identified. These ligands attest to a role for α2M receptor in clearing a range of extracellular, plasma products.

The studies reported here show that the heat shock protein gp96 is an additional ligand for the α2M receptor. The human gp96-coding gene has been mapped previously by us at chromosome 12 (q24.2→q24.3) (Maki et al., 1993, Somatic Cell Mol. Gen. 19:73–81). It is of interest in this regard that the α2M receptor gene has been mapped to the same chromosome and at a not too distant location (ql3 q14) (Hilliker et al. Genomics 13:472–474). Gp96 binds α2M receptor directly and not through other ligands such as α2M. Homogenous preparations of gp96, in solution, or cross-linked to a solid matrix, bind to the α2M receptor. Indeed, the major ligand for the α2M receptor, α2M, actually inhibits interaction of gp96 with α2M receptor, instead of promoting it, providing evidence that gp96 is a direct ligand for the α2M receptor. The 80 kDa protein shown to bind gp96 is clearly an amino terminal degradation product of the α subunit of the α2M receptor. Degradation products of the α2M receptor in this size range have also been observed in previous studies (Jensen et al., 1989, Biochem. Arch. 5:171–176), and may indicate the existence of a discrete ectodomain in the α2M receptor which may be particularly sensitive to proteolytic cleavage.

As shown here, the gp96-α2M receptor interaction provides a new type of function for α2M receptor, a function of a sensor, not only of the extracellular environment with its previously known plasma-based ligands, but also a sensor of the intracellular milieu as well. HSPs such as gp96 are obligate intracellular molecules and are released into the extracellular milieu only under conditions of necrotic (but not apoptotic) cell death. Thus, the α2M receptor may act as a sensor for necrotic cell death (see FIG. 5), just as the scavenger receptor CD36 and the recently identified phosphatidyl serine-binding protein act as sensors of apoptotic cell death and receptors for apoptotic cells (Savill et al., 1992, J. Clin. Invest. 90:1513–1522; Fadok et al., 2000, Nature 405:85–90). Interaction of the macrophages with the apoptotic cells leads to a down-regulation of the inflammatory cytokines such as TNF (Fadok et al., 2000, supra), while gp96-APC interaction leads to re-presentation of gp96-chaperoned peptides by MHC I molecules of the APC, followed by stimulation of antigen-specific T cells (Suto and Srivastava, 1995, supra) and, in addition, secretion of pro-inflammatory cytokines such as TNF, GM-CSF and IL-12. Interestingly, α2M, an independent ligand for the α2M receptor, inhibits representation of gp96-chaperoned peptides by macrophages. This observation suggests that re-presentation of gp96-chaperoned peptides can not occur physiologically in blood, but only within tissues as a result of localized necrotic cell death. This is consistent with the complete absence of gp96 or other HSPs in blood under all conditions tested. Together, these observations point towards a possible mechanism whereby the release of HSPs in the blood as a result of severe tissue injury and lysis will not lead to a systemic and lethal pro-inflammatory cytokine cascade.

It is possible, therefore, that the α2M receptor renders it possible for the APCs to sample (i) the extracellular milieu of the blood through α2M and other plasma ligands and (ii) the intracellular milieu of the tissues through HSPs, particularly of the gp96 family. The former permits APCs to implement their primordial phagocytic function, while the latter allows them to execute its innate and adaptive immunological functions. Viewed in another perspective, recognition of apoptotic cells by APCs through CD36 or phophatidyl serine, leads to anti-inflammatory signals, while interaction of the APC with necrotic cells through α2M receptor leads to pro-inflammatory innate and adaptive immune responses (see Srivastava et al., 1998, Immunity 8: 657–665).

The invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

All references cited herein, including patent applications, patents, and other publications, are incorporated by reference herein in their entireties for all purposes.

What is claimed is:

1. A method for identifying a compound that modulates a process selected from the group consisting of heat shock protein (hereinafter "HSP") binding activity, HSP uptake activity, and HSP-mediated antigen representation activity, comprising:

(a) contacting a test compound with: (i) a ligand-binding fragment of an alpha (2) macroglobulin (hereinafter "α2M") receptor; and (ii) a purified HSP, or a receptor-binding fragment thereof, or a purified HSP-peptide complex; and (b) measuring the level of HSP binding activity, HSP uptake activity, or HSP-mediated antigen representation activity, such that if the level of HSP binding activity, HSP uptake activity, or HSP-mediated antigen representation activity measured in (b) differs from the level of HSP binding activity, HSP uptake activity, or HSP-mediated antigen representation activity in the absence of the test compound, then a compound that modulates said process is identified.

2. The method of claim 1 wherein the ligand-binding fragment of the α2M receptor is immobilized to a solid surface.

3. The method of claim 1 wherein the compound identified is an antagonist that interferes with said process.

4. The method of claim 1 wherein the process affects diabetes or other autoimmune disorder, a disease or disorder involving disruption of antigen presentation or endocytosis, a disease or disorder involving cytokine clearance or inflammation, a proliferative disorder, a viral disorder or other infectious disease, hypercholesterolemia, Alzheimer's disease, or osteoporosis.

5. The method of claim 1 wherein the test compound is an antibody specific for the α2M receptor.

6. The method of claim 1 wherein the test compound is an antibody specific for α2M.

7. The method of claim 1 wherein the test compound is an antibody specific for an HSP.

8. The method of claim 1 wherein the test compound is a small molecule.

9. The method of claim 1 wherein the test compound is a peptide.

10. The method of claim 9 wherein the peptide comprises at least 5 consecutive amino acids of α2M (SEQ ID NO.: 4).

11. The method of claim 9 wherein the peptide comprises at least 5 consecutive amino acids of an HSP.

12. The method of claim 9 wherein the peptide comprises at least 5 consecutive amino acids of the α2M receptor (SEQ ID NO.: 7).

13. The method of claim 1 wherein the activity measured is HSP binding activity.

14. The method of claim 13 wherein the HSP, or receptor-binding fragment thereof, is labeled and contacted with said test compound in step (a), and the amount of bound HSP, or receptor-binding fragment thereof, is measured by detecting the label.

15. The method of claim 13 wherein measuring the level of HSP binding activity of step (b) comprises measuring the amount of HSP, or receptor binding fragment thereof, bound to the ligand-binding fragment of the α2M receptor, such that if the amount of bound HSP, or receptor-binding fragment thereof, measured in (b) differs from the amount of bound HSP, or receptor-binding fragment thereof, measured in the absence of the test compound, then a compound that modulates the binding of an HSP to the α2M receptor is identified.

16. The method of claim 1 wherein the ligand-binding fragment of the α2M receptor is purified.

17. The method of claim 1 wherein HSP uptake activity is measured.

18. The method of claim 1 wherein HSP-mediated antigen representation activity is measured.

19. The method of claim 1 wherein the ligand-binding fragment of the α2M receptor comprises a cluster of complement repeats.

20. The method of claim 19 wherein the cluster of complement repeats comprises the CI–CII complement repeat cluster of the α2M receptor.

21. The method of claim 1 wherein the ligand-binding fragment of the α2M receptor comprises the p80 fragment of the α2M receptor.

22. The method of claim 1 wherein the ligand-binding fragment of the α2M receptor is a peptide consisting of amino acid nos. 25–110 (SEQ ID NO:21) of the human α2M receptor.

23. The method of claim 19 wherein at least one complement repeat is selected from the group consisting of CR3 to CR10.

24. The method of claim 1, wherein the HSP is hsp90.

25. The method of claim 1, wherein the HSP is gp96.

26. The method of claim 1, wherein the HSP is hsp70.

27. The method of claim 1, wherein the HSP is calreticulin.

* * * * *